US012600717B2

(12) United States Patent
Li et al.

(10) Patent No.: US 12,600,717 B2
(45) Date of Patent: Apr. 14, 2026

(54) TRICYCLIC COMPOUNDS AS INHIBITORS OF KRAS

(71) Applicant: Incyte Corporation, Wilmington, DE (US)

(72) Inventors: Zhenwu Li, Wilmington, DE (US); Zhiyong Yu, Hockessin, DE (US); Jeremy Roach, Philadelphia, PA (US); Gia Hoang, Wilmington, DE (US); Bin Hu, Garnet Valley, PA (US); Gencheng Li, Claymont, DE (US); Rory McAtee, Kennett Square, PA (US); Ken Mukai, Wilmington, DE (US); Rocco Policarpo, Wilmington, DE (US); Robert Susick, Wilmington, DE (US); Xiaozhao Wang, Mt. Laurel, NJ (US); Wenqing Yao, Wilmington, DE (US)

(73) Assignee: Incyte Corporation, Wilmington, DE (US)

( * ) Notice: Subject to any disclaimer, the term of this patent is extended or adjusted under 35 U.S.C. 154(b) by 184 days.

(21) Appl. No.: 17/812,310

(22) Filed: Jul. 13, 2022

(65) Prior Publication Data

US 2023/0114765 A1 Apr. 13, 2023

Related U.S. Application Data

(60) Provisional application No. 63/221,595, filed on Jul. 14, 2021.

(51) Int. Cl.

| | |
|---|---|
| ***C07D 471/04*** | (2006.01) |
| ***A61P 35/00*** | (2006.01) |
| ***A61P 35/02*** | (2006.01) |
| ***A61P 35/04*** | (2006.01) |
| ***C07D 519/00*** | (2006.01) |

(52) U.S. Cl.

CPC ............ *C07D 471/04* (2013.01); *A61P 35/00* (2018.01); *A61P 35/02* (2018.01); *A61P 35/04* (2018.01); *C07D 519/00* (2013.01)

(58) Field of Classification Search

CPC .................................................... C07D 471/04

See application file for complete search history.

(56) References Cited

U.S. PATENT DOCUMENTS

| | | | |
|---|---|---|---|
| 7,592,453 | B2 | 9/2009 | Kajino et al. |
| 7,897,609 | B2 | 3/2011 | Niwas et al. |
| 8,034,802 | B2 | 10/2011 | Averett |
| 8,143,270 | B2 | 3/2012 | Kshirsagar et al. |
| 8,158,794 | B2 | 4/2012 | Kshirsagar et al. |
| 8,207,187 | B2 | 6/2012 | Beck et al. |
| 8,513,250 | B2 | 8/2013 | Escaich et al. |
| 8,557,984 | B2 | 10/2013 | Bouillot et al. |
| 8,563,565 | B2 | 10/2013 | Norimine et al. |
| 8,637,670 | B2 | 1/2014 | Kumar et al. |
| 8,658,666 | B2 | 2/2014 | Rice et al. |
| 8,846,710 | B2 | 9/2014 | Kshirsagar et al. |
| 8,895,581 | B2 | 11/2014 | McConnell et al. |
| 9,062,046 | B2 | 6/2015 | Kumar et al. |
| 9,169,246 | B2 | 10/2015 | Benazet et al. |
| 9,550,776 | B2 | 1/2017 | Norimine et al. |
| 9,573,947 | B2 | 2/2017 | Ozaki |
| 9,771,327 | B2 | 9/2017 | Zawistoski et al. |
| 9,873,694 | B2 | 1/2018 | Lipford et al. |
| 10,039,753 | B2 | 8/2018 | Coffman et al. |
| 10,544,138 | B2 | 1/2020 | Gray et al. |
| 11,053,240 | B2 | 7/2021 | Li et al. |
| 2005/0054590 | A1 | 3/2005 | Averett |
| 2011/0230476 | A1 | 9/2011 | Niu et al. |
| 2012/0065187 | A1 | 3/2012 | Borchardt et al. |
| 2012/0108627 | A1 | 5/2012 | Kumar et al. |
| 2012/0232074 | A1 | 9/2012 | Bouillot et al. |
| 2014/0243286 | A1 | 8/2014 | Arnold et al. |
| 2016/0264570 | A1 | 9/2016 | McKew et al. |
| 2017/0197945 | A1 | 7/2017 | Li et al. |

(Continued)

FOREIGN PATENT DOCUMENTS

| | | |
|---|---|---|
| CN | 102399218 A | 4/2012 |
| CN | 103012397 B | 3/2017 |

(Continued)

OTHER PUBLICATIONS

International Search Report and Written Opinion for International Application No. PCT/US2021/012689, mailed Mar. 18, 2021, 11 pages.

(Continued)

*Primary Examiner* — Susanna Moore

(74) *Attorney, Agent, or Firm* — Lathrop GPM LLP; Brian C. Trinque; Nicole Sassu

(57) ABSTRACT

Disclosed are compounds of Formula I (shown below), methods of using the compounds for inhibiting KRAS activity and pharmaceutical compositions comprising such compounds. The compounds are useful in treating, preventing or ameliorating diseases or disorders associated with KRAS activity such as cancer.

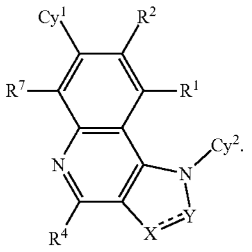

34 Claims, No Drawings

(56) References Cited

U.S. PATENT DOCUMENTS

| | | | |
|---|---|---|---|
| 2017/0217960 | A1 | 8/2017 | Ferguson |
| 2017/0294489 | A1 | 10/2017 | Lim et al. |
| 2019/0144444 | A1 | 5/2019 | Blake et al. |
| 2019/0177338 | A1 | 6/2019 | Kettle et al. |
| 2019/0270743 | A1 | 9/2019 | Marx et al. |
| 2021/0230162 | A1 | 7/2021 | Zhao et al. |
| 2021/0269434 | A1 | 9/2021 | Wang et al. |
| 2021/0308123 | A1 | 10/2021 | Zhang et al. |
| 2021/0317118 | A1 | 10/2021 | Zhang et al. |
| 2021/0355121 | A1 | 11/2021 | Zhu et al. |
| 2021/0355141 | A1 | 11/2021 | Hoang et al. |
| 2022/0064188 | A1 | 3/2022 | Carlsen et al. |
| 2022/0106309 | A1 | 4/2022 | Huang et al. |

FOREIGN PATENT DOCUMENTS

| | | | |
|---|---|---|---|
| CN | 108003153 | A | 5/2018 |
| EP | 1740584 | B1 | 12/2008 |
| EP | 2573073 | B1 | 10/2014 |
| EP | 2760841 | B1 | 8/2016 |
| IN | 201202281 | | 6/2012 |
| WO | WO 2008/056151 | A1 | 5/2008 |
| WO | WO 2009/123967 | A1 | 10/2009 |
| WO | WO 2010/030785 | A2 | 3/2010 |
| WO | WO 2010/049366 | A1 | 5/2010 |
| WO | WO 2010/135571 | A1 | 11/2010 |
| WO | WO 2011/031896 | A2 | 3/2011 |
| WO | WO 2012/011642 | A1 | 1/2012 |
| WO | WO 2012/154731 | A1 | 11/2012 |
| WO | WO 2013/045400 | A1 | 4/2013 |
| WO | WO 2016/161361 | A4 | 10/2016 |
| WO | WO 2016/168540 | A1 | 10/2016 |
| WO | WO 2016/199943 | A1 | 12/2016 |
| WO | WO 2017/058805 | A1 | 4/2017 |
| WO | WO 2017/092413 | A1 | 6/2017 |
| WO | WO 2017/201161 | A1 | 11/2017 |
| WO | WO 2018/119183 | A2 | 6/2018 |
| WO | WO 2018/217651 | A1 | 11/2018 |
| WO | WO 2019/201283 | A1 | 10/2019 |
| WO | WO 2019/209896 | A1 | 10/2019 |
| WO | WO 2019/213516 | A1 | 11/2019 |
| WO | WO 2020/037091 | A1 | 2/2020 |
| WO | WO 2020/037092 | A1 | 2/2020 |
| WO | WO 2020/055755 | A1 | 3/2020 |

OTHER PUBLICATIONS

Korzeniecki et al., "Targeting KRAS mutant cancers by preventing signaling transduction in the MAPK pathway", *European Journal of Medicinal Chemistry* 211, 113006 (2021).

Zhu et al., "Structure-based discovery of selective BRPFI bromodomain inhibitors", *European Journal of Medicinal Chemistry* 155:337-352 (2018).

Chen et al., "Small-Molecule Inhibitors Directly Targeting KRAS as Anticancer Therapeutics", *Journal of Medicinal Chemistry* 63(3):14404-14424 (2020).

Cox et al., "Drugging the undruggable Ras: mission impossible?", *Nature Reviews Drug Discovery* 13(11):828-851 (2014).

Fernandez-Medarde et al., "Ras in Cancer and Developmental Diseases", *Genes & Cancer* 2(3):344-358 (2011).

TRICYCLIC COMPOUNDS AS INHIBITORS OF KRAS

RELATED APPLICATIONS

This application claims priority to U.S. Provisional Application No. 63/221,595 filed on Jul. 14, 2021, the content of which is hereby incorporated in its entirety.

FIELD OF THE INVENTION

The disclosure provides compounds as well as their compositions and methods of use. The compounds modulate KRAS activity and are useful in the treatment of various diseases including cancer.

BACKGROUND OF THE INVENTION

Ras proteins are part of the family of small GTPases that are activated by growth factors and various extracellular stimuli. The Ras family regulates intracellular signaling pathways responsible for growth, migration, survival and differentiation of cells. Activation of RAS proteins at the cell membrane results in the binding of key effectors and initiation of a cascade of intracellular signaling pathways within the cell, including the RAF and PI3K kinase pathways. Somatic mutations in RAS may result in uncontrolled cell growth and malignant transformation while the activation of RAS proteins is tightly regulated in normal cells (Simanshu, D. et al. Cell 170.1 (2017):17-33).

The Ras family is comprised of three members: KRAS, NRAS and HRAS. RAS mutant cancers account for about 25% of human cancers. KRAS is the most frequently mutated isoform accounting for 85% of all RAS mutations whereas NRAS and HRAS are found mutated in 12% and 3% of all Ras mutant cancers respectively (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residue 12, 13, and 61. The frequency of specific mutations varies between RAS gene isoforms and while G12 and Q61 mutations are predominant in KRAS and NRAS respectively, G12, G13 and Q61 mutations are most frequent in HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) while KRAS G12 V mutations are associated with pancreatic cancers (30%), followed by colorectal adenocarcinomas (27%) and lung adenocarcinomas (23%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas, and 2-5% of pancreatic and colorectal adenocarcinomas (Cox, A. D. et al. Nat. Rev. Drug Discov. (2014) 13:828-51). Genomic studies across hundreds of cancer cell lines have demonstrated that cancer cells harboring KRAS mutations are highly dependent on KRAS function for cell growth and survival (McDonald, R. et al. Cell 170 (2017): 577-592). The role of mutant KRAS as an oncogenic driver is further supported by extensive in vivo experimental evidence showing mutant KRAS is required for early tumour onset and maintenance in animal models (Cox, A. D. et al. Nat Rev Drug Discov (2014) 13:828-51).

Taken together, these findings suggest that KRAS mutations play a critical role in human cancers; development of inhibitors targeting mutant KRAS may therefore be useful in the clinical treatment of diseases that are characterized by a KRAS mutation.

SUMMARY

The present disclosure provides, inter alia, a compound of Formula I:

(I)

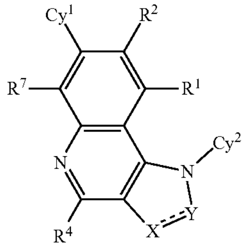

or a pharmaceutically acceptable salt thereof, wherein constituent variables are defined herein.

The present disclosure further provides a pharmaceutical composition comprising a compound of the disclosure, or a pharmaceutically acceptable salt thereof, and at least one pharmaceutically acceptable carrier or excipient.

The present disclosure further provides methods of inhibiting KRAS activity, which comprises administering to an individual a compound of the disclosure, or a pharmaceutically acceptable salt thereof. The present disclosure also provides uses of the compounds described herein in the manufacture of a medicament for use in therapy. The present disclosure also provides the compounds described herein for use in therapy.

The present disclosure further provides methods of treating a disease or disorder in a patient comprising administering to the patient a therapeutically effective amount of a compound of the disclosure, or a pharmaceutically acceptable salt thereof.

DETAILED DESCRIPTION

Compounds

In an aspect, provided herein is a compound having Formula I:

(I)

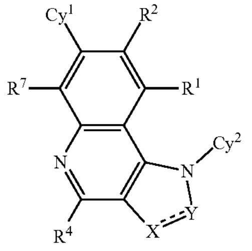

or a pharmaceutically acceptable salt thereof, wherein:

X$\overset{---}{=}$Y is selected from —$NR^5$—C(═O)—, —N═N—, and —N═$CR^6$—;

$R^1$ is selected from H, D, $C_{1-2}$ alkyl, and $C_{1-2}$ haloalkyl; wherein said $C_{1-2}$ alkyl is optionally substituted with 1 or 2 substituents independently selected from $R^{11}$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, or 3 substituents independently selected from $R^{10}$;

$R^4$ is selected from H, $C_{1-3}$ alkyl, $C_{1-3}$ haloalkyl, 5-10 membered heteroaryl, $OR^{a3}$, and $NR^{c3}R^{j3}$; wherein said $C_{1-3}$ alkyl and 5-10 membered heteroaryl, are each optionally substituted with 1 or 2 substituents independently selected from $R^{30}$; or $R^4$ is selected from $R^4$-a

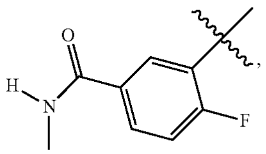

$R^4$-b

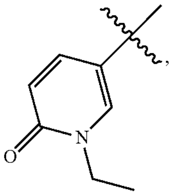

and $R^4$-c

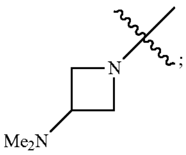

$R^5$ is selected from H, $C_{1-2}$ alkyl, and $C_{1-2}$ haloalkyl;

$R^7$ is selected from H, $C_{1-3}$ alkyl, $C_{1-3}$ haloalkyl, phenyl, 5-6 membered heteroaryl, F, Cl, D, CN, $OR^{a7}$, and $NR^{c7}R^{d7}$; wherein said phenyl, and 5-6 membered heteroaryl, are each optionally substituted with 1 or 2 substituents independently selected from $R^{70}$;

$Cy^2$ is selected from $Cy^2$-a

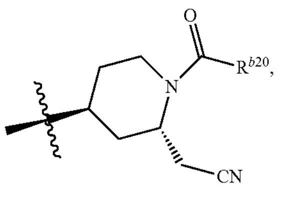

and $Cy^2$-b

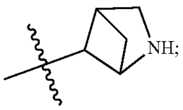

when $Cy^2$ is $Cy^2$-a and X ═ Y is —N═$CR^6$, then, $R^6$ is selected from H, D, $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl, are each optionally substituted with 1 or 2 substituents independently selected from $R^{60}$;

when $Cy^2$ is $Cy^2$-a, then $R^2$ is selected from H, $C_{1-2}$ alkyl, $C_{1-2}$ haloalkyl, F, Cl, and —$CH_2CH_2CN$;

when $Cy^2$ is $Cy^2$-b and X ═ Y is-N═$CR^6$—, then $R^6$ is selected from $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl, are each optionally substituted with 1 or 2 substituents independently selected from $R^{60}$;

when $Cy^2$ is $Cy^2$-b, then $R^2$ is selected from H, $C_{1-2}$ alkyl, $C_{1-2}$ haloalkyl, F, —$CH_2CH_2CN$, $R^2$-a

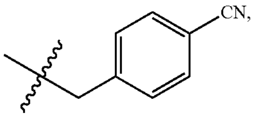

$R^2$-b

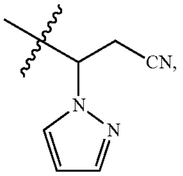

$R^2$-c

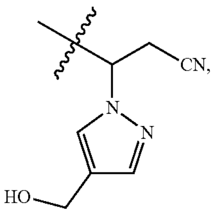

$R^2$-d

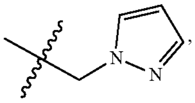

and $R^2$-e

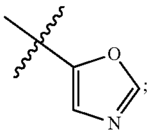

each $R^{10}$ is independently selected from $C_{1-3}$ alkyl, $C_{1-3}$ haloalkyl, $C_{3-6}$ cycloalkyl, halo, D, CN, $OR^{a10}$, C(O) $NR^{c10}R^{d10}$, $NR^{c10}C(O)OR^{a10}$, $NR^{c10}C(O)$ $NR^{c10}R^{d10}$, and $NR^{c10}R^{d10}$; wherein said $C_{1-3}$ alkyl, and $C_{3-6}$ cycloalkyl are each optionally substituted with 1 or 2 substituents independently selected from $R^g$;

each $R^{11}$ is independently selected from $C_{1-2}$ alkyl, $C_{1-2}$ haloalkyl, $C_{3-6}$ cycloalkyl, 4-6 membered heterocycloalkyl, halo, D, CN, $OR^{a1}$, and $NR^{c11}R^{d11}$; wherein said $C_{1-2}$ alkyl, $C_{3-6}$ cycloalkyl, and 4-6 membered heterocycloalkyl, are each optionally substituted with 1 or 2 substituents independently selected from $R^g$;

each $R^{21}$ is independently selected from $C_{1-3}$ alkyl, $C_{1-3}$ haloalkyl, halo, D, CN, $OR^{a21}$, and $NR^{c21}R^{d21}$;

each $R^{30}$ is independently selected from $C_{1-3}$ alkyl, $C_{1-3}$ haloalkyl, 4-10 membered heterocycloalkyl, halo, D, CN, $OR^{a30}$, $C(O)NR^{c30}R^{d30}$, $NR^{c30}C(O)OR^{a30}$, $NR^{c30}C(O)NR^{c30}R^{d30}$ and $NR^{c30}R^{d30}$; wherein said $C_{1-3}$ alkyl, and 4-6 membered heterocycloalkyl, are each optionally substituted with 1 or 2 substituents independently selected from $R^{31}$;

each $R^{31}$ is independently selected from $C_{1-3}$ alkyl, $C_{1-3}$ haloalkyl, halo, D, and CN;

each $R^{60}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a60}$, $C(O)R^{b60}$, $C(O)NR^{c60}R^{d60}$, and $NR^{c60}R^{d60}$; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$;

each $R^{61}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a61}$, $C(O)R^{b61}$, and $NR^{c61}R^{d61}$;

each $R^{70}$ is independently selected from $C_{1-3}$ alkyl, $C_{1-3}$ haloalkyl, phenyl, 5-6 membered heteroaryl, halo, D, CN, $OR^{a70}$, and $NR^{c70}R^{d70}$;

each $R^{a3}$, and $R^{c3}$ is independently selected from H, $C_{1-3}$ alkyl, $C_{1-3}$ haloalkyl, 5-6 membered heteroaryl, and phenyl; wherein said $C_{1-3}$ alkyl, 5-6 membered heteroaryl, and phenyl are each optionally substituted with 1 or 2 substituents independently selected from $R^{30}$;

each $R^{f3}$ is independently selected from $C_{1-3}$ alkyl, and $C_{1-3}$ haloalkyl;

each $R^{a7}$, $R^{c7}$ and $R^{d7}$ is independently selected from H, $C_{1-3}$ alkyl, and $C_{1-3}$ haloalkyl; wherein said $C_{1-3}$ alkyl, is optionally substituted with 1 or 2 substituents independently selected from $R^{70}$;

each $R^{a10}$, $R^{c10}$ and $R^{d10}$ is independently selected from H, $C_{1-3}$ alkyl, and $C_{1-3}$ haloalkyl;

each $R^{a11}$, $R^{c11}$ and $R^{d11}$, is independently selected from H, $C_{1-3}$ alkyl, and $C_{1-3}$ haloalkyl;

$R^{b20}$ is selected from $NH_2$, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{21}$;

each $R^{a21}$, $R^{c21}$ and $R^{d21}$, is independently selected from H, $C_{1-3}$ alkyl, and $C_{1-3}$ haloalkyl;

each $R^{a30}$, $R^{c30}$ and $R^{d30}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$;

or any $R^{c60}$ and $R^{d60}$ attached to the same N atom, together with the N atom to which they are attached, form a 4-, 5-, 6-. 7-, 8-, or 9-membered heterocycloalkyl group optionally substituted with 1 or 2 substituents independently selected from $R^{61}$;

each $R^{a61}$, $R^{b61}$ $R^{c61}$ and $R^{d61}$, is independently selected from H, $C_{1-3}$ alkyl, and $C_{1-3}$ haloalkyl;

each $R^{a70}$, $R^{c70}$ and $R^{d70}$, is independently selected from H, $C_{1-3}$ alkyl, and $C_{1-3}$ haloalkyl; and each $R^g$ is independently selected from D, OH, CN, halo, $C_{1-2}$ alkyl, amino, and $C_{1-2}$ haloalkyl; provided that the compound of Formula I is other than,

| |
|---|
| 3-(1-((endo)-2-azabicyclo[2.1.1]hexan-5-yl)-8-(2-cyanoethyl)-4-(3-(dimethylamino)azetidin-1-yl)-6-fluoro-7-(7-fluoronaphthalen-1-yl)-1H-imidazo[4,5-c]quinolin-2-yl)-N,N-dimethylpropanamide, |
| 3-(1-((endo)-2-azabicyclo[2.1.1]hexan-5-yl)-4-(3-(dimethylamino)azetidin-1-yl)-2-ethyl-6-fluoro-7-(7-fluoro-3-hydroxynaphthalen-1-yl)-1H-imidazo[4,5-c]quinolin-8-yl)propanenitrile, |
| 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-((3-oxomorpholino)methyl)-1H-imidazo[4,5-c]quinolin-8-yl)propanenitrile, |
| 3-(1-((endo)-2-azabicyclo[2.1.1]hexan-5-yl)-8-(2-cyanoethyl)-4-(3-(dimethylamino)azetidin-1-yl)-6-fluoro-7-(3-hydroxynaphthalen-1-yl)-1H-imidazo[4,5-c]quinolin-2-yl)-N-methyl-N-(pyridin-2-ylmethyl)propanamide, and |
| 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(piperazin-1-yl)thiazol-4-yl)-1H-imidazo[4,5-c]quinolin-8-yl)propanenitrile. |

In an embodiment of Formula I, or a pharmaceutically acceptable salt thereof,

X$\overline{---}$Y is selected from —$NR^5$—C(═O)—, —N═N—, and —N═$CR^6$—;

$R^1$ is selected from H, D, $C_{1-2}$ alkyl, and $C_{1-2}$ haloalkyl; wherein said $C_{1-2}$ alkyl is optionally substituted with 1 or 2 substituents independently selected from $R^{11}$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, or 3 substituents independently selected from $R^{10}$;

$R^4$ is selected from $OR^{a3}$;

$R^5$ is selected from H, $C_{1-2}$ alkyl, and $C_{1-2}$ haloalkyl;

$R^7$ is selected from H, $C_{1-3}$ alkyl, $C_{1-3}$ haloalkyl, phenyl, 5-6 membered heteroaryl, F, Cl, D, CN, $OR^{a7}$, and $NR^{c7}R^{d7}$; wherein said phenyl, and 5-6 membered heteroaryl, are each optionally substituted with 1 or 2 substituents independently selected from $R^{70}$;

$Cy^2$ is selected from $Cy^2$-a

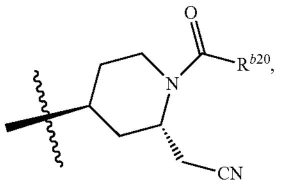

and $Cy^2$-b

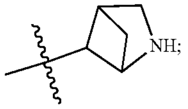

when $Cy^2$ is $Cy^2$-a and X== Y is —N=$CR^6$— then, $R^6$ is selected from H, D, $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl, are each optionally substituted with 1 or 2 substituents independently selected from $R^{60}$;

when $Cy^2$ is $Cy^2$-a, then $R^2$ is selected from H, $C_{1-2}$ alkyl, $C_{1-2}$ haloalkyl, F, Cl, and —$CH_2CH_2CN$;

when $Cy^2$ is $Cy^2$-b and X==is-N=$CR^6$—, then $R^6$ is selected from $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl, are each optionally substituted with 1 or 2 substituents independently selected from $R^{60}$;

when $Cy^2$ is $Cy^2$-b, then $R^2$ is selected from H, $C_{1-2}$ alkyl, $C_{1-2}$ haloalkyl, F, —$CH_2CH_2CN$, $R^2$-a

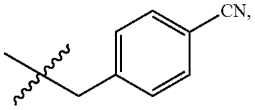

$R^2$-b

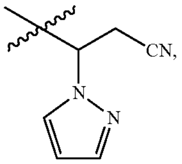

$R^2$-c

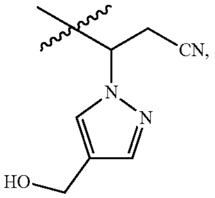

$R^2$-d

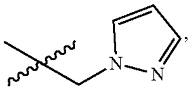

and

-continued $R^2$-e

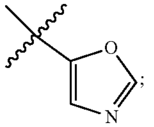

each $R^{10}$ is independently selected from $C_{1-3}$ alkyl, $C_{1-3}$ haloalkyl, $C_{3-6}$ cycloalkyl, halo, D, CN, $OR^{a10}$, C(O) $NR^{c10}R^{d10}$, $NR^{c10}C(O)OR^{a10}$, $NR^{c10}C(O)$ $NR^{c10}R^{d10}$, and $NR^{c10}R^{d10}$; wherein said $C_{1-3}$ alkyl, and $C_{3-6}$ cycloalkyl are each optionally substituted with 1 or 2 substituents independently selected from $R^g$;

each $R^{11}$ is independently selected from $C_{1-2}$ alkyl, $C_{1-2}$ haloalkyl, $C_{3-6}$ cycloalkyl, 4-6 membered heterocycloalkyl, halo, D, CN, $OR^{a1}$, and $NR^{c11}R^{d11}$; wherein said $C_{1-2}$ alkyl, $C_{3-6}$ cycloalkyl, and 4-6 membered heterocycloalkyl, are each optionally substituted with 1 or 2 substituents independently selected from $R^g$;

each $R^{21}$ is independently selected from $C_{1-3}$ alkyl, $C_{1-3}$ haloalkyl, halo, D, CN, $OR^{a21}$ and $NR^{c21}R^{d21}$;

each $R^{30}$ is independently selected from $C_{1-3}$ alkyl, $C_{1-3}$ haloalkyl, 4-10 membered heterocycloalkyl, halo, D, CN, $OR^{a30}$, $C(O)NR^{c30}R^{d30}$, $NR^{c30}C(O)OR^{a30}$, $NR^{c30}C(O)NR^{c30}R^{d30}$ and $NR^{c30}R^{d30}$; wherein said $C_{1-3}$ alkyl, and 4-6 membered heterocycloalkyl, are each optionally substituted with 1 or 2 substituents independently selected from $R^{31}$;

each $R^{31}$ is independently selected from $C_{1-3}$ alkyl, $C_{1-3}$ haloalkyl, halo, D, and CN;

each $R^{60}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a60}$, $C(O)R^{b60}$, $C(O)NR^{c60}R^{d60}$, and $NR^{c60}R^{d60}$; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$;

each $R^{61}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a61}$, $C(O)R^{b61}$, and $NR^{c61}R^{d61}$;

each $R^{70}$ is independently selected from $C_{1-3}$ alkyl, $C_{1-3}$ haloalkyl, phenyl, 5-6 membered heteroaryl, halo, D, CN, $OR^{a70}$, and $NR^{c70}R^{d70}$;

each $R^{a3}$ is independently selected from H, $C_{1-3}$ alkyl, $C_{1-3}$ haloalkyl, 5-6 membered heteroaryl, and phenyl; wherein said $C_{1-3}$ alkyl, 5-6 membered heteroaryl, and phenyl are each optionally substituted with 1 or 2 substituents independently selected from $R^{30}$;

each $R^{a7}$, $R^{c7}$ and $R^{d7}$ is independently selected from H, $C_{1-3}$ alkyl, and $C_{1-3}$ haloalkyl; wherein said $C_{1-3}$ alkyl, is optionally substituted with 1 or 2 substituents independently selected from $R^{70}$;

each $R^{a10}$, $R^{c10}$ and $R^{d10}$ is independently selected from H, $C_{1-3}$ alkyl, and $C_{1-3}$ haloalkyl;

each $R^{a11}$, $R^{c11}$ and $R^{d11}$, is independently selected from H, $C_{1-3}$ alkyl, and $C_{1-3}$ haloalkyl;

$R^{b20}$ is selected from $NH_2$, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{21}$;

each $R^{a21}$, $R^{c21}$ and $R^{d21}$, is independently selected from H, $C_{1-3}$ alkyl, and $C_{1-3}$ haloalkyl;

each $R^{a30}$, $R^{c30}$ and $R^{d30}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$;

or any $R^{c60}$ and $R^{d60}$ attached to the same N atom, together with the N atom to which they are attached, form a 4-, 5-, 6-. 7-, 8-, or 9-membered heterocycloalkyl group optionally substituted with 1 or 2 substituents independently selected from $R^{61}$;

each $R^{a61}$, $R^{b61}$ $R^{c61}$ and $R^{d61}$, is independently selected from H, $C_{1-3}$ alkyl, and $C_{1-3}$ haloalkyl;

each $R^{a70}$, $R^{c70}$ and $R^{d70}$, is independently selected from H, $C_{1-3}$ alkyl, and $C_{1-3}$ haloalkyl; and each $R^g$ is independently selected from D, OH, CN, halo, $C_{1-2}$ alkyl, amino, and $C_{1-2}$ haloalkyl.

In another embodiment of Formula I, or a pharmaceutically acceptable salt thereof, X$\overline{---}$Y is selected from —$NR^5$—C(═O)—, —N═N—, and —N═$CR^6$—;

$R^1$ is selected from H, D, $C_{1-2}$ alkyl, and $C_{1-2}$ haloalkyl; wherein said $C_{1-2}$ alkyl is optionally substituted with 1 or 2 substituents independently selected from $R^{11}$;

$Cy^1$ is selected from $C_{3-10}$ cycloalkyl, 4-10 membered heterocycloalkyl, phenyl and 6-10 membered heteroaryl; wherein the 4-10 membered heterocycloalkyl and 6-10 membered heteroaryl each has at least one ring-forming carbon atom and 1 or 2 ring-forming heteroatoms independently selected from N, O, and S; and wherein the $C_{3-10}$ cycloalkyl, 4-10 membered heterocycloalkyl, phenyl and 6-10 membered heteroaryl are each optionally substituted with 1, 2, or 3 substituents independently selected from $R^{10}$; or $Cy^1$ is selected from $Cy^1$-a

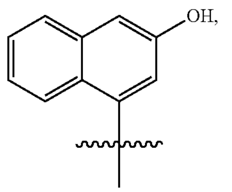

and $Cy^1$-b

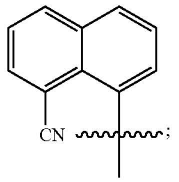

;

$R^4$ is selected from H, $C_{1-3}$ alkyl, $C_{1-3}$ haloalkyl, 5-10 membered heteroaryl, $OR^{a3}$, and $NR^{c3}R^{j3}$; wherein said $C_{1-3}$ alkyl and 5-10 membered heteroaryl, are each optionally substituted with 1 or 2 substituents independently selected from $R^{30}$; or $R^4$ is selected from $R^4$-a

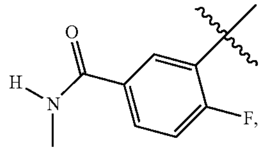

, $R^4$-b

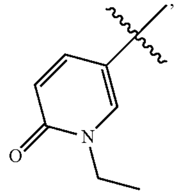

, and $R^4$-c

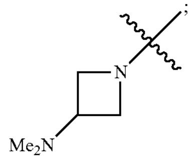

;

$R^5$ is selected from H, $C_{1-2}$ alkyl, and $C_{1-2}$ haloalkyl;

$R^7$ is selected from H, $C_{1-3}$ alkyl, $C_{1-3}$ haloalkyl, phenyl, 5-6 membered heteroaryl, F, Cl, D, CN, $OR^{a7}$, and $NR^{c7}R^{d7}$; wherein said phenyl, and 5-6 membered heteroaryl, are each optionally substituted with 1 or 2 substituents independently selected from $R^{70}$;

$Cy^2$ is selected from $Cy^2$-a

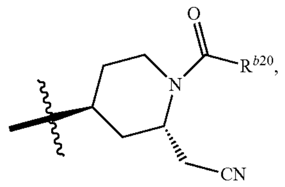

, and $Cy^2$-b

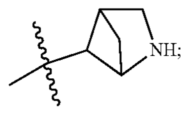

;

when $Cy^2$ is $Cy^2$-a and X$\overline{---}$Y is-N═$CR^6$—, then, $R^6$ is selected from H, $C_{1-3}$ alkyl, $C_{1-3}$ haloalkyl, $C_{3-6}$ cycloalkyl, 4-6 membered heterocycloalkyl, phenyl, 5-10 membered heteroaryl, D; wherein said $C_{1-3}$ alkyl, $C_{3-6}$ cycloalkyl, 4-6 membered heterocycloalkyl, phenyl, and 5-10 membered heteroaryl, are each optionally substituted with 1 or 2 substituents independently selected from $R^{60}$;

when $Cy^2$ is $Cy^2$-a, then $R^2$ is selected from H, $C_{1-2}$ alkyl, $C_{1-2}$ haloalkyl, F, Cl, —$CH_2CH_2CN$;

when $Cy^2$ is $Cy^2$-b and X$\overline{---}$Y is-N═$CR^6$—, then $R^6$ is selected from $C_{1-3}$ alkyl, $C_{1-3}$ haloalkyl, $C_{3-6}$ cycloalkyl, —$CH_2CH_2NHMe$, —$CH_2CH_2C(O)NMe_2$, R⁶-a

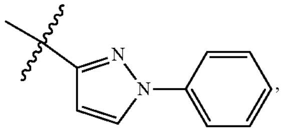

$R^6$-b

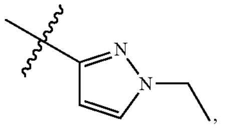

$R^6$-c

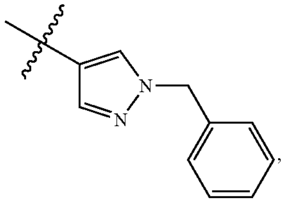

$R^6$-d

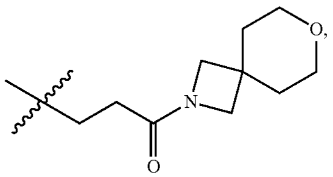

$R^6$-e

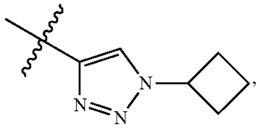

$R^6$-f

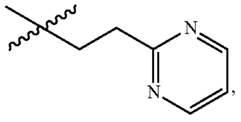

$R^6$-g

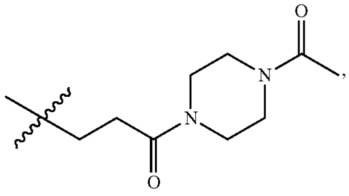

$R^6$-h

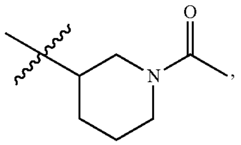

$R^6$-i

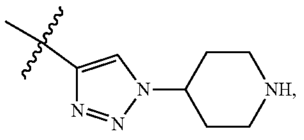

-continued $R^6$-j

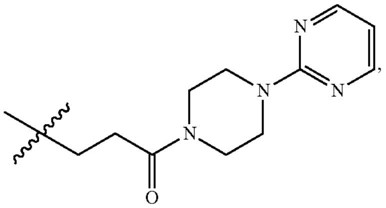

$R^6$-k

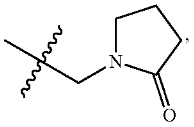

and $R^6$-i

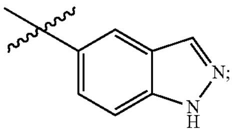

when $Cy^2$ is $Cy^2$-b, then $R^2$ is selected from H, $C_{1-2}$ alkyl, $C_{1-2}$ haloalkyl, F, —$CH_2CH_2CN$, $R^2$-a

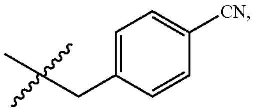

$R^2$-b

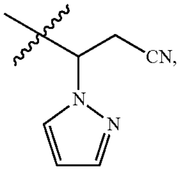

$R^2$-c

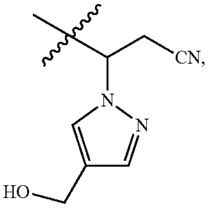

$R^2$-d

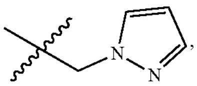

and $R^2$-e

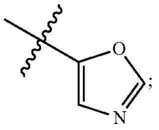

each $R^{10}$ is independently selected from $C_{1-3}$ alkyl, $C_{1-3}$ haloalkyl, $C_{3-6}$ cycloalkyl, halo, D, ON, $OR^{a10}$, C(O)$NR^{c10}R^{d10}$, $NR^{c10}C(O)OR^{a10}$, $NR^{c10}C(O)NR^{c10}R^{d10}$, and $NR^{c10}R^{d10}$; wherein said $C_{1-3}$ alkyl, and $C_{3-6}$ cycloalkyl are each optionally substituted with 1 or 2 substituents independently selected from $R^g$;

each $R^{11}$ is independently selected from $C_{1-2}$ alkyl, $C_{1-2}$ haloalkyl, $C_{3-6}$ cycloalkyl, 4-6 membered heterocycloalkyl, halo, O, ON, $OR^{a11}$, and $NR^{c11}R^{d11}$; wherein said $C_{1-2}$ alkyl, $C_{3-6}$ cycloalkyl, and 4-6 membered heterocycloalkyl, are each optionally substituted with 1 or 2 substituents independently selected from $R^g$;

each $R^{21}$ is independently selected from $C_{1-3}$ alkyl, $C_{1-3}$ haloalkyl, halo, D, CN, $OR^{a21}$, and $NR^{c21}R^{d21}$;

each $R^{30}$ is independently selected from $C_{1-3}$ alkyl, $C_{1-3}$ haloalkyl, 4-10 membered heterocycloalkyl, halo, D, CN, $OR^{a30}$, $C(O)NR^{c30}R^{d30}$, $NR^{c30}C(O)OR^{a30}$, $NR^{c30}C(O)NR^{c30}R^{d30}$, 5-6 membered heteroaryl, and $NR^{c30}R^{d30}$; wherein said $C_{1-3}$ alkyl, and 4-6 membered heterocycloalkyl, are each optionally substituted with 1 or 2 substituents independently selected from $R^{31}$;

each $R^{31}$ is independently selected from $C_{1-3}$ alkyl, $C_{1-3}$ haloalkyl, halo, D, and CN; each $R^{60}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a60}$, $C(O)R^{b60}$, $C(O)NR^{c60}R^{d60}$, and $NR^{c60}R^{d60}$; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$;

each $R^{61}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a61}$, $C(O)R^{b61}$, and $NR^{c61}R^{d61}$;

each $R^{70}$ is independently selected from $C_{1-3}$ alkyl, $C_{1-3}$ haloalkyl, phenyl, 5-6 membered heteroaryl, halo, D, CN, $OR^{a70}$, and $NR^{c70}R^{d70}$;

each $R^{a3}$, and $R^{c3}$ is independently selected from H, $C_{1-3}$ alkyl, $C_{1-3}$ haloalkyl, 5-6 membered heteroaryl, and phenyl; wherein said $C_{1-3}$ alkyl, 5-6 membered heteroaryl, and phenyl are each optionally substituted with 1 or 2 substituents independently selected from $R^{30}$;

each $R^{b3}$ is independently selected from $C_{1-3}$ alkyl, and $C_{1-3}$ haloalkyl;

each $R^{a7}$, $R^{c7}$ and $R^{d7}$ is independently selected from H, $C_{1-3}$ alkyl, and $C_{1-3}$ haloalkyl; wherein said $C_{1-3}$ alkyl, is optionally substituted with 1 or 2 substituents independently selected from $R^{70}$;

each $R^{a10}$, $R^{c10}$ and $R^{d10}$ is independently selected from H, $C_{1-3}$ alkyl, and $C_{1-3}$ haloalkyl;

each $R^{a11}$, $R^{c11}$ and $R^{d11}$, is independently selected from H, $C_{1-3}$ alkyl, and $C_{1-3}$ haloalkyl;

$R^{b20}$ is selected from $NH_2$, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{21}$;

each $R^{a21}$, $R^{c21}$ and $R^{d21}$, is independently selected from H, $C_{1-3}$ alkyl, and $C_{1-3}$ haloalkyl;

each $R^{a30}$, $R^{c30}$ and $R^{d30}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$;

or any $R^{c60}$ and $R^{d60}$ attached to the same N atom, together with the N atom to which they are attached, form a 4-, 5-, 6-. 7-, 8-, or 9-membered heterocycloalkyl group optionally substituted with 1 or 2 substituents independently selected from $R^{61}$;

each $R^{a61}$, $R^{b61}$ $R^{c61}$ and $R^{d61}$, is independently selected from H, $C_{1-3}$ alkyl, and $C_{1-3}$ haloalkyl;

each $R^{a70}$, $R^{c70}$ and $R^{d70}$, is independently selected from H, $C_{1-3}$ alkyl, and $C_{1-3}$ haloalkyl; and each $R^g$ is independently selected from D, OH, CN, halo, $C_{1-2}$ alkyl, amino, and $C_{1-2}$ haloalkyl.

In yet another embodiment of Formula I, or a pharmaceutically acceptable salt thereof, X$\equiv$Y is selected from —$NR^5$—C(═O)—, —N═N—, and —N═$CR^6$—;

$R^1$ is selected from H, D, $C_{1-2}$ alkyl, and $C_{1-2}$ haloalkyl; wherein said $C_{1-2}$ alkyl is optionally substituted with 1 or 2 substituents independently selected from $R^{11}$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, or 3 substituents independently selected from $R^{10}$;

$R^4$ is selected from $OR^{a3}$;

$R^5$ is selected from H, $C_{1-2}$ alkyl, and $C_{1-2}$ haloalkyl;

$R^7$ is selected from H, $C_{1-3}$ alkyl, $C_{1-3}$ haloalkyl, phenyl, 5-6 membered heteroaryl, F, Cl, D, CN, $OR^{a7}$, and $NR^{c7}R^{d7}$; wherein said phenyl, and 5-6 membered heteroaryl, are each optionally substituted with 1 or 2 substituents independently selected from $R^{70}$;

$Cy^2$ is selected from $Cy^2$-a

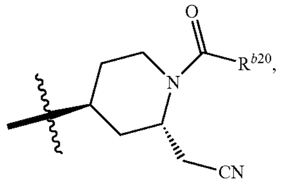

and $Cy^2$-b

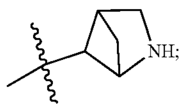

when $Cy^2$ is $Cy^2$-a and X$\equiv$Y is-N═$CR^6$—, then, $R^6$ is selected from H, D, $C_{1-3}$ alkyl, and $C_{1-3}$ haloalkyl; wherein said $C_{1-3}$ alkyl, is optionally substituted with 1 or 2 substituents independently selected from $R^{60}$;

when $Cy^2$ is $Cy^2$-a, then $R^2$ is selected from H, $C_{1-2}$ alkyl, $C_{1-2}$ haloalkyl, F, Cl, and —$CH_2CH_2CN$;

when $Cy^2$ is $Cy^2$-b and X$\equiv$Y is-N═$CR^6$—, then $R^6$ is selected from $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl, are each optionally substituted with 1 or 2 substituents independently selected from $R^{60}$;

when $Cy^2$ is $Cy^2$-b, then $R^2$ is selected from H, $C_{1-2}$ alkyl, $C_{1-2}$ haloalkyl, F, —$CH_2CH_2CN$, $R^2$-a

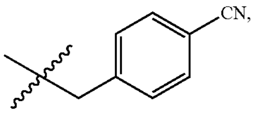

$R^2$-b

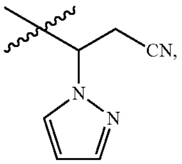

$R^2$-c

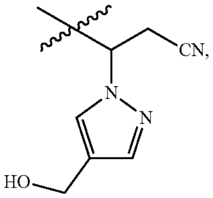

$R^2$-d

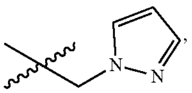

and $R^2$-e

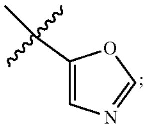

;

each $R^{10}$ is independently selected from $C_{1-3}$ alkyl, $C_{1-3}$ haloalkyl, $C_{3-6}$ cycloalkyl, halo, D, CN, $OR^{a10}$, C(O)$NR^{c10}R^{d10}$, and $NR^{c10}R^{d10}$; wherein said $C_{1-3}$ alkyl, and $C_{3-6}$ cycloalkyl are each optionally substituted with 1 or 2 substituents independently selected from $R^g$;

each $R^{11}$ is independently selected from $C_{1-2}$ alkyl, $C_{1-2}$ haloalkyl, $C_{3-6}$ cycloalkyl, 4-6 membered heterocycloalkyl, halo, D, CN, $OR^{a11}$, and $NR^{c11}R^{d11}$; wherein said $C_{1-2}$ alkyl, $C_{3-6}$ cycloalkyl, and 4-6 membered heterocycloalkyl, are each optionally substituted with 1 or 2 substituents independently selected from $R^g$;

each $R^{21}$ is independently selected from $C_{1-3}$ alkyl, $C_{1-3}$ haloalkyl, halo, D, and CN;

each $R^{30}$ is independently selected from $C_{1-3}$ alkyl, $C_{1-3}$ haloalkyl, 4-10 membered heterocycloalkyl, halo, D, CN, $OR^{a30}$, C(O)$NR^{c30}R^{d30}$, and $NR^{c30}R^{d30}$; wherein said $C_{1-3}$ alkyl, and 4-6 membered heterocycloalkyl, are each optionally substituted with 1 or 2 substituents independently selected from $R^{31}$;

each $R^{31}$ is independently selected from $C_{1-3}$ alkyl, $C_{1-3}$ haloalkyl, halo, D, and CN; each $R^{60}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a60}$, C(O)$R^{b60}$, C(O)$NR^{c60}R^{d60}$, and $NR^{c60}R^{d60}$; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$;

each $R^{61}$ is independently selected from $C_{1-3}$ alkyl, $C_{1-3}$ haloalkyl, phenyl, 5-6 membered heteroaryl, halo, D, CN, $OR^{a61}$, C(O)$R^{b61}$, and $NR^{c61}R^{d61}$;

each $R^{70}$ is independently selected from $C_{1-3}$ alkyl, $C_{1-3}$ haloalkyl, phenyl, 5-6 membered heteroaryl, halo, D, and CN;

each $R^{a3}$, is independently selected from H, $C_{1-3}$ alkyl, $C_{1-3}$ haloalkyl, 5-6 membered heteroaryl, and phenyl; wherein said $C_{1-3}$ alkyl, 5-6 membered heteroaryl, and phenyl are each optionally substituted with 1 or 2 substituents independently selected from $R^{30}$;

each $R^{a7}$, $R^{c7}$ and $R^{d7}$ is independently selected from H, $C_{1-3}$ alkyl, and $C_{1-3}$ haloalkyl; wherein said $C_{1-3}$ alkyl, is optionally substituted with 1 or 2 substituents independently selected from $R^{70}$;

each $R^{a10}$, $R^{c10}$ and $R^{d10}$ is independently selected from H, $C_{1-3}$ alkyl, and $C_{1-3}$ haloalkyl;

each $R^{a11}$, $R^{c11}$ and $R^{d11}$, is independently selected from H, $C_{1-3}$ alkyl, and $C_{1-3}$ haloalkyl;

$R^{b20}$ is selected from $NH_2$, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{21}$; each $R^{a21}$, $R^{c21}$ and $R^{d21}$, is independently selected from H, $C_{1-3}$ alkyl, and $C_{1-3}$ haloalkyl;

each $R^{a30}$, $R^{c30}$ and $R^{d30}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, and $C_{1-3}$ haloalkyl; wherein said $C_{1-3}$ alkyl, is optionally substituted with 1 or 2 substituents independently selected from $R^{61}$;

or any $R^{c60}$ and $R^{d60}$ attached to the same N atom, together with the N atom to which they are attached, form a 4-, 5-, 6-, or 9-membered heterocycloalkyl group optionally substituted with 1 or 2 substituents independently selected from $R^{61}$;

each $R^{a61}$, $R^{b61}$ $R^{c61}$ and $R^{d61}$, is independently selected from H, $C_{1-3}$ alkyl, and $C_{1-3}$ haloalkyl; and each $R^g$ is independently selected from D, OH, CN, halo, $C_{1-2}$ alkyl, amino, and $C_{1-2}$ haloalkyl.

In still another embodiment of Formula I, or a pharmaceutically acceptable salt thereof, X⎓Y is selected from —$NR^5$—C(═O)—, —N═N—, and —N═$CR^6$—;

$R^1$ is selected from H, and $C_{1-2}$ alkyl; wherein said $C_{1-2}$ alkyl is optionally substituted with 1 or 2 substituents independently selected from $R^1$;

$Cy^1$ is selected from $C_{3-10}$ cycloalkyl, $C_{6-10}$ aryl and 6-10 membered heteroaryl; wherein the 6-10 membered heteroaryl each has at least one ring-forming carbon atom and 1, 2, or 3 ring-forming heteroatoms independently selected from N, O, and S; wherein a ring-forming carbon atom of 6-10 membered heteroaryl is optionally substituted by oxo to form a carbonyl group; and wherein the $C_{3-10}$ cycloalkyl, $C_{6-10}$ aryl and 6-10 membered heteroaryl are each optionally substituted with 1, 2, or 3 substituents independently selected from $R^{10}$;

$R^4$ is selected from $OR^{a3}$;

$R^5$ is H;

$R^7$ is selected from phenyl, 5-6 membered heteroaryl, F, and $OR^{a7}$; wherein said phenyl, and 5-6 membered heteroaryl, are each optionally substituted with 1 or 2 substituents independently selected from $R^{70}$;

$Cy^2$ is selected from

Cy²-a

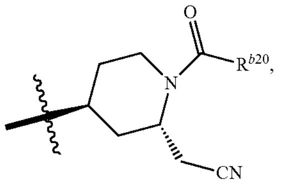

and

Cy²-b

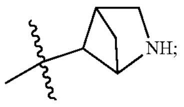

when $Cy^2$ is $Cy^2$-a and X⎓Y is-N═CR$^6$—, then, $R^6$ is H;

when $Cy^2$ is $Cy^2$-a, then $R^2$ is Cl;

when $Cy^2$ is $Cy^2$-b and X⎓Y is-N═CR$^6$—, then $R^6$ is selected from $C_{1-3}$ alkyl, $C_{3-6}$ cycloalkyl, 4-6 membered heterocycloalkyl, and 5-10 membered heteroaryl; wherein said $C_{1-3}$ alkyl, $C_{3-6}$ cycloalkyl, 4-6 membered heterocycloalkyl, and 5-10 membered heteroaryl, are each optionally substituted with 1 or 2 substituents independently selected from $R^{60}$;

when $Cy^2$ is $Cy^2$-b, then $R^2$ is selected from H, $C_{1-2}$ alkyl, —$CH_2CH_2CN$, R²-a

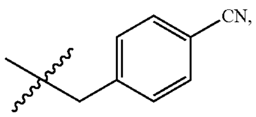

R²-b

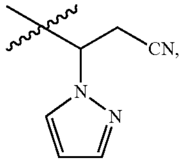

R²-c

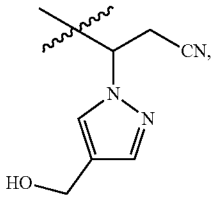

R²-d

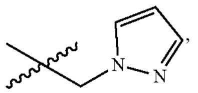

and

R²-e

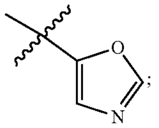

each $R^{10}$ is independently selected from $C_{1-3}$ alkyl, $C_{1-3}$ haloalkyl, $C_{3-6}$ cycloalkyl, halo, CN, $OR^{a10}$, and $NR^{c10}$, $R^{d10}$; wherein said $C_{1-3}$ alkyl, and $C_{3-6}$ cycloalkyl are each optionally substituted with 1 or 2 substituents independently selected from $R^g$;

each $R^{11}$ is independently selected from 4-6 membered heterocycloalkyl, and $OR^a$11; wherein said 4-6 membered heterocycloalkyl, is optionally substituted with 1 or 2 substituents independently selected from $R^g$;

each $R^{21}$ is CN;

each $R^{30}$ is independently selected from 4-10 membered heterocycloalkyl, and $C(O)NR^{c30}R^{d30}$; wherein said 4-6 membered heterocycloalkyl, is optionally substituted with 1 or 2 substituents independently selected from $R^{31}$;

each $R^{31}$ is independently selected from $C_{1-3}$ alkyl;

each $R^{60}$ is independently selected from $C_{1-3}$ alkyl, $C_{3-6}$ cycloalkyl, 4-6 membered heterocycloalkyl, phenyl, 5-6 membered heteroaryl, $C(O)R^{b60}$, $C(O)NR^{c60}R^{d60}$, and $NR^{c60}R^{d60}$; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$;

each $R^{61}$ is independently selected from phenyl, 5-6 membered heteroaryl, and $C(O)R^{b61}$;

each $R^{70}$ is independently selected from phenyl, 5-6 membered heteroaryl, and CN;

each $R^{a3}$, is independently selected from, $C_{1-3}$ alkyl, and phenyl; wherein said $C_{1-3}$ alkyl, and phenyl are each optionally substituted with 1 or 2 substituents independently selected from $R^{30}$;

each $R^{a7}$, is $C_{1-3}$ alkyl; wherein said $C_{1-3}$ alkyl, is optionally substituted with 1 or 2 substituents independently selected from $R^{70}$;

each $R^{a10}$, $R^{c10}$ and $R^{d10}$ is H;

each $R^{a11}$ is H;

$R^{b20}$ is selected from $NH_2$, $C_{1-3}$ alkyl, $C_{3-6}$ cycloalkyl, and 5-6 membered heteroaryl; wherein said $C_{1-3}$ alkyl, $C_{3-6}$ cycloalkyl, and 5-6 membered heteroaryl are each optionally substituted with 1 or 2 substituents independently selected from $R^{21}$;

each $R^{c30}$ and $R^{d30}$ is independently selected from H, and $C_{1-3}$ alkyl;

each $R^{b60}$, $R^{c60}$ and $R^{d60}$ is independently selected from H, and $C_{1-3}$ alkyl; wherein said $C_{1-3}$ alkyl, is optionally substituted with 1 or 2 substituents independently selected from $R^{61}$;

or any $R^{c60}$ and $R^{d60}$ attached to the same N atom, together with the N atom to which they are attached, form a 6-, or 9-membered heterocycloalkyl group optionally substituted with 1 or 2 substituents independently selected from $R^{61}$;

each $R^{b61}$, is $C_{1-3}$ alkyl; and each $R^g$ is CN.

In an embodiment X⎓Y is —NR$^5$—C(═O)—. In another embodiment X⎓Y is —N═N—. In yet another embodiment X⎓Y is —N═CR$^6$—.

In an embodiment, $R^1$ is selected from H and $C_{1-2}$ alkyl; wherein said $C_{1-2}$ alkyl is optionally substituted with 1 or 2 substituents independently selected from $R^{11}$. In another embodiment, $R^1$ is selected from H and $C_{1-2}$ alkyl. In yet another embodiment, $R^1$ is H.

In an embodiment, $Cy^1$ is selected from $C_{3-10}$ cycloalkyl, $C_{6-10}$ aryl and 6-10 membered heteroaryl; wherein the 6-10 membered heteroaryl has at least one ring-forming carbon atom and 1, 2, 3, or 4 ring-forming heteroatoms independently selected from N, O, and S; wherein a ring-forming carbon atom of 6-10 membered heteroaryl is optionally substituted by oxo to form a carbonyl group; and wherein the $C_{3-10}$ cycloalkyl, $C_{6-10}$ aryl and 6-10 membered heteroaryl are each optionally substituted with 1, 2, or 3 substituents independently selected from $R^{10}$.

In another embodiment, $Cy^1$ is selected from $C_{6-10}$ aryl and 6-10 membered heteroaryl; wherein the 6-10 membered heteroaryl has at least one ring-forming carbon atom and 1, 2, 3, or 4 ring-forming heteroatoms independently selected from N, O, and S; wherein a ring-forming carbon atom of 6-10 membered heteroaryl is optionally substituted by oxo to form a carbonyl group; and wherein the $C_{6-10}$ aryl and 6-10 membered heteroaryl are each optionally substituted with 1, 2, or 3 substituents independently selected from $R^{10}$.

In yet another embodiment, $Cy^1$ is selected from $C_{3-10}$ cycloalkyl, phenyl and 6-10 membered heteroaryl; wherein the 6-10 membered heteroaryl has at least one ring-forming carbon atom and 1 or 2 ring-forming heteroatoms independently selected from N, O, and S; and wherein the $C_{3-10}$ cycloalkyl, phenyl and 6-10 membered heteroaryl are each optionally substituted with 1, 2, or 3 substituents independently selected from $R^{10}$.

In still another embodiment, $Cy^1$ is selected from phenyl and 6-10 membered heteroaryl; wherein the 6-10 membered heteroaryl has at least one ring-forming carbon atom and 1 or 2 ring-forming heteroatoms independently selected from N, O, and S; and wherein the phenyl and 6-10 membered heteroaryl are each optionally substituted with 1, 2, or 3 substituents independently selected from $R^{10}$.

In an embodiment, $Cy^1$ is selected from $Cy^1$-a

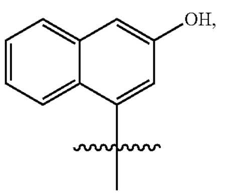

$Cy^1$-b

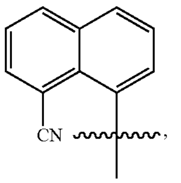

and $Cy^1$-c

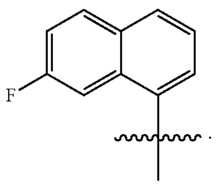

In another embodiment, $Cy^1$ is selected from $Cy^1$-a and $Cy^1$-b. In yet another embodiment, $Cy^1$ is $Cy^1$-a. In still another embodiment, $Cy^1$ is $Cy^1$-b. In an embodiment, $Cy^1$ is $Cy^1$-c.

In another embodiment, $R^4$ is selected from $C_{1-3}$ alkyl, $C_{1-3}$ haloalkyl, 5-10 membered heteroaryl, and $OR^{a3}$; wherein said $C_{1-3}$ alkyl and 5-10 membered heteroaryl, are each optionally substituted with 1 or 2 substituents independently selected from $R^{30}$; or $R^4$ is selected from $R^4$-a

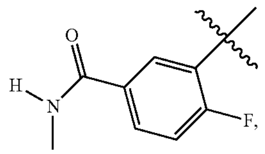

$R^4$-b

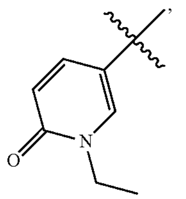

and $R^4$-c

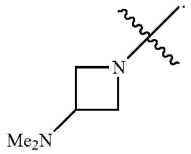

In another embodiment, $R^4$ is selected from H, $C_{1-3}$ alkyl, $C_{1-3}$ haloalkyl, and 5-10 membered heteroaryl; wherein said $C_{1-3}$ alkyl and 5-10 membered heteroaryl, are each optionally substituted with 1 or 2 substituents independently selected from $R^{30}$; or $R^4$ is selected from $R^4$-a, $R^4$-b, and $R^4$-c.

In yet another embodiment, $R^4$ is selected from H, $C_{1-3}$ alkyl, $C_{1-3}$ haloalkyl, 5-10 membered heteroaryl, $OR^{a3}$, and $NR^{c3}R^{d3}$; wherein said $C_{1-3}$ alkyl and 5-10 membered heteroaryl, are each optionally substituted with 1 or 2 substituents independently selected from $R^{30}$.

In still another embodiment, $R^4$ is selected from $C_{1-3}$ alkyl, 5-10 membered heteroaryl, and $OR^{a3}$, wherein said $C_{1-3}$ alkyl and 5-10 membered heteroaryl, are each optionally substituted with 1 or 2 substituents independently selected from $R^{30}$.

In an embodiment, $R^4$ is selected from $C_{1-3}$ alkyl, and 5-10 membered heteroaryl, wherein said $C_{1-3}$ alkyl and 5-10 membered heteroaryl, are each optionally substituted with 1 or 2 substituents independently selected from $R^{30}$. In another embodiment, $R^4$ is $OR^{a3}$.

In yet another embodiment, $R^4$ is selected from $R^4$-a

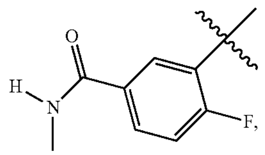

$R^4$-b

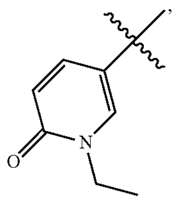

and

-continued

R4-c

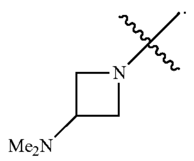

In an embodiment, $R^4$ is $R^4$-c.

In another embodiment, $R^7$ is selected from phenyl, 5-6 membered heteroaryl, F, Cl, CN, $OR^{a7}$, and $NR^{c7}R^{d7}$; wherein said phenyl, and 5-6 membered heteroaryl, are each optionally substituted with 1 or 2 substituents independently selected from $R^{70}$.

In yet another embodiment, $R^7$ is selected from phenyl, 5-6 membered heteroaryl, F, and $OR^{a7}$; wherein said phenyl, and 5-6 membered heteroaryl, are each optionally substituted with 1 or 2 substituents independently selected from $R^{70}$. In still another embodiment, $R^7$ is F.

In another embodiment, $Cy^2$ is $Cy^2$-a. In an embodiment, $Cy^2$ is $Cy^2$-b.

In an embodiment, when $Cy^2$ is $Cy^2$-a and X$\equiv$Y is-N$=$$CR^6$—, then, $R^6$ is selected from 4-6 membered heterocycloalkyl, phenyl, and 5-10 membered heteroaryl; wherein said $C_{3-6}$ cycloalkyl, 4-6 membered heterocycloalkyl, phenyl, and 5-10 membered heteroaryl, are each optionally substituted with 1 or 2 substituents independently selected from $R^{60}$. In another embodiment, when $Cy^2$ is $Cy^2$-a and X$\equiv$Y is-N$=$$CR^6$—, then, $R^6$ is selected from H, D, $C_{1-3}$ alkyl, and $C_{1-3}$ haloalkyl; wherein said $C_{1-3}$ alkyl, is optionally substituted with 1 or 2 substituents independently selected from $R^{60}$.

In yet another embodiment, when $Cy^2$ is $Cy^2$-a and X$\equiv$Y is-N$=$$CR^6$—, then, $R^6$ is selected from H and $C_{1-3}$ alkyl; wherein said $C_{1-3}$ alkyl, is optionally substituted with 1 or 2 substituents independently selected from $R^{60}$. In still another embodiment, when $Cy^2$ is $Cy^2$-a and X$\equiv$Y is-N$=$$CR^6$—, then, $R^6$ is H.

In an embodiment, when $Cy^2$ is $Cy^2$-b and X$\equiv$Y is-N$=$$CR^6$—, then $R^6$ is selected from $C_{1-3}$ alkyl, $C_{3-6}$ cycloalkyl, 4-6 membered heterocycloalkyl, and 5-10 membered heteroaryl; wherein said $C_{1-3}$ alkyl, $C_{3-6}$ cycloalkyl, 4-6 membered heterocycloalkyl, and 5-10 membered heteroaryl, are each optionally substituted with 1 or 2 substituents independently selected from $R^{60}$.

In another embodiment, when $Cy^2$ is $Cy^2$-b and X$\equiv$Y is-N$=$$CR^6$—, then $R^6$ is selected from $C_{3-6}$ cycloalkyl, 4-6 membered heterocycloalkyl, phenyl, and 5-10 membered heteroaryl; wherein said $C_{3-6}$ cycloalkyl, 4-6 membered heterocycloalkyl, phenyl, and 5-10 membered heteroaryl, are each optionally substituted with 1 or 2 substituents independently selected from $R^{60}$.

In yet another embodiment, when $Cy^2$ is $Cy^2$-b and X$\equiv$Y is-N$=$$CR^6$—, then $R^6$ is selected from $C_{1-3}$ alkyl, and $C_{1-3}$ haloalkyl; wherein said $C_{1-3}$ alkyl is optionally substituted with 1 or 2 substituents independently selected from $R^{60}$.

In still another embodiment, when $Cy^2$ is $Cy^2$-b and X$\equiv$Y is-N$=$$CR^6$—, then $R^6$ is $C_{1-3}$ alkyl; wherein said $C_{1-3}$ alkyl is optionally substituted with 1 or 2 substituents independently selected from $R^{60}$.

In an embodiment, when $Cy^2$ is $Cy^2$-b and X$\equiv$Y is-N$=$$CR^6$—, then $R^6$ is selected from —$CH_2CH_2C(O)NMe_2$ and —$CH_2CH_3$. In another embodiment, when $Cy^2$ is $Cy^2$-a, then $R^2$ is selected from H, $C_{1-2}$ alkyl, $C_{1-2}$ haloalkyl, F, Cl, and —$CH_2CH_2CN$. In yet another embodiment, when $Cy^2$ is $Cy^2$-a, then $R^2$ is selected from H, $C_{1-2}$ alkyl, and —$CH_2CH_2CN$. In still another embodiment, when $Cy^2$ is $Cy^2$-a, then $R^2$ is selected from $C_{1-2}$ haloalkyl, F, and Cl.

In an embodiment, when $Cy^2$ is $Cy^2$-a, then $R^2$ is selected from F and Cl. In another embodiment, when $Cy^2$ is $Cy^2$-a, then $R^2$ is Cl.

In yet another embodiment, when $Cy^2$ is $Cy^2$-b, then $R^2$ is selected from H, $C_{1-2}$ alkyl, —$CH_2CH_2CN$, R2-a

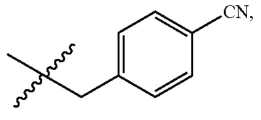

R2-b

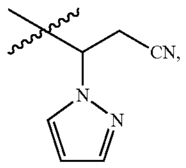

R2-c

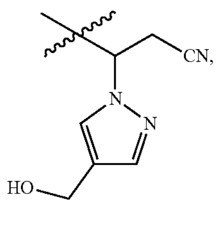

R2-d

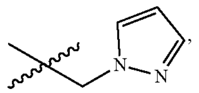

, and

R2-e

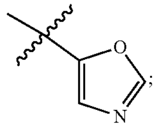

In an embodiment, when $Cy^2$ is $Cy^2$-b, then $R^2$ is selected from $R^2$-a, $R^2$-b, $R^2$-c, $R^2$-d, and $R^2$-e. In another embodiment, when $Cy^2$ is $Cy^2$-b, then $R^2$ is selected from H, $C_{1-2}$ alkyl, —$CH_2CH_2CN$, $R^2$-a, $R^2$-b, and $R^2$-c. In yet another embodiment, when $Cy^2$ is $Cy^2$-b, then $R^2$ is selected from H, $C_{1-2}$ alkyl, and —$CH_2CH_2CN$. In still another embodiment, when $Cy^2$ is $Cy^2$-b, then $R^2$ is —$CH_2CH_2CN$.

In an embodiment, each $R^{10}$ is independently selected from $C_{1-3}$ alkyl, $C_{1-3}$ haloalkyl, $C_{3-6}$ cycloalkyl, halo, D, CN, $OR^{a10}$, $C(O)NR^{c10}R^{d10}$, $NR^{c10}C(O)OR^{a10}$, $NR^{c10}C(O)NR^{c10}R^{d10}$, and $NR^{c10}R^{d10}$; wherein said $C_{1-3}$ alkyl, and $C_{3-6}$ cycloalkyl are each optionally substituted with 1 or 2 substituents independently selected from $R^g$. In another embodiment, each $R^{10}$ is independently selected from $C_{1-3}$ alkyl, $C_{1-3}$ haloalkyl, $C_{3-6}$ cycloalkyl, halo, CN, $OR^{a10}$, $C(O)NR^{c10}R^{d10}$, and $NR^{c10}R^{d10}$; wherein said $C_{1-3}$ alkyl, and $C_{3-6}$ cycloalkyl are each optionally substituted with 1 or 2 substituents independently selected from $R^g$.

In yet another embodiment, each $R^{10}$ is independently selected from $C_{1-3}$ alkyl, $C_{1-3}$ haloalkyl, $C_{3-6}$ cycloalkyl, halo, CN, $OR^{a10}$, and $NR^{c10}R^{d10}$; wherein said $C_{1-3}$ alkyl, and $C_{3-6}$ cycloalkyl are each optionally substituted with 1 or 2 substituents independently selected from $R^g$.

In still another embodiment, each $R^{11}$ is independently selected from 4-6 membered heterocycloalkyl, halo, CN, and $OR^{a11}$, wherein said 4-6 membered heterocycloalkyl, is optionally substituted with 1 or 2 substituents independently selected from $R^g$.

In an embodiment, each $R^{11}$ is independently selected from 4-6 membered heterocycloalkyl, and $OR^{a1}$, wherein said 4-6 membered heterocycloalkyl, is optionally substituted with 1 or 2 substituents independently selected from $R^g$.

In another embodiment, each $R^{21}$ is independently selected from $C_{1-3}$ alkyl, $C_{1-3}$ haloalkyl, halo, CN, $OR^{a21}$, and $NR^{c21}R^{d21}$. In yet another embodiment, each $R^{21}$ is independently selected from halo, CN, and $OR^{a21}$. In still another embodiment, each $R^{21}$ is independently selected from halo, and CN. In an embodiment, each $R^{21}$ is CN.

In an embodiment, each $R^{30}$ is independently selected from $C_{1-3}$ alkyl, $C_{1-3}$ haloalkyl, 4-10 membered heterocycloalkyl, halo, CN, $OR^{a30}$, $C(O)NR^{c30}R^{d30}$, and $NR^{c30}R^{d30}$; wherein said $C_{1-3}$ alkyl, and 4-6 membered heterocycloalkyl, are each optionally substituted with 1 or 2 substituents independently selected from $R^{31}$. In another embodiment, each $R^{30}$ is independently selected from 4-10 membered heterocycloalkyl, and $C(O)NR^{c30}R^{d30}$; wherein said 4-6 membered heterocycloalkyl, is optionally substituted with 1 or 2 substituents independently selected from $R^{31}$.

In yet another embodiment, each $R^{31}$ is independently selected from $C_{1-3}$ alkyl, $C_{1-3}$ haloalkyl, halo, and CN. In still another embodiment, each $R^{31}$ is independently selected from $C_{1-3}$ alkyl, and $C_{1-3}$ haloalkyl.

In an embodiment, each $R^{60}$ is independently selected from $C_{1-3}$ alkyl, $C_{3-6}$ cycloalkyl, 4-6 membered heterocycloalkyl, phenyl, 5-6 membered heteroaryl, $C(O)R^{b60}$, $C(O)NR^{c60}R^{d60}$, and $NR^{c60}R^{d60}$; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$.

In another embodiment, each $R^{60}$ is independently selected from $C_{3-6}$ cycloalkyl, 4-6 membered heterocycloalkyl, phenyl, and 5-6 membered heteroaryl; wherein said $C_{3-6}$ cycloalkyl, 4-6 membered heterocycloalkyl, phenyl, and 5-6 membered heteroaryl, are each optionally substituted with 1 or 2 substituents independently selected from $R^{61}$.

In yet another embodiment, each $R^{60}$ is independently selected from $C_{1-3}$ alkyl, $C_{1-3}$ haloalkyl, halo, D, CN, $OR^{a60}$, $C(O)R^{b60}$, $C(O)NR^{c60}R^{d60}$, and $NR^{c60}R^{d60}$; wherein said $C_{1-3}$ alkyl, is optionally substituted with 1 or 2 substituents independently selected from $R^{61}$.

In still another embodiment, each $R^{60}$ is independently selected from $C_{1-3}$ alkyl, $C(O)NR^{c60}R^{d60}$, and $NR^{c60}R^{d60}$; wherein said $C_{1-3}$ alkyl, is optionally substituted with 1 or 2 substituents independently selected from $R^{61}$.

In an embodiment, each $R^{61}$ is independently selected from $C_{1-3}$ alkyl, $C_{1-3}$ haloalkyl, phenyl, 5-6 membered heteroaryl, halo, CN, $OR^{a61}$, $C(O)R^{b61}$, and $NR^{c61}R^{d61}$. In another embodiment, each $R^{61}$ is independently selected from phenyl, 5-6 membered heteroaryl, and $C(O)R^{b61}$.

In yet another embodiment, each $R^{70}$ is independently selected from $C_{1-3}$ alkyl, $C_{1-3}$ haloalkyl, phenyl, 5-6 membered heteroaryl, halo, and CN. In still another embodiment, each $R^{70}$ is independently selected from phenyl, 5-6 membered heteroaryl, and CN.

In an embodiment, each $R^g$ is independently selected from OH, CN, halo, $C_{1-2}$ alkyl, and amino. In an embodiment, each $R^g$ is independently selected from OH, CN, and halo. In another embodiment, each $R^g$ is CN.

In yet another embodiment, each $R^{a3}$ is independently selected from H, $C_{1-3}$ alkyl, $C_{1-3}$ haloalkyl, 5-6 membered heteroaryl, and phenyl; wherein said $C_{1-3}$ alkyl, 5-6 membered heteroaryl, and phenyl are each optionally substituted with 1 or 2 substituents independently selected from $R^{30}$.

In still another embodiment, each $R^{a3}$ is independently selected from H, $C_{1-3}$ alkyl, and $C_{1-3}$ haloalkyl; wherein said $C_{1-3}$ alkyl is optionally substituted with 1 or 2 substituents independently selected from $R^{30}$.

In an embodiment, each $R^{a3}$ is independently selected from $C_{1-3}$ alkyl; wherein said $C_{1-3}$ alkyl is optionally substituted with 1 or 2 substituents independently selected from $R^{30}$.

In another embodiment, $R^{b20}$ is selected from $NH_2$, $C_{1-3}$ alkyl, $C_{3-6}$ cycloalkyl, and 5-6 membered heteroaryl; wherein said $C_{1-3}$ alkyl, $C_{3-6}$ cycloalkyl, and 5-6 membered heteroaryl are each optionally substituted with 1 or 2 substituents independently selected from $R^{21}$. In yet another embodiment, $R^{b20}$ is selected from $NH_2$, $C_{1-3}$ alkyl, and $C_{1-3}$ haloalkyl; wherein said $C_{1-3}$ alkyl, is optionally substituted with 1 or 2 substituents independently selected from $R^{21}$. In still another embodiment, $R^{b20}$ is selected from $NH_2$ and $C_{1-3}$ alkyl; wherein said $C_{1-3}$ alkyl, is optionally substituted with 1 or 2 substituents independently selected from $R^{21}$.

In an embodiment, each $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl, are each optionally substituted with 1 or 2 substituents independently selected from $R^{61}$; or any $R^{c60}$ and $R^{d60}$ attached to the same N atom, together with the N atom to which they are attached, form a 4-, 5-, 6-. 7-, 8-, or 9-membered heterocycloalkyl group optionally substituted with 1 or 2 substituents independently selected from $R^{61}$.

In another embodiment, each $R^{b60}$, $R^{c60}$ and $R^{d60}$ is independently selected from H, $C_{1-3}$ alkyl, and $C_{1-3}$ haloalkyl; wherein said $C_{1-3}$ alkyl, is optionally substituted with 1 or 2 substituents independently selected from $R^{61}$; or any $R^{c60}$ and $R^{d60}$ attached to the same N atom, together with the N atom to which they are attached, form a 4-, 5-, 6-, or 9-membered heterocycloalkyl group optionally substituted with 1 or 2 substituents independently selected from $R^{61}$.

In yet another embodiment, each $R^{b60}$, $R^{c60}$ and $R^{d60}$ is independently selected from H and $C_{1-3}$ alkyl; wherein said $C_{1-3}$ alkyl, is optionally substituted with 1 or 2 substituents independently selected from $R^{61}$; or any $R^{c60}$ and $R^{d60}$ attached to the same N atom, together with the N atom to which they are attached, form a 6-, or 9-membered heterocycloalkyl group optionally substituted with 1 or 2 substituents independently selected from $R^{61}$.

In still another embodiment, the compound of Formula I is selected from:

1-(3-(1-((endo)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)piperidin-1-yl)ethan-1-one;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)-1-(4-(pyrimidin-2-yl)piperazin-1-yl)propan-1-one;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(3-oxo-3-(7-oxa-2-azaspiro[3.5]nonan-2-yl)propyl)-1H-imidazo[4,5-c]quinolin-8-yl)propanenitrile;

3-(2-(3-(4-acetylpiperazin-1-yl)-3-oxopropyl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-8-yl)propanenitrile;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-((2-oxopyrrolidin-1-yl)methyl)-1H-imidazo[4,5-c]quinolin-8-yl)propanenitrile;

4-(1-((endo)-2-azabicyclo[2.1.1]hexan-5-yl)-4-(3-(dimethylamino)azetidin-1-yl)-2-ethyl-6-fluoro-8-(oxazol-5-yl)-1H-imidazo[4,5-c]quinolin-7-yl)naphthalen-2-ol;

3-(1-((endo)-2-azabicyclo[2.1.1]hexan-5-yl)-4-(3-(dimethylamino)azetidin-1-yl)-2-ethyl-6-fluoro-7-(3-hydroxynaphthalen-1-yl)-1H-imidazo[4,5-c]quinolin-8-yl)-3-(1H-pyrazol-1-yl)propanenitrile;

3-(1-((endo)-2-azabicyclo[2.1.1]hexan-5-yl)-4-(3-(dimethylamino)azetidin-1-yl)-2-ethyl-6-fluoro-7-(3-hydroxynaphthalen-1-yl)-1H-imidazo[4,5-c]quinolin-8-yl)-3-(4-(hydroxymethyl)-1H-pyrazol-1-yl)propanenitrile;

3-(8-((1H-pyrazol-1-yl)methyl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-2-yl)-N,N-dimethylpropanamide;

3-(1-(2-azabicyclo[2.1.1]hexan-5-yl)-8-(2-cyanoethyl)-7-(2,3-dichloro-6-hydroxyphenyl)-4-(3-(dimethylamino)azetidin-1-yl)-6-fluoro-1H-imidazo[4,5-c]quinolin-2-yl)-N,N-dimethylpropanamide;

3-(1-(2-azabicyclo[2.1.1]hexan-5-yl)-7-(3-chloro-2-cyclopropyl-5-hydroxyphenyl)-4-(3-(dimethylamino)azetidin-1-yl)-6-fluoro-1H-imidazo[4,5-c]quinolin-2-yl)-N,N-dimethylpropanamide;

3-(1-((endo)-2-azabicyclo[2.1.1]hexan-5-yl)-8-(2-cyanoethyl)-6-(3-cyanophenyl)-4-(3-(dimethylamino)azetidin-1-yl)-7-(3-hydroxynaphthalen-1-yl)-1H-imidazo[4,5-c]quinolin-2-yl)-N,N-dimethylpropanamide;

3-(1-((endo)-2-azabicyclo[2.1.1]hexan-5-yl)-8-(2-cyanoethyl)-4-(3-(dimethylamino)azetidin-1-yl)-7-(3-hydroxynaphthalen-1-yl)-6-(1-(pyridin-2-yl)-1H-pyrazol-4-yl)-1H-imidazo[4,5-c]quinolin-2-yl)-N,N-dimethylpropanamide;

3-(6-(benzyloxy)-1-((endo)-2-azabicyclo[2.1.1]hexan-5-yl)-8-(2-cyanoethyl)-4-(3-(dimethylamino)azetidin-1-yl)-7-(7-fluoronaphthalen-1-yl)-1H-imidazo[4,5-c]quinolin-2-yl)-N,N-dimethylpropanamide;

3-(1-((endo)2-azabicyclo[2.1.1]hexan-5-yl)-4-(3-(dimethylamino)azetidin-1-yl)-6-fluoro-9-(hydroxymethyl)-7-(3-hydroxynaphthalen-1-yl)-1H-imidazo[4,5-c]quinolin-2-yl)-N,N-dimethylpropanamide;

3-(1-((endo)2-azabicyclo[2.1.1]hexan-5-yl)-9-((3-cyanopyrrolidin-1-yl)methyl)-4-(3-(dimethylamino)azetidin-1-yl)-6-fluoro-7-(3-hydroxynaphthalen-1-yl)-1H-imidazo[4,5-c]quinolin-2-yl)-N,N-dimethylpropanamide;

3-(1-((endo)-2-Azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-4-fluoro-N-methylbenzamide;

3-(1-((endo)-2-Azabicyclo[2.1.1]hexan-5-yl)-2-ethyl-4-(1-ethyl-6-oxo-1,6-dihydropyridin-3-yl)-6-fluoro-7-(3-hydroxynaphthalen-1-yl)-1H-imidazo[4,5-c]quinolin-8-yl)propanenitrile;

5-(1-((endo)-2-Azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-N-methylpicolinamide;

3-(1-((endo)-2-Azabicyclo[2.1.1]hexan-5-yl)-2-ethyl-6-fluoro-7-(3-hydroxynaphthalen-1-yl)-4-(oxazol-2-yl)-1H-imidazo[4,5-c]quinolin-8-yl)propanenitrile;

3-(4-([1,2,4]Triazolo[1,5-a]pyridin-7-yl)-1-((endo)-2-azabicyclo[2.1.1]hexan-5-yl)-2-ethyl-6-fluoro-7-(3-hydroxynaphthalen-1-yl)-1H-imidazo[4,5-c]quinolin-8-yl)propanenitrile;

3-(1-((endo)-2-Azabicyclo[2.1.1]hexan-5-yl)-2-ethyl-6-fluoro-7-(3-hydroxynaphthalen-1-yl)-4-(2-(4-methylpiperazin-1-yl)pyridin-4-yl)-1H-imidazo[4,5-c]quinolin-8-yl)propanenitrile;

3-(1-((endo)-2-Azabicyclo[2.1.1]hexan-5-yl)-2-ethyl-6-fluoro-7-(3-hydroxynaphthalen-1-yl)-4-methyl-1H-imidazo[4,5-c]quinolin-8-yl)propanenitrile;

3-(1-((endo)-2-Azabicyclo[2.1.1]hexan-5-yl)-2-ethyl-6-fluoro-7-(3-hydroxynaphthalen-1-yl)-4-phenoxy-1H-imidazo[4,5-c]quinolin-8-yl)propanenitrile;

3-(1-((endo)-2-Azabicyclo[2.1.1]hexan-5-yl)-2-cyclopropyl-4-(3-(dimethylamino)azetidin-1-yl)-6-fluoro-7-(3-hydroxynaphthalen-1-yl)-1H-imidazo[4,5-c]quinolin-8-yl)propanenitrile;

3-(1-((endo)-2-Azabicyclo[2.1.1]hexan-5-yl)-4-(3-(dimethylamino)azetidin-1-yl)-6-fluoro-7-(3-hydroxynaphthalen-1-yl)-2-(1-(piperidin-4-yl)-1H-1,2,3-triazol-4-yl)-1H-imidazo[4,5-c]quinolin-8-yl)propanenitrile;

3-(1-((endo)-2-Azabicyclo[2.1.1]hexan-5-yl)-2-(1-cyclobutyl-1H-1,2,3-triazol-4-yl)-6-fluoro-7-(3-hydroxynaphthalen-1-yl)-4-(((S)-1-methylpyrrolidin-2-yl)methoxy)-1H-imidazo[4,5-c]quinolin-8-yl)propanenitrile;

3-(1-(2-azabicyclo[2.1.1]hexan-5-yl)-2-ethyl-6-fluoro-4-(((2R,7aS)-2-fluorotetrahydro-1H-pyrrolizin-7a(5H)-yl)methoxy)-7-(5-methyl-1H-indol-3-yl)-1H-imidazo[4,5-c]quinolin-8-yl)propanenitrile;

4-((1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(methylamino)ethyl)-1H-imidazo[4,5-c]quinolin-8-yl)methyl)benzonitrile;

3-(1-((endo)-2-azabicyclo[2.1.1]hexan-5-yl)-2-ethyl-6-fluoro-7-(5-fluoro-1H-indol-3-yl)-4-(((2R,7aS)-2-fluorotetrahydro-1H-pyrrolizin-7a(5H)-yl)methoxy)-1H-imidazo[4,5-c]quinolin-8-yl)propanenitrile;

3-(7-(3-aminoisoquinolin-1-yl)-1-endo-(2-azabicyclo[2.1.1]hexan-5-yl)-8-(2-cyanoethyl)-4-(3-(dimethylamino)azetidin-1-yl)-6-fluoro-1H-imidazo[4,5-c]quinolin-2-yl)-N,N-dimethylpropanamide;

3-(7-(6-amino-3-(trifluoromethyl) pyridin-2-yl)-1-endo-(2-azabicyclo[2.1.1]hexan-5-yl)-8-(2-cyanoethyl)-4-(3-(dimethylamino)azetidin-1-yl)-6-fluoro-1H-imidazo[4,5-c]quinolin-2-yl)-N,N-dimethylpropanamide;

3-(1-endo-(2-azabicyclo[2.1.1]hexan-5-yl)-8-(2-cyanoethyl)-7-(7,7-difluoro-5,6,7,8-tetrahydronaphthalen-1-yl)-4-(3-(dimethylamino)azetidin-1-yl)-6-fluoro-1H-imidazo[4,5-c]quinolin-2-yl)-N,N-dimethylpropanamide;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(1-phenyl-1H-pyrazol-3-yl)-1H-imidazo[4,5-c]quinolin-8-yl)propanenitrile;

3-(1-((endo)-2-azabicyclo[2.1.1]hexan-5-yl)-4-(3-(dimethylamino)azetidin-1-yl)-2-(1-ethyl-1H-pyrazol-3-yl)-6-fluoro-7-(3-hydroxynaphthalen-1-yl)-1H-imidazo[4,5-c]quinolin-8-yl)propanenitrile;

3-(2-(1-benzyl-1H-pyrazol-3-yl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-8-yl)propanenitrile;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(pyrimidin-2-yl)ethyl)-1H-imidazo[4,5-c]quinolin-8-yl)propanenitrile;

(3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(1H-indazol-5-yl)-1H-imidazo[4,5-c]quinolin-8-yl)propanenitrile;

8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-imidazo[4,5-c]quinolin-7-yl)-1-naphthonitrile;

8-(8-chloro-1-((2S,4S)-1-(2-cyanoacetyl)-2-(cyanomethyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

8-(8-chloro-1-((2S,4S)-2-(cyanomethyl)-1-(1H-1,2,4-triazole-3-carbonyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

(2S,4S)-4-(8-chloro-7-(8-cyanonaphthalen-1-yl)-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxamide;

8-(8-chloro-1-((2S,4S)-2-(cyanomethyl)-1-(cyclopropanecarbonyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-[1,2,3]triazolo[4,5-c]quinolin-7-yl)-1-naphthonitrile; and 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-2-oxo-2,3-dihydro-1H-imidazo[4,5-c]quinolin-7-yl)-1-naphthonitrile;

or a pharmaceutically acceptable salt thereof.

In another embodiment, the compound of Formula I is selected from:

3-(1-((endo)-2-Azabicyclo[2.1.1]hexan-5-yl)-2-ethyl-6-fluoro-7-(3-hydroxynaphthalen-1-yl)-4-phenoxy-1H-imidazo[4,5-c]quinolin-8-yl)propanenitrile;

3-(1-((endo)-2-Azabicyclo[2.1.1]hexan-5-yl)-2-(1-cyclobutyl-1H-1,2,3-triazol-4-yl)-6-fluoro-7-(3-hydroxynaphthalen-1-yl)-4-(((S)-1-methylpyrrolidin-2-yl)methoxy)-1H-imidazo[4,5-c]quinolin-8-yl)propanenitrile;

3-(1-(2-azabicyclo[2.1.1]hexan-5-yl)-2-ethyl-6-fluoro-4-(((2R,7aS)-2-fluorotetrahydro-1H-pyrrolizin-7a(5H)-yl)methoxy)-7-(5-methyl-1H-indol-3-yl)-1H-imidazo[4,5-c]quinolin-8-yl)propanenitrile 3-(1-((endo)-2-azabicyclo[2.1.1]hexan-5-yl)-2-ethyl-6-fluoro-7-(5-fluoro-1H-indol-3-yl)-4-(((2R,7aS)-2-fluorotetrahydro-1H-pyrrolizin-7a(5H)-yl)methoxy)-1H-imidazo[4,5-c]quinolin-8-yl)propanenitrile;

8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-imidazo[4,5-c]quinolin-7-yl)-1-naphthonitrile;

8-(8-chloro-1-((2S,4S)-1-(2-cyanoacetyl)-2-(cyanomethyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

8-(8-chloro-1-((2S,4S)-2-(cyanomethyl)-1-(1H-1,2,4-triazole-3-carbonyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

(2S,4S)-4-(8-chloro-7-(8-cyanonaphthalen-1-yl)-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxamide;

8-(8-chloro-1-((2S,4S)-2-(cyanomethyl)-1-(cyclopropanecarbonyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-[1,2,3]triazolo[4,5-c]quinolin-7-yl)-1-naphthonitrile; and 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-2-oxo-2,3-dihydro-1H-imidazo[4,5-c]quinolin-7-yl)-1-naphthonitrile;

or a pharmaceutically acceptable salt thereof.

It is further appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination. Thus, it is contemplated as features described as embodiments of the compounds of Formula I can be combined in any suitable combination.

At various places in the present specification, certain features of the compounds are disclosed in groups or in ranges. It is specifically intended that such a disclosure include each and every individual subcombination of the members of such groups and ranges. For example, the term "$C_{1-6}$ alkyl" is specifically intended to individually disclose (without limitation) methyl, ethyl, $C_3$ alkyl, $C_4$ alkyl, $C_5$ alkyl and $C_6$ alkyl.

The term "n-membered," where n is an integer, typically describes the number of ring-forming atoms in a moiety where the number of ring-forming atoms is n. For example, piperidinyl is an example of a 6-membered heterocycloalkyl ring, pyrazolyl is an example of a 5-membered heteroaryl ring, pyridyl is an example of a 6-membered heteroaryl ring and 1,2,3,4-tetrahydro-naphthalene is an example of a 10-membered cycloalkyl group.

At various places in the present specification, variables defining divalent linking groups may be described. It is specifically intended that each linking substituent include both the forward and backward forms of the linking substituent. For example, $—NR(CR'R'')_n—$ includes both $—NR(CR'R'')_n—$ and $—(CR'R'')_nNR—$ and is intended to disclose each of the forms individually. Where the structure requires a linking group, the Markush variables listed for that group are understood to be linking groups. For example, if the structure requires a linking group and the Markush group definition for that variable lists "alkyl" or "aryl" then it is understood that the "alkyl" or "aryl" represents a linking alkylene group or arylene group, respectively.

The term "substituted" means that an atom or group of atoms formally replaces hydrogen as a "substituent" attached to another group. The term "substituted," unless otherwise indicated, refers to any level of substitution, e.g., mono-, di-, tri-, tetra- or penta-substitution, where such substitution is permitted. The substituents are independently selected, and substitution may be at any chemically accessible position. It is to be understood that substitution at a given atom is limited by valency. It is to be understood that substitution at a given atom results in a chemically stable molecule. The phrase "optionally substituted" means unsubstituted or substituted. The term "substituted" means that a hydrogen atom is removed and replaced by a substituent. A single divalent substituent, e.g., oxo, can replace two hydrogen atoms.

The term "$C_{n-m}$" indicates a range which includes the endpoints, wherein n and m are integers and indicate the number of carbons. Examples include $C_{1-4}$, $C_{1-6}$ and the like.

The term "alkyl" employed alone or in combination with other terms, refers to a saturated hydrocarbon group that may be straight-chained or branched. The term "$C_{n-m}$ alkyl," refers to an alkyl group having n to m carbon atoms. An alkyl group formally corresponds to an alkane with one C—H bond replaced by the point of attachment of the alkyl group to the remainder of the compound. In some embodiments, the alkyl group contains from 1 to 6 carbon atoms, from 1 to 4 carbon atoms, from 1 to 3 carbon atoms, or 1 to 2 carbon atoms. Examples of alkyl moieties include, but are not limited to, chemical groups such as methyl, ethyl, n-propyl, isopropyl, n-butyl, tert-butyl, isobutyl, sec-butyl; higher homologs such as 2-methyl-1-butyl, n-pentyl, 3-pentyl, n-hexyl, 1,2,2-trimethylpropyl and the like.

The term "alkenyl" employed alone or in combination with other terms, refers to a straight-chain or branched hydrocarbon group corresponding to an alkyl group having one or more double carbon-carbon bonds. An alkenyl group formally corresponds to an alkene with one C—H bond replaced by the point of attachment of the alkenyl group to the remainder of the compound. The term "$C_{n-m}$ alkenyl" refers to an alkenyl group having n to m carbons. In some embodiments, the alkenyl moiety contains 2 to 6, 2 to 4, or 2 to 3 carbon atoms. Example alkenyl groups include, but are not limited to, ethenyl, n-propenyl, isopropenyl, n-butenyl, sec-butenyl and the like.

The term "alkynyl" employed alone or in combination with other terms, refers to a straight-chain or branched hydrocarbon group corresponding to an alkyl group having one or more triple carbon-carbon bonds. An alkynyl group formally corresponds to an alkyne with one C—H bond replaced by the point of attachment of the alkyl group to the remainder of the compound. The term "$C_{n-m}$ alkynyl" refers to an alkynyl group having n to m carbons. Example alkynyl groups include, but are not limited to, ethynyl, propyn-1-yl, propyn-2-yl and the like. In some embodiments, the alkynyl moiety contains 2 to 6, 2 to 4, or 2 to 3 carbon atoms.

The term "alkylene," employed alone or in combination with other terms, refers to a divalent alkyl linking group. An alkylene group formally corresponds to an alkane with two C—H bond replaced by points of attachment of the alkylene group to the remainder of the compound. The term "$C_{n-m}$ alkylene" refers to an alkylene group having n to m carbon atoms. Examples of alkylene groups include, but are not limited to, ethan-1,2-diyl, ethan-1,1-diyl, propan-1,3-diyl, propan-1,2-diyl, propan-1,1-diyl, butan-1,4-diyl, butan-1,3-diyl, butan-1,2-diyl, 2-methyl-propan-1,3-diyl and the like.

The term "alkoxy," employed alone or in combination with other terms, refers to a group of formula —O-alkyl, wherein the alkyl group is as defined above. The term "$C_{n-m}$ alkoxy" refers to an alkoxy group, the alkyl group of which has n to m carbons. Example alkoxy groups include methoxy, ethoxy, propoxy (e.g., n-propoxy and isopropoxy), t-butoxy and the like. In some embodiments, the alkyl group has 1 to 6, 1 to 4, or 1 to 3 carbon atoms. The term "$C_{n-m}$ dialkoxy" refers to a linking group of formula —O—($C_{n-m}$ alkyl)-O—, the alkyl group of which has n to m carbons. Example dialkyoxy groups include $—OCH_2CH_2O—$ and $OCH_2CH_2CH_2O—$. In some embodiments, the two O atoms of a $C_{n-m}$ dialkoxy group may be attached to the same B atom to form a 5- or 6-membered heterocycloalkyl group.

The term "alkylthio," employed alone or in combination with other terms, refers to a group of formula —S-alkyl, wherein the alkyl group is as defined above.

The term "amino," employed alone or in combination with other terms, refers to a group of formula $—NH_2$, wherein the hydrogen atoms may be substituted with a substituent described herein. For example, "alkylamino" can refer to —NH(alkyl) and $—N(alkyl)_2$.

The term "carbonyl," employed alone or in combination with other terms, refers to a —C(=O)— group, which also may be written as C(O).

The term "cyano" or "nitrile" refers to a group of formula —C≡N, which also may be written as —CN.

The term "carbamyl," as used herein, refers to a —NHC(O)O— or —OC(O)NH— group, wherein the carbon atom is doubly bound to one oxygen atom, and singly bound to a nitrogen and second oxygen atom.

The terms "halo" or "halogen," used alone or in combination with other terms, refers to fluoro, chloro, bromo and iodo. In some embodiments, "halo" refers to a halogen atom selected from F, Cl, or Br. In some embodiments, halo groups are F.

The term "haloalkyl" as used herein refers to an alkyl group in which one or more of the hydrogen atoms has been replaced by a halogen atom. The term "$C_{n-m}$ haloalkyl" refers to a Cn-m alkyl group having n to m carbon atoms and from at least one up to {2(n to m)+1}halogen atoms, which may either be the same or different. In some embodiments, the halogen atoms are fluoro atoms. In some embodiments, the haloalkyl group has 1 to 6 or 1 to 4 carbon atoms. Example haloalkyl groups include $CF_3$, $C_2F_5$, $CHF_2$, $CH_2F$, $CCl_3$, $CHCl_2$, $C_2Cl_5$ and the like. In some embodiments, the haloalkyl group is a fluoroalkyl group.

The term "haloalkoxy," employed alone or in combination with other terms, refers to a group of formula —O-haloalkyl, wherein the haloalkyl group is as defined above. The term "$C_{n-m}$ haloalkoxy" refers to a haloalkoxy group, the haloalkyl group of which has n to m carbons. Example haloalkoxy groups include trifluoromethoxy and the like. In some embodiments, the haloalkoxy group has 1 to 6, 1 to 4, or 1 to 3 carbon atoms.

The term "oxo" or "oxy" refers to an oxygen atom as a divalent substituent, forming a carbonyl group when attached to carbon, or attached to a heteroatom forming a sulfoxide or sulfone group, or an N-oxide group. In some embodiments, heterocyclic groups may be optionally substituted by 1 or 2 oxo (=O) substituents.

The term "sulfido" refers to a sulfur atom as a divalent substituent, forming a thiocarbonyl group (C=S) when attached to carbon.

The term "sulfonyl" refers to a $—SO_2—$ group wherein a sulfur atom is doubly bound to two oxygen atoms.

The term "oxidized" in reference to a ring-forming N atom refers to a ring-forming N-oxide.

The term "oxidized" in reference to a ring-forming S atom refers to a ring-forming sulfonyl or ring-forming sulfinyl.

The term "aromatic" refers to a carbocycle or heterocycle having one or more polyunsaturated rings having aromatic character (i.e., having (4n+2) delocalized □ (pi) electrons where n is an integer).

The term "aryl," employed alone or in combination with other terms, refers to an aromatic hydrocarbon group, which may be monocyclic or polycyclic (e.g., having 2 fused rings). The term "$C_{n-m}$ aryl" refers to an aryl group having from n to m ring carbon atoms. Aryl groups include, e.g., phenyl, naphthyl, and the like. In some embodiments, aryl groups have from 6 to about 10 carbon atoms. In some embodiments, aryl groups have 6 carbon atoms. In some embodiments, aryl groups have 10 carbon atoms. In some embodiments, the aryl group is phenyl. In some embodiments, the aryl group is naphthyl.

The term "heteroaryl" or "heteroaromatic," employed alone or in combination with other terms, refers to a monocyclic or polycyclic aromatic heterocycle having at least one heteroatom ring member selected from sulfur, oxygen and nitrogen. In some embodiments, the heteroaryl ring has 1, 2, 3 or 4 heteroatom ring members independently selected from nitrogen, sulfur and oxygen. In some embodiments, any ring-forming N in a heteroaryl moiety can be an N-oxide. In some embodiments, the heteroaryl has 5-14 ring atoms including carbon atoms and 1, 2, 3 or 4 heteroatom ring members independently selected from nitrogen, sulfur and oxygen. In some embodiments, the heteroaryl has 5-10 ring atoms including carbon atoms and 1, 2, 3 or 4 heteroatom ring members independently selected from nitrogen, sulfur and oxygen. In some embodiments, the heteroaryl has 5-6 ring atoms and 1 or 2 heteroatom ring members independently selected from nitrogen, sulfur and oxygen. In some embodiments, the heteroaryl is a five-membered or six-membered heteroaryl ring. In other embodiments, the heteroaryl is an eight-membered, nine-membered or ten-membered fused bicyclic heteroaryl ring. Example heteroaryl groups include, but are not limited to, pyridinyl (pyridyl), pyrimidinyl, pyrazinyl, pyridazinyl, pyrrolyl, pyrazolyl, azolyl, oxazolyl, isoxazolyl, thiazolyl, imidazolyl, furanyl, thiophenyl, quinolinyl, isoquinolinyl, naphthyridinyl (including 1,2-, 1,3-, 1,4-, 1,5-, 1,6-, 1,7-, 1,8-, 2,3- and 2,6-naphthyridine), indolyl, isoindolyl, benzothiophenyl, benzofuranyl, benzisoxazolyl, imidazo[1,2-b]thiazolyl, purinyl, and the like. In some embodiments, the heteroaryl group is pyridone (e.g., 2-pyridone).

A five-membered heteroaryl ring is a heteroaryl group having five ring atoms wherein one or more (e.g., 1, 2 or 3) ring atoms are independently selected from N, O and S. Exemplary five-membered ring heteroaryls include thienyl, furyl, pyrrolyl, imidazolyl, thiazolyl, oxazolyl, pyrazolyl, isothiazolyl, isoxazolyl, 1,2,3-triazolyl, tetrazolyl, 1,2,3-thiadiazolyl, 1,2,3-oxadiazolyl, 1,2,4-triazolyl, 1,2,4-thiadiazolyl, 1,2,4-oxadiazolyl, 1,3,4-triazolyl, 1,3,4-thiadiazolyl and 1,3,4-oxadiazolyl.

A six-membered heteroaryl ring is a heteroaryl group having six ring atoms wherein one or more (e.g., 1, 2 or 3) ring atoms are independently selected from N, O and S. Exemplary six-membered ring heteroaryls are pyridyl, pyrazinyl, pyrimidinyl, triazinyl, isoindolyl, and pyridazinyl.

The term "cycloalkyl," employed alone or in combination with other terms, refers to a non-aromatic hydrocarbon ring system (monocyclic, bicyclic or polycyclic), including cyclized alkyl and alkenyl groups. The term "$C_{n-m}$ cycloalkyl" refers to a cycloalkyl that has n to m ring member carbon atoms. Cycloalkyl groups can include mono- or polycyclic (e.g., having 2, 3 or 4 fused rings) groups and spirocycles. Cycloalkyl groups can have 3, 4, 5, 6 or 7 ring-forming carbons ($C_{3-7}$). In some embodiments, the cycloalkyl group has 3 to 6 ring members, 3 to 5 ring members, or 3 to 4 ring members. In some embodiments, the cycloalkyl group is monocyclic. In some embodiments, the cycloalkyl group is monocyclic or bicyclic. In some embodiments, the cycloalkyl group is a $C_{3-6}$ monocyclic cycloalkyl group. Ring-forming carbon atoms of a cycloalkyl group can be optionally oxidized to form an oxo or sulfido group. Cycloalkyl groups also include cycloalkylidenes. In some embodiments, cycloalkyl is cyclopropyl, cyclobutyl, cyclopentyl or cyclohexyl. Also included in the definition of cycloalkyl are moieties that have one or more aromatic rings fused (i.e., having a bond in common with) to the cycloalkyl ring, e.g., benzo or thienyl derivatives of cyclopentane, cyclohexane and the like. A cycloalkyl group containing a fused aromatic ring can be attached through any ring-forming atom including a ring-forming atom of the fused aromatic ring. Examples of cycloalkyl groups include cyclopropyl, cyclobutyl, cyclopentyl, cyclohexyl, cycloheptyl, cyclopentenyl, cyclohexenyl, cyclohexadienyl, cycloheptatrienyl, norbornyl, norpinyl, norcarnyl, bicyclo[1.1.1]pentanyl, bicyclo[2.1.1]hexanyl, and the like. In some embodiments, the cycloalkyl group is cyclopropyl, cyclobutyl, cyclopentyl, or cyclohexyl.

The term "heterocycloalkyl," employed alone or in combination with other terms, refers to a non-aromatic ring or ring system, which may optionally contain one or more alkenylene groups as part of the ring structure, which has at least one heteroatom ring member independently selected from nitrogen, sulfur, oxygen and phosphorus, and which has 4-10 ring members, 4-7 ring members, or 4-6 ring members. Included within the term "heterocycloalkyl" are monocyclic 4-, 5-, 6- and 7-membered heterocycloalkyl groups. Heterocycloalkyl groups can include mono- or bicyclic (e.g., having two fused or bridged rings) or spirocyclic ring systems. In some embodiments, the heterocycloalkyl group is a monocyclic group having 1, 2 or 3 heteroatoms independently selected from nitrogen, sulfur and oxygen. Ring-forming carbon atoms and heteroatoms of a heterocycloalkyl group can be optionally oxidized to form an oxo or sulfido group or other oxidized linkage (e.g., C(O), S(O), C(S) or $S(O)_2$, N-oxide etc.) or a nitrogen atom can be quaternized. The heterocycloalkyl group can be attached through a ring-forming carbon atom or a ring-forming heteroatom. In some embodiments, the heterocycloalkyl group contains 0 to 3 double bonds. In some embodiments, the heterocycloalkyl group contains 0 to 2 double bonds. Also included in the definition of heterocycloalkyl are moieties that have one or more aromatic rings fused (i.e., having a bond in common with) to the heterocycloalkyl ring, e.g., benzo or thienyl derivatives of piperidine, morpholine, azepine, etc. A heterocycloalkyl group containing a fused aromatic ring can be attached through any ring-forming atom including a ring-forming atom of the fused aromatic ring. Examples of heterocycloalkyl groups include 2,5-diazobicyclo[2.2.1]heptanyl; pyrrolidinyl; hexahydropyrrolo[3,4-b]pyrrol-1(2H)-yl; 1,6-dihydropyridinyl; morpholinyl; azetidinyl; piperazinyl; and 4,7-diazaspiro[2.5]octan-7-yl.

At certain places, the definitions or embodiments refer to specific rings (e.g., an azetidine ring, a pyridine ring, etc.). Unless otherwise indicated, these rings can be attached to any ring member provided that the valency of the atom is not exceeded. For example, an azetidine ring may be attached at any position of the ring, whereas an azetidin-3-yl ring is attached at the 3-position.

The compounds described herein can be asymmetric (e.g., having one or more stereocenters). All stereoisomers, such as enantiomers and diastereomers, are intended unless otherwise indicated. Compounds of the present invention that contain asymmetrically substituted carbon atoms can be isolated in optically active or racemic forms. Methods on how to prepare optically active forms from optically inactive starting materials are known in the art, such as by resolution of racemic mixtures or by stereoselective synthesis. Many geometric isomers of olefins, C═N double bonds and the like can also be present in the compounds described herein, and all such stable isomers are contemplated in the present invention. Cis and trans geometric isomers of the compounds of the present invention are described and may be isolated as a mixture of isomers or as separated isomeric forms.

Resolution of racemic mixtures of compounds can be carried out by any of numerous methods known in the art. One method includes fractional recrystallization using a chiral resolving acid which is an optically active, salt-forming organic acid. Suitable resolving agents for fractional recrystallization methods are, e.g., optically active acids, such as the D and L forms of tartaric acid, diacetyltartaric acid, dibenzoyltartaric acid, mandelic acid, malic acid, lactic acid or the various optically active camphorsulfonic acids such as Q-camphorsulfonic acid. Other resolving agents suitable for fractional crystallization methods include stereoisomerically pure forms of Q-methylbenzylamine (e.g., S and R forms, or diastereomerically pure forms), 2-phenylglycinol, norephedrine, ephedrine, N-methylephedrine, cyclohexylethylamine, 1,2-diaminocyclohexane and the like.

Resolution of racemic mixtures can also be carried out by elution on a column packed with an optically active resolving agent (e.g., dinitrobenzoylphenylglycine). Suitable elution solvent composition can be determined by one skilled in the art.

In some embodiments, the compounds of the invention have the (R)-configuration. In other embodiments, the compounds have the (S)-configuration. In compounds with more than one chiral centers, each of the chiral centers in the compound may be independently (R) or (S), unless otherwise indicated.

Compounds of the invention also include tautomeric forms. Tautomeric forms result from the swapping of a single bond with an adjacent double bond together with the concomitant migration of a proton. Tautomeric forms include prototropic tautomers which are isomeric protonation states having the same empirical formula and total charge.

Example prototropic tautomers include ketone-enol pairs, amide-imidic acid pairs, lactam-lactim pairs, enamine-imine pairs, and annular forms where a proton can occupy two or more positions of a heterocyclic system, e.g., 1H- and 3H-imidazole, 1H-, 2H- and 4H-1,2,4-triazole, 1H- and 2H-isoindole and 1H- and 2H-pyrazole. Tautomeric forms can be in equilibrium or sterically locked into one form by appropriate substitution.

Compounds of the invention can also include all isotopes of atoms occurring in the intermediates or final compounds. Isotopes include those atoms having the same atomic number but different mass numbers. For example, isotopes of hydrogen include tritium and deuterium. One or more constituent atoms of the compounds of the invention can be replaced or substituted with isotopes of the atoms in natural or non-natural abundance. In some embodiments, the compound includes at least one deuterium atom. For example, one or more hydrogen atoms in a compound of the present disclosure can be replaced or substituted by deuterium. In some embodiments, the compound includes two or more deuterium atoms. In some embodiments, the compound includes 1, 2, 3, 4, 5, 6, 7, 8, 9, 10, 11 or 12 deuterium atoms. Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can used in various studies such as NMR spectroscopy, metabolism experiments, and/or assays.

Substitution with heavier isotopes such as deuterium, may afford certain therapeutic advantages resulting from greater metabolic stability, for example, increased in vivo half-life or reduced dosage requirements, and hence may be preferred in some circumstances. (A. Kerekes et. al. *J. Med. Chem.* 2011, 54, 201-210; R. Xu et. al. *J. Label Compd. Radiopharm.* 2015, 58, 308-312).

The term "compound" as used herein is meant to include all stereoisomers, geometric isomers, tautomers and isotopes of the structures depicted. The term is also meant to refer to compounds of the inventions, regardless of how they are prepared, e.g., synthetically, through biological process (e.g., metabolism or enzyme conversion), or a combination thereof.

All compounds, and pharmaceutically acceptable salts thereof, can be found together with other substances such as water and solvents (e.g., hydrates and solvates) or can be isolated. When in the solid state, the compounds described herein and salts thereof may occur in various forms and may, e.g., take the form of solvates, including hydrates. The compounds may be in any solid state form, such as a polymorph or solvate, so unless clearly indicated otherwise, reference in the specification to compounds and salts thereof should be understood as encompassing any solid state form of the compound.

In some embodiments, the compounds of the invention, or salts thereof, are substantially isolated. By "substantially isolated" is meant that the compound is at least partially or substantially separated from the environment in which it was formed or detected. Partial separation can include, e.g., a composition enriched in the compounds of the invention. Substantial separation can include compositions containing at least about 50%, at least about 60%, at least about 70%, at least about 80%, at least about 90%, at least about 95%, at least about 97%, or at least about 99% by weight of the compounds of the invention, or salt thereof.

The phrase "pharmaceutically acceptable" is employed herein to refer to those compounds, materials, compositions and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

The expressions "ambient temperature" and "room temperature," as used herein, are understood in the art, and refer generally to a temperature, e.g., a reaction temperature, that is about the temperature of the room in which the reaction is carried out, e.g., a temperature from about 20° C. to about 30° C.

The present invention also includes pharmaceutically acceptable salts of the compounds described herein. The term "pharmaceutically acceptable salts" refers to derivatives of the disclosed compounds wherein the parent compound is modified by converting an existing acid or base moiety to its salt form. Examples of pharmaceutically acceptable salts include, but are not limited to, mineral or organic acid salts of basic residues such as amines; alkali or organic salts of acidic residues such as carboxylic acids; and the like. The pharmaceutically acceptable salts of the present invention include the non-toxic salts of the parent compound formed, e.g., from non-toxic inorganic or organic acids. The pharmaceutically acceptable salts of the present invention can be synthesized from the parent compound which contains a basic or acidic moiety by conventional chemical methods. Generally, such salts can be prepared by reacting the free acid or base forms of these compounds with a stoichiometric amount of the appropriate base or acid in water or in an organic solvent, or in a mixture of the two; generally, non-aqueous media like ether, ethyl acetate, alcohols (e.g., methanol, ethanol, iso-propanol or butanol) or acetonitrile (MeCN) are preferred. Lists of suitable salts are found in *Remington's Pharmaceutical Sciences*, 17th Ed., (Mack Publishing Company, Easton, 1985), p. 1418, Berge et al., *J. Pharm. Sci.*, 1977, 66(1), 1-19 and in Stahl et al., *Handbook of Pharmaceutical Salts: Properties, Selection, and Use*, (Wiley, 2002). In some embodiments, the compounds described herein include the N-oxide forms.

Synthesis

Compounds of the invention, including salts thereof, can be prepared using known organic synthesis techniques and can be synthesized according to any of numerous possible synthetic routes, such as those in the Schemes below.

The reactions for preparing compounds of the invention can be carried out in suitable solvents which can be readily selected by one of skill in the art of organic synthesis. Suitable solvents can be substantially non-reactive with the starting materials (reactants), the intermediates or products at the temperatures at which the reactions are carried out, e.g., temperatures which can range from the solvent's freezing temperature to the solvent's boiling temperature. A given reaction can be carried out in one solvent or a mixture of more than one solvent. Depending on the particular reaction step, suitable solvents for a particular reaction step can be selected by the skilled artisan.

Preparation of compounds of the invention can involve the protection and deprotection of various chemical groups. The need for protection and deprotection, and the selection of appropriate protecting groups, can be readily determined by one skilled in the art. The chemistry of protecting groups is described, e.g., in Kocienski, Protecting Groups, (Thieme, 2007); Robertson, *Protecting Group Chemistry*, (Oxford University Press, 2000); Smith et al., *March's Advanced Organic Chemistry: Reactions, Mechanisms, and Structure*, 6th Ed. (Wiley, 2007); Petursson et al., "Protecting Groups in Carbohydrate Chemistry," *J.* Chem. Educ., 1997, 74(11), 1297; and Wuts et al., *Protective Groups in Organic Synthesis*, 4th Ed., (Wiley, 2006).

Reactions can be monitored according to any suitable method known in the art. For example, product formation can be monitored by spectroscopic means, such as nuclear magnetic resonance spectroscopy (e.g., $^{1}H$ or $^{13}C$), infrared spectroscopy, spectrophotometry (e.g., UV-visible), mass spectrometry or by chromatographic methods such as high-performance liquid chromatography (HPLC) or thin layer chromatography (TLC).

The Schemes below provide general guidance in connection with preparing the compounds of the invention. One skilled in the art would understand that the preparations shown in the Schemes can be modified or optimized using general knowledge of organic chemistry to prepare various compounds of the invention.

Scheme 1

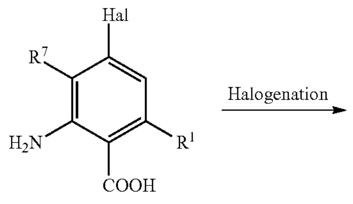

1-1

-continued

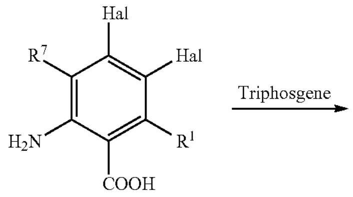

1-2

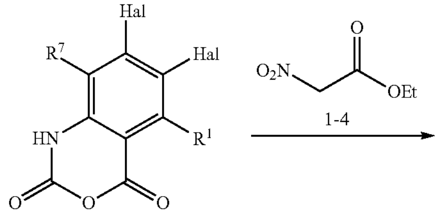

1-3

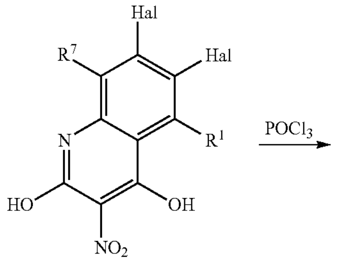

1-5

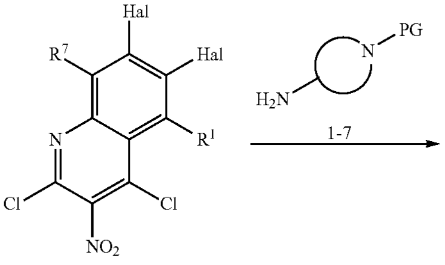

1-6

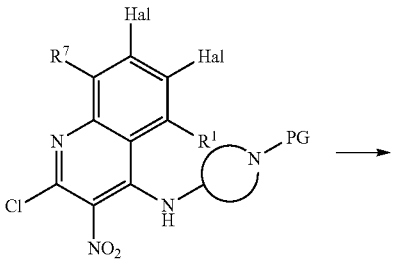

1-8

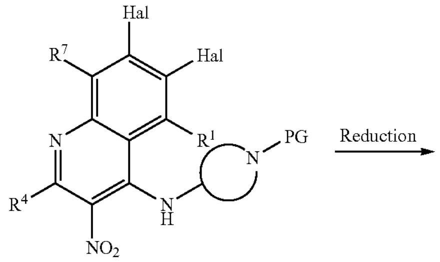

1-9

-continued

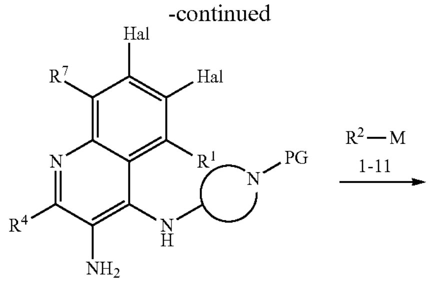

1-10

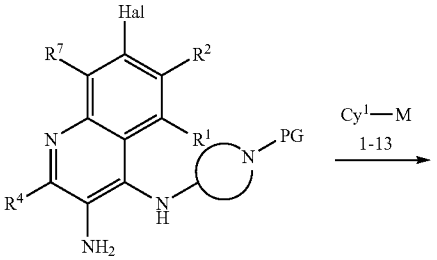

1-12

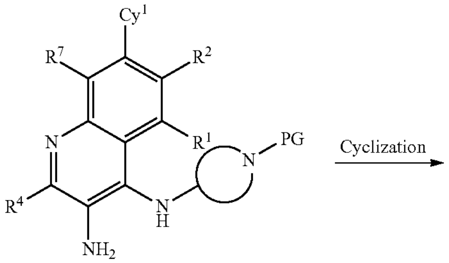

1-14

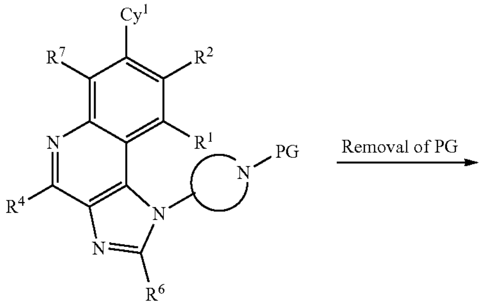

1-15

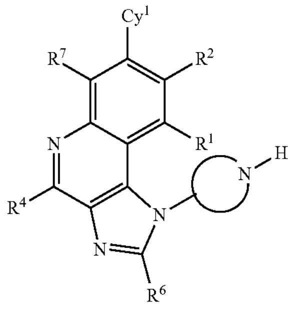

1-16

Compounds of formula 1-16 can be prepared via the synthetic route outlined in Scheme 1. Halogenation of starting material 1-1 (Hal is a halide, such as F, Cl, Br, or I) with an appropriate reagent, such as N-chloro-succinimide (NCS), affords intermediate 1-2 (Hal is a halide, such as F, Cl, Br, or I). Compound 1-3 can be prepared by treating 1-2 with reagents such as triphosgene. Intermediate 1-3 can then react with ester 1-4 to deliver the nitro compound 1-5, which can be treated with an appropriate reagent (e.g., $POCl_3$) to afford compound 1-6. A $S_NAr$ reaction of intermediate 1-6 with amine 1-7 (PG is an appropriate protecting group, such as Boc) can be carried out to generate compound 1-8, followed by a $S_NAr$ reaction to provide 1-9. The nitro group in 1-9 can be reduced to $NH_2$ in the presence reducing agents (e.g., Fe in acetic acid or sodium dithionite). A cross-coupling reaction with 1-11, in which M is a boronic acid, boronic ester or an appropriately substituted metal or metalloid [e.g., M is $B(OR)_2$, $Sn(Alkyl)_3$, Zn-Hal, or $CF_3TMS$], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), or trifluoromethylation conditions (e.g., in the presence of a copper catalyst) yields 1-12. Intermediate 1-14 can be prepared by a cross-coupling reaction between 1-12 and an adduct of formula 1-13, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). Intermediate 1-14 can then undergo a cyclization reaction (e.g., using triethyl orthoformate) to yield intermediate 1-15. Removal of the protecting group in 1-15 affords the desired product 1-16. The order of the above described chemical reactions can be rearranged or omitted as appropriate to suit the preparation of different analogues.

Scheme 2

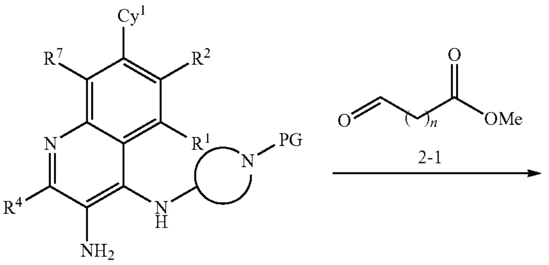

1-14

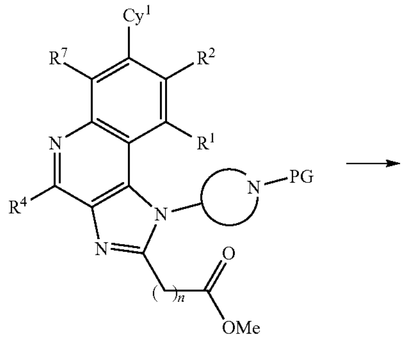

2-2

-continued

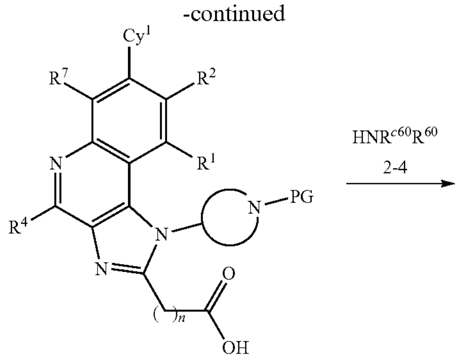

2-3

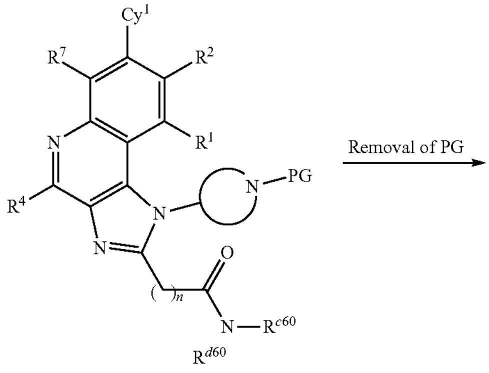

2-5

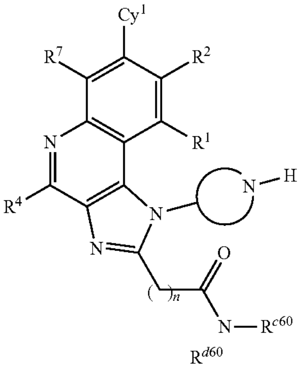

2-6

Scheme 3

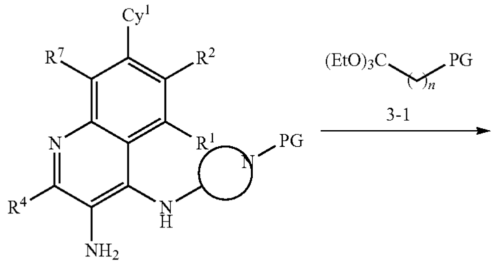

1-14

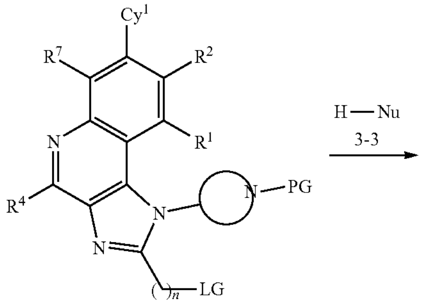

3-2

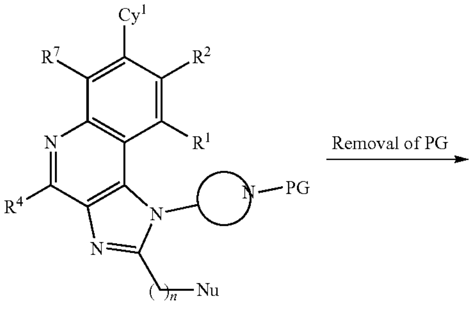

3-4

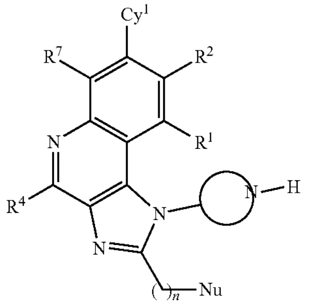

3-5

Compounds of formula 2-6 can be prepared via the synthetic route outlined in Scheme 2. Cyclization of starting material 1-14 with an appropriate ester bearing aldehyde 2-1 affords intermediate 2-2, which can be converted to acid 2-3 upon saponification. Coupling with amine 2-4 under standard amide coupling conditions (e.g., in the presence of HATU and a suitable base) yields 2-5. Removal of the protecting group in 2-5 affords the desired product 2-6. The order of the above described chemical reactions can be rearranged or omitted as appropriate to suit the preparation of different analogues.

Alternatively, compounds of formula 3-5 can be prepared via the synthetic route outlined in Scheme 3. Condensation of starting material 1-14 with an appropriate leaving group substituted triethyl orthoformate 3-1 (e.g., 2-chloro-1,1,1-triethoxyethane) affords intermediate 3-2. Replacement of the leaving group in 3-2 with a nucleophile 3-3 in the presence of a suitable base yields 3-4. Removal of the protecting group in 3-4 affords the desired product 3-5. The order of the above described chemical reactions can be rearranged or omitted as appropriate to suit the preparation of different analogues.

Scheme 4

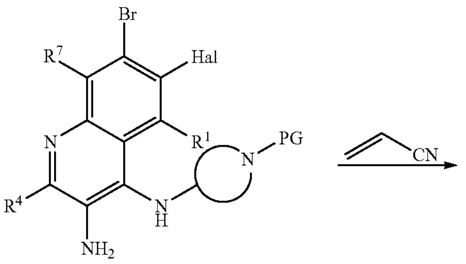

1-10

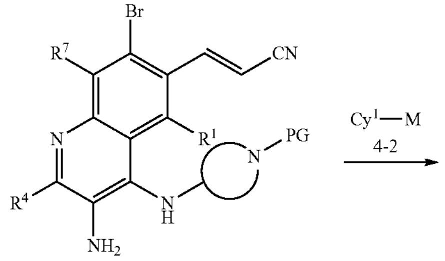

4-1

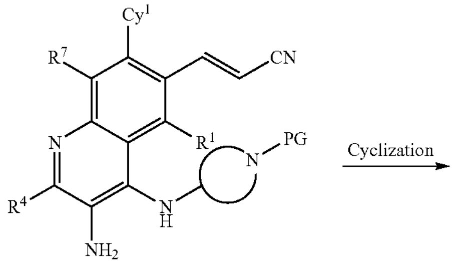

4-3

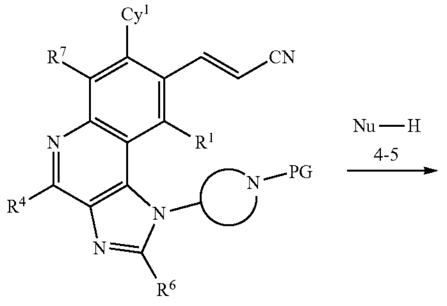

4-4

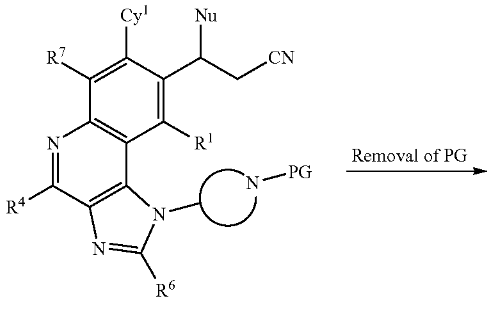

4-6

-continued

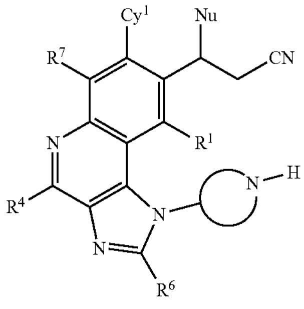

4-7

Compounds of formula 4-7 can be prepared via the synthetic route outlined in Scheme 4. Coupling of starting material 1-10 with acrylonitrile under standard Heck reaction conditions (e.g., in the presence of a palladium catalyst and a suitable base) affords intermediate 4-1. A cross-coupling reaction with 4-2, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) affords 4-3. Intermediate 4-3 can then undergo a cyclization reaction (e.g., using triethyl orthoformate) to yield intermediate 4-4. Michael addition of a nucleophile 4-5 to the olefin in 4-4 with the assistance of a suitable base can afford 4-6. Removal of the protecting group in 1-15 affords the desired product 1-16. The order of the above described chemical reactions can be rearranged or omitted as appropriate to suit the preparation of different analogues.

Scheme 5

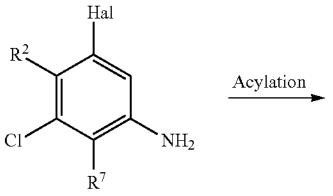

5-1

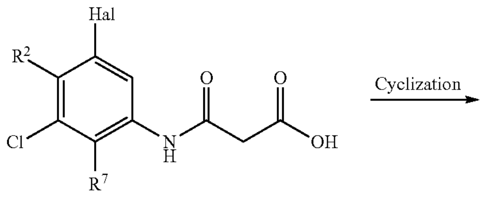

5-2

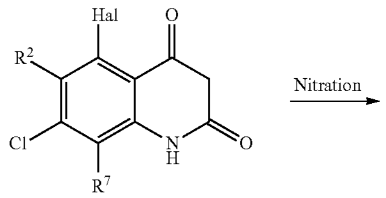

5-3

-continued

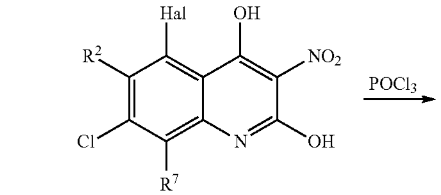

5-4

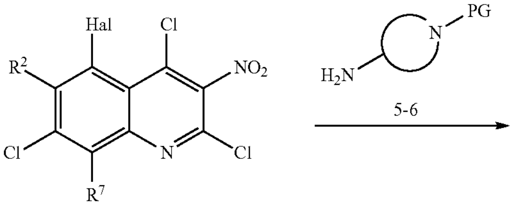

5-5

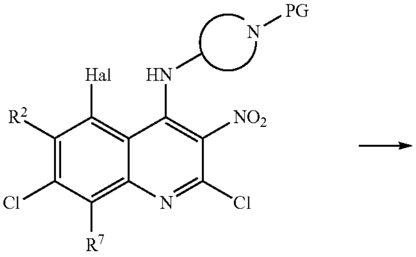

5-7

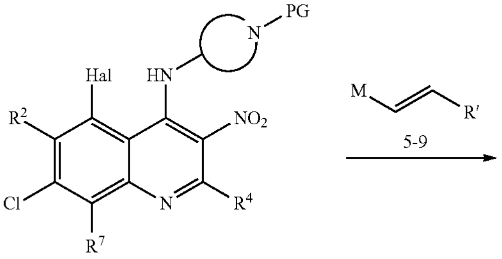

5-8

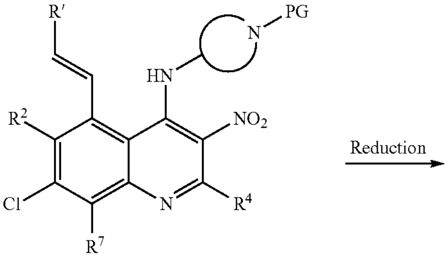

5-10

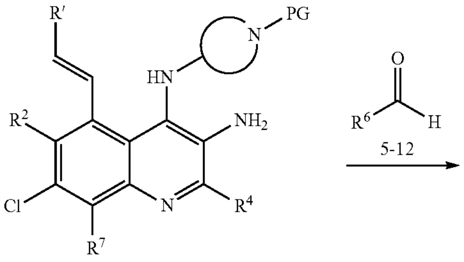

5-11

-continued

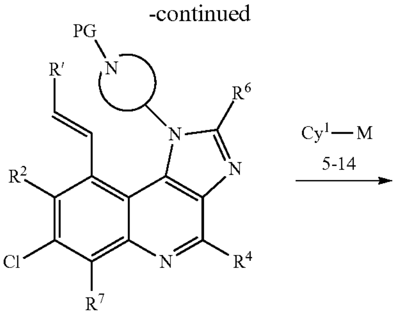

5-13

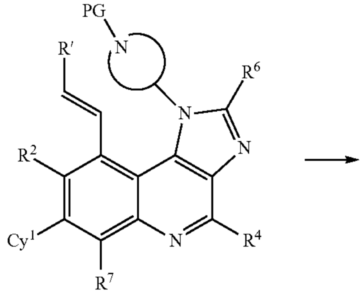

5-15

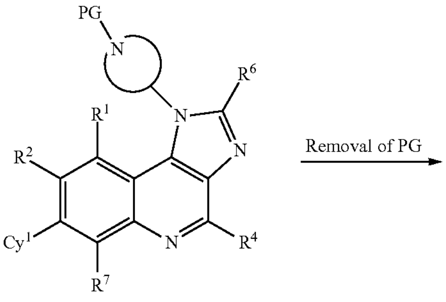

5-16

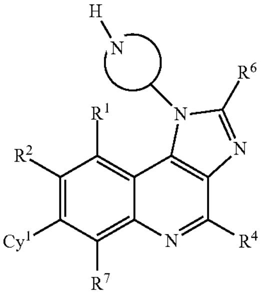

5-17

Compounds of formula 5-17 can be prepared following the synthetic route in scheme 5. Acylation of starting material 5-1 with ethyl malonyl chloride, followed by hydrolysis of the ester group in the presence of an appropriate base, such as LiOH, can generate intermediate 5-2. Compound 5-3 can be prepared by treating 5-2 with dehydrating reagents, such as Eaton's reagent or polyphosphric acid (PPA). Nitration of 5-3 with nitric acid in acetic acid can deliver the nitro-containing compound 5-4, which can be treated with an appropriate reagent (e.g., $POCl_3$) to afford compound 5-5. A $S_NAr$ reaction of intermediate 5-5 with amine 5-6 (PG is an appropriate protecting group, such as Boc) can be carried out to generate compound 5-7, followed by a second $S_NAr$ reaction to provide 5-8. Compound 5-10 can be prepared by a cross-coupling with vinyl metallic reagents of formula 5-9, where M is a hydrogen atom, boronic acid, boronic ester or an appropriately substituted metal or metalloid [e.g., M is $B(OR)_2$, $Sn(Alkyl)_3$, Zn-Hal], under standard Heck reaction conditions (e.g., in the presence of a palladium catalyst), or standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst). The nitro group in 5-10 can be reduced to $NH_2$ in the presence reducing agents (e.g., Fe or sodium dithionite) to deliver intermediate 5-11, which can undergo a cyclization reaction with aldehyde 5-12 or a suitable surrogate (e.g. triethyl orthoformate) to yield intermediate 5-13. A cross-coupling reaction between 5-13 and adduct of formula 5-14, in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst), can generate compound 5-15. The double bond in 5-15 can be reduced with reducing agents (e.g. palladium on carbon under hydrogen atmosphere or lithium borohydrides), or be oxidatively cleaved with an oxidant (e.g. $NaIO_4$ with catalytic amount of $OsO_4$) to aldehyde which can be subsequently reduced to alcohol or be converted to an amine under standard reductive amination conditions, to deliver compound 5-16. Removal of the protecting group in 5-16 affords the desired product 5-17. The order of the above described chemical reactions can be rearranged or omitted as appropriate to suit the preparation of different analogues.

Scheme 6

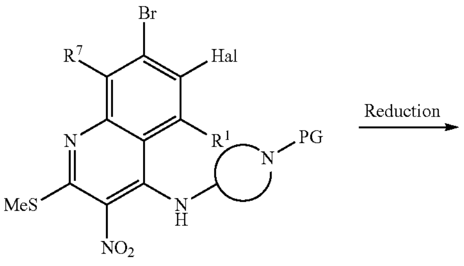

1-9a

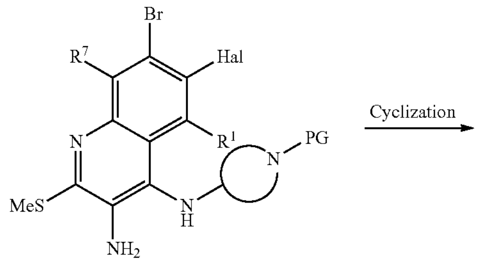

6-1

-continued

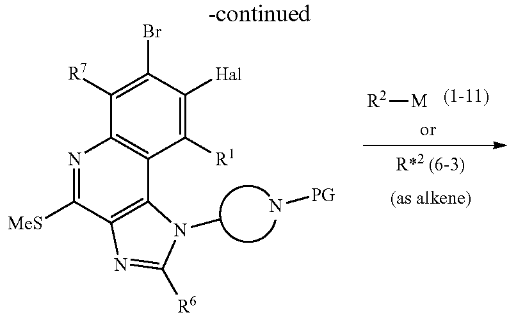

6-2

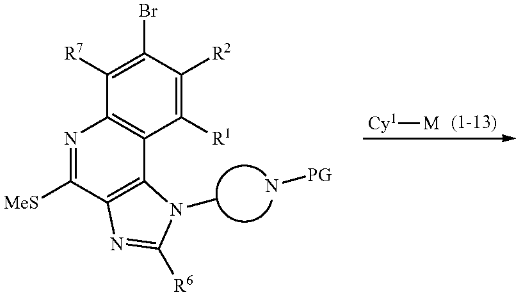

6-4

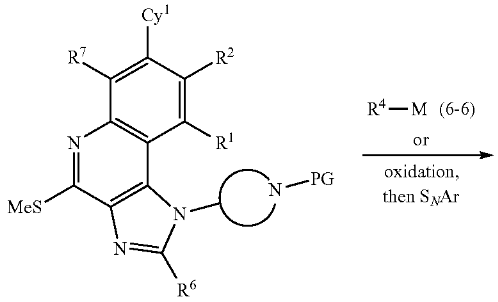

6-5

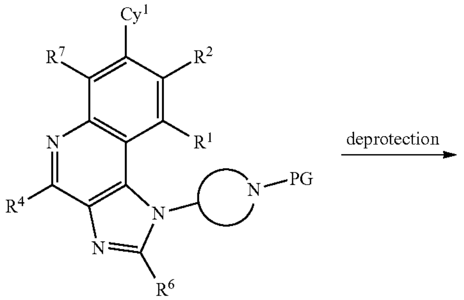

6-7

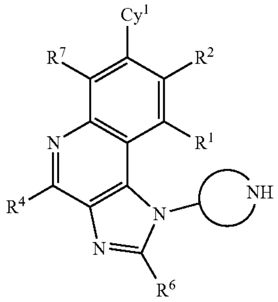

6-8

Alternatively, compounds of formula 6-8 can be prepared via the synthetic route outlined in Scheme 6. Thioether 1-9a (as prepared in Scheme 1, where $R^4$ is SMe) can undergo nitro reduction to $NH_2$ in the presence of reducing agents (e.g. Fe in acetic acid or sodium dithionate). Intermediate 6-1 can undergo a cyclization reaction (e.g. using triethyl orthoformate or an appropriate aldehyde) to provide tricycle 6-2. Subsequent coupling with an adduct of formula 1-11 in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) provides compounds of formula 6-4. Alternatively, coupling with an appropriate alkene $R^{*2}$ (6-3) under standard Heck conditions (e.g., in the presence of a palladium catalyst and base), or reductive Heck conditions (e.g., in the presence of a palladium catalyst and a hydride source) also provides compounds of formula 6-4. Intermediates 6-4 can then undergo coupling with an adduct $Cy^1$-M (1-13) in which M is a boronic acid, boronic ester or an appropriately substituted metal [e.g., M is $B(OR)_2$, $Sn(Alkyl)_3$, or Zn-Hal], under standard Suzuki cross-coupling conditions (e.g., in the presence of a palladium catalyst and a suitable base), or standard Stille cross-coupling conditions (e.g., in the presence of a palladium catalyst), or standard Negishi cross-coupling conditions (e.g., in the presence of a palladium catalyst) to provide compounds of formula 6-5. The thioether moiety of compounds 6-5 can then undergo coupling with an adduct of formula $R^4$-M (6-6), in which M is a boronic acid, boronic ester or an appropriately substituted metal [e.g., M is $B(OR)_2$, $Sn(Alkyl)_3$, Mg-Hal, or Zn-Hal], under standard Liebeskind-Srogl conditions (e.g., in the presence of a palladium catalyst and copper(I) source). Alternatively, the desired compounds 6-7 can be prepared by a two-step protocol, wherein the aryl thioether 6-5 is oxidized to the corresponding sulfoxide or sulfone by a suitable oxidant (e.g., m-CPBA) and then displaced by the appropriate $R^4$—H nucleophile in an $S_NAr$ reaction. Finally, the title compounds 6-8 can be prepared by removal of the protecting group. The order of the above described chemical reactions can be rearranged as appropriate to suit the preparation of different analogues.

KRAS Protein

The Ras family is comprised of three members: KRAS, NRAS and HRAS. RAS mutant cancers account for about 25% of human cancers. KRAS is the most frequently mutated isoform in human cancers: 85% of all RAS mutations are in KRAS, 12% in NRAS, and 3% in HRAS (Simanshu, D. et al. Cell 170.1 (2017):17-33). KRAS mutations are prevalent amongst the top three most deadly cancer types: pancreatic (97%), colorectal (44%), and lung (30%) (Cox, A. D. et al. Nat Rev Drug Discov (2014) 13:828-51). The majority of RAS mutations occur at amino acid residues/codons 12, 13, and 61; Codon 12 mutations are most frequent in KRAS. The frequency of specific mutations varied between RAS genes and G12D mutations are most predominant in KRAS whereas Q61R and G12R mutations are most frequent in NRAS and HRAS. Furthermore, the spectrum of mutations in a RAS isoform differs between cancer types. For example, KRAS G12D mutations predominate in pancreatic cancers (51%), followed by colorectal adenocarcinomas (45%) and lung cancers (17%) (Cox, A. D. et al. Nat Rev Drug Discov (2014) 13:828-51). In contrast, KRAS G12C mutations predominate in non-small cell lung cancer (NSCLC) comprising 11-16% of lung adenocarcinomas (nearly half of mutant KRAS is G12C), as well as 2-5% of pancreatic and colorectal adenocarcinomas, respectively (Cox, A. D. et al. Nat. Rev. Drug Discov. (2014) 13:828-51). Using shRNA knockdown thousands of genes across hundreds of cancer cell lines, genomic studies have demonstrated that cancer cells exhibiting KRAS mutations are highly dependent on KRAS function for cell growth (McDonald, R. et al. Cell 170 (2017): 577-592). Taken together, these findings suggested that KRAS mutations play a critical role in human cancers, therefore development of the inhibitors targeting mutant KRAS may be useful in the clinical treatment of diseases that have characterized by a KRAS mutation.

Methods of Use

The cancer types in which KRAS harboring G12C, G12V and 12D mutations are implicated include, but are not limited to: carcinomas (e.g., pancreatic, colorectal, lung, bladder, gastric, esophageal, breast, head and neck, cervical skin, thyroid); hematopoietic malignancies (e.g., myeloproliferative neoplasms (MPN), myelodysplastic syndrome (MDS), chronic and juvenile myelomonocytic leukemia (CMML and JMML), acute myeloid leukemia (AML), acute lymphocytic leukemia (ALL) and multiple myeloma (MM)); and other neoplasms (e.g., glioblastoma and sarcomas). In addition, KRAS mutations were found in acquired resistance to anti-EGFR therapy (Knickelbein, K. et al. Genes & Cancer, (2015): 4-12). KRAS mutations were found in immunological and inflammatory disorders (Fernandez-Medarde, A. et al. Genes & Cancer, (2011): 344-358) such as Ras-associated lymphoproliferative disorder (RALD) or juvenile myelomonocytic leukemia (JMML) caused by somatic mutations of KRAS or NRAS.

Compounds of the present disclosure can inhibit the activity of the KRAS protein. For example, compounds of the present disclosure can be used to inhibit activity of KRAS in a cell or in an individual or patient in need of inhibition of the enzyme by administering an inhibiting amount of one or more compounds of the present disclosure to the cell, individual, or patient.

As KRAS inhibitors, the compounds of the present disclosure are useful in the treatment of various diseases associated with abnormal expression or activity of KRAS. Compounds which inhibit KRAS will be useful in providing a means of preventing the growth or inducing apoptosis in tumors, or by inhibiting angiogenesis. It is therefore anticipated that compounds of the present disclosure will prove useful in treating or preventing proliferative disorders such as cancers. In particular, tumors with activating mutants of receptor tyrosine kinases or upregulation of receptor tyrosine kinases may be particularly sensitive to the inhibitors.

In an aspect, provided herein is a method of inhibiting KRAS activity, said method comprising contacting a compound of the instant disclosure with KRAS. In an embodiment, the contacting comprises administering the compound to a patient.

In an aspect, provided herein is a method of inhibiting a KRAS protein harboring a G12C mutation, said method comprising contacting a compound of the instant disclosure with KRAS.

In an aspect, provided herein is a method of inhibiting a KRAS protein harboring a G12D mutation, said method comprising contacting a compound of the instant disclosure with KRAS.

In an aspect, provided herein is a method of inhibiting a KRAS protein harboring a G12V mutation, said method comprising contacting a compound of the instant disclosure with KRAS.

In another aspect, provided herein a is method of treating a disease or disorder associated with inhibition of KRAS interaction, said method comprising administering to a patient in need thereof a therapeutically effective amount of a compound of any of the formulae disclosed herein, or pharmaceutically acceptable salt thereof.

In yet another aspect, provided herein is a method of treating a disease or disorder associated with inhibiting a KRAS protein harboring a G12D mutation, said method comprising administering to a patient in need thereof a therapeutically effective amount of a compound of any of the formulae disclosed herein, or pharmaceutically acceptable salt thereof.

In still another aspect, provided herein is also a method of treating cancer in a patient in need thereof comprising administering to the patient a therapeutically effective amount of the compounds disclosed herein wherein the cancer is characterized by an interaction with a KRAS protein harboring a G12D mutation.

In yet another aspect, provided herein is a method for treating a cancer in a patient, said method comprising administering to the patient a therapeutically effective amount of any one of the compounds disclosed herein, or pharmaceutically acceptable salt thereof.

In an aspect, provided herein is a method for treating a disease or disorder associated with inhibition of KRAS interaction or a mutant thereof, in a patient in need thereof, comprising the step of administering to the patient a compound disclosed herein, or a pharmaceutically acceptable salt thereof, or a composition comprising a compound disclosed herein or a pharmaceutically acceptable salt thereof, in combination with another therapy or therapeutic agent as described herein.

In an embodiment, the cancer is selected from hematological cancers, sarcomas, lung cancers, gastrointestinal cancers, genitourinary tract cancers, liver cancers, bone cancers, nervous system cancers, gynecological cancers, and skin cancers.

In another embodiment, the lung cancer is selected from non-small cell lung cancer (NSCLC), small cell lung cancer, bronchogenic carcinoma, squamous cell bronchogenic carcinoma, undifferentiated small cell bronchogenic carcinoma, undifferentiated large cell bronchogenic carcinoma, adenocarcinoma, bronchogenic carcinoma, alveolar carcinoma, bronchiolar carcinoma, bronchial adenoma, chondromatous hamartoma, mesothelioma, pavicellular and non-pavicellular carcinoma, bronchial adenoma, and pleuropulmonary blastoma.

In yet another embodiment, the lung cancer is non-small cell lung cancer (NSCLC). In still another embodiment, the lung cancer is adenocarcinoma.

In an embodiment, the gastrointestinal cancer is selected from esophagus squamous cell carcinoma, esophagus adenocarcinoma, esophagus leiomyosarcoma, esophagus lymphoma, stomach carcinoma, stomach lymphoma, stomach leiomyosarcoma, exocrine pancreatic carcinoma, pancreatic ductal adenocarcinoma, pancreatic insulinoma, pancreatic glucagonoma, pancreatic gastrinoma, pancreatic carcinoid tumors, pancreatic vipoma, small bowel adenocarcinoma, small bowel lymphoma, small bowel carcinoid tumors, Kaposi's sarcoma, small bowel leiomyoma, small bowel hemangioma, small bowel lipoma, small bowel neurofibroma, small bowel fibroma, large bowel adenocarcinoma, large bowel tubular adenoma, large bowel villous adenoma, large bowel hamartoma, large bowel leiomyoma, colorectal cancer, gall bladder cancer, and anal cancer.

In an embodiment, the gastrointestinal cancer is colorectal cancer.

In another embodiment, the cancer is a carcinoma. In yet another embodiment, the carcinoma is selected from pancreatic carcinoma, colorectal carcinoma, lung carcinoma, bladder carcinoma, gastric carcinoma, esophageal carcinoma, breast carcinoma, head and neck carcinoma, cervical skin carcinoma, and thyroid carcinoma.

In still another embodiment, the cancer is a hematopoietic malignancy. In an embodiment, the hematopoietic malignancy is selected from multiple myeloma, acute myelogenous leukemia, and myeloproliferative neoplasms.

In another embodiment, the cancer is a neoplasm. In yet another embodiment, the neoplasm is glioblastoma or sarcomas.

In certain embodiments, the disclosure provides a method for treating a KRAS-mediated disorder in a patient in need thereof, comprising the step of administering to said patient a compound according to the invention, or a pharmaceutically acceptable composition thereof.

In some embodiments, diseases and indications that are treatable using the compounds of the present disclosure include, but are not limited to hematological cancers, sarcomas, lung cancers, gastrointestinal cancers, genitourinary tract cancers, liver cancers, bone cancers, nervous system cancers, gynecological cancers, and skin cancers.

Exemplary hematological cancers include lymphomas and leukemias such as acute lymphoblastic leukemia (ALL), acute myelogenous leukemia (AML), acute promyelocytic leukemia (APL), chronic lymphocytic leukemia (CLL), chronic myelogenous leukemia (CML), diffuse large B-cell lymphoma (DLBCL), mantle cell lymphoma, Non-Hodgkin lymphoma (including relapsed or refractory NHL and recurrent follicular), Hodgkin lymphoma, myeloproliferative diseases (e.g., primary myelofibrosis (PMF), polycythemia vera (PV), essential thrombocytosis (ET), 8p11 myeloproliferative syndrome, myelodysplasia syndrome (MDS), T-cell acute lymphoblastic lymphoma (T-ALL), multiple myeloma, cutaneous T-cell lymphoma, adult T-cell leukemia, Waldenstrom's Macroglubulinemia, hairy cell lymphoma, marginal zone lymphoma, chronic myelogenic lymphoma and Burkitt's lymphoma.

Exemplary sarcomas include chondrosarcoma, Ewing's sarcoma, osteosarcoma, rhabdomyosarcoma, angiosarcoma, fibrosarcoma, liposarcoma, myxoma, rhabdomyoma, rhabdosarcoma, fibroma, lipoma, harmatoma, lymphosarcoma, leiomyosarcoma, and teratoma.

Exemplary lung cancers include non-small cell lung cancer (NSCLC), small cell lung cancer, bronchogenic carcinoma (squamous cell, undifferentiated small cell, undifferentiated large cell, adenocarcinoma), alveolar (bronchiolar) carcinoma, bronchial adenoma, chondromatous hamartoma, mesothelioma, pavicellular and non-pavicellular carcinoma, bronchial adenoma and pleuropulmonary blastoma.

Exemplary gastrointestinal cancers include cancers of the esophagus (squamous cell carcinoma, adenocarcinoma, leiomyosarcoma, lymphoma), stomach (carcinoma, lymphoma, leiomyosarcoma), pancreas (exocrine pancreatic carcinoma, ductal adenocarcinoma, insulinoma, glucagonoma, gastrinoma, carcinoid tumors, vipoma), small bowel (adenocarcinoma, lymphoma, carcinoid tumors, Kaposi's sarcoma, leiomyoma, hemangioma, lipoma, neurofibroma, fibroma), large bowel (adenocarcinoma, tubular adenoma, villous adenoma, hamartoma, leiomyoma), colorectal cancer, gall bladder cancer and anal cancer.

Exemplary genitourinary tract cancers include cancers of the kidney (adenocarcinoma, Wilm's tumor [nephroblastoma], renal cell carcinoma), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma) and urothelial carcinoma.

Exemplary liver cancers include hepatoma (hepatocellular carcinoma), cholangiocarcinoma, hepatoblastoma, angiosarcoma, hepatocellular adenoma, and hemangioma.

Exemplary bone cancers include, for example, osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma, and giant cell tumors Exemplary nervous system cancers include cancers of the skull (osteoma, hemangioma, granuloma, xanthoma, osteitis deformans), meninges (meningioma, meningiosarcoma, gliomatosis), brain (astrocytoma, meduoblastoma, glioma, ependymoma, germinoma (pinealoma), glioblastoma, glioblastoma multiform, oligodendroglioma, schwannoma, retinoblastoma, congenital tumors, neuro-ectodermal tumors), and spinal cord (neurofibroma, meningioma, glioma, sarcoma), neuroblastoma, Lhermitte-Duclos disease and pineal tumors.

Exemplary gynecological cancers include cancers of the breast (ductal carcinoma, lobular carcinoma, breast sarcoma, triple-negative breast cancer, HER2-positive breast cancer, inflammatory breast cancer, papillary carcinoma), uterus (endometrial carcinoma), cervix (cervical carcinoma, pretumor cervical dysplasia), ovaries (ovarian carcinoma (serous cystadenocarcinoma, mucinous cystadenocarcinoma, unclassified carcinoma), granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), and fallopian tubes (carcinoma).

Exemplary skin cancers include melanoma, basal cell carcinoma, squamous cell carcinoma, Kaposi's sarcoma, Merkel cell skin cancer, moles dysplastic nevi, lipoma, angioma, dermatofibroma, and keloids.

Exemplary head and neck cancers include glioblastoma, melanoma, rhabdosarcoma, lymphosarcoma, osteosarcoma, squamous cell carcinomas, adenocarcinomas, oral cancer, laryngeal cancer, nasopharyngeal cancer, nasal and paranasal cancers, thyroid and parathyroid cancers, tumors of the eye, tumors of the lips and mouth and squamous head and neck cancer.

The compounds of the present disclosure can also be useful in the inhibition of tumor metastases.

In addition to oncogenic neoplasms, the compounds of the invention are useful in the treatment of skeletal and chondrocyte disorders including, but not limited to, achrondroplasia, hypochondroplasia, dwarfism, thanatophoric dysplasia (TD) (clinical forms TD I and TD II), Apert syndrome, Crouzon syndrome, Jackson-Weiss syndrome, Beare-Stevenson cutis gyrate syndrome, Pfeiffer syndrome, and craniosynostosis syndromes. In some embodiments, the present disclosure provides a method for treating a patient suffering from a skeletal and chondrocyte disorder.

In some embodiments, compounds described herein can be used to treat Alzheimer's disease, HIV, or tuberculosis.

As used herein, the term "8p11 myeloproliferative syndrome" is meant to refer to myeloid/lymphoid neoplasms associated with eosinophilia and abnormalities of FGFR1.

As used herein, the term "cell" is meant to refer to a cell that is in vitro, ex vivo or in vivo. In some embodiments, an ex vivo cell can be part of a tissue sample excised from an organism such as a mammal. In some embodiments, an in vitro cell can be a cell in a cell culture. In some embodiments, an in vivo cell is a cell living in an organism such as a mammal.

As used herein, the term "contacting" refers to the bringing together of indicated moieties in an in vitro system or an in vivo system. For example, "contacting" KRAS with a compound described herein includes the administration of a compound described herein to an individual or patient, such as a human, having KRAS, as well as, for example, introducing a compound described herein into a sample containing a cellular or purified preparation containing KRAS.

As used herein, the term "individual," "subject," or "patient," used interchangeably, refers to any animal, including mammals, preferably mice, rats, other rodents, rabbits, dogs, cats, swine, cattle, sheep, horses, or primates, and most preferably humans.

As used herein, the phrase "therapeutically effective amount" refers to the amount of active compound or pharmaceutical agent such as an amount of any of the solid forms or salts thereof as disclosed herein that elicits the biological or medicinal response in a tissue, system, animal, individual or human that is being sought by a researcher, veterinarian, medical doctor or other clinician. An appropriate "effective" amount in any individual case may be determined using techniques known to a person skilled in the art.

The phrase "pharmaceutically acceptable" is used herein to refer to those compounds, materials, compositions, and/or dosage forms which are, within the scope of sound medical judgment, suitable for use in contact with the tissues of human beings and animals without excessive toxicity, irritation, allergic response, immunogenicity or other problem or complication, commensurate with a reasonable benefit/risk ratio.

As used herein, the phrase "pharmaceutically acceptable carrier or excipient" refers to a pharmaceutically-acceptable material, composition, or vehicle, such as a liquid or solid filler, diluent, solvent, or encapsulating material. Excipients or carriers are generally safe, non-toxic and neither biologically nor otherwise undesirable and include excipients or carriers that are acceptable for veterinary use as well as human pharmaceutical use. In one embodiment, each component is "pharmaceutically acceptable" as defined herein. See, e.g., *Remington: The Science and Practice of Pharmacy,* 21st ed.; Lippincott Williams & Wilkins: Philadelphia, Pa., 2005; *Handbook of Pharmaceutical Excipients,* 6th ed.; Rowe et al., Eds.; The Pharmaceutical Press and the American Pharmaceutical Association: 2009; *Handbook of Pharmaceutical Additives,* 3rd ed.; Ash and Ash Eds.; Gower Publishing Company: 2007; *Pharmaceutical Preformulation and Formulation,* 2nd ed.; Gibson Ed.; CRC Press LLC: Boca Raton, Fla., 2009.

As used herein, the term "treating" or "treatment" refers to inhibiting a disease; for example, inhibiting a disease, condition, or disorder in an individual who is experiencing or displaying the pathology or symptomology of the disease, condition, or disorder (i.e., arresting further development of the pathology and/or symptomology) or ameliorating the disease; for example, ameliorating a disease, condition, or disorder in an individual who is experiencing or displaying the pathology or symptomology of the disease, condition, or disorder (i.e., reversing the pathology and/or symptomology) such as decreasing the severity of the disease.

The term "prevent," "preventing," or "prevention" as used herein, comprises the prevention of at least one symptom associated with or caused by the state, disease or disorder being prevented.

It is appreciated that certain features of the invention, which are, for clarity, described in the context of separate embodiments, can also be provided in combination in a single embodiment (while the embodiments are intended to be combined as if written in multiply dependent form). Conversely, various features of the invention which are, for brevity, described in the context of a single embodiment, can also be provided separately or in any suitable subcombination.

Combination Therapy

I. Cancer Therapies

Cancer cell growth and survival can be impacted by dysfunction in multiple signaling pathways. Thus, it is useful to combine different enzyme/protein/receptor inhibitors, exhibiting different preferences in the targets which they modulate the activities of, to treat such conditions. Targeting more than one signaling pathway (or more than one biological molecule involved in a given signaling pathway) may reduce the likelihood of drug-resistance arising in a cell population, and/or reduce the toxicity of treatment.

One or more additional pharmaceutical agents such as, for example, chemotherapeutics, anti-inflammatory agents, steroids, immunosuppressants, immune-oncology agents, metabolic enzyme inhibitors, chemokine receptor inhibitors, and phosphatase inhibitors, as well as targeted therapies such as Bcr-Abl, Flt-3, EGFR, HER2, JAK, c-MET, VEGFR, PDGFR, c-Kit, IGF-1R, RAF, FAK, and CDK4/6 kinase inhibitors such as, for example, those described in WO 2006/056399 can be used in combination with the compounds of the present disclosure for treatment of CDK2-associated diseases, disorders or conditions. Other agents such as therapeutic antibodies can be used in combination with the compounds of the present disclosure for treatment of CDK2-associated diseases, disorders or conditions. The one or more additional pharmaceutical agents can be administered to a patient simultaneously or sequentially.

In some embodiments, the CDK2 inhibitor is administered or used in combination with a BCL2 inhibitor or a CDK4/6 inhibitor.

The compounds as disclosed herein can be used in combination with one or more other enzyme/protein/receptor inhibitors therapies for the treatment of diseases, such as cancer and other diseases or disorders described herein. Examples of diseases and indications treatable with combination therapies include those as described herein. Examples of cancers include solid tumors and non-solid tumors, such as liquid tumors, blood cancers. Examples of infections include viral infections, bacterial infections, fungus infections or parasite infections. For example, the compounds of the present disclosure can be combined with one or more inhibitors of the following kinases for the treatment of cancer: Akt1, Akt2, Akt3, BCL2, CDK4/6, TGF-PR, PKA, PKG, PKC, CaM-kinase, phosphorylase kinase, MEKK, ERK, MAPK, mTOR, EGFR, HER2, HER3, HER4, INS-R, IDH2, IGF-1R, IR-R, PDGFαR, PDGFβR, PI3K (alpha, beta, gamma, delta, and multiple or selective), CSF1R, KIT, FLK-II, KDR/FLK-1, FLK-4, flt-1, FGFR1, FGFR2, FGFR3, FGFR4, c-Met, PARP, Ron, Sea, TRKA, TRKB, TRKC, TAM kinases (Ax1, Mer, Tyro3), FLT3, VEGFR/Flt2, Flt4, EphA1, EphA2, EphA3, EphB2, EphB4, Tie2, Src, Fyn, Lck, Fgr, Btk, Fak, SYK, FRK, JAK, ABL, ALK and B-Raf. In some embodiments, the compounds of the present disclosure can be combined with one or more of the following inhibitors for the treatment of cancer or infections. Non-limiting examples of inhibitors that can be combined with the compounds of the present disclosure for treatment of cancer and infections include an FGFR inhibitor (FGFR1, FGFR2, FGFR3 or FGFR4, e.g., pemigatinib (INCB54828), INCB62079), an EGFR inhibitor (also known as ErB-1 or HER-1; e.g., erlotinib, gefitinib, vandetanib, orsimertinib, cetuximab, necitumumab, or panitumumab), a VEGFR inhibitor or pathway blocker (e.g. bevacizumab, pazopanib, sunitinib, sorafenib, axitinib, regorafenib, ponatinib, cabozantinib, vandetanib, ramucirumab, lenvatinib, ziv-aflibercept), a PARP inhibitor (e.g., olaparib, rucaparib, veliparib or niraparib), a JAK inhibitor (JAK1 and/or JAK2; e.g., ruxolitinib or baricitinib; or JAK1; e.g., itacitinib (INCB39110), INCB052793, or INCB054707), an IDO inhibitor (e.g., epacadostat, NLG919, or BMS-986205, MK7162), an LSD1 inhibitor (e.g., GSK2979552, INCB59872 and INCB60003), a TDO inhibitor, a PI3K-delta inhibitor (e.g., parsaclisib (INCB50465) or INCB50797), a PI3K-gamma inhibitor such as PI3K-gamma selective inhibitor, a Pim inhibitor (e.g., INCB53914), a CSF1R inhibitor, a TAM receptor tyrosine kinases (Tyro-3, Ax1, and Mer; e.g., INCB081776), an adenosine receptor antagonist (e.g., A2a/A2b receptor antagonist), an HPK1 inhibitor, a chemokine receptor inhibitor (e.g., CCR2 or CCR5 inhibitor), a SHP1/2 phosphatase inhibitor, a histone deacetylase inhibitor (HDAC) such as an HDAC8 inhibitor, an angiogenesis inhibitor, an interleukin receptor inhibitor, bromo and extra terminal family members inhibitors (for example, bromodomain inhibitors or BET inhibitors such as INCB54329 and INCB57643), c-MET inhibitors (e.g., capmatinib), an anti-CD19 antibody (e.g., tafasitamab), an ALK2 inhibitor (e.g., INCB00928); or combinations thereof.

In some embodiments, the compound or salt described herein is administered with a PI3Kδ inhibitor. In some embodiments, the compound or salt described herein is administered with a JAK inhibitor. In some embodiments, the compound or salt described herein is administered with a JAK1 or JAK2 inhibitor (e.g., baricitinib or ruxolitinib). In some embodiments, the compound or salt described herein is administered with a JAK1 inhibitor. In some embodiments, the compound or salt described herein is administered with a JAK1 inhibitor, which is selective over JAK2.

Example antibodies for use in combination therapy include, but are not limited to, trastuzumab (e.g., anti-HER2), ranibizumab (e.g., anti-VEGF-A), bevacizumab (AVASTIN™, e.g., anti-VEGF), panitumumab (e.g., anti-EGFR), cetuximab (e.g., anti-EGFR), rituxan (e.g., anti-CD20), and antibodies directed to c-MET.

One or more of the following agents may be used in combination with the compounds of the present disclosure and are presented as a non-limiting list: a cytostatic agent, cisplatin, doxorubicin, taxotere, taxol, etoposide, irinotecan, camptosar, topotecan, paclitaxel, docetaxel, epothilones, tamoxifen, 5-fluorouracil, methotrexate, temozolomide, cyclophosphamide, SCH 66336, R115777, L778,123, BMS 214662, IRESSA™ (gefitinib), TARCEVA™ (erlotinib), antibodies to EGFR, intron, ara-C, adriamycin, cytoxan, gemcitabine, uracil mustard, chlormethine, ifosfamide, melphalan, chlorambucil, pipobroman, triethylenemelamine, triethylenethiophosphoramine, busulfan, carmustine, lomustine, streptozocin, dacarbazine, floxuridine, cytarabine, 6-mercaptopurine, 6-thioguanine, fludarabine phosphate, oxaliplatin, leucovirin, ELOXATIN™ (oxaliplatin), pentostatine, vinblastine, vincristine, vindesine, bleomycin, dactinomycin, daunorubicin, doxorubicin, epirubicin, idarubicin, mithramycin, deoxycoformycin, mitomycin-C, L-asparaginase, teniposide 17.alpha.-ethinylestradiol, diethylstilbestrol, testosterone, Prednisone, Fluoxymesterone, Dromostanolone propionate, testolactone, megestrolacetate, methylprednisolone, methyltestosterone, prednisolone, triamcinolone, chlorotrianisene, hydroxyprogesterone, aminoglutethimide, estramustine, medroxyprogesteroneacetate, leuprolide, flutamide, toremifene, goserelin, carboplatin, hydroxyurea, amsacrine, procarbazine, mitotane, mitoxantrone, levamisole, navelbene, anastrazole, letrazole, capecitabine, reloxafine, droloxafine, hexamethylmelamine, avastin, HERCEPTIN™ (trastuzumab), BEXXAR™ (tositumomab), VELCADE™ (bortezomib), ZEVALIN™ (ibritumomab tiuxetan), TRISENOX™ (arsenic trioxide), XELODA™ (capecitabine), vinorelbine, porfimer, ERBITUX™ (cetuximab), thiotepa, altretamine, melphalan, trastuzumab, Ierozole, fulvestrant, exemestane, ifosfomide, rituximab, C225 (cetuximab), Campath (alemtuzumab), clofarabine, cladribine, aphidicolon, rituxan, sunitinib, dasatinib, tezacitabine, Sml1, fludarabine, pentostatin, triapine, didox, trimidox, amidox, 3-AP, and MDL-101,731.

The compounds of the present disclosure can further be used in combination with other methods of treating cancers, for example by chemotherapy, irradiation therapy, tumor-targeted therapy, adjuvant therapy, immunotherapy or surgery. Examples of immunotherapy include cytokine treatment (e.g., interferons, GM-CSF, G-CSF, IL-2), CRS-207 immunotherapy, cancer vaccine, monoclonal antibody, bispecific or multi-specific antibody, antibody drug conjugate, adoptive T cell transfer, Toll receptor agonists, RIG-1 agonists, oncolytic virotherapy and immunomodulating small molecules, including thalidomide or JAK1/2 inhibitor, PI3Kδ inhibitor and the like. The compounds can be administered in combination with one or more anti-cancer drugs, such as a chemotherapeutic agent. Examples of chemotherapeutics include any of: abarelix, aldesleukin, alemtuzumab, alitretinoin, allopurinol, altretamine, anastrozole, arsenic trioxide, asparaginase, azacitidine, bevacizumab, bexarotene, baricitinib, bleomycin, bortezomib, busulfan intravenous, busulfan oral, calusterone, capecitabine, carboplatin, carmustine, cetuximab, chlorambucil, cisplatin, cladribine, clofarabine, cyclophosphamide, cytarabine, dacarbazine, dactinomycin, dalteparin sodium, dasatinib, daunorubicin, decitabine, denileukin, denileukin diftitox, dexrazoxane, docetaxel, doxorubicin, dromostanolone propionate, eculizumab, epirubicin, erlotinib, estramustine, etoposide phosphate, etoposide, exemestane, fentanyl citrate, filgrastim, floxuridine, fludarabine, fluorouracil, fulvestrant, gefitinib, gemcitabine, gemtuzumab ozogamicin, goserelin acetate, histrelin acetate, ibritumomab tiuxetan, idarubicin, ifosfamide, imatinib mesylate, interferon alfa 2a, irinotecan, lapatinib ditosylate, lenalidomide, letrozole, leucovorin, leuprolide acetate, levamisole, lomustine, meclorethamine, megestrol acetate, melphalan, mercaptopurine, methotrexate, methoxsalen, mitomycin C, mitotane, mitoxantrone, nandrolone phenpropionate, nelarabine, nofetumomab, oxaliplatin, paclitaxel, pamidronate, panitumumab, pegaspargase, pegfilgrastim, pemetrexed disodium, pentostatin, pipobroman, plicamycin, procarbazine, quinacrine, rasburicase, rituximab, ruxolitinib, sorafenib, streptozocin, sunitinib, sunitinib maleate, tamoxifen, temozolomide, teniposide, testolactone, thalidomide, thioguanine, thiotepa, topotecan, toremifene, tositumomab, trastuzumab, tretinoin, uracil mustard, valrubicin, vinblastine, vincristine, vinorelbine, vorinostat, and zoledronate.

Additional examples of chemotherapeutics include proteasome inhibitors (e.g., bortezomib), thalidomide, revlimid, and DNA-damaging agents such as melphalan, doxorubicin, cyclophosphamide, vincristine, etoposide, carmustine, and the like.

Example steroids include corticosteroids such as dexamethasone or prednisone.

Example Bcr-Abl inhibitors include imatinib mesylate (GLEEVAC™), nilotinib, dasatinib, bosutinib, and ponatinib, and pharmaceutically acceptable salts. Other example suitable Bcr-Abl inhibitors include the compounds, and pharmaceutically acceptable salts thereof, of the genera and species disclosed in U.S. Pat. No. 5,521,184, WO 04/005281, and U.S. Ser. No. 60/578,491.

Example suitable Flt-3 inhibitors include midostaurin, lestaurtinib, linifanib, sunitinib, sunitinib, maleate, sorafenib, quizartinib, crenolanib, pacritinib, tandutinib, PLX3397 and ASP2215, and their pharmaceutically acceptable salts. Other example suitable Flt-3 inhibitors include compounds, and their pharmaceutically acceptable salts, as disclosed in WO 03/037347, WO 03/099771, and WO 04/046120.

Example suitable RAF inhibitors include dabrafenib, sorafenib, and vemurafenib, and their pharmaceutically acceptable salts. Other example suitable RAF inhibitors include compounds, and their pharmaceutically acceptable salts, as disclosed in WO 00/09495 and WO 05/028444.

Example suitable FAK inhibitors include VS-4718, VS-5095, VS-6062, VS-6063, B1853520, and GSK2256098, and their pharmaceutically acceptable salts. Other example suitable FAK inhibitors include compounds, and their pharmaceutically acceptable salts, as disclosed in WO 04/080980, WO 04/056786, WO 03/024967, WO 01/064655, WO 00/053595, and WO 01/014402.

Example suitable CDK4/6 inhibitors include palbociclib, ribociclib, trilaciclib, lerociclib, and abemaciclib, and their pharmaceutically acceptable salts. Other example suitable CDK4/6 inhibitors include compounds, and their pharmaceutically acceptable salts, as disclosed in WO 09/085185, WO 12/129344, WO 11/101409, WO 03/062236, WO 10/075074, and WO 12/061156.

In some embodiments, the compounds of the disclosure can be used in combination with one or more other kinase inhibitors including imatinib, particularly for treating patients resistant to imatinib or other kinase inhibitors.

In some embodiments, the compounds of the disclosure can be used in combination with a chemotherapeutic in the treatment of cancer and may improve the treatment response as compared to the response to the chemotherapeutic agent alone, without exacerbation of its toxic effects. In some embodiments, the compounds of the disclosure can be used in combination with a chemotherapeutic provided herein. For example, additional pharmaceutical agents used in the treatment of multiple myeloma, can include, without limitation, melphalan, melphalan plus prednisone [MP], doxorubicin, dexamethasone, and Velcade (bortezomib). Further additional agents used in the treatment of multiple myeloma include Bcr-Abl, Flt-3, RAF and FAK kinase inhibitors. In some embodiments, the agent is an alkylating agent, a proteasome inhibitor, a corticosteroid, or an immunomodulatory agent. Examples of an alkylating agent include cyclophosphamide (CY), melphalan (MEL), and bendamustine. In some embodiments, the proteasome inhibitor is carfilzomib. In some embodiments, the corticosteroid is dexamethasone (DEX). In some embodiments, the immunomodulatory agent is lenalidomide (LEN) or pomalidomide (POM). Additive or synergistic effects are desirable outcomes of combining a CDK2 inhibitor of the present disclosure with an additional agent.

The agents can be combined with the present compound in a single or continuous dosage form, or the agents can be administered simultaneously or sequentially as separate dosage forms.

The compounds of the present disclosure can be used in combination with one or more other inhibitors or one or more therapies for the treatment of infections. Examples of infections include viral infections, bacterial infections, fungus infections or parasite infections.

In some embodiments, a corticosteroid such as dexamethasone is administered to a patient in combination with the compounds of the disclosure where the dexamethasone is administered intermittently as opposed to continuously.

The compounds of Formula (I) or any of the formulas as described herein, a compound as recited in any of the claims and described herein, or salts thereof can be combined with another immunogenic agent, such as cancerous cells, purified tumor antigens (including recombinant proteins, peptides, and carbohydrate molecules), cells, and cells transfected with genes encoding immune stimulating cytokines. Non-limiting examples of tumor vaccines that can be used include peptides of melanoma antigens, such as peptides of gp100, MAGE antigens, Trp-2, MARTI and/or tyrosinase, or tumor cells transfected to express the cytokine GM-CSF.

The compounds of Formula (I) or any of the formulas as described herein, a compound as recited in any of the claims and described herein, or salts thereof can be used in combination with a vaccination protocol for the treatment of cancer. In some embodiments, the tumor cells are transduced to express GM-CSF. In some embodiments, tumor vaccines include the proteins from viruses implicated in human cancers such as Human Papilloma Viruses (HPV), Hepatitis Viruses (HBV and HCV) and Kaposi's Herpes Sarcoma Virus (KHSV). In some embodiments, the compounds of the present disclosure can be used in combination with tumor specific antigen such as heat shock proteins isolated from tumor tissue itself. In some embodiments, the compounds of Formula (I) or any of the formulas as described herein, a compound as recited in any of the claims and described herein, or salts thereof can be combined with dendritic cells immunization to activate potent anti-tumor responses.

The compounds of the present disclosure can be used in combination with bispecific macrocyclic peptides that target Fe alpha or Fe gamma receptor-expressing effectors cells to tumor cells. The compounds of the present disclosure can also be combined with macrocyclic peptides that activate host immune responsiveness.

In some further embodiments, combinations of the compounds of the disclosure with other therapeutic agents can be administered to a patient prior to, during, and/or after a bone marrow transplant or stem cell transplant. The compounds of the present disclosure can be used in combination with bone marrow transplant for the treatment of a variety of tumors of hematopoietic origin.

The compounds of Formula (I) or any of the formulas as described herein, a compound as recited in any of the claims and described herein, or salts thereof can be used in combination with vaccines, to stimulate the immune response to pathogens, toxins, and self-antigens. Examples of pathogens for which this therapeutic approach may be particularly useful, include pathogens for which there is currently no effective vaccine, or pathogens for which conventional vaccines are less than completely effective. These include, but are not limited to, HIV, Hepatitis (A, B, & C), Influenza, Herpes, Giardia, Malaria, *Leishmania, Staphylococcus aureus, Pseudomonas Aeruginosa.*

Viruses causing infections treatable by methods of the present disclosure include, but are not limit to human papillomavirus, influenza, hepatitis A, B, C or D viruses, adenovirus, poxvirus, herpes simplex viruses, human cytomegalovirus, severe acute respiratory syndrome virus, Ebola virus, measles virus, herpes virus (e.g., VZV, HSV-1, HAV-6, HSV-II, and CMV, Epstein Barr virus), flaviviruses, echovirus, rhinovirus, coxsackie virus, cornovirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus and arboviral encephalitis virus.

Pathogenic bacteria causing infections treatable by methods of the disclosure include, but are not limited to, *chlamydia*, rickettsial bacteria, mycobacteria, staphylococci, streptococci, pneumococci, meningococci and conococci, *klebsiella, proteus, serratia, pseudomonas, legionella*, diphtheria, *salmonella*, bacilli, cholera, tetanus, botulism, anthrax, plague, leptospirosis, and Lyme's disease bacteria.

Pathogenic fungi causing infections treatable by methods of the disclosure include, but are not limited to, *Candida* (*albicans, krusei, glabrata, tropicalis*, etc.), *Cryptococcus neoformans, Aspergillus* (*fumigatus, niger*, etc.), Genus Mucorales (*mucor, absidia*, rhizophus), *Sporothrix schenkii, Blastomyces dermatitidis, Paracoccidioides brasiliensis, Coccidioides immitis* and *Histoplasma capsulatum.*

Pathogenic parasites causing infections treatable by methods of the disclosure include, but are not limited to, *Entamoeba histolytica, Balantidium coli, Naegleria fowleri, Acanthamoeba* sp., *Giardia lambia, Cryptosporidium* sp., *Pneumocystis carinii, Plasmodium vivax, Babesia microti, Trypanosoma brucei, Trypanosoma cruzi, Leishmania donovani, Toxoplasma gondi*, and *Nippostrongylus brasiliensis.*

When more than one pharmaceutical agent is administered to a patient, they can be administered simultaneously, separately, sequentially, or in combination (e.g., for more than two agents).

Methods for the safe and effective administration of most of these chemotherapeutic agents are known to those skilled in the art. In addition, their administration is described in the standard literature. For example, the administration of many of the chemotherapeutic agents is described in the "Physicians' Desk Reference" (PDR, e.g., 1996 edition, Medical Economics Company, Montvale, N.J.), the disclosure of which is incorporated herein by reference as if set forth in its entirety.

II. Immune-Checkpoint Therapies

Compounds of the present disclosure can be used in combination with one or more immune checkpoint inhibitors for the treatment of diseases, such as cancer or infections. Exemplary immune checkpoint inhibitors include inhibitors against immune checkpoint molecules such as CBL-B, CD20, CD28, CD40, CD70, CD122, CD96, CD73, CD47, CDK2, GITR, CSF1R, JAK, PI3K delta, PI3K gamma, TAM, arginase, HPK1, CD137 (also known as 4-1BB), ICOS, A2AR, B7-H3, B7-H4, BTLA, CTLA-4, LAG3, TIM3, TLR (TLR7/8), TIGIT, CD112R, VISTA, PD-1, PD-L1 and PD-L2. In some embodiments, the immune checkpoint molecule is a stimulatory checkpoint molecule selected from CD27, CD28, CD40, ICOS, OX40, GITR and CD137. In some embodiments, the immune checkpoint molecule is an inhibitory checkpoint molecule selected from A2AR, B7-H3, B7-H4, BTLA, CTLA-4, IDO, KIR, LAG3, PD-1, TIM3, TIGIT, and VISTA. In some embodiments, the compounds provided herein can be used in combination with one or more agents selected from KIR inhibitors, TIGIT inhibitors, LAIR1 inhibitors, CD160 inhibitors, 2B4 inhibitors and TGFR beta inhibitors.

In some embodiments, the compounds provided herein can be used in combination with one or more agonists of immune checkpoint molecules, e.g., OX40, CD27, GITR, and CD137 (also known as 4-1BB).

In some embodiments, the inhibitor of an immune checkpoint molecule is anti-PD1 antibody, anti-PD-L1 antibody, or anti-CTLA-4 antibody.

In some embodiments, the inhibitor of an immune checkpoint molecule is an inhibitor of PD-1 or PD-L1, e.g., an anti-PD-1 or anti-PD-L1 monoclonal antibody. In some embodiments, the anti-PD-1 or anti-PD-L1 antibody is nivolumab, pembrolizumab, atezolizumab, durvalumab, avelumab, cemiplimab, atezolizumab, avelumab, tislelizumab, spartalizumab (PDR001), cetrelimab (JNJ-63723283), toripalimab (JS001), camrelizumab (SHR-1210), sintilimab (1B1308), AB122 (GLS-010), AMP-224, AMP-514/MEDI-0680, BMS936559, JTX-4014, BGB-108, SHR-1210, MEDI4736, FAZ053, BCD-100, KN035, CS1001, BAT1306, LZM009, AK105, HLX10, SHR-1316, CBT-502 (TQB2450), A167 (KL-A167), STI-A101 (ZKAB001), CK-301, BGB-A333, MSB-2311, HLX20, TSR-042, or LY3300054. In some embodiments, the inhibitor of PD-1 or PD-L1 is one disclosed in U.S. Pat. Nos. 7,488,802, 7,943,743, 8,008,449, 8,168,757, 8,217, 149, or 10,308,644; U.S. Publ. Nos. 2017/0145025, 2017/0174671, 2017/0174679, 2017/0320875, 2017/0342060, 2017/0362253, 2018/0016260, 2018/0057486, 2018/0177784, 2018/0177870, 2018/0179179, 2018/0179201, 2018/0179202, 2018/0273519, 2019/0040082, 2019/0062345, 2019/0071439, 2019/0127467, 2019/0144439, 2019/0202824, 2019/0225601, 2019/0300524, or 2019/0345170; or PCT Pub. Nos. WO 03042402, WO 2008156712, WO 2010089411, WO 2010036959, WO 2011066342, WO 2011159877, WO 2011082400, or WO 2011161699, which are each incorporated herein by reference in their entirety. In some embodiments, the inhibitor of PD-L1 is INCB086550.

In some embodiments, the antibody is an anti-PD-1 antibody, e.g., an anti-PD-1 monoclonal antibody. In some embodiments, the anti-PD-1 antibody is nivolumab, pembrolizumab, cemiplimab, spartalizumab, camrelizumab, cetrelimab, toripalimab, sintilimab, AB122, AMP-224, JTX-4014, BGB-108, BCD-100, BAT1306, LZM009, AK105, HLX10, or TSR-042. In some embodiments, the anti-PD-1 antibody is nivolumab, pembrolizumab, cemiplimab, spartalizumab, camrelizumab, cetrelimab, toripalimab, or sintilimab. In some embodiments, the anti-PD-1 antibody is pembrolizumab. In some embodiments, the anti-PD-1 antibody is nivolumab. In some embodiments, the anti-PD-1 antibody is cemiplimab. In some embodiments, the anti-PD-1 antibody is spartalizumab. In some embodiments, the anti-PD-1 antibody is camrelizumab. In some embodiments, the anti-PD-1 antibody is cetrelimab. In some embodiments, the anti-PD-1 antibody is toripalimab. In some embodiments, the anti-PD-1 antibody is sintilimab. In some embodiments, the anti-PD-1 antibody is AB122. In some embodiments, the anti-PD-1 antibody is AMP-224. In some embodiments, the anti-PD-1 antibody is JTX-4014. In some embodiments, the anti-PD-1 antibody is BGB-108. In some embodiments, the anti-PD-1 antibody is BCD-100. In some embodiments, the anti-PD-1 antibody is BAT1306. In some embodiments, the anti-PD-1 antibody is LZM009. In some embodiments, the anti-PD-1 antibody is AK105. In some embodiments, the anti-PD-1 antibody is HLX10. In some embodiments, the anti-PD-1 antibody is TSR-042. In some embodiments, the anti-PD-1 monoclonal antibody is nivolumab or pembrolizumab. In some embodiments, the anti-PD-1 monoclonal antibody is MGA012 (INCMGA0012; retifanlimab). In some embodiments, the anti-PD1 antibody is SHR-1210. Other anti-cancer agent(s) include antibody therapeutics such as 4-1BB (e.g., urelumab, utomilumab). In some embodiments, the inhibitor of an immune checkpoint molecule is an inhibitor of PD-L1, e.g., an anti-PD-L1 monoclonal antibody. In some embodiments, the anti-PD-L1 monoclonal antibody is atezolizumab, avelumab, durvalumab, tislelizumab, BMS-935559, MEDI4736, atezolizumab (MPDL3280A; also known as RG7446), avelumab (MSB0010718C), FAZ053, KN035, CS1001, SHR-1316, CBT-502, A167, STI-A101, CK-301, BGB-A333, MSB-2311, HLX20, or LY3300054. In some embodiments, the anti-PD-L1 antibody is atezolizumab, avelumab, durvalumab, or tislelizumab. In some embodiments, the anti-PD-L1 antibody is atezolizumab. In some embodiments, the anti-PD-L1 antibody is avelumab. In some embodiments, the anti-PD-L1 antibody is durvalumab. In some embodiments, the anti-PD-L1 antibody is tislelizumab. In some embodiments, the anti-PD-L1 antibody is BMS-935559. In some embodiments, the anti-PD-L1 antibody is MEDI4736. In some embodiments, the anti-PD-L1 antibody is FAZ053. In some embodiments, the anti-PD-L1 antibody is KN035. In some embodiments, the anti-PD-L1 antibody is CS1001. In some embodiments, the anti-PD-L1 antibody is SHR-1316. In some embodiments, the anti-PD-L1 antibody is CBT-502. In some embodiments, the anti-PD-L1 antibody is A167. In some embodiments, the anti-PD-L1 antibody is STI-A101. In some embodiments, the anti-PD-L1 antibody is CK-301. In some embodiments, the anti-PD-L1 antibody is BGB-A333. In some embodiments, the anti-PD-L1 antibody is MSB-2311. In some embodiments, the anti-PD-L1 antibody is HLX20. In some embodiments, the anti-PD-L1 antibody is LY3300054.

In some embodiments, the inhibitor of an immune checkpoint molecule is a small molecule that binds to PD-L1, or a pharmaceutically acceptable salt thereof. In some embodiments, the inhibitor of an immune checkpoint molecule is a small molecule that binds to and internalizes PD-L1, or a pharmaceutically acceptable salt thereof. In some embodiments, the inhibitor of an immune checkpoint molecule is a compound selected from those in US 2018/0179201, US 2018/0179197, US 2018/0179179, US 2018/0179202, US 2018/0177784, US 2018/0177870, U.S. Ser. No. 16/369,654 (filed Mar. 29, 2019), and U.S. Ser. No. 62/688,164, or a pharmaceutically acceptable salt thereof, each of which is incorporated herein by reference in its entirety.

In some embodiments, the inhibitor of an immune checkpoint molecule is an inhibitor of KIR, TIGIT, LAIR1, CD160, 2B4 and TGFR beta.

In some embodiments, the inhibitor is MCLA-145.

In some embodiments, the inhibitor of an immune checkpoint molecule is an inhibitor of CTLA-4, e.g., an anti-CTLA-4 antibody. In some embodiments, the anti-CTLA-4 antibody is ipilimumab, tremelimumab, AGEN1884, or CP-675,206.

In some embodiments, the inhibitor of an immune checkpoint molecule is an inhibitor of LAG3, e.g., an anti-LAG3 antibody. In some embodiments, the anti-LAG3 antibody is BMS-986016, LAG525, INCAGN2385, or eftilagimod alpha (IMP321).

In some embodiments, the inhibitor of an immune checkpoint molecule is an inhibitor of CD73. In some embodiments, the inhibitor of CD73 is oleclumab.

In some embodiments, the inhibitor of an immune checkpoint molecule is an inhibitor of TIGIT. In some embodiments, the inhibitor of TIGIT is OMP-31M32.

In some embodiments, the inhibitor of an immune checkpoint molecule is an inhibitor of VISTA. In some embodiments, the inhibitor of VISTA is JNJ-61610588 or CA-170.

In some embodiments, the inhibitor of an immune checkpoint molecule is an inhibitor of B7-H3. In some embodiments, the inhibitor of B7-H3 is enoblituzumab, MGD009, or 8H9.

In some embodiments, the inhibitor of an immune checkpoint molecule is an inhibitor of KIR. In some embodiments, the inhibitor of KIR is lirilumab or IPH4102.

In some embodiments, the inhibitor of an immune checkpoint molecule is an inhibitor of A2aR. In some embodiments, the inhibitor of A2aR is CPI-444.

In some embodiments, the inhibitor of an immune checkpoint molecule is an inhibitor of TGF-beta. In some embodiments, the inhibitor of TGF-beta is trabedersen, galusertinib, or M7824.

In some embodiments, the inhibitor of an immune checkpoint molecule is an inhibitor of PI3K-gamma. In some embodiments, the inhibitor of PI3K-gamma is IPI-549.

In some embodiments, the inhibitor of an immune checkpoint molecule is an inhibitor of CD47. In some embodiments, the inhibitor of CD47 is Hu5F9-G4 or TTI-621.

In some embodiments, the inhibitor of an immune checkpoint molecule is an inhibitor of CD73. In some embodiments, the inhibitor of CD73 is MEDI9447.

In some embodiments, the inhibitor of an immune checkpoint molecule is an inhibitor of CD70. In some embodiments, the inhibitor of CD70 is cusatuzumab or BMS-936561.

In some embodiments, the inhibitor of an immune checkpoint molecule is an inhibitor of TIM3, e.g., an anti-TIM3 antibody. In some embodiments, the anti-TIM3 antibody is INCAGN2390, MBG453, or TSR-022.

In some embodiments, the inhibitor of an immune checkpoint molecule is an inhibitor of CD20, e.g., an anti-CD20 antibody. In some embodiments, the anti-CD20 antibody is obinutuzumab or rituximab.

In some embodiments, the agonist of an immune checkpoint molecule is an agonist of OX40, CD27, CD28, GITR, ICOS, CD40, TLR7/8, and CD137 (also known as 4-1BB).

In some embodiments, the agonist of CD137 is urelumab. In some embodiments, the agonist of CD137 is utomilumab.

In some embodiments, the agonist of an immune checkpoint molecule is an inhibitor of GITR. In some embodiments, the agonist of GITR is TRX518, MK-4166, INCAGN1876, MK-1248, AMG228, BMS-986156, GWN323, MED11873, or MEDI6469. In some embodiments, the agonist of an immune checkpoint molecule is an agonist of OX40, e.g., OX40 agonist antibody or OX40L fusion protein. In some embodiments, the anti-OX40 antibody is INCAGN01949, MED10562 (tavolimab), MOXR-0916, PF-04518600, GSK3174998, BMS-986178, or 9B12. In some embodiments, the OX40L fusion protein is MEDI6383.

In some embodiments, the agonist of an immune checkpoint molecule is an agonist of CD40. In some embodiments, the agonist of CD40 is CP-870893, ADC-1013, CDX-1140, SEA-CD40, RO7009789, JNJ-64457107, APX-005M, or Chi Lob 7/4.

In some embodiments, the agonist of an immune checkpoint molecule is an agonist of ICOS. In some embodiments, the agonist of ICOS is GSK-3359609, JTX-2011, or MEDI-570.

In some embodiments, the agonist of an immune checkpoint molecule is an agonist of CD28. In some embodiments, the agonist of CD28 is theralizumab.

In some embodiments, the agonist of an immune checkpoint molecule is an agonist of CD27. In some embodiments, the agonist of CD27 is varlilumab.

In some embodiments, the agonist of an immune checkpoint molecule is an agonist of TLR7/8. In some embodiments, the agonist of TLR7/8 is MEDI9197.

The compounds of the present disclosure can be used in combination with bispecific antibodies. In some embodiments, one of the domains of the bispecific antibody targets PD-1, PD-L1, CTLA-4, GITR, OX40, TIM3, LAG3, CD137, ICOS, CD3 or TGFβ receptor. In some embodiments, the bispecific antibody binds to PD-1 and PD-L1. In some embodiments, the bispecific antibody that binds to PD-1 and PD-L1 is MCLA-136. In some embodiments, the bispecific antibody binds to PD-L1 and CTLA-4. In some embodiments, the bispecific antibody that binds to PD-L1 and CTLA-4 is AK104.

In some embodiments, the compounds of the disclosure can be used in combination with one or more metabolic enzyme inhibitors. In some embodiments, the metabolic enzyme inhibitor is an inhibitor of IDO1, TDO, or arginase. Examples of IDO1 inhibitors include epacadostat, NLG919, BMS-986205, PF-06840003, IOM2983, RG-70099 and LY338196. Inhibitors of arginase inhibitors include INCB1158.

As provided throughout, the additional compounds, inhibitors, agents, etc. can be combined with the present compound in a single or continuous dosage form, or they can be administered simultaneously or sequentially as separate dosage forms.

Formulation, Dosage Forms and Administration

When employed as pharmaceuticals, the compounds of the present disclosure can be administered in the form of pharmaceutical compositions. Thus, the present disclosure provides a composition comprising a compound of Formula I, II, or any of the formulas as described herein, a compound as recited in any of the claims and described herein, or a pharmaceutically acceptable salt thereof, or any of the embodiments thereof, and at least one pharmaceutically acceptable carrier or excipient. These compositions can be prepared in a manner well known in the pharmaceutical art, and can be administered by a variety of routes, depending upon whether local or systemic treatment is indicated and upon the area to be treated. Administration may be topical (including transdermal, epidermal, ophthalmic and to mucous membranes including intranasal, vaginal and rectal delivery), pulmonary (e.g., by inhalation or insufflation of powders or aerosols, including by nebulizer; intratracheal or intranasal), oral or parenteral. Parenteral administration includes intravenous, intraarterial, subcutaneous, intraperitoneal intramuscular or injection or infusion; or intracranial, e.g., intrathecal or intraventricular, administration. Parenteral administration can be in the form of a single bolus dose, or may be, e.g., by a continuous perfusion pump. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable.

This invention also includes pharmaceutical compositions which contain, as the active ingredient, the compound of the present disclosure or a pharmaceutically acceptable salt thereof, in combination with one or more pharmaceutically acceptable carriers or excipients. In some embodiments, the composition is suitable for topical administration. In making the compositions of the invention, the active ingredient is typically mixed with an excipient, diluted by an excipient or enclosed within such a carrier in the form of, e.g., a capsule, sachet, paper, or other container. When the excipient serves as a diluent, it can be a solid, semi-solid, or liquid material, which acts as a vehicle, carrier or medium for the active ingredient. Thus, the compositions can be in the form of tablets, pills, powders, lozenges, sachets, cachets, elixirs, suspensions, emulsions, solutions, syrups, aerosols (as a solid or in a liquid medium), ointments containing, e.g., up to 10% by weight of the active compound, soft and hard gelatin capsules, suppositories, sterile injectable solutions and sterile packaged powders.

In preparing a formulation, the active compound can be milled to provide the appropriate particle size prior to combining with the other ingredients. If the active compound is substantially insoluble, it can be milled to a particle size of less than 200 mesh. If the active compound is substantially water soluble, the particle size can be adjusted by milling to provide a substantially uniform distribution in the formulation, e.g., about 40 mesh.

The compounds of the invention may be milled using known milling procedures such as wet milling to obtain a particle size appropriate for tablet formation and for other formulation types. Finely divided (nanoparticulate) preparations of the compounds of the invention can be prepared by processes known in the art see, e.g., WO 2002/000196.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water, syrup and methyl cellulose. The formulations can additionally include: lubricating agents such as talc, magnesium stearate and mineral oil; wetting agents; emulsifying and suspending agents; preserving agents such as methyl- and propylhydroxy-benzoates; sweetening agents; and flavoring agents. The compositions of the invention can be formulated so as to provide quick, sustained or delayed release of the active ingredient after administration to the patient by employing procedures known in the art.

In some embodiments, the pharmaceutical composition comprises silicified microcrystalline cellulose (SMCC) and at least one compound described herein, or a pharmaceutically acceptable salt thereof. In some embodiments, the silicified microcrystalline cellulose comprises about 98% microcrystalline cellulose and about 2% silicon dioxide w/w.

In some embodiments, the composition is a sustained release composition comprising at least one compound described herein, or a pharmaceutically acceptable salt thereof, and at least one pharmaceutically acceptable carrier or excipient. In some embodiments, the composition comprises at least one compound described herein, or a pharmaceutically acceptable salt thereof, and at least one component selected from microcrystalline cellulose, lactose monohydrate, hydroxypropyl methylcellulose and polyethylene oxide. In some embodiments, the composition comprises at least one compound described herein, or a pharmaceutically acceptable salt thereof, and microcrystalline cellulose, lactose monohydrate and hydroxypropyl methylcellulose. In some embodiments, the composition comprises at least one compound described herein, or a pharmaceutically acceptable salt thereof, and microcrystalline cellulose, lactose monohydrate and polyethylene oxide. In some embodiments, the composition further comprises magnesium stearate or silicon dioxide. In some embodiments, the microcrystalline cellulose is Avicel PH102™. In some embodiments, the lactose monohydrate is Fast-flo 316™. In some embodiments, the hydroxypropyl methylcellulose is hydroxypropyl methylcellulose 2208 K4M (e.g., Methocel K4 M Premier™) and/or hydroxypropyl methylcellulose 2208 K100LV (e.g., Methocel K00LV™). In some embodiments, the polyethylene oxide is polyethylene oxide WSR 1105 (e.g., Polyox WSR 1105™).

In some embodiments, a wet granulation process is used to produce the composition. In some embodiments, a dry granulation process is used to produce the composition.

The compositions can be formulated in a unit dosage form, each dosage containing from about 5 to about 1,000 mg (1 g), more usually about 100 mg to about 500 mg, of the active ingredient. In some embodiments, each dosage contains about 10 mg of the active ingredient. In some embodiments, each dosage contains about 50 mg of the active ingredient. In some embodiments, each dosage contains about 25 mg of the active ingredient. The term "unit dosage forms" refers to physically discrete units suitable as unitary dosages for human subjects and other mammals, each unit containing a predetermined quantity of active material calculated to produce the desired therapeutic effect, in association with a suitable pharmaceutical excipient.

The components used to formulate the pharmaceutical compositions are of high purity and are substantially free of potentially harmful contaminants (e.g., at least National Food grade, generally at least analytical grade, and more typically at least pharmaceutical grade). Particularly for human consumption, the composition is preferably manufactured or formulated under Good Manufacturing Practice standards as defined in the applicable regulations of the U.S. Food and Drug Administration. For example, suitable formulations may be sterile and/or substantially isotonic and/or in full compliance with all Good Manufacturing Practice regulations of the U.S. Food and Drug Administration.

The active compound may be effective over a wide dosage range and is generally administered in a therapeutically effective amount. It will be understood, however, that the amount of the compound actually administered will usually be determined by a physician, according to the relevant circumstances, including the condition to be treated, the chosen route of administration, the actual compound administered, the age, weight, and response of the individual patient, the severity of the patient's symptoms and the like.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

For preparing solid compositions such as tablets, the principal active ingredient is mixed with a pharmaceutical excipient to form a solid preformulation composition containing a homogeneous mixture of a compound of the present invention. When referring to these preformulation compositions as homogeneous, the active ingredient is typically dispersed evenly throughout the composition so that the composition can be readily subdivided into equally effective unit dosage forms such as tablets, pills and capsules. This solid preformulation is then subdivided into unit dosage forms of the type described above containing from, e.g., about 0.1 to about 1000 mg of the active ingredient of the present invention.

The tablets or pills of the present invention can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol and cellulose acetate.

The liquid forms in which the compounds and compositions of the present invention can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Compositions for inhalation or insufflation include solutions and suspensions in pharmaceutically acceptable, aqueous or organic solvents, or mixtures thereof, and powders. The liquid or solid compositions may contain suitable pharmaceutically acceptable excipients as described supra. In some embodiments, the compositions are administered by the oral or nasal respiratory route for local or systemic effect. Compositions can be nebulized by use of inert gases. Nebulized solutions may be breathed directly from the nebulizing device or the nebulizing device can be attached to a face mask, tent, or intermittent positive pressure breathing machine. Solution, suspension, or powder compositions can be administered orally or nasally from devices which deliver the formulation in an appropriate manner.

Topical formulations can contain one or more conventional carriers. In some embodiments, ointments can contain water and one or more hydrophobic carriers selected from, e.g., liquid paraffin, polyoxyethylene alkyl ether, propylene glycol, white Vaseline, and the like. Carrier compositions of creams can be based on water in combination with glycerol and one or more other components, e.g., glycerinemonostearate, PEG-glycerinemonostearate and cetylstearyl alcohol. Gels can be formulated using isopropyl alcohol and water, suitably in combination with other components such as, e.g., glycerol, hydroxyethyl cellulose, and the like. In some embodiments, topical formulations contain at least about 0.1, at least about 0.25, at least about 0.5, at least about 1, at least about 2 or at least about 5 wt % of the compound of the invention. The topical formulations can be suitably packaged in tubes of, e.g., 100 g which are optionally associated with instructions for the treatment of the select indication, e.g., psoriasis or other skin condition.

The amount of compound or composition administered to a patient will vary depending upon what is being administered, the purpose of the administration, such as prophylaxis or therapy, the state of the patient, the manner of administration and the like. In therapeutic applications, compositions can be administered to a patient already suffering from a disease in an amount sufficient to cure or at least partially arrest the symptoms of the disease and its complications. Effective doses will depend on the disease condition being treated as well as by the judgment of the attending clinician depending upon factors such as the severity of the disease, the age, weight and general condition of the patient and the like.

The compositions administered to a patient can be in the form of pharmaceutical compositions described above. These compositions can be sterilized by conventional sterilization techniques, or may be sterile filtered. Aqueous solutions can be packaged for use as is, or lyophilized, the lyophilized preparation being combined with a sterile aqueous carrier prior to administration. The pH of the compound preparations typically will be between 3 and 11, more preferably from 5 to 9 and most preferably from 7 to 8. It will be understood that use of certain of the foregoing excipients, carriers or stabilizers will result in the formation of pharmaceutical salts.

The therapeutic dosage of a compound of the present invention can vary according to, e.g., the particular use for which the treatment is made, the manner of administration of the compound, the health and condition of the patient, and the judgment of the prescribing physician. The proportion or concentration of a compound of the invention in a pharmaceutical composition can vary depending upon a number of factors including dosage, chemical characteristics (e.g., hydrophobicity), and the route of administration. For example, the compounds of the invention can be provided in an aqueous physiological buffer solution containing about 0.1 to about 10% w/v of the compound for parenteral administration. Some typical dose ranges are from about 1 μg/kg to about 1 g/kg of body weight per day. In some embodiments, the dose range is from about 0.01 mg/kg to about 100 mg/kg of body weight per day. The dosage is likely to depend on such variables as the type and extent of progression of the disease or disorder, the overall health status of the particular patient, the relative biological efficacy of the compound selected, formulation of the excipient, and its route of administration. Effective doses can be extrapolated from dose-response curves derived from in vitro or animal model test systems.

Labeled Compounds and Assay Methods

Another aspect of the present invention relates to labeled compounds of the disclosure (radio-labeled, fluorescent-labeled, etc.) that would be useful not only in imaging techniques but also in assays, both in vitro and in vivo, for localizing and quantitating KRAS protein in tissue samples, including human, and for identifying KRAS ligands by inhibition binding of a labeled compound. Substitution of one or more of the atoms of the compounds of the present disclosure can also be useful in generating differentiated ADME (Adsorption, Distribution, Metabolism and Excretion). Accordingly, the present invention includes KRAS binding assays that contain such labeled or substituted compounds.

The present disclosure further includes isotopically-labeled compounds of the disclosure. An "isotopically" or "radio-labeled" compound is a compound of the disclosure where one or more atoms are replaced or substituted by an atom having an atomic mass or mass number different from the atomic mass or mass number typically found in nature (i.e., naturally occurring). Suitable radionuclides that may be incorporated in compounds of the present disclosure include but are not limited to $^{2}H$ (also written as D for deuterium), $^{3}H$ (also written as T for tritium), $^{11}C$ $^{13}C$, $^{14}C$ $^{13}N$, $^{15}N$, $^{15}O$, $^{17}O$, $^{18}O$, $^{18}F$, $^{35}S$, $^{36}Cl$, $^{82}Br$, $^{75}Br$, $^{76}Br$, $^{77}Br$, $^{123}I$, $^{124}I$, $^{125}I$ and $^{131}I$. For example, one or more hydrogen atoms in a compound of the present disclosure can be replaced by deuterium atoms (e.g., one or more hydrogen atoms of a $C_{1-6}$ alkyl group of Formula I, II, or any formulae provided herein can be optionally substituted with deuterium atoms, such as —$CD_3$ being substituted for —$CH_3$). In some embodiments, alkyl groups in Formula I, II, or any formulae provided herein can be perdeuterated.

One or more constituent atoms of the compounds presented herein can be replaced or substituted with isotopes of the atoms in natural or non-natural abundance. In some embodiments, the compound includes at least one deuterium atom. In some embodiments, the compound includes two or more deuterium atoms. In some embodiments, the compound includes 1-2, 1-3, 1-4, 1-5, or 1-6 deuterium atoms. In some embodiments, all of the hydrogen atoms in a compound can be replaced or substituted by deuterium atoms.

Synthetic methods for including isotopes into organic compounds are known in the art (Deuterium Labeling in Organic Chemistry by Alan F. Thomas (New York, N.Y., Appleton-Century-Crofts, 1971; The Renaissance of H/D Exchange by Jens Atzrodt, Volker Derdau, Thorsten Fey and Jochen Zimmermann, Angew. Chem. Int. Ed. 2007, 7744-7765; The Organic Chemistry of Isotopic Labelling by James R. Hanson, Royal Society of Chemistry, 2011). Isotopically labeled compounds can be used in various studies such as NMR spectroscopy, metabolism experiments, and/or assays.

Substitution with heavier isotopes, such as deuterium, may afford certain therapeutic advantages resulting from greater metabolic stability, for example, increased in vivo half-life or reduced dosage requirements, and hence may be preferred in some circumstances. (see e.g., A. Kerekes et. al. *J. Med. Chem.* 2011, 54, 201-210; R. Xu et. al. *J. Label Compd. Radiopharm.* 2015, 58, 308-312). In particular, substitution at one or more metabolism sites may afford one or more of the therapeutic advantages.

The radionuclide that is incorporated in the instant radio-labeled compounds will depend on the specific application of that radio-labeled compound. For example, for in vitro adenosine receptor labeling and competition assays, compounds that incorporate $^{3}H$, $^{14}C$, $^{82}Br$, $^{125}I$, $^{131}I$ or $^{35}S$ can be useful. For radio-imaging applications $^{11}C$, $^{18}F$, $^{125}I$, $^{123}I$, $^{124}I$, $^{131}I$, $^{75}Br$, $^{76}Br$ or $^{77}Br$ can be useful.

It is understood that a "radio-labeled" or "labeled compound" is a compound that has incorporated at least one radionuclide. In some embodiments, the radionuclide is selected from $^{3}H$, $^{14}C$ $^{125}I$, $^{35}S$ and $^{82}Br$.

The present disclosure can further include synthetic methods for incorporating radio-isotopes into compounds of the disclosure. Synthetic methods for incorporating radio-isotopes into organic compounds are well known in the art, and an ordinary skill in the art will readily recognize the methods applicable for the compounds of disclosure.

A labeled compound of the invention can be used in a screening assay to identify and/or evaluate compounds. For example, a newly synthesized or identified compound (i.e., test compound) which is labeled can be evaluated for its ability to bind a KRAS protein by monitoring its concentration variation when contacting with the KRAS, through tracking of the labeling. For example, a test compound (labeled) can be evaluated for its ability to reduce binding of another compound which is known to bind to a KRAS protein (i.e., standard compound). Accordingly, the ability of a test compound to compete with the standard compound for binding to the KRAS protein directly correlates to its binding affinity. Conversely, in some other screening assays, the standard compound is labeled and test compounds are unlabeled. Accordingly, the concentration of the labeled standard compound is monitored in order to evaluate the competition between the standard compound and the test compound, and the relative binding affinity of the test compound is thus ascertained.

Kits

The present disclosure also includes pharmaceutical kits useful, e.g., in the treatment or prevention of diseases or disorders associated with the activity of KRAS, such as cancer or infections, which include one or more containers containing a pharmaceutical composition comprising a therapeutically effective amount of a compound of Formula I, II, or any of the embodiments thereof. Such kits can further include one or more of various conventional pharmaceutical kit components, such as, e.g., containers with one or more pharmaceutically acceptable carriers, additional containers, etc., as will be readily apparent to those skilled in the art. Instructions, either as inserts or as labels, indicating quantities of the components to be administered, guidelines for administration, and/or guidelines for mixing the components, can also be included in the kit.

The invention will be described in greater detail by way of specific examples. The following examples are offered for illustrative purposes, and are not intended to limit the invention in any manner. Those of skill in the art will readily recognize a variety of non-critical parameters which can be changed or modified to yield essentially the same results. The compounds of the Examples have been found to inhibit the activity of KRAS according to at least one assay described herein.

EXAMPLES

Experimental procedures for compounds of the invention are provided below. Preparatory LC-MS purifications of some of the compounds prepared were performed on Waters mass directed fractionation systems. The basic equipment setup, protocols, and control software for the operation of these systems have been described in detail in the literature. See e.g. "Two-Pump At Column Dilution Configuration for Preparative LC-MS", K. Blom, *J. Combi. Chem.,* 4, 295 (2002); "Optimizing Preparative LC-MS Configurations and Methods for Parallel Synthesis Purification", K. Blom, R. Sparks, J. Doughty, G. Everlof, T. Haque, A. Combs, *J. Combi. Chem.,* 5, 670 (2003); and "Preparative LC-MS Purification: Improved Compound Specific Method Optimization", K. Blom, B. Glass, R. Sparks, A. Combs, *J. Combi. Chem.,* 6, 874-883 (2004). The compounds separated were typically subjected to analytical liquid chromatography mass spectrometry (LCMS) for purity check.

The compounds separated were typically subjected to analytical liquid chromatography mass spectrometry (LCMS) for purity check under the following conditions: Instrument; Agilent 1100 series, LC/MSD, Column: Waters Sunfire™ $C_{18}$ 5 μm particle size, 2.1×5.0 mm, Buffers: mobile phase A: 0.025% TFA in water and mobile phase B: acetonitrile; gradient 2% to 80% of B in 3 minutes with flow rate 2.0 mL/minute.

Some of the compounds prepared were also separated on a preparative scale by reverse-phase high performance liquid chromatography (RP-HPLC) with MS detector or flash chromatography (silica gel) as indicated in the Examples. Typical preparative reverse-phase high performance liquid chromatography (RP-HPLC) column conditions are as follows:

pH=2 purifications: Waters Sunfire™ $C_{18}$ 5 μm particle size, 19×100 mm column, eluting with mobile phase A: 0.1% TFA (trifluoroacetic acid) in water and mobile phase B: acetonitrile; the flow rate was 30 mL/minute, the separating gradient was optimized for each compound using the Compound Specific Method Optimization protocol as described in the literature [see "Preparative LCMS Purification: Improved Compound Specific Method Optimization", K. Blom, B. Glass, R. Sparks, A. Combs, J. Comb. Chem., 6, 874-883 (2004)]. Typically, the flow rate used with the 30×100 mm column was 60 mL/minute.

pH=10 purifications: Waters XBridge $C_{18}$ 5 μm particle size, 19×100 mm column, eluting with mobile phase A: 0.15% $NH_4OH$ in water and mobile phase B: acetonitrile; the flow rate was 30 mL/minute, the separating gradient was optimized for each compound using the Compound Specific Method Optimization protocol as described in the literature [See "Preparative LCMS Purification: Improved Compound Specific Method Optimization", K. Blom, B. Glass, R. Sparks, A. Combs, J. Comb. Chem., 6, 874-883 (2004)]. Typically, the flow rate used with 30×100 mm column was 60 mL/minute."

The following abbreviations may be used herein: AcOH (acetic acid); $Ac_2O$ (acetic anhydride); aq. (aqueous); atm. (atmosphere(s)); Boc (t-butoxycarbonyl); BOP ((benzotriazol-1-yloxy)tris(dimethylamino)phosphonium hexafluorophosphate); br (broad); Cbz (carboxybenzyl); calc. (calculated); d (doublet); dd (doublet of doublets); DBU (1,8-diazabicyclo[5.4.0]undec-7-ene); DCM (dichloromethane); DIAD (N, N'-diisopropyl azidodicarboxylate); DIEA (N,N-diisopropylethylamine); DIPEA (N, N-diisopropylethylamine); DIBAL (diisobutylaluminium hydride); DMF (N, N-dimethylformamide); Et (ethyl); EtOAc (ethyl acetate); FCC (flash column chromatography); g (gram(s)); h (hour(s)); HATU (N, N, N', N'-tetramethyl-O-(7-azabenzotriazol-1-yl)uronium hexafluorophosphate); HCl (hydrochloric acid); HPLC (high performance liquid chromatography); Hz (hertz); J (coupling constant); LCMS (liquid chromatography-mass spectrometry); LDA (lithium diisopropylamide); m (multiplet); M (molar); mCPBA (3-chloroperoxybenzoic acid); MS (Mass spectrometry); Me (methyl); MeCN (acetonitrile); MeOH (methanol); mg (milligram(s)); min. (minutes(s)); mL (milliliter(s)); mmol (millimole(s)); N (normal); NCS (N-chlorosuccinimide); $NEt_3$ (triethylamine); nM (nanomolar); NMP (N-methylpyrrolidinone); NMR (nuclear magnetic resonance spectroscopy); OTf (trifluoromethanesulfonate); Ph (phenyl); pM (picomolar); PPT (precipitate); RP-HPLC (reverse phase high performance liquid chromatography); r.t. (room temperature), s (singlet); t (triplet or tertiary); TBS (tert-butyldimethylsilyl); tert (tertiary); tt (triplet of triplets); TFA (trifluoroacetic acid); THF (tetrahydrofuran); μg (microgram(s)); μL (microliter(s)); μM (micromolar); wt % (weight percent). Brine is saturated aqueous sodium chloride. In vacuo is under vacuum.

Intermediate 1. 7-bromo-2,4-dichloro-8-fluoro-6-iodo-3-nitroquinoline

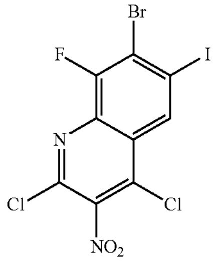 [SMILES: O=[N+]([O-])c1c(Cl)nc2c(F)c(Br)c(I)cc2c1Cl]

Step 1. 2-amino-4-bromo-3-fluoro-5-iodobenzoic acid

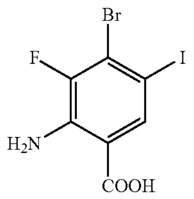 [SMILES: Nc1c(C(=O)O)cc(I)c(Br)c1F]

NIS (9.61 g, 42.7 mmol) was added to a solution of 2-amino-4-bromo-3-fluorobenzoic acid (10.0 g, 42.7 mmol) in DMF (100 mL) and then the reaction was stirred at 80° C. for 6 h. The mixture was cooled with ice water and then water (150 mL) was added and stirred for 20 min, the precipitate was filtered and washed with water, dried to provide the desired product as a solid. LCMS calculated for $C_7H_5BrFINO_2$ $(M+H)^+$: m/z=359.9; found 359.8.

Step 2. 7-bromo-8-fluoro-6-iodo-2H-benzo[d][1,3]oxazine-2,4(1H)-dione

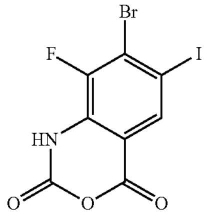 [SMILES: O=c1[nH]c2c(F)c(Br)c(I)cc2c(=O)o1]

To a solution of 2-amino-4-bromo-3-fluoro-5-iodobenzoic acid (8.4 g, 23.34 mmol) in 1,4-dioxane (200 mL) was added triphosgene (6.34 g, 21.37 mmol), and stirred at 100° C. for 1 h. After cooling to r.t., ice was added until a solid precipitated. The mixture was then fully diluted with water (final volume ~400 mL) and the solid collected by filtration then air dried. The crude product was used in the next step without further purification.

Step 3. 7-bromo-8-fluoro-6-iodo-3-nitroquinoline-2,4-diol

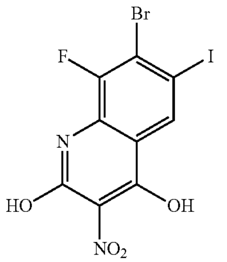 [SMILES: O=[N+]([O-])c1c(O)nc2c(F)c(Br)c(I)cc2c1O]

DIPEA (6.06 ml, 34.7 mmol) was added to a solution of ethyl 2-nitroacetate (4.62 g, 17.36 mmol) in toluene (10.0 mL) at r.t. and stirred for 10 min. 7-Bromo-8-fluoro-6-iodo-2H-benzo[d][1,3]oxazine-2,4(1H)-dione (6.7 g, 17.36 mmol) was then added to the reaction mixture and the reaction was stirred at 95° C. for 3 h. The reaction was cooled with ice water and then 1 N HCl (40 mL) was added. The solid precipitate was collected via filtration then washed with small amount of ethyl acetate to provide the desired product as a yellow solid (6 g, 81%). LCMS calculated for $C_9H_4BrFIN_2O_4(M+H)^+$: m/z=428.8; found 428.8.

Step 4. 7-bromo-2,4-dichloro-8-fluoro-6-iodo-3-nitroquinoline

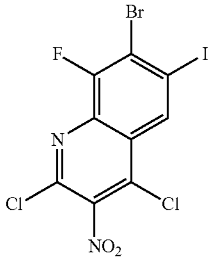 [SMILES: O=[N+]([O-])c1c(Cl)nc2c(F)c(Br)c(I)cc2c1Cl]

DIPEA (3.67 mL, 21.03 mmol) was added to 7-bromo-8-fluoro-6-iodo-3-nitroquinoline-2,4-diol (4.51 g, 10.51 mmol) in $POCl_3$ (4.9 mL, 52.6 mmol) and the reaction was stirred at 105° C. for 3 h. The solvent was removed under vacuum and then azeotroped with toluene 3 times to provide the crude material which was used in the next step without further purification.

Intermediate 2. tert-butyl (endo)-5-((3-amino-7-bromo-2-(3-(dimethylamino)azetidin-1-yl)-8-fluoro-6-iodoquinolin-4-yl)amino)-2-azabicyclo[2.1.1]hexane-2-carboxylate

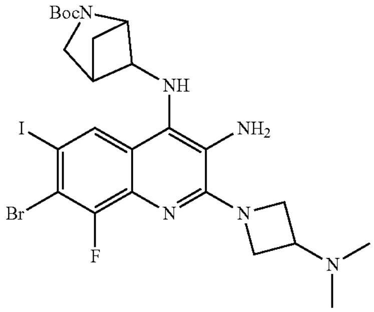

Step 1. tert-butyl (endo)-5-((7-bromo-2-(3-(dimethylamino)azetidin-1-yl)-8-fluoro-6-iodo-3-nitroquinolin-4-yl)amino)-2-azabicyclo[2.1.1]hexane-2-carboxylate

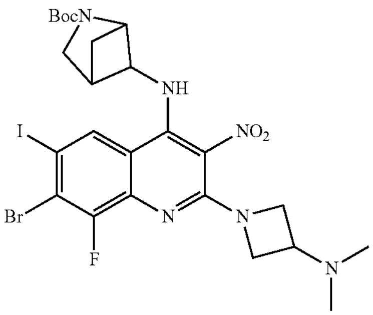

To a mixture of 7-bromo-2,4-dichloro-8-fluoro-6-iodo-3-nitroquinoline (1.53 g, 3.28 mmol) in $CH_2Cl_2$ (16.4 ml) was added tert-butyl (endo)-5-amino-2-azabicyclo[2.1.1]hexane-2-carboxylate (651 mg, 3.28 mmol) and DIPEA (2.87 mL, 16.4 mmol) and the reaction was stirred at 55° C. for 4 h. Then N,N-dimethylazetidin-3-amine dihydrochloride (739 mg, 4.27 mmol) was added. After heating at 55° C. for another 4 h, the mixture was concentrated to dryness, and used without further purification. LCMS calculated for $C_{24}H_{30}BrFIN_6O_4(M+H)^+$: m/z=691.1; found 691.2.

Step 2. tert-butyl (endo)-5-((3-amino-7-bromo-2-(3-(dimethylamino)azetidin-1-yl)-8-fluoro-6-iodoquinolin-4-yl)amino)-2-azabicyclo[2.1.1]hexane-2-carboxylate Sodium hydrosulfite (2.86 g, 16.4 mmol) in water (2.5 mL) was added to a solution of above crude mixture and 30% aq. ammonium hydroxide (4.26 mL, 32.8 mmol) in MeOH (30 mL) at 0° C. After 10 min, water (30 mL) was added to the reaction mixture followed by extraction with dichloromethane (30 mL×3). The combined organic layers were dried $Na_2SO_4$, filtered and concentrated. The crude product was added to a silica gel column and was eluted with methanol/dichloromethane from 0% to 10% to give tert-butyl (endo)-5-((3-amino-7-bromo-2-(3-(dimethylamino)azetidin-1-yl)-8-fluoro-6-iodoquinolin-4-yl)amino)-2-azabicyclo[2.1.1]hexane-2-carboxylate (1.9 g, 88% yield). LCMS calculated for $C_{24}H_{32}BrFIN_6O_2(M+H)^+$: m/z=661.1; found 661.2.

Intermediate 3. tert-butyl (endo)-5-((3-amino-7-bromo-6-(2-cyanoethyl)-2-(3-(dimethylamino)azetidin-1-yl)-8-fluoroquinolin-4-yl)amino)-2-azabicyclo[2.1.1]hexane-2-carboxylate

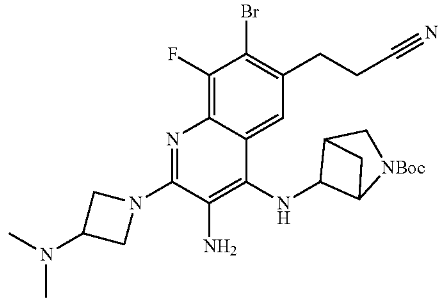 [SMILES: CN(C)C1CN(c2nc3c(F)c(Br)c(CCC#N)cc3c(NC3C4CC3N(C(=O)OC(C)(C)C)C4)c2N)C1]

In a 10 dram vial tert-butyl (endo)-5-((3-amino-7-bromo-2-(3-(dimethylamino)-azetidin-1-yl)-8-fluoro-6-iodoquinolin-4-yl)amino)-2-azabicyclo[2.1.1]hexane-2-carboxylate (Intermediate 2, 1.17 g, 1.76 mmol), acrylonitrile (468 mg, 8.82 mmol) and aq. tetramethylammonium formate (25%, 1.24 mL, 2.65 mmol) in DMF (3.5 mL) was added DIPEA (616 μL, 3.53 mmol) and $Pd(PPh_3)_4$(204 mg, 0.176 mmol). The reaction mixture was heated at 80° C. for 2 h, then concentrated to dryness and added to a silica gel column and was eluted with methanol/dichloromethane from 0% to 5% to give tert-butyl (endo)-5-((3-amino-7-bromo-6-(2-cyanoethyl)-2-(3-(dimethylamino)azetidin-1-yl)-8-fluoroquinolin-4-yl)amino)-2-azabicyclo[2.1.1]hexane-2-carboxylate (782 mg, 70% yield). LCMS calculated for $C_{27}H_{36}BrFN_7O_2$ $(M+H)^+$: m/z=588.2/590.2; found 588.2/590.2.

Intermediate 4. 2-(3-(Methoxymethoxy)naphthalen-1-yl)-4,4,5,5-tetramethyl-1,3,2-dioxaborolane

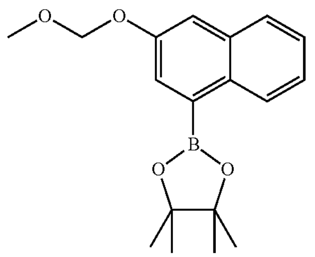 [SMILES: COCOc1cc(B2OC(C)(C)C(C)(C)O2)c2ccccc2c1]

Step 1: 1-bromo-3-(methoxymethoxy)naphthalene

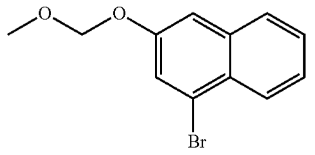

A sample of 4-bromonaphthalen-2-ol (1.57 g, 7.04 mmol) was dissolved in DCM (14 mL) and stirred at room temperature. The solution was treated with N,N-diisopropylethylamine (1.4 mL, 7.8 mmol) and chloromethyl methyl ether (0.6 mL, 7.8 mmol). After 20 min, LCMS indicated complete conversion to the desired product. The reaction was quenched with saturated aq. $NH_4Cl$ and diluted with DCM. The layers were separated, and the aqueous layer was extracted with additional DCM. The combined organic layers were dried over $MgSO_4$, filtered, and concentrated in vacuo. The crude material was dissolved in 50% DCM in hexanes and filtered through a silica plug. The filtrate was concentrated in vacuo to provide 1-bromo-3-(methoxymethoxy)naphthalene (1.76 g, 6.59 mmol, 94% yield). LCMS calculated for $C_1H_5BrO_4$ $(M-MeOH)^+$: m/z=235.0, 237.0; found: 235.0, 237.0.

Step 2: 2-(3-(Methoxymethoxy)naphthalen-1-yl)-4,4,5,5-tetramethyl-1,3,2-dioxaborolane A sample of 1-bromo-3-(methoxymethoxy)naphthalene (1.76 g, 6.59 mmol) was dissolved in dioxane (19 mL) and stirred at room temperature. The solution was treated with potassium acetate (1.9 g, 19.8 mmol) and bis(pinacolato) diboron (2.5 g, 9.9 mmol). Finally, [1,1'-bis(diphenylphosphino)ferrocene]dichloropalladium(II), DCM complex (0.270 g, 0.329 mmol) was added to the solution, which was then stirred at 100° C. After 16 hours, LCMS indicated complete conversion to the product. The reaction mixture was diluted with EtOAc, filtered to remove solids, and concentrated in vacuo. The crude material was purified by flash column chromatography (0-40% EtOAc/hexanes) to give 2-(3-(methoxymethoxy)naphthalen-1-yl)-4,4,5,5-tetramethyl-1,3,2-dioxaborolane (1.74 g, 5.53 mmol, 84% yield). LCMS calculated for $C_{17}H_{20}BO_3$ $(M-MeOH)^+$: m/z=283.2; found: 283.1.

Intermediate 5. tert-butyl (endo)-5-((3-amino-6-((E)-2-cyanovinyl)-2-(3-(dimethylamino)azetidin-1-yl)-8-fluoro-7-(3-(methoxymethoxy)naphthalen-1-yl)quinolin-4-yl)amino)-2-azabicyclo[2.1.1]hexane-2-carboxylate

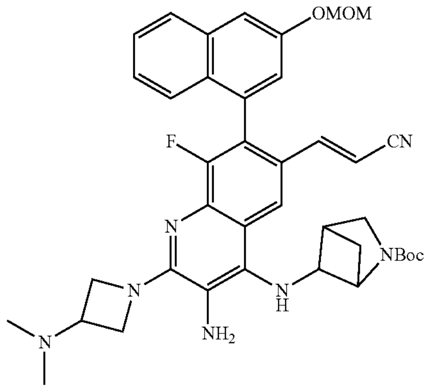

In a 10 dram vial, a solution of tert-butyl (endo)-5-((3-amino-7-bromo-2-(3-(dimethylamino)azetidin-1-yl)-8-fluoro-6-iodoquinolin-4-yl)amino)-2-azabicyclo[2.1.1]hexane-2-carboxylate (Intermediate 2, 1.59 g, 2.40 mmol), acrylonitrile (230 mg, 4.33 mmol) and triethylamine (670 μL, 4.81 mmol) in DMF (12 mL) was added $PdOAc_2$ (54.0 mg, 0.240 mmol) and tri-o-tolylphosphine (146 mg, 0.481 mmol). The reaction mixture was heated at 80° C. for 2 h. Then the reaction was diluted with water (10 mL) and dioxane (10 mL). (3-(methoxymethoxy)naphthalen-1-yl)boronic acid (Intermediate 4, 1.12 g, 4.81 mmol), $Pd(PPh_3)_4$ (278 mg, 0.240 mmol) and $Na_2CO_3$ (510 mg, 4.81 mmol) were added. The reaction mixture was heated at 105° C. for 15 h. Then $H_2O$ (50 mL) was added to the reaction mixture followed by extraction with dichloromethane (50 mL×3). The combined organic layers were washed with $H_2O$ (50 mL), dried with $Na_2SO_4$, filtered and concentrated. The crude product was added to a silica gel column and was eluted with methanol/dichloromethane from 0% to 10% to give tert-butyl (endo)-5-((3-amino-6-((E)-2-cyanovinyl)-2-(3-(dimethylamino)azetidin-1-yl)-8-fluoro-7-(3-(methoxymethoxy)naphthalen-1-yl)quinolin-4-yl)amino)-2-azabicyclo[2.1.1]hexane-2-carboxylate (1.25 g, 75% yield) as a yellow solid. LCMS calculated for $C_{39}H_{45}FN_7O_4$$(M+H)^+$: m/z=694.4; found 694.3.

Intermediate 6. tert-butyl (endo)-5-((3-amino-6-(2-cyanoethyl)-2-(3-(dimethylamino)azetidin-1-yl)-8-fluoro-7-(3-hydroxynaphthalen-1-yl)quinolin-4-yl)amino)-2-azabicyclo[2.1.1]hexane-2-carboxylate

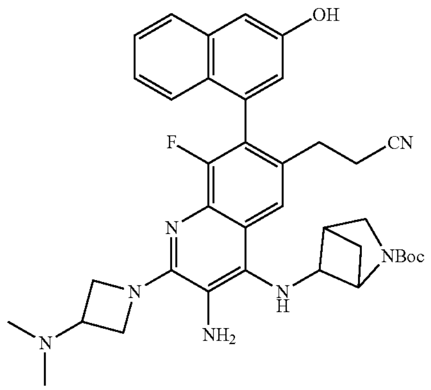 [SMILES: CN(C)C1CN(c2nc3c(F)c(-c4cc(O)cc5ccccc45)c(CCC#N)cc3c(NC3C4CC3N(C(=O)OC(C)(C)C)C4)c2N)C1]

To a solution of tert-butyl (endo)-5-((3-amino-7-bromo-6-(2-cyanoethyl)-2-(3-(dimethylamino)azetidin-1-yl)-8-fluoroquinolin-4-yl)amino)-2-azabicyclo[2.1.1]hexane-2-carboxylate (Intermediate 3, 1038 mg, 1.76 mmol) in water (2 mL) and dioxane (4 mL), (3-hydroxynaphthalen-1-yl) boronic acid (763 mg, 4.06 mmol), $Pd(PPh_3)_4$(204 mg, 0.176 mmol) and $Na_2CO_3$ (374 mg, 3.53 mmol) were added. The reaction mixture was heated to 100° C. for 4 h. $H_2O$ (5 mL) was added to the reaction mixture followed by extraction with dichloromethane (10 mL×3) and then the combined organic layers were washed with $H_2O$ (20 mL), dried with $Na_2SO_4$, filtered and concentrated. The crude product was added to a silica gel column and was eluted with methanol/dichloromethane from 0% to 5% to give tert-butyl (endo)-5-((3-amino-6-(2-cyanoethyl)-2-(3-(dimethylamino)azetidin-1-yl)-8-fluoro-7-(3-hydroxynaphthalen-1-yl)quinolin-4-yl)amino)-2-azabicyclo[2.1.1]hexane-2-carboxylate (0.93 g, 81% yield). LCMS calculated for $C_{37}H_{43}FN_7O_3$ $(M+H)^+$: m/z=652.3; found 652.3.

Intermediate 7. 7-bromo-2,4,6-trichloro-8-fluoro-3-nitroquinoline

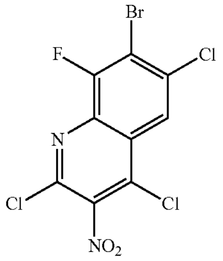 [SMILES: O=[N+]([O-])c1c(Cl)nc2c(F)c(Br)c(Cl)cc2c1Cl]

This compound was prepared according to the procedure described for Intermediate 1, replacing NIS with NCS in Step 1.

Intermediate 8. tert-butyl (endo)-5-((3-amino-7-bromo-6-chloro-2-(3-(dimethylamino)azetidin-1-yl)-8-fluoroquinolin-4-yl)amino)-2-azabicyclo[2.1.1]hexane-2-carboxylate

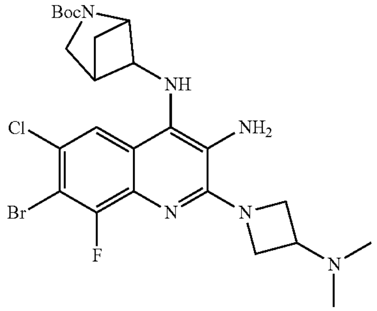

This compound was prepared according to the procedure described for Intermediate 2, replacing 7-bromo-2,4-dichloro-8-fluoro-6-iodo-3-nitroquinoline with 7-bromo-2,4,6-trichloro-8-fluoro-3-nitroquinoline (Intermediate 7) in Step 1. LCMS calculated for $C_{24}H_{32}BrClFN_6O_2(M+H)^+$: m/z=569.1; found 569.2.

Intermediate 9. tert-butyl 5-(7-bromo-8-(2-cyanoethyl)-2-(3-(dimethylamino)-3-oxopropyl)-4-(3-(dimethylamino)azetidin-1-yl)-6-fluoro-1H-imidazo[4,5-c]quinolin-1-yl)-2-endo-azabicyclo[2.1.1]hexane-2-carboxylate

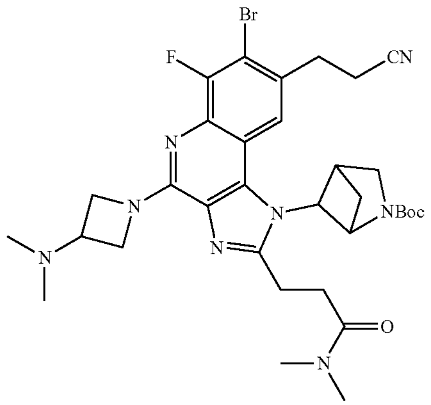 [SMILES: CN(C)C(=O)CCc1nc2c(N3CC(N(C)C)C3)nc3c(F)c(Br)c(CCC#N)cc3c2n1C1C2CC1N(C(=O)OC(C)(C)C)C2]

Step 1. tert-butyl 5-(7-bromo-2-(3-(dimethylamino)-3-oxopropyl)-4-(3-(dimethylamino)azetidin-1-yl)-6-fluoro-8-iodo-1H-imidazo[4,5-c]quinolin-1-yl)-2-endo-azabicyclo[2.1.1]hexane-2-carboxylate

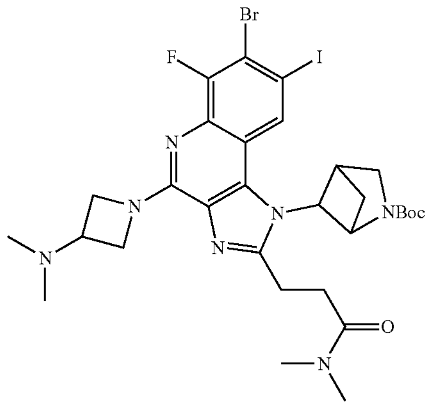 [SMILES: CN(C)C(=O)CCc1nc2c(N3CC(N(C)C)C3)nc3c(F)c(Br)c(I)cc3c2n1C1C2CC1N(C(=O)OC(C)(C)C)C2]

A solution of tert-butyl 5-((3-amino-7-bromo-2-(3-(dimethylamino)azetidin-1-yl)-8-fluoro-6-iodoquinolin-4-yl)amino)-2-endo-azabicyclo[2.1.1]hexane-2-carboxylate (Intermediate 2, 3.00 g, 4.54 mmol, 1.0 equiv.) and N,N-dimethyl-4-oxobutanamide (0.615 g, 4.76 mmol, 1.05 equiv.) in ethanol (9.1 ml) was heated to 85° C. in a sealed vial under air for 3 h. The vial was cooled to 22° C. and n-butanol (9 mL) was added, the vial uncapped, and the mixture stirred vigorously overnight (open to air) at 65° C. The following day LCMS revealed complete conversion to the desired product. Volatiles were removed in vacuo and the product was used without further purification (quant. yield assume). LCMS calculated for $C_{30}H_{39}BrFIN_7O_3(M+H)^+$: m/z=770.1; found: 770.1.

Step 2. tert-butyl 5-(7-bromo-8-(2-cyanoethyl)-2-(3-(dimethylamino)-3-oxopropyl)-4-(3-(dimethylamino)azetidin-1-yl)-6-fluoro-1H-imidazo[4,5-c]quinolin-1-yl)-2-endo-azabicyclo[2.1.1]hexane-2-carboxylate Part A: In a 40 mL vial tert-butyl 5-(7-bromo-2-(3-(dimethylamino)-3-oxopropyl)-4-(3-(dimethylamino)azetidin-1-yl)-6-fluoro-8-iodo-1H-imidazo[4,5-c]quinolin-1-yl)-2-endo-azabicyclo[2.1.1]hexane-2-carboxylate (3.50 g, 4.54 mmol) and bis(tri-o-tolylphosphine)palladium(0) (0.325 g, 0.454 mmol) were dissolved in DMF (15 ml). Triethylamine (1.266 ml, 9.09 mmol) and acrylonitrile (0.598 ml, 9.09 mmol) were added to the reaction mixture at once. The headspace was purged with nitrogen and the vial was capped and stirred at 80° C. for 1 h. At this time LCMS indicated completion of the reaction. The reaction mixture was cooled to RT and poured into rapidly stirring ice water to precipitate a yellow solid. The solid was filtered and dried on the filter for 72 h. The filter cake was used in the following reaction without further purification. LCMS calculated for $C_{33}H_{41}BrFN_8O_3(M+H)^+$: m/z=695.2; found: 695.3.

Part B: The filter cake from Part A was dissolved in THF (40 mL) and cooled to 0° C. Lithium triethylborohydride (8.2 mL, 1M in THF, 1.81 equiv.) was added in four portions over 30 min with LCMS monitoring after each addition. Water was slowly added to the reaction mixture (20 mL) and the mixture was extracted with DCM (3×20 mL), dried over $MgSO_4$, and volatiles removed in vacuo. The residue was dried under high vacuum overnight to yield a crumbly brown/orange solid that was used without further purification in subsequent steps (3.24 g, quant.). LCMS calculated for $C_{33}H_{43}BrFN_8O_3(M+H)^+$: m/z=697.3; found: 697.4.

Intermediate 10. 8-bromo-2,4,7-trichloro-6-iodo-3-nitroquinoline

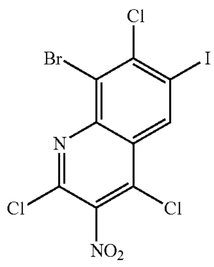 [SMILES: O=[N+]([O-])c1c(Cl)nc2c(Br)c(Cl)c(I)cc2c1Cl]

Step 1. 2-amino-3-bromo-4-chloro-5-iodobenzoic acid

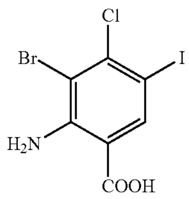 [SMILES: Nc1c(C(=O)O)cc(I)c(Cl)c1Br]

To a solution of 2-amino-4-chlorobenzoic acid (10.0 g, 58.3 mmol) in DMF (194 mL) was added NIS (14.4 g, 64.1 mmol). The resulting mixture was stirred at 70° C. for 16 h and was cooled to room temperature before adding NBS (11.4 g, 64.1 mmol). The resulting mixture was stirred at 70° C. overnight. The mixture was cooled with ice water and then water (150 mL) was added and stirred for 20 min, the precipitate was filtered and washed with water, dried to provide the desired product as a solid. LCMS calculated for $C_7HsBrClINO_2$ $(M+H)^+$: m/z=375.8; found 375.8.

Step 2. 8-bromo-2,4,7-trichloro-6-iodo-3-nitroquinoline

This compound was prepared according to the procedure described for Intermediate 1, replacing 2-amino-4-bromo-3-fluoro-5-iodobenzoic acid with 2-amino-3-bromo-4-chloro-5-iodobenzoic acid in Step 2.

Intermediate 11. tert-butyl (endo)-5-(6-bromo-7-chloro-8-(2-cyanoethyl)-2-(3-(dimethylamino)-3-oxopropyl)-4-(3-(dimethylamino)azetidin-1-yl)-1H-imidazo[4,5-c]quinolin-1-yl)-2-azabicyclo[2.1.1]hexane-2-carboxylate

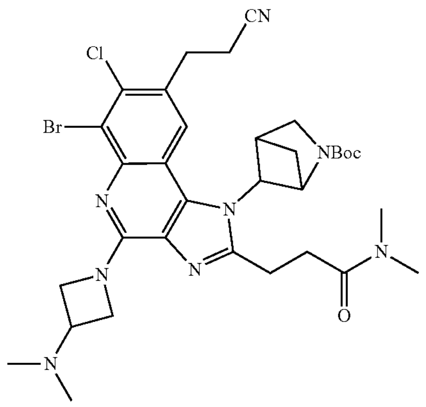

Step 1. tert-butyl (endo)-5-((3-amino-8-bromo-7-chloro-2-(3-(dimethylamino)azetidin-1-yl)-6-iodoquinolin-4-yl)amino)-2-azabicyclo[2.1.1]hexane-2-carboxylate

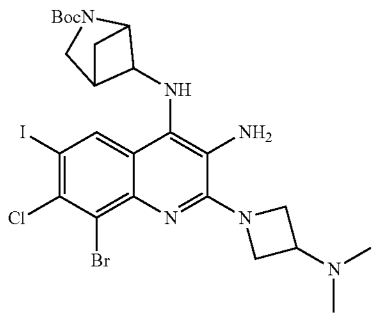 [SMILES: CN(C)C1CN(c2nc3c(Br)c(Cl)c(I)cc3c(NC3C4CC3N(C(=O)OC(C)(C)C)C4)c2N)C1]

This compound was prepared according to the procedure described for Intermediate 2, replacing 7-bromo-2,4-dichloro-8-fluoro-6-iodo-3-nitroquinoline with 8-bromo-2,4,7-trichloro-6-iodo-3-nitroquinoline (Intermediate 10) in Step 1. LCMS calculated for $C_{24}H_{32}BrClIN_6O_2(M+H)^+$: m/z=677.1; found 677.1.

Step 2. tert-butyl (endo)-5-(6-bromo-7-chloro-2-(3-(dimethylamino)-3-oxopropyl)-4-(3-(dimethylamino)azetidin-1-yl)-8-iodo-1H-imidazo[4,5-c]quinolin-1-yl)-2-azabicyclo[2.1.1]hexane-2-carboxylate

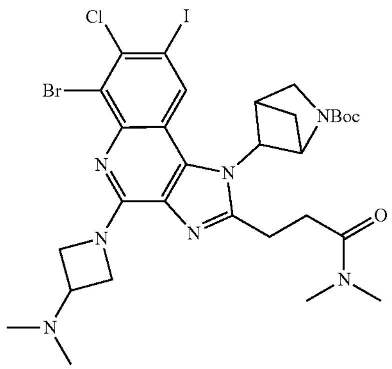

A mixture of tert-butyl (endo)-5-((3-amino-8-bromo-7-chloro-2-(3-(dimethylamino)azetidin-1-yl)-6-iodoquinolin-4-yl)amino)-2-azabicyclo[2.1.1]hexane-2-carboxylate (780 mg, 1.151 mmol) and N,N-dimethyl-4-oxobutanamide (178 mg, 1.38 mmol) in EtOH (3.84 mL)/AcOH (0.767 mL) was stirred at 80° C. overnight. The resultant mixture was concentrated under reduced pressure and purified by column chromatography (0-20% MeOH:DCM) to yield the desired product. LCMS calculated for $C_{30}H_{39}BrClIN_7O_3(M+H)^+$: m/z=786.1; found 786.2.

Step 3. tert-butyl (endo)-5-(6-bromo-7-chloro-8-(2-cyanovinyl)-2-(3-(dimethylamino)-3-oxopropyl)-4-(3-(dimethylamino)azetidin-1-yl)-1H-imidazo[4,5-c]quinolin-1-yl)-2-azabicyclo[2.1.1]hexane-2-carboxylate

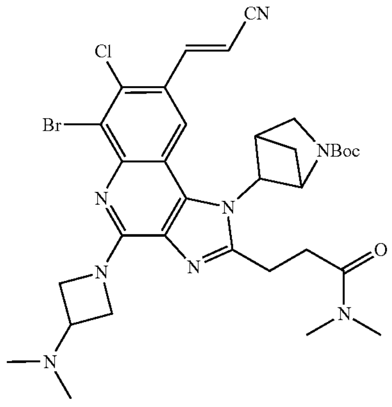

To a 40 mL vial, tert-butyl (endo)-5-(6-bromo-7-chloro-2-(3-(dimethylamino)-3-oxopropyl)-4-(3-(dimethylamino)azetidin-1-yl)-8-iodo-1H-imidazo[4,5-c]quinolin-1-yl)-2-azabicyclo[2.1.1]hexane-2-carboxylate (1.58 g, 2.01 mmol), $Pd(OAc)_2$ (0.045 g, 0.201 mmol) and tri-o-tolylphosphane (0.122 g, 0.402 mmol) were dissolved in DMF (5 mL). TEA (560 μL, 4.02 mmol) and acrylonitrile (264 μL, 4.02 mmol) were added to the reaction mixture in one portion. The headspace was purged with nitrogen and the vial was capped and stirred at 80° C. for two hours. At this time LCMS indicated completion. The reaction mixture was cooled to room temperature and water was added followed by DCM. The mixture was extracted with DCM and the combined organic extracts were washed with brine, dried and concentrated under reduced pressure. Flash column chromatography (0-20% MeOH:DCM) afforded the desired product. LCMS calculated for $C_{33}H_{41}BrClN_8O_3(M+H)^+$: m/z=711.2; found 711.3.

Step 4. tert-butyl (endo)-5-(6-bromo-7-chloro-8-(2-cyanoethyl)-2-(3-(dimethylamino)-3-oxopropyl)-4-(3-(dimethylamino)azetidin-1-yl)-1H-imidazo[4,5-c]quinolin-1-yl)-2-azabicyclo[2.1.1]hexane-2-carboxylate To a solution of tert-butyl (endo)-5-(6-bromo-7-chloro-8-(2-cyanovinyl)-2-(3-(dimethylamino)-3-oxopropyl)-4-(3-(dimethylamino)azetidin-1-yl)-1H-imidazo[4,5-c]quinolin-1-yl)-2-azabicyclo[2.1.1]hexane-2-carboxylate (800 mg, 1.12 mmol) in THF (5.60 mL) at 0° C. was added Super-Hydride (1M in THF) (1.70 mL, 1.70 mmol) dropwise. The resulting mixture was stirred at 0° C. for 5 min. Additional Super-Hydride was added as necessary while the reaction was monitored by LCMS (ca. 5 min after hydride addition) until completion. The resultant mixture was quenched with water and extracted with DCM. The combined organic extracts were dried and concentrated under reduced pressure. Flash column chromatography (0-20% MeOH:DCM) afforded the desired product. LCMS calculated for $C_{33}H_{43}BrClNaO_3$ $(M+H)^+$: m/z=713.2; found 713.3.

Intermediate 12. tert-butyl (endo)-5-(2-(3-(dimethylamino)-3-oxopropyl)-4-(3-(dimethylamino)azetidin-1-yl)-6-fluoro-9-formyl-7-(3-(methoxymethoxy)naphthalen-1-yl)-1H-imidazo[4,5-c]quinolin-1-yl)-2-azabicyclo[2.1.1]hexane-2-carboxylate

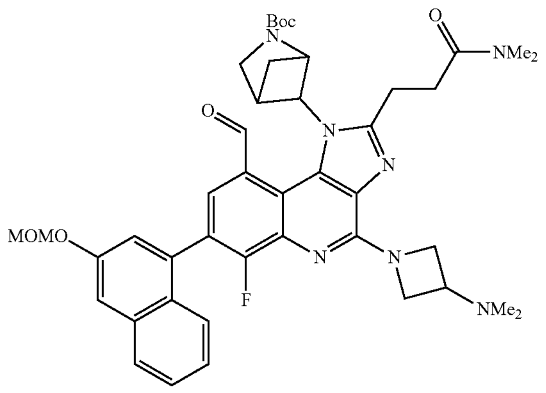

Step 1: 3-((5-bromo-3-chloro-2-fluorophenyl)amino)-3-oxopropanoic acid

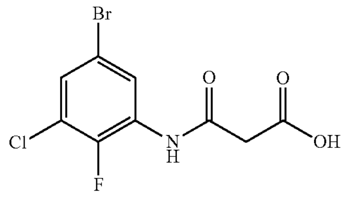 [SMILES: O=C(O)CC(=O)Nc1cc(Br)cc(Cl)c1F]

Ethyl malonyl chloride (9.41 g, 62.5 mmol) was added dropwise to a solution of 5-bromo-3-chloro-2-fluoroaniline (11.2 g, 50 mmol) in EtOAc (100 mL) and saturated $NaHCO_3$ aqueous solution (100 mL) at 0° C., and the resulting mixture was stirred for 30 minutes. The reaction mixture was diluted with EtOAc, and the organic layer was washed with brine, dried over $Na_2SO_4$, and concentrated in vacuo. The crude material was dissolved in THF (100 mL), and 2N LiOH solution (50 mL) was added, followed by the addition of MeOH (10 mL). The mixture was stirred vigorously at ambient temperature for 2 h. The reaction mixture was acidified with 1N HCl and then extracted with EtOAc, washed with brine, dried over $Na_2SO_4$, and concentrated in vacuo to give the product (14.5 g, 93% yield), which was used in the next step without further purification.

Step 2. 5-bromo-7-chloro-8-fluoroquinoline-2,4(1H,3H)-dione

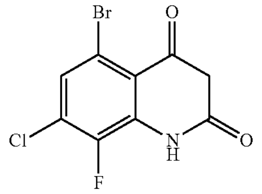 [SMILES: O=C1CC(=O)c2c(Br)cc(Cl)c(F)c2N1]

Methanesulfonic anhydride (16.3 g, 93 mmol) was added to a solution of 3-((5-bromo-3-chloro-2-fluorophenyl)amino)-3-oxopropanoic acid (14.5 g, 46.7 mmol) in Eaton's reagent (10 wt % phosphorus pentoxide solution in methanesulfonic acid, 100 mL), and the resulting mixture was stirred at 60° C. overnight. Upon completion, the reaction solution was poured into cold water, and the precipitates were collected by filtration and air dried to give the crude product (13.4 g, 98% yield), which was used in the next step without further purification.

Step 3. 5-bromo-7-chloro-8-fluoro-3-nitroquinoline-2,4-diol

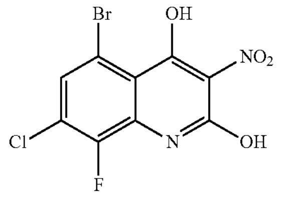 [SMILES: O=[N+]([O-])c1c(O)nc2c(F)c(Cl)cc(Br)c2c1O]

Nitric acid (92 wt %, 3.9 mL, 80 mmol) was added dropwise to a solution of 5-bromo-7-chloro-8-fluoroquinoline-2,4(1H,3H)-dione (13.4 g, 45.8 mmol) in acetic acid (100 mL), and the mixture was stirred at ambient temperature with LCMS monitoring. Upon completion, the reaction solution was poured into cold water with stirring, and the precipitates were collected by filtration, washed with ether, and air dried to give the crude product (13.8 g, 89% yield), which was used in the next step without further purification.

Step 4. 5-bromo-2,4,7-trichloro-8-fluoro-3-nitroquinoline

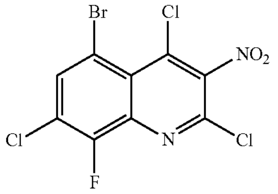 [SMILES: O=[N+]([O-])c1c(Cl)nc2c(F)c(Cl)cc(Br)c2c1Cl]

DIPEA (2.070 ml, 11.85 mmol) was added to a solution of 5-bromo-7-chloro-8-fluoro-3-nitroquinoline-2,4-diol (1.0 g, 2.96 mmol) and $POCl_3$ (2.2 ml, 23.7 mmol) in toluene (8 ml), and the mixture was stirred at 110° C. for 1 h. The solvent was removed under vacuum and then azeotroped with toluene 3 times to remove excess $POCl_3$, the residue was purified by flash chromatography (0-40% DCM in hexanes) to give the product (377 mg, 34% yield).

Step 5. tert-butyl (endo)-5-((5-bromo-7-chloro-2-(3-(dimethylamino)azetidin-1-yl)-8-fluoro-3-nitroquinolin-4-yl)amino)-2-azabicyclo[2.1.1]hexane-2-carboxylate

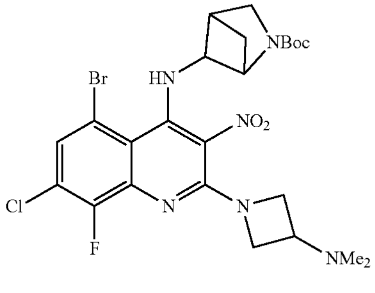 [SMILES: CN(C)C1CN(c2nc3c(F)c(Cl)cc(Br)c3c(NC3C4CC3N(C(=O)OC(C)(C)C)C4)c2[N+](=O)[O-])C1]

To a mixture of 5-bromo-2,4,7-trichloro-8-fluoro-3-nitroquinoline (250 mg, 0.67 mmol) in DCM (5 ml) was added tert-butyl (endo)-5-amino-2-azabicyclo[2.1.1]hexane-2-carboxylate (132 mg, 0.67 mmol) and DIPEA (0.58 mL, 3.34 mmol) and the reaction was stirred at 80° C. for 30 minutes. The reaction was cooled to room temperature, and N,N-dimethylazetidin-3-amine dihydrochloride (173 mg, 1.0 mmol) was added. After stirring at 80° C. for an additional 1 h, the reaction mixture was concentrated in vacuo to give the crude product, which was used in the next step without further purification. LCMS calculated for $C_{24}H_{30}BrClFN_6O_4(M+H)^+$: m/z=599.1; found 599.1.

Step 6. tert-butyl (endo)-5-((7-chloro-2-(3-(dimethylamino)azetidin-1-yl)-8-fluoro-3-nitro-5-vinylquinolin-4-yl)amino)-2-azabicyclo[2.1.1]hexane-2-carboxylate

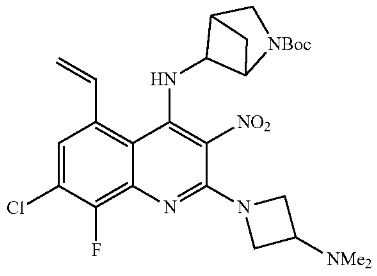

A solution of tert-butyl (endo)-5-((5-bromo-7-chloro-2-(3-(dimethylamino)azetidin-1-yl)-8-fluoro-3-nitroquinolin-4-yl)amino)-2-azabicyclo[2.1.1]hexane-2-carboxylate (0.45 g, 0.75 mmol) and 4,4,5,5-tetramethyl-2-vinyl-1,3,2-dioxaborolane (0.46 g, 3.0 mmol), $PdCl_2(dppf)$-$CH_2Cl_2$ adduct (61 mg, 75 mol), $K_3PO_4$ (0.32 g, 1.5 mmol) in dioxane (5 ml) and water (1 ml) was stirred at 100° C. for 5 h. The reaction was extracted with EtOAc, and the organic layer was washed with brine, dried over $Na_2SO_4$, and concentrated in vacuo. The residue was purified by flash chromatography to give the product (338 mg, 82% yield). LCMS calculated for $C_{26}H_{33}ClFN_6O_4(M+H)^+$: m/z=547.2; found 547.2.

Step 7. tert-butyl (endo)-5-((3-amino-7-chloro-2-(3-(dimethylamino)azetidin-1-yl)-8-fluoro-5-vinylquinolin-4-yl)amino)-2-azabicyclo[2.1.1]hexane-2-carboxylate

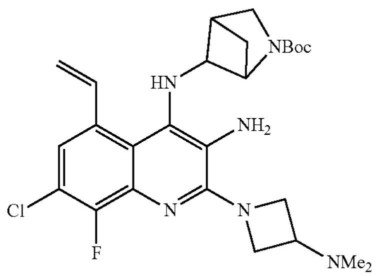 [SMILES: C=Cc1cc(Cl)c(F)c2nc(N3CC(N(C)C)C3)c([N+](=O)[O-])c(NC3C4CC3N(C(=O)OC(C)(C)C)C4)c12]

Sodium hydrosulfite (382 mg, 1.85 mmol) in water (1 mL) was added to a solution of tert-butyl (endo)-5-((7-chloro-2-(3-(dimethylamino)azetidin-1-yl)-8-fluoro-3-nitro-5-vinylquinolin-4-yl)amino)-2-azabicyclo[2.1.1]hexane-2-carboxylate (338 mg, 0.62 mmol) and 30% aq. ammonium hydroxide (0.8 mL, 6.18 mmol) in meOH (5 mL) at room temperature. After 10 min, the reaction was diluted with water and extracted with DCM for 3 times. The combined organic layers were dried $Na_2SO_4$, filtered and concentrated to give the crude product, which was used in the next step without further purification.

Step 8. tert-butyl (endo)-5-(7-chloro-2-(3-(dimethylamino)-3-oxopropyl)-4-(3-(dimethylamino)azetidin-1-yl)-6-fluoro-9-vinyl-1H-imidazo[4,5-c]quinolin-1-yl)-2-azabicyclo[2.1.1]hexane-2-carboxylate

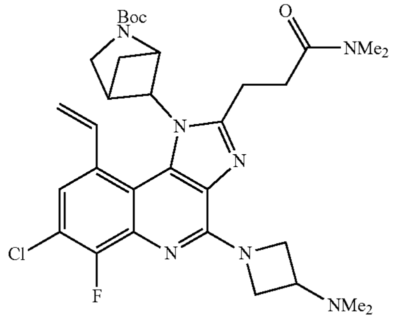 [SMILES: C=Cc1cc(Cl)c(F)c2nc(N3CC(N(C)C)C3)c3nc(CCC(=O)N(C)C)n(C4C5CC4N(C(=O)OC(C)(C)C)C5)c3c12]

A solution of tert-butyl 5-((3-amino-7-chloro-2-(3-(dimethylamino)azetidin-1-yl)-8-fluoro-5-vinylquinolin-4-yl)amino)-2-azabicyclo[2.1.1]hexane-2-carboxylate (0.26 g, 0.5 mmol) and N,N-dimethyl-4-oxobutanamide (0.193 g, 1.5 mmol) in i-PrOH (4 mL) was stirred at 80° C. for 4 h. The reaction mixture was concentrated and the residue was purified by flash chromatography (0-10% MeOH in DCM) to give the product (156 mg, 50% yield). LCMS calculated for $C_{32}H_{42}ClFN_7O_3(M+H)^+$: m/z=626.3; found 626.3.

Step 9. tert-butyl (endo)-5-(2-(3-(dimethylamino)-3-oxopropyl)-4-(3-(dimethylamino)azetidin-1-yl)-6-fluoro-7-(3-(methoxymethoxy)naphthalen-1-yl)-9-vinyl-1H-imidazo[4,5-c]quinolin-1-yl)-2-azabicyclo[2.1.1]hexane-2-carboxylate

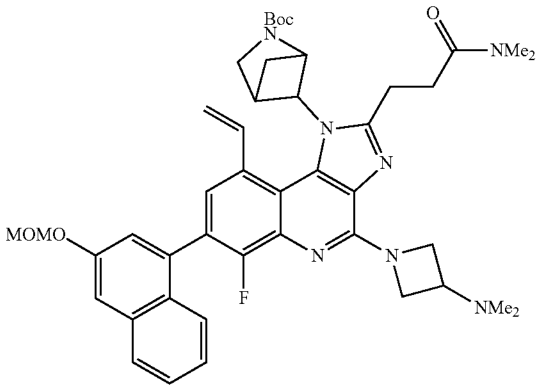

A mixture of tert-butyl 5-(7-chloro-2-(3-(dimethylamino)-3-oxopropyl)-4-(3-(dimethylamino)azetidin-1-yl)-6-fluoro-9-vinyl-1H-imidazo[4,5-c]quinolin-1-yl)-2-azabicyclo[2.1.1]hexane-2-carboxylate (100 mg, 0.16 mmol), 2-(3-(methoxymethoxy)naphthalen-1-yl)-4,4,5,5-tetramethyl-1,3,2-dioxaborolane (100 mg, 0.32 mmol), Xphos Pd G2 (12.57 mg, 0.016 mmol), and $K_3PO_4$ (102 mg, 0.48 mmol) in dioxane (1.6 ml) and water (0.4 ml) was stirred at 100° C. for 5 h with LCMS monitoring. The reaction mixture was diluted with water and extracted with EtOAc. The Organic layer was washed with brine, dried over $Na_2SO_4$, and concentrated in vacuo. The residue was purified by flash chromatography (0-10% MeOH in DCM) to give the product (87 mg, 70% yield). LCMS calculated for $C_{44}H_{53}FN_7O_5(M+H)^+$: m/z=778.4; found 778.4.

Step 10. tert-butyl (endo)-5-(2-(3-(dimethylamino)-3-oxopropyl)-4-(3-(dimethylamino)azetidin-1-yl)-6-fluoro-9-formyl-7-(3-(methoxymethoxy)naphthalen-1-yl)-1H-imidazo[4,5-c]quinolin-1-yl)-2-azabicyclo[2.1.1]hexane-2-carboxylate

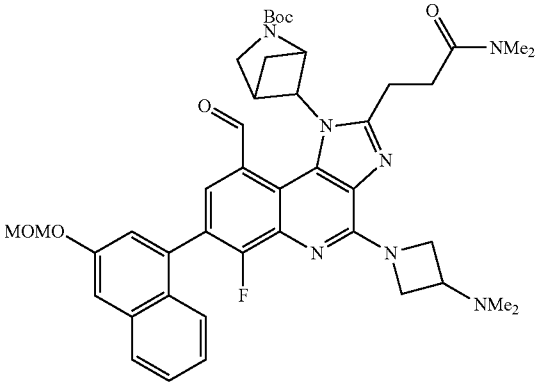

To a 10 dram vial, tert-butyl (endo)-5-(2-(3-(dimethylamino)-3-oxopropyl)-4-(3-(dimethylamino)azetidin-1-yl)-6-fluoro-7-(3-(methoxymethoxy)naphthalen-1-yl)-9-vinyl-1H-imidazo[4,5-c]quinolin-1-yl)-2-azabicyclo[2.1.1]hexane-2-carboxylate (87 mg, 0.11 mmol) and sodium periodate (70.6 mg, 0.33 mmol) in THF (1.0 mL) and water (10.0 ml) was added 0.4% aq. osmium tetroxide (35 μL, 5.5 μmol). The reaction mixture was stirred for 3 h. The reaction was diluted with water and extracted with EtOAc. The organic layers were washed with water and brine, dried over $Na_2SO_4$, concentrated in vacuo. The residue was purified by flash chromatography (0-10% MeOH in DCM) to give the Intermediate 12 (70 mg, 82% yield). LCMS calculated for $C_{43}H_{51}FN_7O_6(M+H)^+$: m/z=780.4; found 780.4.

Example 1a, Example 1b and Example 1c. 1-(3-(1-((endo)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)piperidin-1-yl)ethan-1-one

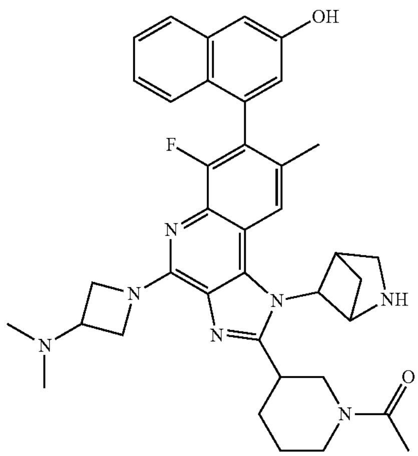 [SMILES: CC(=O)N1CCCC(c2nc3c(N4CC(N(C)C)C4)nc4c(F)c(-c5cc(O)cc6ccccc56)c(C)cc4c3n2C2C3CNC2C3)C1]

Step 1. tert-butyl (endo)-5-((3-amino-2-(3-(dimethylamino)azetidin-1-yl)-8-fluoro-7-(3-hydroxynaphthalen-1-yl)-6-methylquinolin-4-yl)amino)-2-azabicyclo[2.1.1]hexane-2-carboxylate

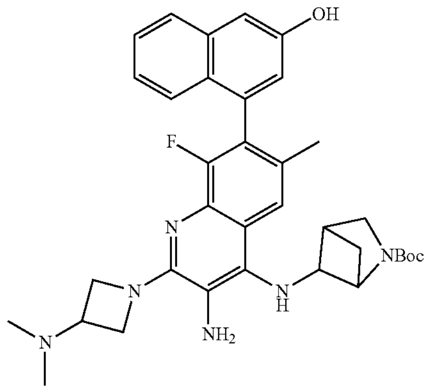 [SMILES: Cc1cc2c(NC3C4CC3N(C(=O)OC(C)(C)C)C4)c(N)c(N3CC(N(C)C)C3)nc2c(F)c1-c1cc(O)cc2ccccc12]

In a 10 dram vial tert-butyl (endo)-5-((3-amino-7-bromo-2-(3-(dimethylamino)azetidin-1-yl)-8-fluoro-6-iodoquinolin-4-yl)amino)-2-azabicyclo[2.1.1]hexane-2-carboxylate (Intermediate 2: 1.070 g, 1.618 mmol) and methylboronic acid (0.107 g, 1.780 mmol), $Pd(PPh_3)_4$(0.187 g, 0.162 mmol), sodium carbonate (0.514 g, 4.85 mmol) in water (5 mL) and dioxane (10 mL) were added. The reaction mixture was heated to 80° C. for 5 h. After cooling the reaction to room temperature, 4-(4,4,5,5-tetramethyl-1,3,2-dioxaborolan-2-yl)naphthalen-2-ol (0.437 g, 1.620 mmol) was added. The reaction mixture was heated to 100° C. for another 5 h. Then water (10 mL) was added to the reaction mixture followed by extraction with dichloromethane (10 mL×4). The combined organic layers were dried $Na_2SO_4$, filtered and concentrated. The crude product was added to a silica gel column and was eluted with methanol/dichloromethane from 0% to 10% to give tert-butyl (endo)-5-((3-amino-2-(3-(dimethylamino)azetidin-1-yl)-8-fluoro-7-(3-hydroxynaphthalen-1-yl)-6-methylquinolin-4-yl)amino)-2-azabicyclo [2.1.1]hexane-2-carboxylate (0.9 g, 91% yield). LCMS calculated for $C_{35}H_{42}FN_6O_3(M+H)^+$: m/z=613.3; found 613.2.

Step 2. 1-(3-(1-((endo)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)piperidin-1-yl)ethan-1-one In a 1 dram vial tert-butyl (endo)-5-((3-amino-2-(3-(dimethylamino)azetidin-1-yl)-8-fluoro-7-(3-hydroxynaphthalen-1-yl)-6-methylquinolin-4-yl)amino)-2-azabicyclo[2.1.1]hexane-2-carboxylate (15 mg, 0.024 mmol) and 1-acetylpiperidine-3-carbaldehyde (3.90 mg, 0.024 mmol) in ethanol (0.2 mL) was stirred at 60° C. for 18 h, then concentrated HCl (0.5 mL) was added. After 30 min, the mixture was diluted with acetonitrile/water and purified using prep-LCMS (XBridge C18 column, eluting with a gradient of acetonitrile/water containing 0.1% TFA, at flow rate of 60 mL/min) to afford the desired products as a TFA salt. The product was isolated as a pair of diastereomers.

Example 1a. Diastereomer 1. Peak 1. LCMS calculated for $C_{38}H_{43}FN_7O_2(M+H)^+$ m/z=648.3; found 648.2.

Example 1b. Diastereomer 2. Peak 2. LCMS calculated for $C_{38}H_{43}FN_7O_2(M+H)^+$ m/z=648.3; found 648.2.

Example 1c. Diastereomer 3. Peak 3. LCMS calculated for $C_{38}H_{43}FN_7O_2(M+H)^+$ m/z=648.3; found 648.2.

Example 2a and Example 2b. 3-(1-((endo)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)-1-(4-(pyrimidin-2-yl)piperazin-1-yl)propan-1-one

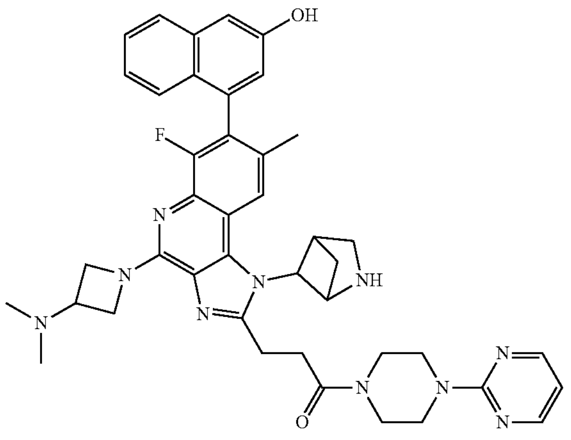 [SMILES: Cc1cc2c(nc(N3CC(N(C)C)C3)c3nc(CCC(=O)N4CCN(c5ncccn5)CC4)n(C4C5CNC4C5)c32)c(F)c1-c1cc(O)cc2ccccc12]

Step 1. tert-butyl (endo)-5-((3-amino-2-(3-(dimethylamino)azetidin-1-yl)-8-fluoro-7-(3-hydroxynaphthalen-1-yl)-6-methylquinolin-4-yl)amino)-2-azabicyclo[2.1.1]hexane-2-carboxylate

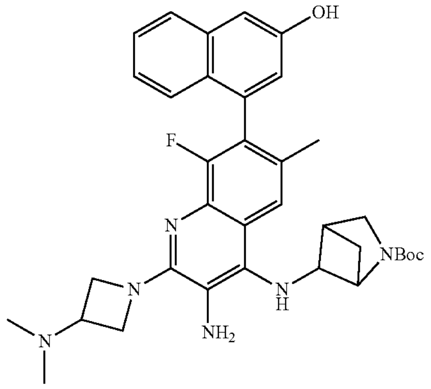 [SMILES: Cc1cc2c(NC3C4CC3N(C(=O)OC(C)(C)C)C4)c(N)c(N3CC(N(C)C)C3)nc2c(F)c1-c1cc(O)cc2ccccc12]

In a 10 dram vial, tert-butyl (endo)-5-((3-amino-7-bromo-2-(3-(dimethylamino)azetidin-1-yl)-8-fluoro-6-iodoquinolin-4-yl)amino)-2-azabicyclo[2.1.1]hexane-2-carboxylate (Intermediate 2: 1.070 g, 1.618 mmol) and methylboronic acid (0.107 g, 1.780 mmol), $Pd(Ph_3P)_4$ (0.187 g, 0.162 mmol), sodium carbonate (0.514 g, 4.85 mmol) in water (5 mL) and dioxane (10 mL) were added. The reaction mixture was heated to 80° C. for 5 h.

After cooling to room temperature, 4-(4,4,5,5-tetramethyl-1,3,2-dioxaborolan-2-yl)naphthalen-2-ol (0.437 g, 1.620 mmol) was added. The reaction mixture was heated to 100° C. for another 5 h. Then water (10 mL) was added to the reaction mixture followed by extraction with dichloromethane (10 mL×4). The combined organic layers were dried $Na_2SO_4$, filtered and concentrated. The crude product was added to a silica gel column and was eluted with methanol/dichloromethane from 0% to 10% to give tert-butyl (endo)-5-((3-amino-2-(3-(dimethylamino)azetidin-1-yl)-8-fluoro-7-(3-hydroxynaphthalen-1-yl)-6-methylquinolin-4-yl)amino)-2-azabicyclo[2.1.1]hexane-2-carboxylate (0.9 g, 91% yield). LCMS calculated for $C_{35}H_{42}FN_6O_3$ $(M+H)^+$: m/z=613.3; found 613.2.

Step 2. 3-(1-((endo)-2-(tert-butoxycarbonyl)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)propanoic acid

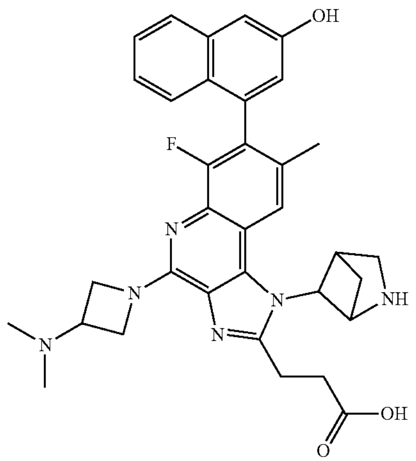 [SMILES: Cc1cc2c(nc(N3CC(N(C)C)C3)c3nc(CCC(=O)O)n(C4C5CNC4C5)c32)c(F)c1-c1cc(O)cc2ccccc12]

In a 10 dram vial tert-butyl (endo)-5-((3-amino-2-(3-(dimethylamino)azetidin-1-yl)-8-fluoro-7-(3-hydroxynaphthalen-1-yl)-6-methylquinolin-4-yl)amino)-2-azabicyclo[2.1.1]hexane-2-carboxylate (650 mg, 1.061 mmol) and methyl 4-oxobutanoate (370 mg, 3.18 mmol) in ethanol (5.3 mL) was stirred at 60° C. for 18 h. LiOH (203 mg, 8.49 mmol) in water (0.5 mL) was added. The reaction mixture was stirred at r.t. for another 1 h. The reaction mixture was diluted with acetonitrile/water and purified using prep-LCMS (XBridge C18 column, eluting with a gradient of acetonitrile/water containing 0.1% TFA, at flow rate of 60 mL/min) to give the desired product 3-(1-((endo)-2-(tert-butoxycarbonyl)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)propanoic acid (290 mg, 39.3% yield) as the TFA salt. LCMS calculated for $C_{34}H_{36}FN_6O_3(M+H)^+$: m/z=595.3; found 595.2.

Step 3. 3-(1-((endo)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)-1-(4-(pyrimidin-2-yl)piperazin-1-yl)propan-1-one In a 1 dram vial 3-(1-((endo)-2-(tert-butoxycarbonyl)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)propanoic acid (7 mg, 10.07 μmol), 2-(piperazin-1-yl)pyrimidine (4 mg, 20.1 μmol) and DIPEA (5.28 μl, 0.030 mmol) in DCM (0.50 mL) was added BOP (5.79 mg, 0.013 mmol). The reaction mixture was stirred for 1 h. Then concentrated HCl (50 uL) was added. After cooling to room temperature, the mixture was diluted with acetonitrile/water and purified using prep-LCMS (XBridge C18 column, eluting with a gradient of acetonitrile/water containing 0.1% TFA, at flow rate of 60 mL/min) to afford the desired products as a TFA salt. The product was isolated as a pair of diastereomers.

Example 2a. Diastereomer 1. Peak 1. LCMS calculated for $C_{42}H_{46}FN_{10}O_2$(M+H)+m/z=741.4; found 741.3.

Example 2b. Diastereomer 2. Peak 2. LCMS calculated for $C_{42}H_{46}FN_{10}O_2(M+H)^+$ m/z=741.4; found 741.3.

Example 3a and Example 3b. 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(3-oxo-3-(7-oxa-2-azaspiro[3.5]nonan-2-yl)propyl)-1H-imidazo[4,5-c]quinolin-8-yl)propanenitrile

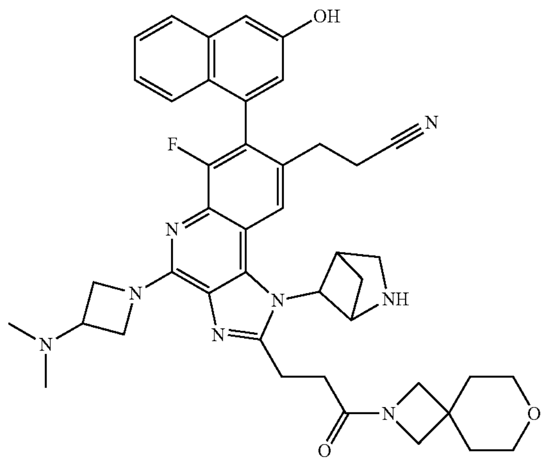 [SMILES: CN(C)C1CN(c2nc3c(F)c(-c4cc(O)cc5ccccc45)c(CCC#N)cc3c3c2nc(CCC(=O)N2CC4(CCOCC4)C2)n3C2C3CNC2C3)C1]

Step 1. 3-(1-((endo)-2-(tert-butoxycarbonyl)-2-azabicyclo[2.1.1]hexan-5-yl)-8-(2-cyanoethyl)-4-(3-(dimethylamino)azetidin-1-yl)-6-fluoro-7-(3-(methoxymethoxy)naphthalen-1-yl)-1H-imidazo[4,5-c]quinolin-2-yl)propanoic acid

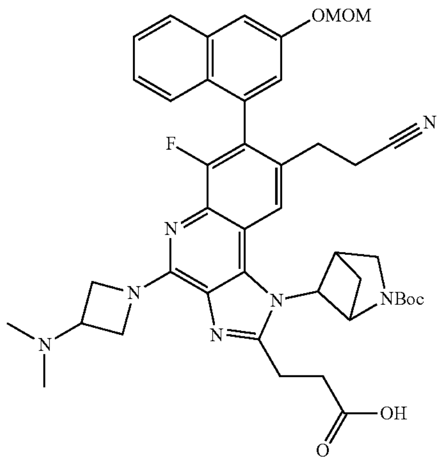

Part A: In a 10 dram vial tert-butyl (endo)-5-((3-amino-6-((E)-2-cyanovinyl)-2-(3-(dimethylamino)azetidin-1-yl)-8-fluoro-7-(3-(methoxymethoxy)naphthalen-1-yl)quinolin-4-yl)amino)-2-azabicyclo[2.1.1]hexane-2-carboxylate (Intermediate 5, 2.0 g, 2.88 mmol) in THF (14 mL) was added L-Selectride (5.77 ml, 1 M in THF, 5.77 mmol) dropwise at 0° C. for 1 h. Then $H_2O$ (30 mL) was added to the reaction mixture followed by extraction with dichloromethane (30 mL×3). The combined organic layers were dried $Na_2SO_4$, filtered and concentrated. The crude product was used directly without further purification.

Part B: To a solution of the above crude product in EtOH (20 mL) was added methyl 4-oxobutanoate (1.0 g, 8.65 mmol). The reaction mixture was stirred at 60° C. for 18 h. Then LiOH (0.414 g, 17.30 mmol) in water (2 mL) was added. After another 1 h, the reaction mixture was diluted with MeOH then purified by prep-HPLC (pH=2, acetonitrile/water+TFA) to give the desired product 3-(1-((endo)-2-(tert-butoxycarbonyl)-2-azabicyclo[2.1.1]hexan-5-yl)-8-(2-cyanoethyl)-4-(3-(dimethylamino)azetidin-1-yl)-6-fluoro-7-(3-(methoxymethoxy)naphthalen-1-yl)-1H-imidazo[4,5-c]quinolin-2-yl)propanoic acid (270 mg, 12.0% yield) as the TFA salt. LCMS calculated for $C_{43}H_{49}FN_7O_6$ $(M+H)^+$: m/z=778.4; found 778.3.

Step 2. 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(3-oxo-3-(7-oxa-2-azaspiro[3.5]nonan-2-yl)propyl)-1H-imidazo[4,5-c]quinolin-8-yl)propanenitrile In a 1 dram vial 3-(1-((endo)-2-(tert-butoxycarbonyl)-2-azabicyclo[2.1.1]hexan-5-yl)-8-(2-cyanoethyl)-4-(3-(dimethylamino)azetidin-1-yl)-6-fluoro-7-(3-(methoxymethoxy)naphthalen-1-yl)-1H-imidazo[4,5-c]quinolin-2-yl)propanoic acid (10 mg, 0.013 mmol), 7-oxa-2-azaspiro[3.5]nonane (3.2 mg, 0.026 mmol) and DIPEA (6.74 μL, 0.039 mmol) in DMF (0.5 mL) was added BOP (7.4 mg, 0.017 mmol). The reaction mixture was stirred for 1 h. Then concentrated HCl (50 uL) was added. After 30 min, the mixture was diluted with acetonitrile/water and purified using prep-LCMS (XBridge C18 column, eluting with a gradient of acetonitrile/water containing 0.1% TFA, at flow rate of 60 mL/min) to afford the desired products as a TFA salt. The product was isolated as a pair of diastereomers.

Example 3a. Diastereomer 1. Peak 1. LCMS calculated for $C_{43}H_{48}FN_8O_3(M+H)^+$ m/z=743.4; found 743.3.

Example 3b. Diastereomer 2. Peak 2. LCMS calculated for $C_{43}H_{48}FN_8O_3(M+H)^+$ m/z=743.4; found 743.3.

Example 4a and Example 4b. 3-(2-(3-(4-acetylpiperazin-1-yl)-3-oxopropyl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-8-yl)propanenitrile

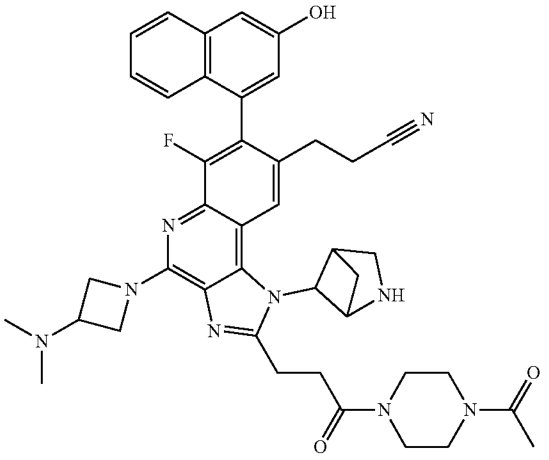 [SMILES: CC(=O)N1CCN(C(=O)CCc2nc3c(N4CC(N(C)C)C4)nc4c(F)c(-c5cc(O)cc6ccccc56)c(CCC#N)cc4c3n2C2C3CNC2C3)CC1]

This compound was prepared according to the procedure described in Example 3, Step 2, replacing 7-oxa-2-azaspiro[3.5]nonane with 1-(piperazin-1-yl)ethan-1-one. The product 3-(2-(3-(4-acetylpiperazin-1-yl)-3-oxopropyl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-8-yl)propanenitrile was isolated as a pair of diastereomers.

Example 4a. Diastereomer 1. Peak 1. LCMS calculated for $C_{42}H_{47}FN_9O_3(M+H)^+$ m/z=744.4; found 744.3.

Example 4b. Diastereomer 2. Peak 2. LCMS calculated for $C_{42}H_{47}FN_9O_3(M+H)^+$ m/z=744.4; found 744.3.

Example 5a and Example 5b. 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-((2-oxopyrrolidin-1-yl)methyl)-1H-imidazo[4,5-c]quinolin-8-yl)propanenitrile

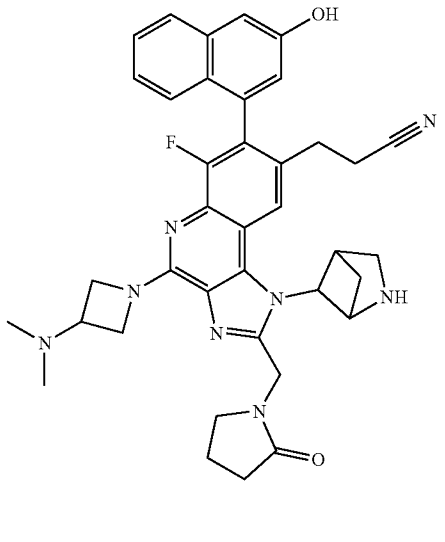 [SMILES: CN(C)C1CN(c2nc3c(F)c(-c4cc(O)cc5ccccc45)c(CCC#N)cc3c3c2nc(CN2CCCC2=O)n3C2C3CNC2C3)C1]

Step 1. tert-butyl (endo)-5-(2-(chloromethyl)-8-(2-cyanoethyl)-4-(3-(dimethylamino)azetidin-1-yl)-6-fluoro-7-(3-hydroxynaphthalen-1-yl)-1H-imidazo[4,5-c]quinolin-1-yl)-2-azabicyclo[2.1.1]hexane-2-carboxylate

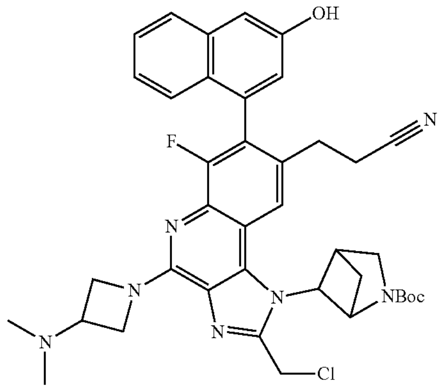 [SMILES: CN(C)C1CN(c2nc3c(F)c(-c4cc(O)cc5ccccc45)c(CCC#N)cc3c3c2nc(CCl)n3C2C3CC2N(C(=O)OC(C)(C)C)C3)C1]

In a 10 dram vial tert-butyl (endo)-5-((3-amino-6-(2-cyanoethyl)-2-(3-(dimethylamino)azetidin-1-yl)-8-fluoro-7-(3-hydroxynaphthalen-1-yl)quinolin-4-yl)amino)-2-azabicyclo[2.1.1]hexane-2-carboxylate (Intermediate 6, 774 mg, 0.891 mmol) and 2-chloro-1,1,1-triethoxyethane (525 mg, 2.67 mmol) in acetic acid (4.45 mL) was stirred at 100° C. for 0.5 h. The reaction mixture was concentrated and diluted with DCM. Saturated $NaHCO_3$ (15 mL) was added to the reaction mixture followed by extraction with dichloromethane (10 mL×3). The combined organic layers were dried $Na_2SO_4$, filtered and concentrated. The crude product was added to a silica gel column and was eluted with methanol/dichloromethane from 0% to 5% to give tert-butyl (endo)-5-(2-(chloromethyl)-8-(2-cyanoethyl)-4-(3-(dimethylamino)azetidin-1-yl)-6-fluoro-7-(3-hydroxynaphthalen-1-yl)-1H-imidazo[4,5-c]quinolin-1-yl)-2-azabicyclo[2.1.1]hexane-2-carboxylate (440 mg, 70% yield). LCMS calculated for $C_{39}H_{42}ClFN_7O_3(M+H)^+$: m/z=710.3; found 710.3.

Step 2. 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-((2-oxopyrrolidin-1-yl)methyl)-1H-imidazo[4,5-c]quinolin-8-yl)propanenitrile In a 1 dram vial 2.5 M nBuLi in hexanes (56.3 μl, 0.141 mmol) was added to pyrrolidin-2-one (10.3 mg, 0.141 mmol) in THF (0.141 ml). After 15 min, tert-butyl (endo)-5-(2-(chloromethyl)-8-(2-cyanoethyl)-4-(3-(dimethylamino)azetidin-1-yl)-6-fluoro-7-(3-hydroxynaphthalen-1-yl)-1H-imidazo[4,5-c]quinolin-1-yl)-2-azabicyclo[2.1.1]hexane-2-carboxylate (20 mg, 0.028 mmol) in THF (0.5 mL) was added. The resulted mixture was stirred at 60° C. for 5 h. Then concentrated HCl (50 uL) was added. After 30 min, the mixture was diluted with acetonitrile/water and purified using prep-LCMS (XBridge C18 column, eluting with a gradient of acetonitrile/water containing 0.1% TFA, at flow rate of 60 mL/min) to afford the desired products as a TFA salt. The product was isolated as a pair of diastereomers.

Example 5a. Diastereomer 1. Peak 1. LCMS calculated for $C_{38}H_{40}FN_8O_2$ $(M+H)^+$ m/z=659.3; found 659.3.

Example 5b. Diastereomer 2. Peak 2. LCMS calculated for $C_{38}H_{40}FN_8O_2$ $(M+H)^+$ m/z=659.3; found 659.3.

Example 6a and Example 6b. 4-(1-((endo)-2-azabicyclo[2.1.1]hexan-5-yl)-4-(3-(dimethylamino)azetidin-1-yl)-2-ethyl-6-fluoro-8-(oxazol-5-yl)-1H-imidazo[4,5-c]quinolin-7-yl)naphthalen-2-ol

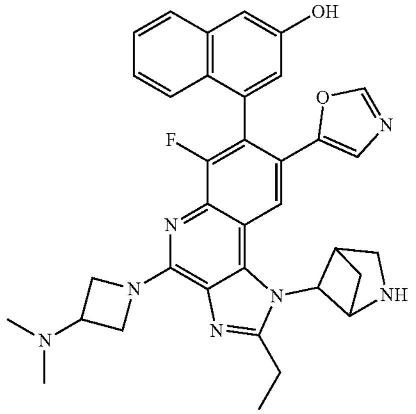 [SMILES: CCc1nc2c(N3CC(N(C)C)C3)nc3c(F)c(-c4cc(O)cc5ccccc45)c(-c4cnco4)cc3c2n1C1C2CNC1C2]

Step 1. tert-butyl (endo)-5-(7-bromo-8-chloro-4-(3-(dimethylamino)azetidin-1-yl)-2-ethyl-6-fluoro-1H-imidazo[4,5-c]quinolin-1-yl)-2-azabicyclo[2.1.1]hexane-2-carboxylate

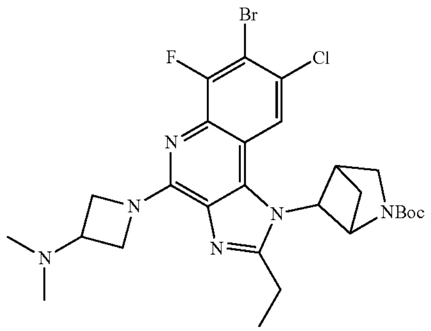 [SMILES: CCc1nc2c(N3CC(N(C)C)C3)nc3c(F)c(Br)c(Cl)cc3c2n1C1C2CC1N(C(=O)OC(C)(C)C)C2]

In a 10 dram vial tert-butyl (endo)-5-((3-amino-7-bromo-6-chloro-2-(3-(dimethylamino)azetidin-1-yl)-8-fluoroquinolin-4-yl)amino)-2-azabicyclo[2.1.1]hexane-2-carboxylate (Intermediate 8, 2720 mg, 4.77 mmol) and 1,1,1-triethoxypropane (2881 μl, 14.32 mmol) in acetic acid (23 mL) was stirred at 80° C. for 0.5 h. The reaction mixture was concentrated and diluted with DCM. Saturated $NaHCO_3$ (30 mL) was added to the reaction mixture followed by extraction with dichloromethane (20 mL×3). The combined organic layers were dried $Na_2SO_4$, filtered and concentrated. The crude product was added to a silica gel column and was eluted with methanol/dichloromethane from 0% to 5% to give tert-butyl (endo)-5-(7-bromo-8-chloro-4-(3-(dimethylamino)azetidin-1-yl)-2-ethyl-6-fluoro-1H-imidazo[4,5-c]quinolin-1-yl)-2-azabicyclo[2.1.1]hexane-2-carboxylate (3.9 g, 100% yield). LCMS calculated for $C_{27}H_{34}BrClFN_6O_2(M+H)^+$: m/z=607.2; found 607.3.

Step 2. tert-butyl (endo)-5-(8-chloro-4-(3-(dimethylamino)azetidin-1-yl)-2-ethyl-6-fluoro-7-(3-(methoxymethoxy)naphthalen-1-yl)-1H-imidazo[4,5-c]quinolin-1-yl)-2-azabicyclo[2.1.1]hexane-2-carboxylate

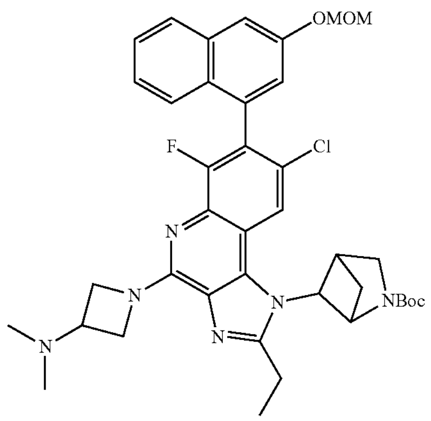

In a 10 dram vial tert-butyl (endo)-5-(7-bromo-8-chloro-4-(3-(dimethylamino)azetidin-1-yl)-2-ethyl-6-fluoro-1H-imidazo[4,5-c]quinolin-1-yl)-2-azabicyclo[2.1.1]hexane-2-carboxylate (1.5 g, 1.850 mmol), 2-(3-(methoxymethoxy)naphthalen-1-yl)-4,4,5,5-tetramethyl-1,3,2-dioxaborolane (Intermediate 4, 1.163 g, 3.70 mmol) and $Na_2CO_3$ (0.981 g, 9.25 mmol) in 1,4-dioxane (10 mL) and water (2 mL) was added $Pd(Ph_3P)_4$ (0.214 g, 0.185 mmol). The reaction mixture was heated to 100° C. for 2 h. $H_2O$ (5 mL) was added to the reaction mixture followed by extraction with dichloromethane (10 mL×3) and then the combined organic layers were washed with $H_2O$ (10 mL), dried with $Na_2SO_4$, filtered and concentrated. The crude product was added to a silica gel column and was eluted with methanol/dichloromethane from 0% to 5% to give tert-butyl (endo)-5-(8-chloro-4-(3-(dimethylamino)azetidin-1-yl)-2-ethyl-6-fluoro-7-(3-(methoxymethoxy)naphthalen-1-yl)-1H-imidazo[4,5-c]quinolin-1-yl)-2-azabicyclo[2.1.1]hexane-2-carboxylate (1.36 g, 100% yield). LCMS calculated for $C_{39}H_{45}ClFN_6O_4$(M+H)$^+$: m/z=715.3; found 715.3.

Step 3. 4-(1-((endo)-2-azabicyclo[2.1.1]hexan-5-yl)-4-(3-(dimethylamino)azetidin-1-yl)-2-ethyl-6-fluoro-8-(oxazol-5-yl)-1H-imidazo[4,5-c]quinolin-7-yl)naphthalen-2-ol In a 1 dram vial tert-butyl (endo)-5-(8-chloro-4-(3-(dimethylamino)azetidin-1-yl)-2-ethyl-6-fluoro-7-(3-(methoxymethoxy)naphthalen-1-yl)-1H-imidazo[4,5-c]quinolin-1-yl)-2-azabicyclo[2.1.1]hexane-2-carboxylate (20 mg, 0.028 mmol) and oxazol-5-ylboronic acid (5.66 mg, 0.034 mmol) were dissolved in 1,4-dioxane (0.5 mL) and water (0.1 mL). $K_3PO_4$ (11.9 mg, 0.056 mmol) and XPhos Pd G2 (2.200 mg, 2.80 μmol) were added to the reaction mixture. The reaction mixture was heated to 105° C. for 2 h. Then concentrated HCl (50 uL) was added. After 30 min, the mixture was diluted with acetonitrile/water and purified using prep-LCMS (XBridge C18 column, eluting with a gradient of acetonitrile/water containing 0.1% TFA, at flow rate of 60 mL/min) to afford the desired products as a TFA salt. The product was isolated as a pair of diastereomers.

Example 6a. Diastereomer 1. Peak 1. LCMS calculated for $C_{35}H_{35}FN_7O_2$(M+H)$^+$ m/z=604.3; found 604.3.

Example 6b. Diastereomer 2. Peak 2. LCMS calculated for $C_{35}H_{35}FN_7O_2$(M+H)$^+$ m/z=604.3; found 604.3.

Example 7a, Example 7b and Example 7c. 3-(1-((endo)-2-azabicyclo[2.1.1]hexan-5-yl)-4-(3-(dimethylamino)azetidin-1-yl)-2-ethyl-6-fluoro-7-(3-hydroxynaphthalen-1-yl)-1H-imidazo[4,5-c]quinolin-8-yl)-3-(1H-pyrazol-1-yl)propanenitrile

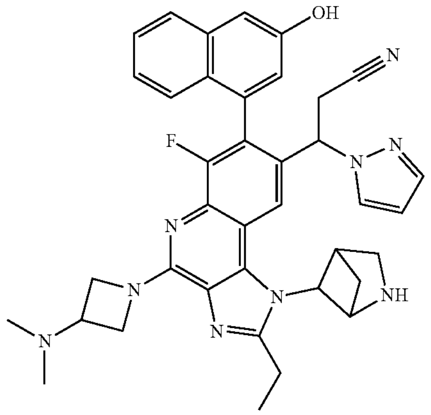 [SMILES: CCc1nc2c(N3CC(N(C)C)C3)nc3c(F)c(-c4cc(O)cc5ccccc45)c(C(CC#N)n4cccn4)cc3c2n1C1C2CNC1C2]

Step 1. tert-butyl (endo)-5-(8-((E)-2-cyanovinyl)-4-(3-(dimethylamino)azetidin-1-yl)-2-ethyl-6-fluoro-7-(3-(methoxymethoxy)naphthalen-1-yl)-1H-imidazo[4,5-c]quinolin-1-yl)-2-azabicyclo[2.1.1]hexane-2-carboxylate

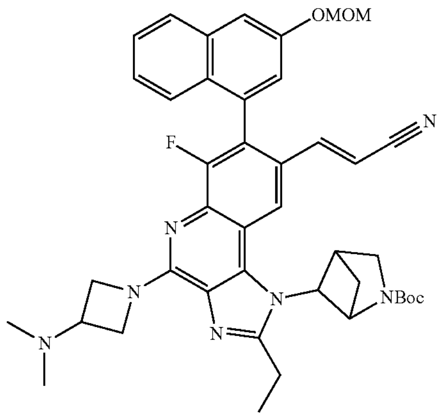

In a 10 dram vial, tert-butyl (endo)-5-((3-amino-6-((E)-2-cyanovinyl)-2-(3-(dimethylamino)azetidin-1-yl)-8-fluoro-7-(3-(methoxymethoxy)naphthalen-1-yl)quinolin-4-yl)amino)-2-azabicyclo[2.1.1]hexane-2-carboxylate (Intermediate 5, 2720 mg, 4.77 mmol) and 1,1,1-triethoxypropane (2881 μl, 14.32 mmol) in acetic acid (23 mL) was stirred at 80° C. for 0.5 h. The reaction mixture was concentrated and diluted with DCM. Saturated $NaHCO_3$ (30 mL) was added to the reaction mixture followed by extraction with dichloromethane (20 mL×3). The combined organic layers were dried $Na_2SO_4$, filtered and concentrated.

The crude product was added to a silica gel column and was eluted with methanol/dichloromethane from 0% to 5% to give tert-butyl (endo)-5-(8-((E)-2-cyanovinyl)-4-(3-(dimethylamino)azetidin-1-yl)-2-ethyl-6-fluoro-7-(3-(methoxymethoxy)naphthalen-1-yl)-1H-imidazo[4,5-c]quinolin-1-yl)-2-azabicyclo[2.1.1]hexane-2-carboxylate (1.36 g, 100% yield). LCMS calculated for $C_{42}H_{47}FN_7O_4(M+H)^-$: m/z=732.4; found 732.3.

Step 2. 3-(1-((endo)-2-azabicyclo[2.1.1]hexan-5-yl)-4-(3-(dimethylamino)azetidin-1-yl)-2-ethyl-6-fluoro-7-(3-hydroxynaphthalen-1-yl)-1H-imidazo[4,5-c]quinolin-8-yl)-3-(1H-pyrazol-1-yl)propanenitrile In a 1 dram vial, tert-butyl (endo)-5-(8-((E)-2-cyanovinyl)-4-(3-(dimethylamino)azetidin-1-yl)-2-ethyl-6-fluoro-7-(3-(methoxymethoxy)naphthalen-1-yl)-1H-imidazo[4,5-c]quinolin-1-yl)-2-azabicyclo[2.1.1]hexane-2-carboxylate (10 mg, 0.014 mmol) in acetonitrile (0.137 ml) was added pyrrazole (10 mg, 0.14 mmol) and DBU (20.6 uL, 0.14 mmol). The reaction mixture was stirred at 95° C. for 5 h. Then concentrated HCl (50 uL) was added. After 30 min, the mixture was diluted with acetonitrile/water and purified using prep-LCMS (XBridge C18 column, eluting with a gradient of acetonitrile/water containing 0.1% TFA, at flow rate of 60 mL/min) to afford the desired products as a TFA salt. The product was isolated as a pair of diastereomers.

Example 7a. Diastereomer 1. Peak 1. LCMS calculated for $C_{38}H_{39}FN_9O$ $(M+H)^+$ m/z=656.3; found 656.3.

Example 7b. Diastereomer 2. Peak 2. LCMS calculated for $C_{38}H_{39}FN_9O$ $(M+H)^+$ m/z=656.3; found 656.3.

Example 7c. Diastereomer 3. Peak 2. LCMS calculated for $C_{38}H_{39}FN_9O$ $(M+H)^+$ m/z=656.3; found 656.3.

Example 8a, Example 8b and Example 8c. 3-(1-((endo)-2-azabicyclo[2.1.1]hexan-5-yl)-4-(3-(dimethylamino)azetidin-1-yl)-2-ethyl-6-fluoro-7-(3-hydroxynaphthalen-1-yl)-1H-imidazo[4,5-c]quinolin-8-yl)-3-(4-(hydroxymethyl)-1H-pyrazol-1-yl)propanenitrile

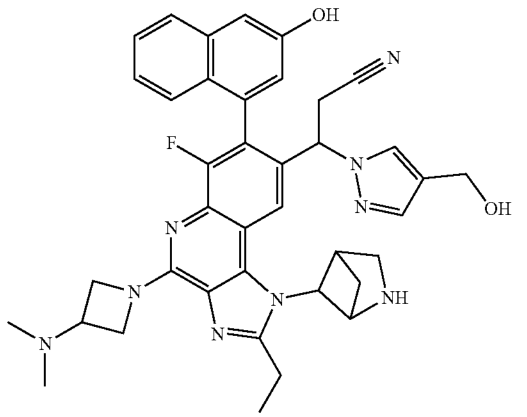 [SMILES: CCc1nc2c(N3CC(N(C)C)C3)nc3c(F)c(-c4cc(O)cc5ccccc45)c(C(CC#N)n4cc(CO)cn4)cc3c2n1C1C2CNC1C2]

This compound was prepared according to the procedure described for Example 7, replacing pyrazole with (1H-pyrazol-4-yl)methanol in Step 2. The product 3-(1-((endo)-2-azabicyclo[2.1.1]hexan-5-yl)-4-(3-(dimethylamino)azetidin-1-yl)-2-ethyl-6-fluoro-7-(3-hydroxynaphthalen-1-yl)-1H-imidazo[4,5-c]quinolin-8-yl)-3-(4-(hydroxymethyl)-1H-pyrazol-1-yl)propanenitrile was isolated as a pair of diastereomers.

Example 8a. Diastereomer 1. Peak 1. LCMS calculated for $C_{39}H_{41}FN_9O_2(M+H)^+$ m/z=686.3; found 686.3.

Example 8b. Diastereomer 1. Peak 1. LCMS calculated for $C_{39}H_{41}FN_9O_2(M+H)^+$ m/z=686.3; found 686.3.

Example 8c. Diastereomer 1. Peak 1. LCMS calculated for $C_{39}H_{41}FN_9O_2(M+H)^+$ m/z=686.3; found 686.3.

Example 9. 3-(8-((1H-pyrazol-1-yl)methyl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-2-yl)-N,N-dimethylpropanamide

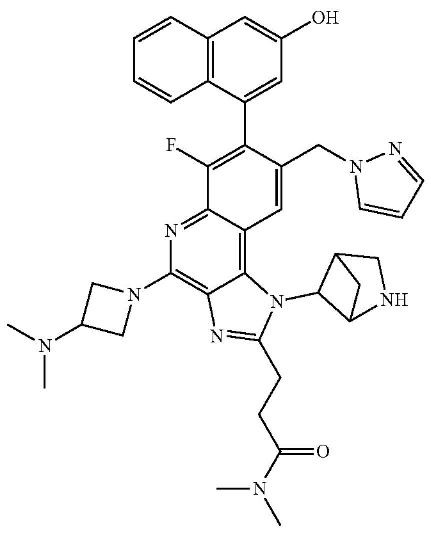 [SMILES: CN(C)C(=O)CCc1nc2c(N3CC(N(C)C)C3)nc3c(F)c(-c4cc(O)cc5ccccc45)c(Cn4cccn4)cc3c2n1C1C2CNC1C2]

Step 1. tert-butyl (endo)-5-(7-bromo-8-chloro-2-(3-(dimethylamino)-3-oxopropyl)-4-(3-(dimethylamino)azetidin-1-yl)-6-fluoro-1H-imidazo[4,5-c]quinolin-1-yl)-2-azabicyclo[2.1.1]hexane-2-carboxylate

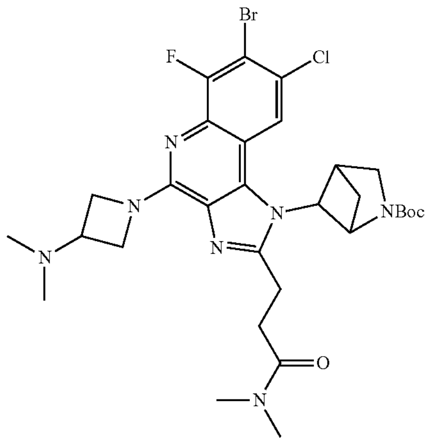 [SMILES: CN(C)C(=O)CCc1nc2c(N3CC(N(C)C)C3)nc3c(F)c(Br)c(Cl)cc3c2n1C1C2CC1N(C(=O)OC(C)(C)C)C2]

In a 10 dram vial, tert-butyl (endo)-5-((3-amino-7-bromo-6-chloro-2-(3-(dimethylamino)azetidin-1-yl)-8-fluoroquinolin-4-yl)amino)-2-azabicyclo[2.1.1]hexane-2-carboxylate (Intermediate 8, 1153 mg, 2.023 mmol) in ethanol (10 mL)

was added N,N-dimethyl-4-oxobutanamide (523 mg, 4.05 mmol). The reaction mixture was stirred at 70° C. for 18 h. The reaction mixture was concentrated to dryness and added to a silica gel column and was eluted with methanol/dichloromethane from 0% to 5% to give tert-butyl (endo)-5-(7-bromo-8-chloro-2-(3-(dimethylamino)-3-oxopropyl)-4-(3-(dimethylamino)azetidin-1-yl)-6-fluoro-1H-imidazo[4,5-c]quinolin-1-yl)-2-azabicyclo[2.1.1]hexane-2-carboxylate (884 mg, 1.302 mmol, 64.3% yield). LCMS calculated for $C_{30}H_{39}BrClFN_7O_3(M+H)^+$: m/z=678.2; found 678.3.

Step 2. tert-butyl (endo)-5-(8-chloro-2-(3-(dimethylamino)-3-oxopropyl)-4-(3-(dimethylamino)azetidin-1-yl)-6-fluoro-7-(3-(methoxymethoxy)naphthalen-1-yl)-1H-imidazo[4,5-c]quinolin-1-yl)-2-azabicyclo[2.1.1]hexane-2-carboxylate

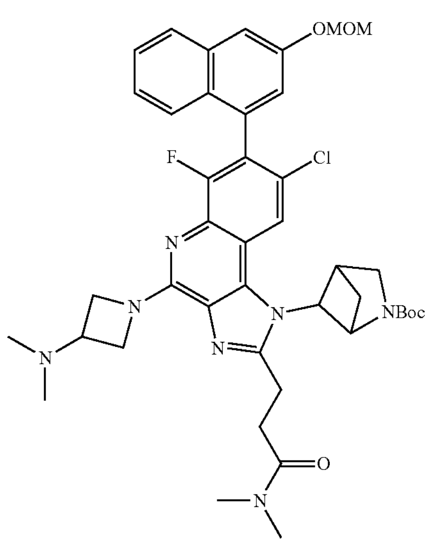

In a 10 dram vial, tert-butyl (endo)-5-(7-bromo-8-chloro-2-(3-(dimethylamino)-3-oxopropyl)-4-(3-(dimethylamino)azetidin-1-yl)-6-fluoro-1H-imidazo[4,5-c]quinolin-1-yl)-2-azabicyclo[2.1.1]hexane-2-carboxylate (0.884 g, 1.302 mmol), 2-(3-(methoxymethoxy)naphthalen-1-yl)-4,4,5,5-tetramethyl-1,3,2-dioxaborolane (Intermediate 4, 0.614 g, 1.953 mmol) and $Na_2CO_3$ (0.690 g, 6.51 mmol) in 1,4-dioxane (6.5 mL) and water (1.1 mL) was added $Pd(Ph_3P)_4$ (0.301 g, 0.260 mmol). The reaction mixture was heated to 105° C. for 2 h. $H_2O$ (10 mL) was added to the reaction mixture followed by extraction with dichloromethane (10 mL×3) and then the combined organic layers were washed with $H_2O$ (20 mL), dried with $Na_2SO_4$, filtered and concentrated. The crude product was added to a silica gel column and was eluted with methanol/dichloromethane from 0% to 5% to give tert-butyl (endo)-5-(8-chloro-2-(3-(dimethylamino)-3-oxopropyl)-4-(3-(dimethylamino)azetidin-1-yl)-6-fluoro-7-(3-(methoxymethoxy)naphthalen-1-yl)-1H-imidazo[4,5-c]quinolin-1-yl)-2-azabicyclo[2.1.1]hexane-2-carboxylate (0.895 g, 87% yield). LCMS calculated for $C_{42}H_{50}ClFN_7O_5(M+H)^+$: m/z=786.4; found 786.3.

Step 3. tert-butyl (endo)-5-(2-(3-(dimethylamino)-3-oxopropyl)-4-(3-(dimethylamino)azetidin-1-yl)-6-fluoro-7-(3-(methoxymethoxy)naphthalen-1-yl)-8-vinyl-1H-imidazo[4,5-c]quinolin-1-yl)-2-azabicyclo[2.1.1]hexane-2-carboxylate

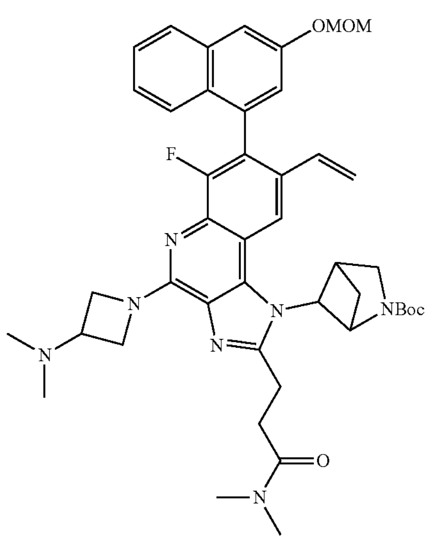

In a 10 dram vial, tert-butyl (endo)-5-(8-chloro-2-(3-(dimethylamino)-3-oxopropyl)-4-(3-(dimethylamino)azetidin-1-yl)-6-fluoro-7-(3-(methoxymethoxy)naphthalen-1-yl)-1H-imidazo[4,5-c]quinolin-1-yl)-2-azabicyclo[2.1.1]hexane-2-carboxylate (880 mg, 1.119 mmol), 4,4,5,5-tetramethyl-2-vinyl-1,3,2-dioxaborolane (862 mg, 5.60 mmol) and $K_3PO_4$ (712 mg, 3.36 mmol) in 1,4-dioxane (5.60 ml) and water (1.1 mL) was added XPhos Pd G2 (176 mg, 0.224 mmol). The reaction mixture was heated to 110° C. for 2 h. $H_2O$ (5 mL) was added to the reaction mixture followed by extraction with dichloromethane (10 mL×3) and then the combined organic layers were washed with $H_2O$ (20 mL), dried with $Na_2SO_4$, filtered and concentrated. The crude product was added to a silica gel column and was eluted with methanol/dichloromethane from 0% to 5% to give tert-butyl (endo)-5-(2-(3-(dimethylamino)-3-oxopropyl)-4-(3-(dimethylamino)azetidin-1-yl)-6-fluoro-7-(3-(methoxymethoxy)naphthalen-1-yl)-8-vinyl-1H-imidazo[4,5-c]quinolin-1-yl)-2-azabicyclo[2.1.1]hexane-2-carboxylate (480 mg, 55.1% yield). LCMS calculated for $C_{44}H_{53}FN_7O_5$ (M+H)$^+$: m/z=778.4; found 778.3.

Step 4. tert-butyl (endo)-5-(2-(3-(dimethylamino)-3-oxopropyl)-4-(3-(dimethylamino)azetidin-1-yl)-6-fluoro-8-formyl-7-(3-(methoxymethoxy)naphthalen-1-yl)-1H-imidazo[4,5-c]quinolin-1-yl)-2-azabicyclo[2.1.1]hexane-2-carboxylate

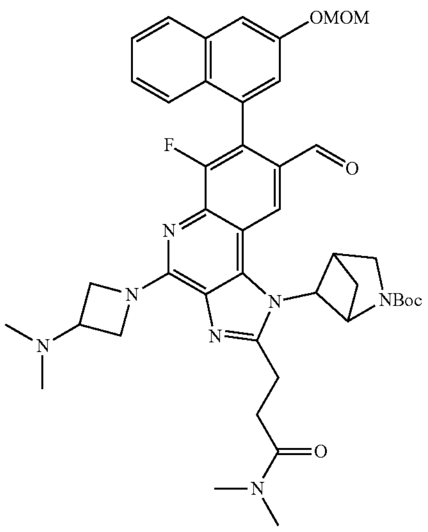

In a 10 dram vial, tert-butyl (endo)-5-(2-(3-(dimethylamino)-3-oxopropyl)-4-(3-(dimethylamino)azetidin-1-yl)-6-fluoro-7-(3-(methoxymethoxy)naphthalen-1-yl)-8-vinyl-1H-imidazo[4,5-c]quinolin-1-yl)-2-azabicyclo[2.1.1]hexane-2-carboxylate (462 mg, 0.594 mmol) and sodium periodate (191 mg, 0.891 mmol) in THF (3.0 mL) and water (3.0 ml) was added 0.4% aq. osmium tetroxide (466 μL, 5.94 μmol). The reaction mixture was stirred for 3 h. $H_2O$ (10 mL) was added to the reaction mixture followed by extraction with ethyl acetate (10 mL×3) and then the combined organic layers were washed with $H_2O$ (20 mL), dried with $Na_2SO_4$, concentrated and used for the next step without further purification. LCMS calculated for $C_{43}H_{51}FN_7O_6$ $(M+H)^+$: m/z=780.4; found 780.3.

Step 5. tert-butyl (endo)-5-(2-(3-(dimethylamino)-3-oxopropyl)-4-(3-(dimethylamino)azetidin-1-yl)-6-fluoro-8-(hydroxymethyl)-7-(3-(methoxymethoxy)naphthalen-1-yl)-1H-imidazo[4,5-c]quinolin-1-yl)-2-azabicyclo[2.1.1]hexane-2-carboxylate

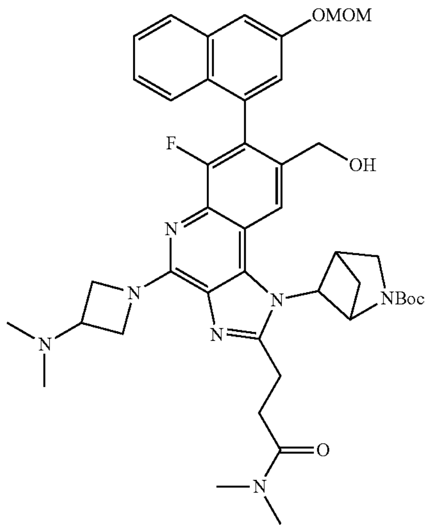

In a 10 dram vial, tert-butyl (endo)-5-(2-(3-(dimethylamino)-3-oxopropyl)-4-(3-(dimethylamino)azetidin-1-yl)-6-fluoro-8-formyl-7-(3-(methoxymethoxy)naphthalen-1-yl)-1H-imidazo[4,5-c]quinolin-1-yl)-2-azabicyclo[2.1.1]hexane-2-carboxylate (0.234 g, 0.3 mmol) in MeOH (3.0 mL) was added $NaBH_4$ (0.011 g, 0.300 mmol). The reaction mixture was stirred for 30 min. $H_2O$ (15 mL) was added to the reaction mixture followed by extraction with dichloromethane (10 mL×3) and then the combined organic layers were washed with $H_2O$ (20 mL), dried with $Na_2SO_4$, filtered and concentrated. The crude product was added to a silica gel column and was eluted with methanol/dichloromethane from 0% to 5% to give tert-butyl (endo)-5-(2-(3-(dimethylamino)-3-oxopropyl)-4-(3-(dimethylamino)azetidin-1-yl)-6-fluoro-8-(hydroxymethyl)-7-(3-(methoxymethoxy)naphthalen-1-yl)-1H-imidazo[4,5-c]quinolin-1-yl)-2-azabicyclo[2.1.1]hexane-2-carboxylate (80 mg, 34.1% yield). LCMS calculated for $C_{43}H_{53}FN_7O_6(M+H)^+$: m/z=782.4; found 782.3.

Step 6. 3-(8-((1H-pyrazol-1-yl)methyl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-2-yl)-N,N-dimethylpropanamide In a 1 dram vial, tert-butyl (endo)-5-(2-(3-(dimethylamino)-3-oxopropyl)-4-(3-(dimethylamino)azetidin-1-yl)-6-fluoro-8-(hydroxymethyl)-7-(3-(methoxymethoxy)naphthalen-1-yl)-1H-imidazo[4,5-c]quinolin-1-yl)-2-azabicyclo[2.1.1]hexane-2-carboxylate (0.02 g, 0.026 mmol) in DCM (0.5 mL) was added TEA (0.021 mL, 0.153 mmol) and Ms-Cl (5.98 μl, 0.077 mmol) at −78° C. After 15 min, pyrazole (4.4 mg, 0.077 mmol) was added. The resulting mixture was allowed to warm up slowly and stirred at r.t. After 16 h, the reaction mixture was concentrated to dryness and dissolved in MeOH (0.5 mL). Conc. HCl (0.5 mL) was added to the reaction mixture. After 30 min, the mixture was diluted with acetonitrile/water and purified using prep-LCMS (XBridge C18 column, eluting with a gradient of acetonitrile/water containing 0.1% TFA, at flow rate of 60 mL/min) to afford the desired product as a TFA salt and a mixture of diastereomers. LCMS calculated for $C_{39}H_{43}FN_9O_2(M+H)^+$ m/z=688.4; found 688.3.

Examples 10. 3-(1-(2-azabicyclo[2.1.1]hexan-5-yl)-8-(2-cyanoethyl)-7-(2,3-dichloro-6-hydroxyphenyl)-4-(3-(dimethylamino)azetidin-1-yl)-6-fluoro-1H-imidazo[4,5-c]quinolin-2-yl)-N,N-dimethylpropanamide

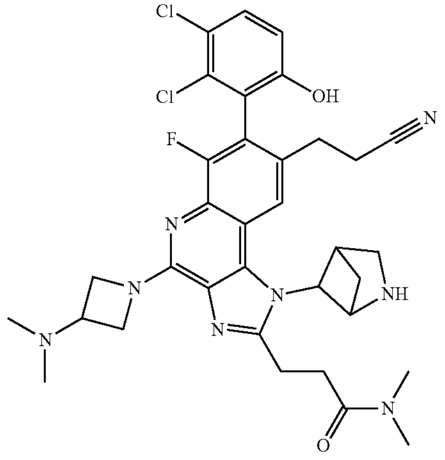 [SMILES: CN(C)C(=O)CCc1nc2c(N3CC(N(C)C)C3)nc3c(F)c(-c4c(O)ccc(Cl)c4Cl)c(CCC#N)cc3c2n1C1C2CNC1C2]

Step 1. tert-butyl 5-(8-(2-cyanoethyl)-2-(3-(dimethylamino)-3-oxopropyl)-4-(3-(dimethylamino)azetidin-1-yl)-6-fluoro-7-(4,4,5,5-tetramethyl-1,3,2-dioxaborolan-2-yl)-1H-imidazo[4,5-c]quinolin-1-yl)-2-azabicyclo[2.1.1]hexane-2-carboxylate

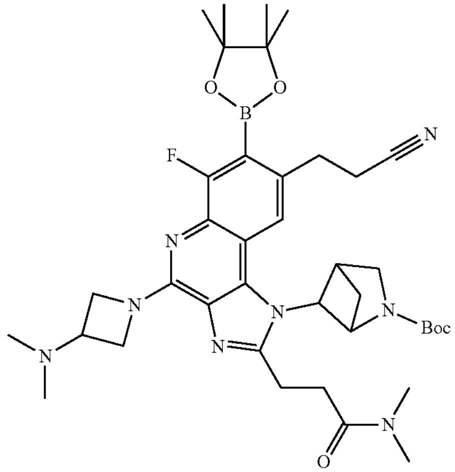 [SMILES: CN(C)C(=O)CCc1nc2c(N3CC(N(C)C)C3)nc3c(F)c(B4OC(C)(C)C(C)(C)O4)c(CCC#N)cc3c2n1C1C2CC1N(C(=O)OC(C)(C)C)C2]

To a 10 dram vial, tert-butyl 5-(7-bromo-8-(2-cyanoethyl)-2-(3-(dimethylamino)-3-oxopropyl)-4-(3-(dimethylamino)azetidin-1-yl)-6-fluoro-1H-imidazo[4,5-c]quinolin-1-yl)-2-azabicyclo[2.1.1]hexane-2-carboxylate (Intermediate 9: 1.2 g, 1.7 mmol),bis(pinacolato)diboron (2.6 g, 10.3 mmol), PCy3 Pd G4 (0.228 g, 0.344 mmol), potassium acetate (1.013 g, 10.3 mmol) in DMF (17.2 mL) were added. The reaction mixture was heated to 85° C. for 5 h. After cooling to room temperature, the reaction mixture was poured into water and extracted with ethyl acetated. The organic phase was concentrated and purified through flash chromatography (DCM/MeOH=0-20%) to give tert-butyl 5-(8-(2-cyanoethyl)-2-(3-(dimethylamino)-3-oxopropyl)-4-(3-(dimethylamino)azetidin-1-yl)-6-fluoro-7-(4,4,5,5-tetramethyl-1,3,2-dioxaborolan-2-yl)-1H-imidazo[4,5-c]quinolin-1-yl)-2-azabicyclo[2.1.1]hexane-2-carboxylate (0.5 g, 39% yield). LCMS calculated for $C_{39}H_{55}BFN_8O_5(M+H)^+$: m/z=745.4; found 745.4.

Step 2. 3-(1-(2-azabicyclo[2.1.1]hexan-5-yl)-8-(2-cyanoethyl)-7-(2,3-dichloro-6-hydroxyphenyl)-4-(3-(dimethylamino)azetidin-1-yl)-6-fluoro-1H-imidazo[4,5-c]quinolin-2-yl)-N,N-dimethylpropanamide To a 1 dram vial 3-(1-(2-azabicyclo[2.1.1]hexan-5-yl)-8-(2-cyanoethyl)-4-(3-(dimethylamino)azetidin-1-yl)-6-fluoro-7-(4,4,5,5-tetramethyl-1,3,2-dioxaborolan-2-yl)-1H-imidazo[4,5-c]quinolin-2-yl)-N,N-dimethylpropanamide (30 mg, 0.04 mmol), 2-bromo-3,4-dichlorophenol (19.5 mg, 0.08 mmol), RuPhos Pd G3 (6.7 mg, 8.1 μmol) and RuPhos (3.8 mg, 8.1 μmol) in dioxane/water (4/1, a total of 0.5 mL) was stirred at 80° C. for 3 h. The reaction mixture was filtered through a SiliaPrep SPE Thiol Cartridge. The filtrate was concentrated and then dissolved in DCM/TFA (1/1, a total of 2.0 mL). The mixture was then concentrated, diluted with acetonitrile/water and purified using prep-LCMS (XBridge C18 column, eluting with a gradient of acetonitrile/water containing 0.1% TFA, at flow rate of 60 mL/min) to afford the desired product as a TFA salt and a mixture of diastereomers. LCMS calculated for $C_{34}H_{38}Cl_2FN_8O_2(M+H)^+$ m/z=678.2; found 678.2.

Examples 11. 3-(1-(2-azabicyclo[2.1.1]hexan-5-yl)-7-(3-chloro-2-cyclopropyl-5-hydroxyphenyl)-4-(3-(dimethylamino)azetidin-1-yl)-6-fluoro-1H-imidazo[4,5-c]quinolin-2-yl)-N,N-dimethylpropanamide

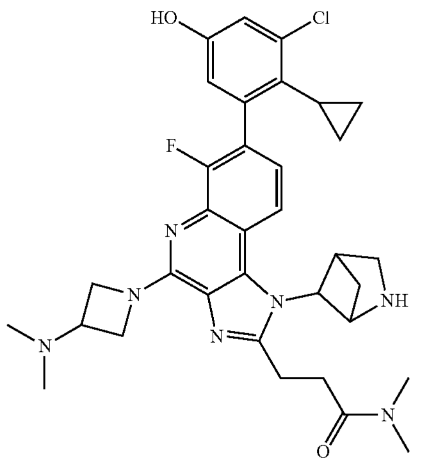

Step 1. 7-bromo-8-fluoro-2H-benzo[d][1,3]oxazine-2,4(1H)-dione

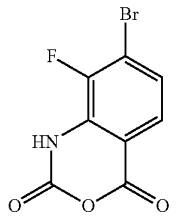

To a solution of 2-amino-4-bromo-3-fluorobenzoic acid (10.0 g, 42.7 mmol) in 1,4-dioxane (300 mL) was added triphosgene (12.68 g, 42.7 mmol), and stirred at 100° C. for 1 h. After cooling to r.t., ice was added until a solid precipitated. The mixture was then fully diluted with water (final volume ~600 mL) and the solid collected by filtration then air dried. The crude product was used in the next step without further purification.

Step 2. 7-bromo-8-fluoro-3-nitroquinoline-2,4-diol

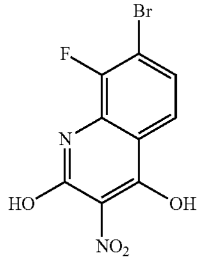

DIPEA (11.4 ml, 65.4 mmol) was added to a solution of ethyl 2-nitroacetate (4.35 g, 32.7 mmol) in toluene (20.0 mL) at r.t. and stirred for 10 min. 7-bromo-8-fluoro-2H-benzo[d][1,3]oxazine-2,4(1H)-dione (8.5 g, 32.7 mmol) was then added to the reaction mixture and the reaction was stirred at 95° C. for 3 h. The reaction was cooled with ice water and then 1 N HCl (70 mL) was added. The solid precipitate was collected via filtration then washed with small amount of ethyl acetate to provide the desired product as a yellow solid (7.5 g, 76%). LCMS calculated for $C_9H_5rFN_2O_4(M+H)^+$: m/z=302.9; found 302.9.

Step 3. 7-bromo-2,4-dichloro-8-fluoro-3-nitroquinoline

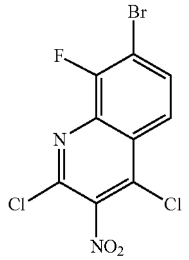 [SMILES: O=[N+]([O-])c1c(Cl)nc2c(F)c(Br)ccc2c1Cl]

DIPEA (8.1 mL, 46.2 mmol) was added to a mixture of 7-bromo-8-fluoro-3-nitroquinoline-2,4-diol (7.0 g, 23.1 mmol) in $POCl_3$ (10.8 mL, 115 mmol) and then the reaction was stirred at 105° C. for 3 h. The solvent was removed under vacuum and then azeotroped with toluene 3 times to provide the crude material which was used in the next step without further purification.

Step 4. tert-butyl 5-((3-amino-7-bromo-2-(3-(dimethylamino)azetidin-1-yl)-8-fluoroquinolin-4-yl)amino)-2-azabicyclo[2.1.1]hexane-2-carboxylate

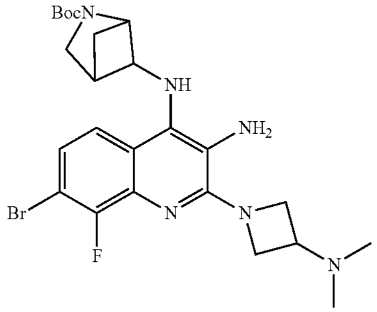 [SMILES: CN(C)C1CN(c2nc3c(F)c(Br)ccc3c(NC3C4CC3N(C(=O)OC(C)(C)C)C4)c2N)C1]

To a mixture of 7-bromo-2,4-dichloro-8-fluoro-3-nitroquinoline (5.0 g, 14.7 mmol) in $CH_2Cl_2$ (100 ml) was added tert-butyl (endo)-5-amino-2-azabicyclo[2.1.1]hexane-2-carboxylate (3.06 g, 15.44 mmol) and DIPEA (15.4 mL, 88 mmol) and the reaction was stirred at 55° C. for 1 h. Then N,N-dimethylazetidin-3-amine dihydrochloride (3.01 g, 22.06 mmol) was added. After heating at 55° C. for another 2 h, the mixture was concentrated to dryness. Sodium hydrosulfite (13.6 g, 66.2 mmol) in water (50.0 mL) was added to a solution of above crude mixture and 30% aq. ammonium hydroxide (50 mL) in MeOH (100 mL) at 0° C. After 10 min, water (100 mL) was added to the reaction mixture followed by extraction with dichloromethane (100 mL×3). The combined organic layers were dried $Na_2SO_4$, filtered and concentrated. The crude product was added to a silica gel column and was eluted with methanol/dichloromethane from 0% to 10% to give tert-butyl 5-((3-amino-7-bromo-2-(3-(dimethylamino)azetidin-1-yl)-8-fluoroquinolin-4-yl)amino)-2-azabicyclo[2.1.1]hexane-2-carboxylate (6.5 g, 83% yield). LCMS calculated for $C_{24}H_{33}BrFN_6O_2$ $(M+H)^+$: m/z=535.2; found 535.2.

Step 5. tert-butyl 5-(7-bromo-2-(3-(dimethylamino)-3-oxopropyl)-4-(3-(dimethylamino)azetidin-1-yl)-6-fluoro-1H-imidazo[4,5-c]quinolin-1-yl)-2-azabicyclo[2.1.1]hexane-2-carboxylate

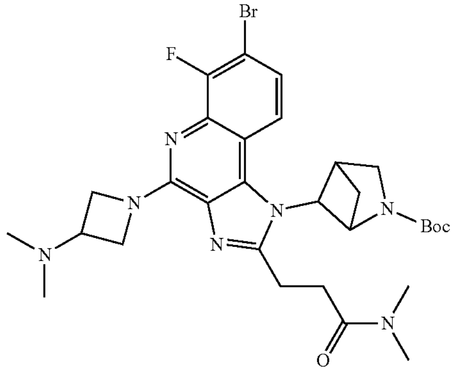 [SMILES: CN(C)C(=O)CCc1nc2c(N3CC(N(C)C)C3)nc3c(F)c(Br)ccc3c2n1C1C2CC1N(C(=O)OC(C)(C)C)C2]

In a 1 dram vial, tert-butyl 5-((3-amino-7-bromo-2-(3-(dimethylamino)azetidin-1-yl)-8-fluoroquinolin-4-yl)amino)-2-azabicyclo[2.1.1]hexane-2-carboxylate (0.5 g, 0.934 mmol), N,N-dimethyl-4-oxobutanamide (0.18 g, 1.4 mmol) in ethanol (5 mL) was stirred at 80° C. for 2 hours with the cap on and then stirred open to air for another 4 hours. The reaction was concentrated and used directly in the next step without further purification. LCMS calculated for $C_{30}H_{40}BrFN_7O_3(M+H)^+$: m/z=644.2; found 644.3.

Step 6. 3-(1-(2-azabicyclo[2.1.1]hexan-5-yl)-7-(3-chloro-2-cyclopropyl-5-hydroxyphenyl)-4-(3-(dimethylamino)azetidin-1-yl)-6-fluoro-1H-imidazo[4,5-c]quinolin-2-yl)-N,N-dimethylpropanamide In a 1 dram vial, tert-butyl 5-(7-bromo-2-(3-(dimethylamino)-3-oxopropyl)-4-(3-(dimethylamino)azetidin-1-yl)-6-fluoro-1H-imidazo[4,5-c]quinolin-1-yl)-2-azabicyclo[2.1.1]hexane-2-carboxylate (30 mg, 0.047 mmol), 2-(3-chloro-2-cyclopropyl-5-(methoxymethoxy)phenyl)-4,4,5,5-tetramethyl-1,3,2-dioxaborolane (31.5 mg, 0.093 mmol), $Pd(PPh_3)_4$(10.8 mg, 9.31 μmol) and potassium carbonate (19.3 mg, 0.14 mmol) were added in dioxane/water (4/1, a total of 0.5 mL). The reaction mixture was refluxed for 3 h. After cooling to room temperature, the reaction mixture was filtered through a SiliaPrep SPE Thiol Cartridge. The filtrate was concentrated and then dissolved in DCM/TFA (1/1 ratio, a total of 2.0 mL). The mixture was then concentrated, diluted with acetonitrile/water and purified using prep-LCMS (XBridge C18 column, eluting with a gradient of acetonitrile/water containing 0.1% TFA, at flow rate of 60 mL/min) to afford the desired product as a TFA salt and a mixture of diastereomers. LCMS calculated for $C_{34}H_{40}ClFN_7O_2(M+H)^+$ m/z=632.3; found 632.3.

Example 12. 3-(1-((endo)-2-azabicyclo[2.1.1]hexan-5-yl)-8-(2-cyanoethyl)-6-(3-cyanophenyl)-4-(3-(dimethylamino)azetidin-1-yl)-7-(3-hydroxynaphthalen-1-yl)-1H-imidazo[4,5-c]quinolin-2-yl)-N,N-dimethylpropanamide

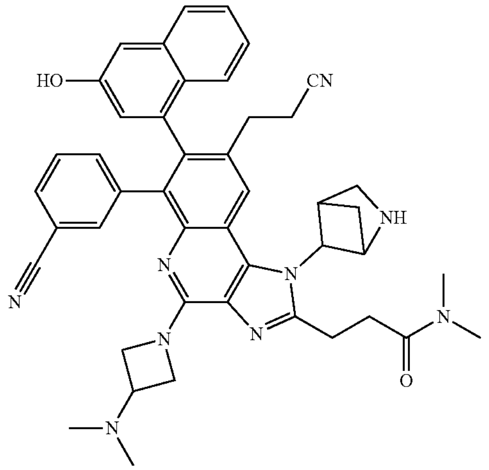 [SMILES: CN(C)C(=O)CCc1nc2c(N3CC(N(C)C)C3)nc3c(-c4cccc(C#N)c4)c(-c4cc(O)cc5ccccc45)c(CCC#N)cc3c2n1C1C2CNC1C2]

A solution of tert-butyl (endo)-5-(6-bromo-7-chloro-8-(2-cyanoethyl)-2-(3-(dimethylamino)-3-oxopropyl)-4-(3-(dimethylamino)azetidin-1-yl)-1H-imidazo[4,5-c]quinolin-1-yl)-2-azabicyclo[2.1.1]hexane-2-carboxylate (Intermediate 11, 30 mg, 0.042 mmol), (3-cyanophenyl)boronic acid (9.3 mg, 0.063 mmol), palladium tetrakis (9.7 mg, 8.4 μmol) and $K_3PO_4$ (26.8 mg, 0.126 mmol) in dioxane (1.0 mL)/water (0.2 mL) was flushed with $N_2$ for 2 min and stirred at 100° C. for 1 h. The resulting mixture was cooled to room temp and quenched with water and extracted with EtOAc. The combined organic extracts were dried and concentrated under reduced pressure and used without further purification. LCMS calculated for $C_{40}H_{47}ClN_9O_3(M+H)^+$: m/z=736.4; found 736.4.

A solution of the above residue, (4-(4,4,5,5-tetramethyl-1,3,2-dioxaborolan-2-yl)naphthalen-2-ol (17 mg, 0.063 mmol), XPhos Pd G2 (6.6 mg, 8.4 μmol) and $K_3PO_4$ (26.8 mg, 0.126 mmol) in dioxane (1.0 mL)/water (0.2 mL) was flushed with $N_2$ for 2 min and stirred at 100° C. for 1 h. The resulting mixture was filtered through a thiol cartridge and concentrated. DCM (1 mL) was then added followed by slow addition of TFA (1 mL). The mixture was stirred at room temperature for 30 min, diluted with MeOH and purified using prep-LCMS (XBridge C18 column, eluting with a gradient of acetonitrile/water containing 0.1% TFA, at flow rate of 60 mL/min) to afford the desired products as a TFA salt. The product was isolated as a mixture of diastereomers. LCMS calculated for $C_{45}H_{46}ClN_9O_2(M+H)^+$: m/z=744.4; found 744.4.

Example 13. 3-(1-((endo)-2-azabicyclo[2.1.1]hexan-5-yl)-8-(2-cyanoethyl)-4-(3-(dimethylamino)azetidin-1-yl)-7-(3-hydroxynaphthalen-1-yl)-6-(1-(pyridin-2-yl)-1H-pyrazol-4-yl)-1H-imidazo[4,5-c]quinolin-2-yl)-N,N-dimethylpropanamide

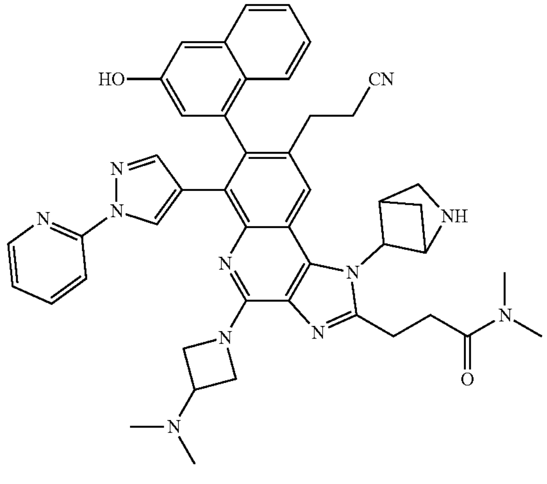 [SMILES: CN(C)C(=O)CCc1nc2c(N3CC(N(C)C)C3)nc3c(-c4cnn(-c5ccccn5)c4)c(-c4cc(O)cc5ccccc45)c(CCC#N)cc3c2n1C1C2CNC1C2]

This compound was prepared according to the procedure described for Example 12, replacing (3-cyanophenyl)boronic acid with 2-(4-(4,4,5,5-tetramethyl-1,3,2-dioxaborolan-2-yl)-1H-pyrazol-1-yl)pyridine. The product was isolated as a TFA salt and a mixture of diastereomers. LCMS calculated for $C_{46}H_{48}N_{11}O_2(M+H)^+$: m/z=786.4; found 786.4.

Example 14. 3-(6-(benzyloxy)-1-((endo)-2-azabicyclo[2.1.1]hexan-5-yl)-8-(2-cyanoethyl)-4-(3-(dimethylamino)azetidin-1-yl)-7-(7-fluoronaphthalen-1-yl)-1H-imidazo[4,5-c]quinolin-2-yl)-N,N-dimethylpropanamide

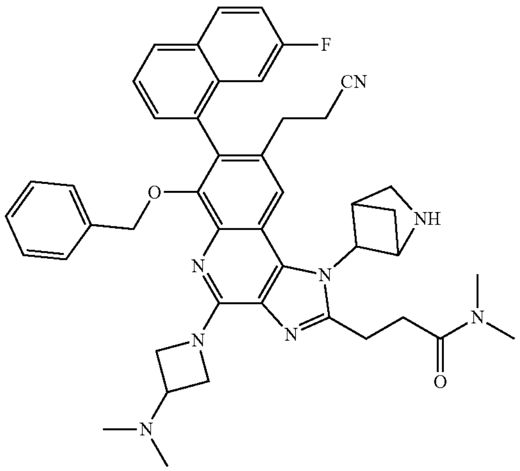 [SMILES: CN(C)C(=O)CCc1nc2c(N3CC(N(C)C)C3)nc3c(OCc4ccccc4)c(-c4cccc5ccc(F)cc45)c(CCC#N)cc3c2n1C1C2CNC1C2]

Step 1. tert-butyl (endo)-5-(7-chloro-8-(2-cyanoethyl)-2-(3-(dimethylamino)-3-oxopropyl)-4-(3-(dimethylamino)azetidin-1-yl)-6-hydroxy-1H-imidazo[4,5-c]quinolin-1-yl)-2-azabicyclo[2.1.1]hexane-2-carboxylate

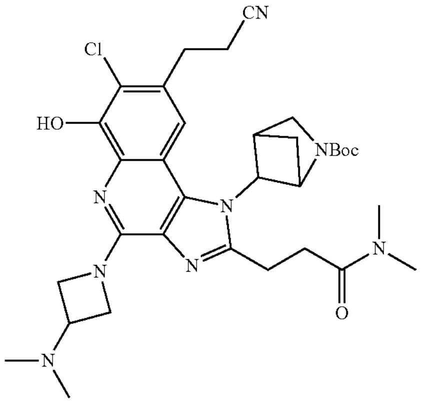

In a 1 dram vial, a solution of tert-butyl (endo)-5-(6-bromo-7-chloro-8-(2-cyanoethyl)-2-(3-(dimethylamino)-3-oxopropyl)-4-(3-(dimethylamino)azetidin-1-yl)-1H-imidazo[4,5-c]quinolin-1-yl)-2-azabicyclo[2.1.1]hexane-2-carboxylate (Intermediate 11, 220 mg, 0.308 mmol) and 40% aq. tetrabutylammonium hydroxide (799 mg, 1.232 mmol) in 1,4-dioxane (3.0 mL) was added tBuBrettPhos Gd G3 (40 mg, 0.046 mmol). The reaction mixture was flushed with $N_2$ for 2 min and heated to 100° C. for 1 h. The resulting mixture was quenched with water, extracted EtOAc, dried and concentrated under reduced pressure. The residue was redissolved in THF (3.0 mL) and then TEA (429 μL, 3.08 mmol) was added. The reaction mixture was cooled to 0° C. and then TFAA (131 μL, 0.924 mmol) was added dropwise. The resultant mixture was stirred at room temperature for 1 h, quenched with saturated aq. $NaHCO_3$ and extracted with EtOAc The combined organic extracts were dried and concentrated under reduced pressure. Flash column chromatography (0-20% MeOH:DCM) affords the desired product. LCMS calculated for $C_{33}H_{44}ClN_8O_4(M+H)^+$: m/z=651.3; found 651.4.

Step 2. tert-butyl (endo)-5-(8-(2-cyanoethyl)-2-(3-(dimethylamino)-3-oxopropyl)-4-(3-(dimethylamino)azetidin-1-yl)-7-(7-fluoronaphthalen-1-yl)-6-hydroxy-1H-imidazo[4,5-c]quinolin-1-yl)-2-azabicyclo[2.1.1]hexane-2-carboxylate

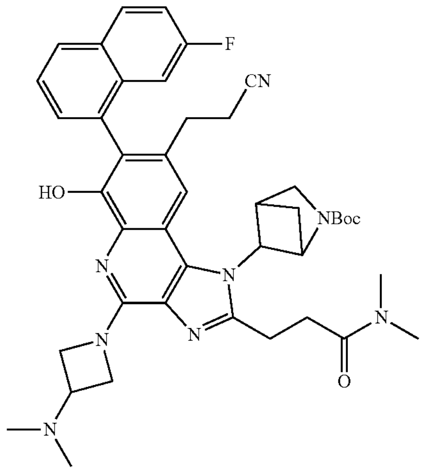

A solution of tert-butyl (endo)-5-(7-chloro-8-(2-cyanoethyl)-2-(3-(dimethylamino)-3-oxopropyl)-4-(3-(dimethylamino)azetidin-1-yl)-6-hydroxy-1H-imidazo[4,5-c]quinolin-1-yl)-2-azabicyclo[2.1.1]hexane-2-carboxylate (125 mg, 0.192 mmol), 2-(7-fluoronaphthalen-1-yl)-4,4,5,5-tetramethyl-1,3,2-dioxaborolane (78 mg, 0.29 mmol), XPhos Pd G2 (30 mg, 0.038 mmol) and $K_3PO_4$ (122 mg, 0.576 mmol) in dioxane (1.0 mL)/water (0.2 mL). The reaction mixture was flushed with $N_2$ for 2 min. and stirred at 100° C. for 1 h. The resultant mixture was cooled to room temperature, quenched with water and extracted with EtOAc. The combined organic extracts were dried and concentrated under reduced pressure and used without further purification. LCMS calculated for $C_{43}H_{50}FN_8O_4$ $(M+H)^+$: m/z=761.4; found 761.5.

Step 3. 3-(6-(benzyloxy)-1-((endo)-2-azabicyclo[2.1.1]hexan-5-yl)-8-(2-cyanoethyl)-4-(3-(dimethylamino)azetidin-1-yl)-7-(7-fluoronaphthalen-1-yl)-1H-imidazo[4,5-c]quinolin-2-yl)-N,N-dimethylpropanamide A solution of tert-butyl (endo)-5-(8-(2-cyanoethyl)-2-(3-(dimethylamino)-3-oxopropyl)-4-(3-(dimethylamino)azetidin-1-yl)-7-(7-fluoronaphthalen-1-yl)-6-hydroxy-1H-imidazo[4,5-c]quinolin-1-yl)-2-azabicyclo[2.1.1]hexane-2-carboxylate (30 mg, 0.039 mmol), benzyl bromide (13 mg, 0.079 mmol) and $Cs_2CO_3$ (38.5 mg, 0.118 mmol) in MeCN (1.0 mL) was stirred at 70° C. for 1 h. The resulting mixture was cooled to room temperature and filtered through a PTFE syringe filter and concentrated. The residue was diluted with DCM (1 mL) and then TFA (1 mL) was added slowly. The resultant mixture was stirred at room temperature for 15 min and diluted with MeOH and purified using prep-LCMS (XBridge C18 column, eluting with a gradient of acetonitrile/water containing 0.1% TFA, at flow rate of 60 mL/min)

to afford the desired products as a TFA salt. The product was isolated as a mixture of diastereomers. LCMS calculated for $C_{45}H_{48}FN_8O_2$ $(M+H)^+$: m/z=751.4; found 751.5.

Example 15. 3-(1-((endo)2-azabicyclo[2.1.1]hexan-5-yl)-4-(3-(dimethylamino)azetidin-1-yl)-6-fluoro-9-(hydroxymethyl)-7-(3-hydroxynaphthalen-1-yl)-1H-imidazo[4,5-c]quinolin-2-yl)-N,N-dimethylpropanamide

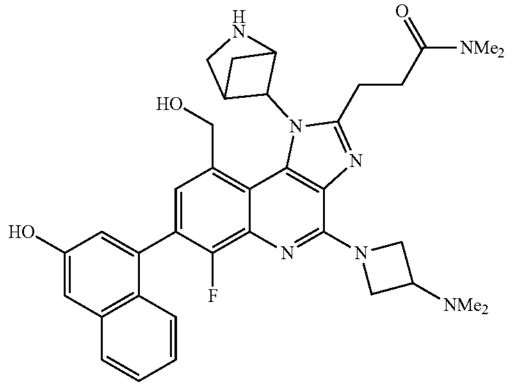 [SMILES: CN(C)C(=O)CCc1nc2c(N3CC(N(C)C)C3)nc3c(F)c(-c4cc(O)cc5ccccc45)cc(CO)c3c2n1C1C2CNC1C2]

$NaBH_4$ (3.64 mg, 0.1 mmol) was added to a solution of tert-butyl (endo)5-(2-(3-(dimethylamino)-3-oxopropyl)-4-(3-(dimethylamino)azetidin-1-yl)-6-fluoro-9-formyl-7-(3-(methoxymethoxy)naphthalen-1-yl)-1H-imidazo[4,5-c]quinolin-1-yl)-2-azabicyclo[2.1.1]hexane-2-carboxylate (Intermediate 12, 25 mg, 0.03 mmol) in MeOH (1 ml), and the mixture was stirred for 1 h. The reaction was concentrated in vacuo, then TFA (1 mL) added, and the resulting mixture was stirred for 10 minutes to remove Boc and MOM. Upon completion, the reaction was diluted with MeOH and purified using prep-LCMS (XBridge C18 column, eluting with a gradient of acetonitrile/water containing 0.1% TFA, at flow rate of 60 mL/min) to afford Example 15 as a TFA salt. The product was isolated as a mixture of diastereomers. LCMS calculated for $C_{36}H_{41}FN_7O_3(M+H)^+$ m/z=638.3; found 638.3.

Example 16. 3-(1-((endo)2-azabicyclo[2.1.1]hexan-5-yl)-9-((3-cyanopyrrolidin-1-yl)methyl)-4-(3-(dimethylamino)azetidin-1-yl)-6-fluoro-7-(3-hydroxynaphthalen-1-yl)-1H-imidazo[4,5-c]quinolin-2-yl)-N,N-dimethylpropanamide

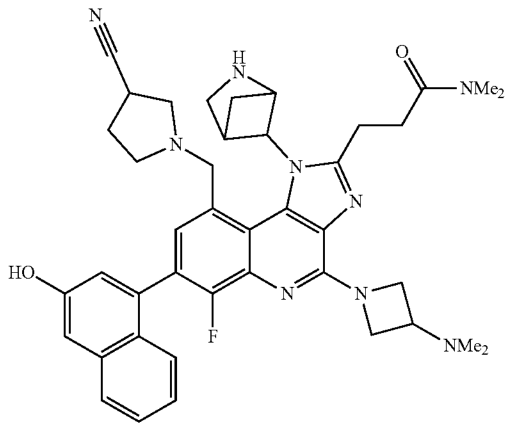 [SMILES: CN(C)C(=O)CCc1nc2c(N3CC(N(C)C)C3)nc3c(F)c(-c4cc(O)cc5ccccc45)cc(CN4CCC(C#N)C4)c3c2n1C1C2CNC1C2]

Sodium triacetoxyborohydride (8.15 mg, 0.038 mmol) was added to a solution of tert-butyl (endo)5-(2-(3-(dimethylamino)-3-oxopropyl)-4-(3-(dimethylamino)azetidin-1-yl)-6-fluoro-9-formyl-7-(3-(methoxymethoxy)naphthalen-1-yl)-1H-imidazo[4,5-c]quinolin-1-yl)-2-azabicyclo[2.1.1]hexane-2-carboxylate (Intermediate 12, 15 mg, 0.02 mmol) and pyrrolidine-3-carbonitrile (3.80 mg, 0.04 mmol) in DCE (1 mL), and the reaction mixture was stirred at room temperature overnight. The reaction was concentrated in vacuo, then TFA (1 mL) added, and the resulting mixture was stirred for 10 minutes to remove Boc and MOM. Upon completion, the reaction was diluted with MeOH and purified using prep-LCMS (XBridge C18 column, eluting with a gradient of acetonitrile/water containing 0.1% TFA, at flow rate of 60 mL/min) to afford Example 16 as a TFA salt. The product was isolated as a mixture of diastereomers. LCMS calculated for $C_{41}H_{47}FN_9O_2(M+H)^+$ m/z=716.4; found 716.4.

Example 17a and Example 17b. 3-(1-((endo)-2-Azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-4-fluoro-N-methylbenzamide

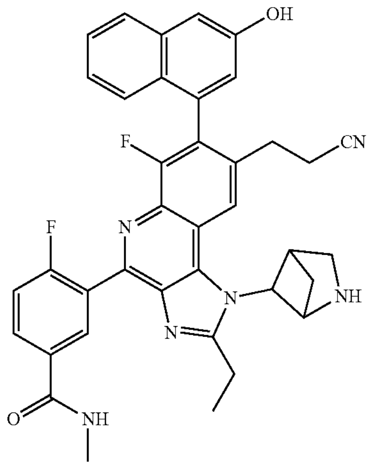 [SMILES: CCc1nc2c(-c3cc(C(=O)NC)ccc3F)nc3c(F)c(-c4cc(O)cc5ccccc45)c(CCC#N)cc3c2n1C1C2CNC1C2]

Step 1. tert-Butyl (endo)-5-((7-bromo-2-chloro-8-fluoro-6-iodo-3-nitroquinolin-4-yl)amino)-2-azabicyclo[2.1.1]hexane-2-carboxylate

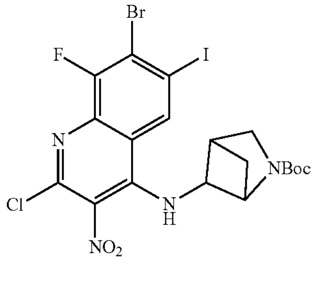 [SMILES: CC(C)(C)OC(=O)N1CC2CC1C2Nc1c(N)c(Cl)nc2c(F)c(Br)c(I)cc12]

A sample of tert-butyl (endo)-5-amino-2-azabicyclo[2.1.1]hexane-2-carboxylate (10.6 g, 54 mmol) was dissolved in NMP (270 mL) and stirred at room temperature.

The solution was treated with N,N-diisopropylethylamine (19 mL, 110 mmol) and 7-bromo-2,4-dichloro-8-fluoro-6-iodo-3-nitroquinoline (Intermediate 1, 25 g, 54 mmol). The reaction mixture was heated to 80° C. and stirred with a magnetic stir bar.

After 30 minutes, LCMS indicated complete conversion to the product, with ~5-10% double addition. The solution was cooled to room temperature and poured into a mixture of water (300 mL) and saturated $NH_4Cl$ (100 mL). The mixture was stirred at room temperature for 30 minutes, at which point the resultant suspension was vacuum filtered and the solid was dried with continued air flow to provide tert-butyl (endo)-5-((7-bromo-2-chloro-8-fluoro-6-iodo-3-nitroquinolin-4-yl)amino)-2-azabicyclo[2.1.1]hexane-2-carboxylate (36 g, 57 mmol, assumed quantitative yield) as a yellow powder. LCMS calculated for $C_{19}H_{19}BrClFIN_4O_4$ $(M+H)^+$: m/z=626.9, 628.9; found 626.8, 628.8.

Step 2. tert-Butyl (endo)-5-((3-amino-7-bromo-2-chloro-8-fluoro-6-iodoquinolin-4-yl)amino)-2-azabicyclo[2.1.1]hexane-2-carboxylate

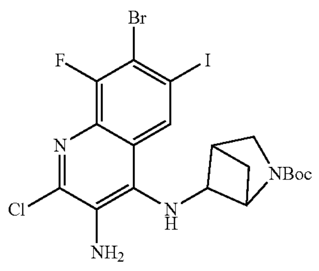

A sample of tert-butyl (endo)-5-((7-bromo-2-chloro-8-fluoro-6-iodo-3-nitroquinolin-4-yl)amino)-2-azabicyclo[2.1.1]hexane-2-carboxylate (36 g, 57 mmol) was dissolved in methanol (240 mL) and water (40 mL) and stirred at room temperature. The solution was treated with ammonium hydroxide (8.1 mL, 62 mmol). Sodium dithionate (53 g, 260 mmol) was then added as a powder to the solution in five portions, every 5 minutes. After 1 hour, LCMS showed complete reduction of the starting material, with two product peaks (possibly reflecting different protonation states). The reaction was quenched with water and diluted with DCM. The layers were separated, and the aqueous layer was repeatedly extracted with additional DCM, and finally with 25% isopropanol in chloroform. The combined organic layers were dried over $MgSO_4$, filtered, and concentrated in vacuo. The product tert-butyl (endo)-5-((3-amino-7-bromo-2-chloro-8-fluoro-6-iodoquinolin-4-yl)amino)-2-azabicyclo[2.1.1]hexane-2-carboxylate (36 g, 61 mmol, assumed quantitative yield) was not purified further and was used as crude in Step 3. LCMS calculated for $C_{19}H_{21}BrClFIN_4O_2$ $(M+H)^+$: m/z=597.0, 599.0; found: 596.9, 598.9.

Step 3. tert-Butyl (endo)-5-(7-bromo-4-chloro-2-ethyl-6-fluoro-8-iodo-1H-imidazo[4,5-c]quinolin-1-yl)-2-azabicyclo[2.1.1]hexane-2-carboxylate

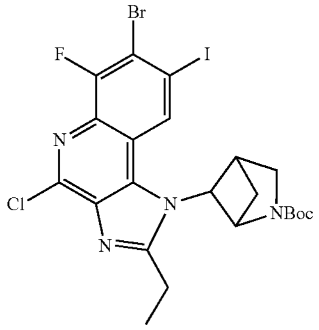 [SMILES: CCc1nc2c(Cl)nc3c(F)c(Br)c(I)cc3c2n1C1C2CC1N(C(=O)OC(C)(C)C)C2]

A crude sample of tert-butyl (endo)-5-((3-amino-7-bromo-2-chloro-8-fluoro-6-iodoquinolin-4-yl)amino)-2-azabicyclo[2.1.1]hexane-2-carboxylate (5.5 g, 9.2 mmol) was dissolved in DMF (46 mL) and acetic acid (23 mL) in a round-bottomed flask and stirred at room temperature. The solution was treated with propionaldehyde (1.9 g, 32 mmol), warmed to 80° C., and stirred open to air.

After 16 hours, LCMS indicated complete conversion to the desired product. The reaction was cooled to room temperature, quenched with water and diluted with EtOAc. The layers were separated, and the aqueous layer was extracted with additional EtOAc. The combined organic layers were washed with saturated aq. $NaHCO_3$, dried over $MgSO_4$, filtered, and concentrated in vacuo. The crude material was purified by flash column chromatography (0-100% EtOAc/Hexanes) to give tert-butyl (endo)-5-(7-bromo-4-chloro-2-ethyl-6-fluoro-8-iodo-1H-imidazo[4,5-c]quinolin-1-yl)-2-azabicyclo[2.1.1]hexane-2-carboxylate (1.4 g, 2.1 mmol, 23% yield). LCMS calculated for $C_{25}H_{23}BrClFIN_4O_2(M+H)^+$: m/z=635.0, 637.0; found: 635.0, 637.0.

Step 4. tert-Butyl (endo)-5-(7-bromo-4-chloro-8-(2-cyanoethyl)-2-ethyl-6-fluoro-1H-imidazo[4,5-c]quinolin-1-yl)-2-azabicyclo[2.1.1]hexane-2-carboxylate

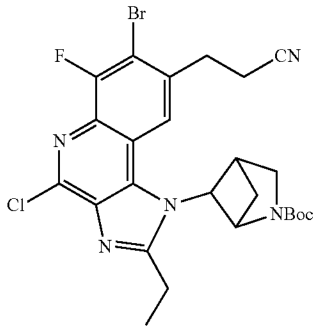 [SMILES: CCc1nc2c(Cl)nc3c(F)c(Br)c(CCC#N)cc3c2n1C1C2CC1N(C(=O)OC(C)(C)C)C2]

A sample of tert-butyl (endo)-5-(7-bromo-4-chloro-2-ethyl-6-fluoro-8-iodo-1H-imidazo[4,5-c]quinolin-1-yl)-2-azabicyclo[2.1.1]hexane-2-carboxylate (1.35 g, 2.12 mmol) was dissolved in DMF (4.5 mL) and stirred at room temperature. The solution was treated with N,N-diisopropylethylamine (0.8 mL, 4.3 mmol) and acrylonitrile (340 μL, 8.6 mmol). Tetramethylammonium formate (1.5 mL, 3.2 mmol) was added as a 30% w/w solution in water. The solution was de-gassed by bubbling nitrogen gas while sonicating. Lastly, the solution was treated with tetrakis(triphenylphosphine) palladium(0) (125 mg, 0.11 mmol) and stirred at 80° C.

After 150 minutes, LCMS showed complete conversion to the products (appears to be 70/30 desired coupling to proto-dehalogenation). The reaction was cooled to room temperature, quenched with saturated aq. $NH_4Cl$ and diluted with EtOAc. The layers were separated, and the aqueous layer was extracted with additional EtOAc. The combined organic layers were dried over $MgSO_4$, filtered, and concentrated in vacuo. The crude material was purified by flash column chromatography (0-100% EtOAc/DCM) to give tert-butyl (endo)-5-(7-bromo-4-chloro-8-(2-cyanoethyl)-2-ethyl-6-fluoro-1H-imidazo[4,5-c]quinolin-1-yl)-2-azabicyclo[2.1.1]hexane-2-carboxylate (700 mg, 1.25 mmol, 59% yield). LCMS calculated for $C_{25}H_{27}BrClFN_5O_2(M+H)^+$: m/z=562.1, 564.1; found: 562.2, 564.2.

Step 5. tert-Butyl (endo)-5-(7-bromo-8-(2-cyanoethyl)-2-ethyl-6-fluoro-4-(2-fluoro-5-(methylcarbamoyl)phenyl)-1H-imidazo[4,5-c]quinolin-1-yl)-2-azabicyclo[2.1.1]hexane-2-carboxylate

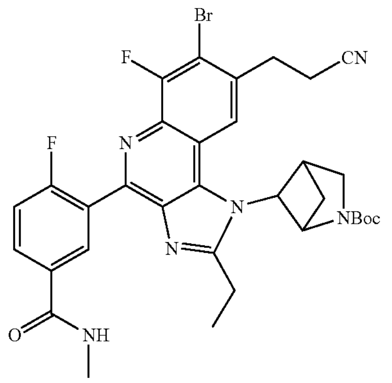 [SMILES: CCc1nc2c(-c3cc(C(=O)NC)ccc3F)nc3c(F)c(Br)c(CCC#N)cc3c2n1C1C2CC1N(C(=O)OC(C)(C)C)C2]

A sample of tert-butyl (endo)-5-(7-bromo-4-chloro-8-(2-cyanoethyl)-2-ethyl-6-fluoro-1H-imidazo[4,5-c]quinolin-1-yl)-2-azabicyclo[2.1.1]hexane-2-carboxylate (50 mg, 0.089 mmol) was dissolved in NMP (0.5 mL) and water (0.1 mL) and stirred at room temperature. The solution was treated with $K_2CO_3$ (37 mg, 0.27 mmol) and (2-fluoro-5-(methylcarbamoyl)phenyl)boronic acid (35 mg, 0.18 mmol), and finally with tetrakis(triphenylphosphine)palladium(0) (10 mg, 9 μmol). The solution was then warmed to 80° C.

After 1 hour, LCMS showed complete conversion to the desired product. The solution was cooled to room temperature, diluted with 4:1 acetonitrile/water, filtered through a SiliaPrep Thiol cartridge, and purified by HPLC (pH=6.5 method) to give tert-butyl 5-(7-bromo-8-(2-cyanoethyl)-2-ethyl-6-fluoro-4-(2-fluoro-5-(methylcarbamoyl)phenyl)-1H-imidazo[4,5-c]quinolin-1-yl)-2-azabicyclo[2.1.1]hexane-2-carboxylate (12 mg, 0.018 mmol, 20% yield). LCMS calculated for $C_{33}H_{34}BrF_2N_6O_3$ $(M+H)^+$: m/z=679.2, 681.2; found: 679.3, 681.3.

Step 6. 3-(1-((endo)-2-Azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-4-fluoro-N-methylbenzamide A sample of tert-butyl (endo)-5-(7-bromo-8-(2-cyanoethyl)-2-ethyl-6-fluoro-4-(2-fluoro-5-(methylcarbamoyl)phenyl)-1H-imidazo[4,5-c]quinolin-1-yl)-2-azabicyclo[2.1.1]hexane-2-carboxylate (12 mg, 0.018 mmol) was dissolved in 1,4-dioxane (0.2 mL) and water (0.05 mL) and stirred at room temperature. The solution was treated with $K_2CO_3$ (7 mg, 0.05 mmol) and (3-hydroxynaphthalen-1-yl) boronic acid (10 mg, 0.05 mmol). The solution was de-gassed by bubbling with nitrogen gas and sonicating for 5 minutes. Finally, the solution was treated with Pd XPhos G2 (2 mg, 3 μmol) and stirred at 80° C.

After 90 minutes, LCMS indicated complete conversion to the intermediate. The reaction was cooled to RT, quenched with saturated aq. $NH_4Cl$ and diluted with EtOAc. The layers were separated, and the aqueous layer was extracted with 25% IPA/$CHCl_3$. The combined organic layers were dried over $MgSO_4$, filtered, and concentrated in vacuo. LCMS calculated for $C_{43}H_{41}F2N_6O_4(M+H)^+$: m/z=743.3; found: 743.3.

The crude material was dissolved in 1 mL of 50% TFA in DCM and stirred at room temperature. After 90 minutes, LCMS indicated complete deprotection. The solution was concentrated in vacuo, diluted with 4:1 acetonitrile/water, filtered through a SiliaPrep Thiol cartridge, and purified by HPLC (pH=2 method) to afford 3-(1-((endo)-2-azabicyclo[2.1.1]hexan-5-yl)-8-(2-cyanoethyl)-2-ethyl-6-fluoro-7-(7-fluoronaphthalen-1-yl)-1H-imidazo[4,5-c]quinolin-4-yl)-N-methylbenzamide as two diastereomers (Peak 1: 2.5 mg, 4 μmol, 18% yield; Peak 2: 3.3 mg, 5.3 μmol, 23% yield). Both isomers were isolated as their corresponding TFA salt.

Example 17a. Diastereomer 1. Peak 1. LCMS calculated for $C_{38}H_{33}F_2N_6O_2$(M+H)+m/z=643.3; found 643.3. *More potent peak.

Example 17b. Diastereomer 2. Peak 2. LCMS calculated for $C_{38}H_{33}F_2N_6O_2$(M+H)+m/z=643.3; found 643.3.

Example 18. 3-(1-((endo)-2-Azabicyclo[2.1.1]hexan-5-yl)-2-ethyl-4-(1-ethyl-6-oxo-1,6-dihydropyridin-3-yl)-6-fluoro-7-(3-hydroxynaphthalen-1-yl)-1H-imidazo[4,5-c]quinolin-8-yl)propanenitrile

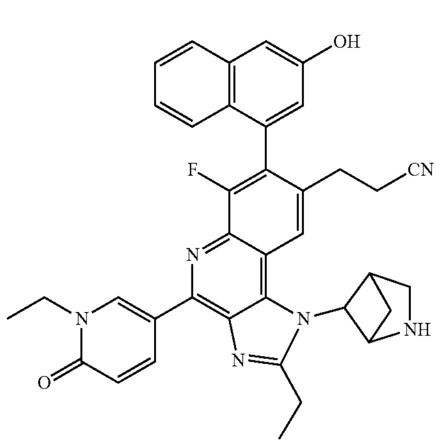 [SMILES: CCc1nc2c(-c3ccc(=O)n(CC)c3)nc3c(F)c(-c4cc(O)cc5ccccc45)c(CCC#N)cc3c2n1C1C2CNC1C2]

Step 1. tert-Butyl (endo)-5-((7-bromo-8-fluoro-6-iodo-2-(methylthio)-3-nitroquinolin-4-yl)amino)-2-azabicyclo[2.1.1]hexane-2-carboxylate

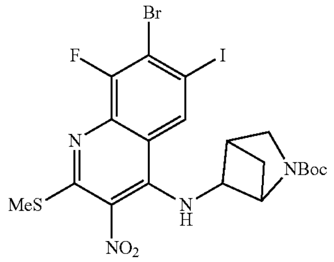

A sample of tert-butyl (endo)-5-amino-2-azabicyclo[2.1.1]hexane-2-carboxylate (22 g, 110 mmol) was dissolved in acetonitrile (540 mL) and stirred at room temperature. The solution was treated with N,N-diisopropylethylamine (23 mL, 130 mmol) and 7-bromo-2,4-dichloro-8-fluoro-6-iodo-3-nitroquinoline (Intermediate 1, 50.3 g, 110 mmol). The reaction mixture was heated to 60° C. and stirred. After 30 minutes, LCMS indicated full conversion to the $S_NAr$ adduct. LCMS calculated for $C_{19}H_{19}BrClFIN_4O_4(M+H)^+$: m/z=626.9, 628.9; found 626.8, 628.8.

The mixture was then cooled to 0° C. and sodium thiomethoxide (120 mL, 360 mmol) was added as a 21% w/w solution in water. DMF (20 mL) was added to aid solubility of the resulting suspension. The mixture was allowed to warm to 22° C. and stirred overnight. After 16 hours, LCMS indicated complete conversion from the intermediate to the desired product. The mixture was poured into 1.8 L of ice water and stirred for 1 h. The suspension was filtered and the solid washed with additional water. The solid was dried with continued air flow overnight to give tert-butyl (endo)-5-((7-bromo-8-fluoro-6-iodo-2-(methylthio)-3-nitroquinolin-4-yl)amino)-2-azabicyclo[2.1.1]hexane-2-carboxylate (66 g, 104 mmol, 96% yield). LCMS calculated for $C_{20}H_{22}BrFIN_4O_4S$ $(M+H)^+$: m/z=639.0, 641.0; found 638.9, 640.9.

Step 2. tert-Butyl (endo)-5-((3-amino-7-bromo-8-fluoro-6-iodo-2-(methylthio)quinolin-4-yl)amino)-2-azabicyclo[2.1.1]hexane-2-carboxylate

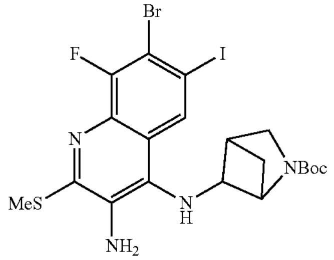 [SMILES: CSc1nc2c(F)c(Br)c(I)cc2c(NC2C3CC2N(C(=O)OC(C)(C)C)C3)c1[N+](=O)[O-]]

A sample of tert-butyl (endo)-5-((7-bromo-8-fluoro-6-iodo-2-(methylthio)-3-nitroquinolin-4-yl)amino)-2-azabicyclo[2.1.1]hexane-2-carboxylate (16 g, 25 mmol) was dissolved in ethanol (125 mL) and stirred at room temperature. The solution was treated with sodium dithionate as a 1.0 M solution in water (75 mL, 75 mmol) and warmed to 70° C. After 90 minutes, LCMS showed the reaction was complete. Two product peaks appear, possibly reflecting different protonation states. The mixture was cooled to room temperature and quenched with aqueous ammonium hydroxide (8.6 ml, 125 mmol). The mixture was concentrated in vacuo until the total volume was approximately 100 mL. The resulting solution was extracted repeatedly with 10% methanol in dichloromethane until an LCMS aliquot of the aqueous phase no longer indicated any product remained. The combined organic fractions were dried with $MgSO_4$, filtered, and concentrated in vacuo to give tert-butyl (endo)-5-((3-amino-7-bromo-8-fluoro-6-iodo-2-(methylthio)quinolin-4-yl)amino)-2-azabicyclo[2.1.1]hexane-2-carboxylate (13.1 g, 22 mmol, 86% yield). LCMS calculated for $C_{20}H_{24}BrFIN_4O_2S$ $(M+H)^+$: m/z=609.0, 611.0; found: 608.9, 610.9.

Step 3. tert-Butyl (endo)-5-(7-bromo-2-ethyl-6-fluoro-8-iodo-4-(methylthio)-1H-imidazo[4,5-c]quinolin-1-yl)-2-azabicyclo[2.1.1]hexane-2-carboxylate

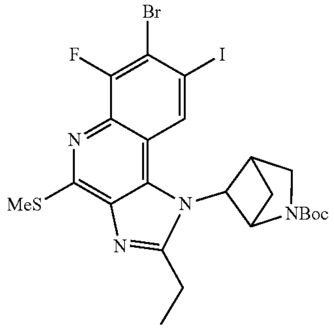 [SMILES: CCc1nc2c(SC)nc3c(F)c(Br)c(I)cc3c2n1C1C2CC1N(C(=O)OC(C)(C)C)C2]

This compound was prepared on 9 g (14.8 mmol) scale according to the procedure described in Example 17, Step 3, with the workup and purification altered as follows.

The reaction was cooled to RT and poured into 800 mL of ice water. The mixture was stirred for 1 h, at which point the suspension was filtered. The solid was dried with continued air flow to give tert-butyl (endo)-5-(7-bromo-2-ethyl-6-fluoro-8-iodo-4-(methylthio)-1H-imidazo[4,5-c]quinolin-1-yl)-2-azabicyclo[2.1.1]hexane-2-carboxylate (8.6 g, 13 mmol, 90% yield). LCMS calculated for $C_{23}H_{26}BrFIN_4O_2S$ $(M+H)^+$: m/z=647.0, 649.0; found: 646.9, 648.9.

Step 4. tert-Butyl (endo)-5-(7-bromo-8-(2-cyanoethyl)-2-ethyl-6-fluoro-4-(methylthio)-1H-imidazo[4,5-c]quinolin-1-yl)-2-azabicyclo[2.1.1]hexane-2-carboxylate

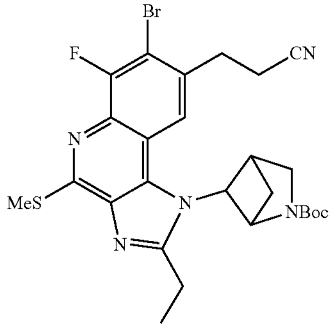 [SMILES: CCc1nc2c(SC)nc3c(F)c(Br)c(CCC#N)cc3c2n1C1C2CC1N(C(=O)OC(C)(C)C)C2]

This compound was prepared on 8.6 g (13.3 mmol) scale according to the procedure described in Example 17, Step 4, with the purification altered as follows.

After concentrating to dryness, the crude material was dissolved in methanol, filtered through a SiliaPrep Thiol cartridge, and purified by supercritical fluid chromatography (SFC) to give tert-butyl (endo)-5-(7-bromo-4-chloro-8-(2-cyanoethyl)-2-ethyl-6-fluoro-1H-imidazo[4,5-c]quinolin-1-yl)-2-azabicyclo[2.1.1]hexane-2-carboxylate (500 mg, 0.90 mmol, 12% yield). LCMS calculated for $C_{26}H_{30}BrFN_5O_2S$ $(M+H)^+$: m/z=574.1, 576.1; found: 574.2, 576.2.

Step 5. tert-Butyl (endo)-5-(8-(2-cyanoethyl)-2-ethyl-6-fluoro-7-(3-(methoxymethoxy)naphthalen-1-yl)-4-(methylthio)-1H-imidazo[4,5-c]quinolin-1-yl)-2-azabicyclo[2.1.1]hexane-2-carboxylate

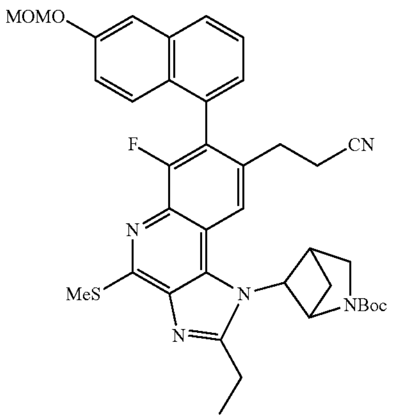

A sample of tert-butyl (endo)-5-(7-bromo-8-(2-cyanoethyl)-2-ethyl-6-fluoro-4-(methylthio)-1H-imidazo[4,5-c]quinolin-1-yl)-2-azabicyclo[2.1.1]hexane-2-carboxylate (2 g, 3.5 mmol) was dissolved in 1,4-dioxane (28 mL) and water (7 mL) and stirred at room temperature. The solution was treated with $K_2CO_3$ (1.4 g, 10 mmol) and 2-(3-(methoxymethoxy)naphthalen-1-yl)-4,4,5,5-tetramethyl-1,3,2-dioxaborolane (Intermediate 4, 2.7 g, 8.7 mmol). The solution was de-gassed by bubbling with nitrogen and sonicating for 5 minutes. Finally, the solution was treated with Pd XPhos G2 (410 mg, 0.52 mmol) and stirred at 65° C.

After 90 min, LCMS indicated complete conversion to the product. The reaction was cooled to RT, quenched with saturated aq. $NH_4Cl$ and diluted with EtOAc. The layers were separated, and the aqueous layer was extracted with EtOAc several times. The combined organic layers were dried over $MgSO_4$, filtered, and concentrated in vacuo.

The crude material was purified by flash column chromatography (0-100% EtOAc/hexanes) to give tert-butyl (endo)-5-(8-(2-cyanoethyl)-2-ethyl-6-fluoro-7-(3-(methoxymethoxy)naphthalen-1-yl)-4-(methylthio)-1H-imidazo[4,5-c]quinolin-1-yl)-2-azabicyclo[2.1.1]hexane-2-carboxylate (1.9 g, 2.7 mmol, 79% yield). LCMS calculated for $C_{38}H_{41}FN_5O_4S$ $(M+H)^+$: m/z=682.3; found: 682.3.

Step 6. 3-(1-((endo)-2-Azabicyclo[2.1.1]hexan-5-yl)-2-ethyl-4-(1-ethyl-6-oxo-1,6-dihydropyridin-3-yl)-6-fluoro-7-(3-hydroxynaphthalen-1-yl)-1H-imidazo[4,5-c]quinolin-8-yl)propanenitrile A sample of tert-butyl (endo)-5-(8-(2-cyanoethyl)-2-ethyl-6-fluoro-7-(3-(methoxymethoxy)naphthalen-1-yl)-4-(methylthio)-1H-imidazo[4,5-c]quinolin-1-yl)-2-azabicyclo[2.1.1]hexane-2-carboxylate (20 mg, 0.03 mmol) was dissolved in 1,4-dioxane (0.3 mL) in a vial with a stir bar and stirred at room temperature. The solution was treated with tetrakis(triphenylphosphine)palladium(0) (7 mg, 6 μmol) and copper(I) 3-methylsalicylate (23 mg, 0.11 mmol). Lastly, 1-ethyl-5-(4,4,5,5-tetramethyl-1,3,2-dioxaborolan-2-yl)pyridin-2(1H)-one (18 mg, 0.073 mmol) was added, the vial was capped, and the solution was stirred at 120° C.

After 16 hours, LCMS showed complete conversion to the desired intermediate. The reaction was cooled to RT, quenched with aq. $NH_4OH$ and diluted with DCM. The layers were separated, and the aqueous layer was extracted with additional DCM. The combined organic fractions were dried over $MgSO_4$, filtered, and concentrated in vacuo. LCMS calculated for $C_{44}H_{45}FN_6O_5(M+H)^+$: m/z=757.4; found: 757.5.

The crude material was dissolved in 1 mL of 50% TFA in DCM and stirred at room temperature. After 20 minutes, LCMS indicated complete deprotection. The solution was concentrated in vacuo and diluted with 4:1 acetonitrile/water, filtered through a SiliaPrep Thiol cartridge, and purified by HPLC (pH=2 method) to afford 3-(1-((endo)-2-azabicyclo[2.1.1]hexan-5-yl)-2-ethyl-4-(1-ethyl-6-oxo-1,6-dihydropyridin-3-yl)-6-fluoro-7-(3-hydroxynaphthalen-1-yl)-1H-imidazo[4,5-c]quinolin-8-yl)propanenitrile as two diastereomers (Peak 1: 2.7 mg, 4.4 μmol, 15% yield; Peak 2: contaminated, yield not determined). Peak 1 was isolated as its corresponding TFA salt.

Example 18. Diastereomer 1. Peak 1. LCMS calculated for $C_{37}H_{34}FN_6O_2(M+H)^+$ m/z=613.3; found 613.4.

Example 19a and Example 19b. 5-(1-((endo)-2-Azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-N-methylpicolinamide

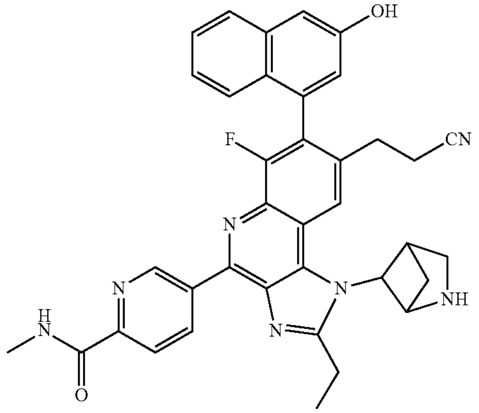 [SMILES: CCc1nc2c(-c3ccc(C(=O)NC)nc3)nc3c(F)c(-c4cc(O)cc5ccccc45)c(CCC#N)cc3c2n1C1C2CNC1C2]

A sample of tert-butyl (endo)-5-(8-(2-cyanoethyl)-2-ethyl-6-fluoro-7-(3-(methoxymethoxy)naphthalen-1-yl)-4-(methylthio)-1H-imidazo[4,5-c]quinolin-1-yl)-2-azabicyclo[2.1.1]hexane-2-carboxylate (Example 18, Step 5; 40 mg, 0.06 mmol) was dissolved in 1,4-dioxane (0.6 mL) in a vial with a stir bar and stirred at room temperature. The solution was treated with tetrakis(triphenylphosphine)palladium(0) (14 mg, 0.012 mmol) and copper(I) 3-methylsalicylate (45 mg, 0.21 mmol). Lastly, N-methyl-5-(4,4,5,5-tetramethyl-1, 3,2-dioxaborolan-2-yl)picolinamide (77 mg, 0.29 mmol) was added, the vial was capped, and the solution was stirred at 120° C.

After 45 minutes, LCMS showed complete conversion to the desired intermediate. The reaction was cooled to RT, quenched with aq. $NH_4OH$ and diluted with DCM. The layers were separated, and the aqueous layer was extracted with additional DCM. The combined organic fractions were dried over $MgSO_4$, filtered, and concentrated in vacuo. LCMS calculated for $C_{44}H_{45}FN_7O_5(M+H)^+$: m/z=770.4; found: 770.3.

The crude material was dissolved in 1 mL of 50% TFA in DCM and stirred at room temperature. After 30 minutes, LCMS indicated complete deprotection. The solution was concentrated in vacuo and diluted with 4:1 acetonitrile/water, filtered through a SiliaPrep Thiol cartridge, and purified by HPLC (pH=2 method) to afford 5-(1-((endo)-2-azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-N-methylpicolinamide as two diastereomers (Peak 1: 3.9 mg, 6 μmol, 11% yield; Peak 2: 6.7 mg, 11 μmol, 18% yield). Both isomers were isolated as their corresponding TFA salt.

Example 19a. Diastereomer 1. Peak 1. LCMS calculated for $C_{37}H_{33}FN_7O_2(M+H)^+$ m/z=626.3; found 626.2.

Example 19b. Diastereomer 2. Peak 2. LCMS calculated for $C_{37}H_{33}FN_7O_2(M+H)^+$ m/z=626.3; found 626.2.

Example 20a and Example 20b. 3-(1-((endo)-2-Azabicyclo[2.1.1]hexan-5-yl)-2-ethyl-6-fluoro-7-(3-hydroxynaphthalen-1-yl)-4-(oxazol-2-yl)-1H-imidazo[4,5-c]quinolin-8-yl)propanenitrile

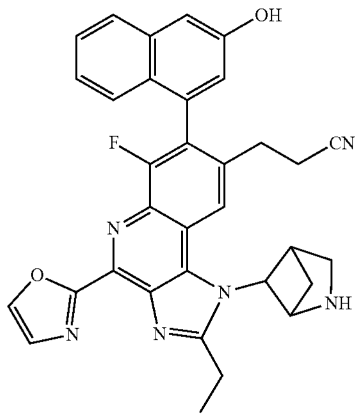 [SMILES: CCc1nc2c(-c3ncco3)nc3c(F)c(-c4cc(O)cc5ccccc45)c(CCC#N)cc3c2n1C1C2CNC1C2]

A sample of tert-butyl (endo)-5-(8-(2-cyanoethyl)-2-ethyl-6-fluoro-7-(3-(methoxymethoxy)naphthalen-1-yl)-4-(methylthio)-1H-imidazo[4,5-c]quinolin-1-yl)-2-azabicyclo[2.1.1]hexane-2-carboxylate (Example 18, Step 5; 20 mg, 0.03 mmol) was dissolved in 1,4-dioxane (0.3 mL) in a vial with a stir bar and stirred at room temperature. The solution was treated with tetrakis(triphenylphosphine)palladium(0) (7 mg, 0.006 mmol) and copper(I) 3-methylsalicylate (23 mg, 0.11 mmol). Lastly, 2-(tributylstannyl)oxazole (26 mg, 0.073 mmol) was added, the vial was capped, and the solution was stirred at 90° C.

After 3 hours, LCMS showed complete conversion to the desired intermediate. The reaction was cooled to RT, quenched with aq. $NH_4OH$ and diluted with DCM. The layers were separated, and the aqueous layer was extracted with additional DCM. The combined organic fractions were dried over $MgSO_4$, filtered, and concentrated in vacuo. LCMS calculated for $C_{40}H_{40}FN_6O_5$ $(M+H)^+$: m/z=703.3; found: 703.3.

The crude material was dissolved in 1 mL of 50% TFA in DCM and stirred at room temperature. After 30 minutes, LCMS indicated complete deprotection. The solution was concentrated in vacuo and diluted with 4:1 acetonitrile/water, filtered through a SiliaPrep Thiol cartridge, and purified by HPLC (pH=2 method) to afford 3-(1-((endo)-2-azabicyclo[2.1.1]hexan-5-yl)-2-ethyl-6-fluoro-7-(3-hydroxynaphthalen-1-yl)-4-(oxazol-2-yl)-1H-imidazo[4,5-c]quinolin-8-yl)propanenitrile as two diastereomers. Diastereomer 1 was contaminated and further purified by HPLC (pH=6.5 method). (Peak 1: 0.4 mg, 0.7 μmol, 2% yield; Peak 2: 1.4 mg, 2.5 μmol, 9% yield). Peak 2 was isolated as its corresponding TFA salt.

Example 20a. Diastereomer 1. Peak 1. LCMS calculated for $C_{33}H_{28}FN_6O_2(M+H)^+$ m/z=559.2; found 559.1.

Example 20b. Diastereomer 2. Peak 2. LCMS calculated for $C_{33}H_{28}FN_6O_2(M+H)^+$ m/z=559.2; found 559.1.

Example 21a and Example 21b. 3-(4-([1,2,4]Triazolo[1,5-a]pyridin-7-yl)-1-((endo)-2-azabicyclo[2.1.1]hexan-5-yl)-2-ethyl-6-fluoro-7-(3-hydroxynaphthalen-1-yl)-1H-imidazo[4,5-c]quinolin-8-yl)propanenitrile

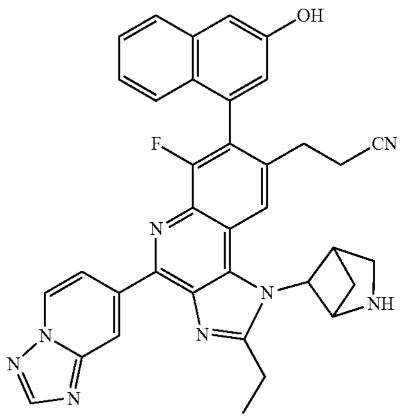 [SMILES: CCc1nc2c(-c3ccn4ncnc4c3)nc3c(F)c(-c4cc(O)cc5ccccc45)c(CCC#N)cc3c2n1C1C2CNC1C2]

This compound was prepared on 20 mg (0.029 mmol) scale according to the procedure described in Example 20, replacing 2-(tributylstannyl)oxazole with 7-(tributylstannyl)-[1,2,4]triazolo[1,5-a]pyridine (30 mg, 0.073 mmol), and with the purification altered as described below. LCMS calculated for intermediate $C_{43}H_{42}FN_8O_4(M+H)^+$: m/z=753.3; found: 753.3.

After deprotection as described above, the solution was concentrated in vacuo and diluted with 4:1 acetonitrile/water, filtered through a SiliaPrep Thiol cartridge, and purified by HPLC (pH=2 method) to afford 3-(4-([1,2,4]triazolo[1,5-a]pyridin-7-yl)-1-((endo)-2-azabicyclo[2.1.1]hexan-5-yl)-2-ethyl-6-fluoro-7-(3-hydroxynaphthalen-1-yl)-1H-imidazo[4,5-c]quinolin-8-yl)propanenitrile as two diastereomers (Peak 1: 1.2 mg, 2.0 μmol, 7% yield; Peak 2: 2.8 mg, 4.6 μmol, 16% yield). Both diastereomers were isolated as their corresponding TFA salt.

Example 21a. Diastereomer 1. Peak 1. LCMS calculated for $C_{36}H_{30}FN_8O$ $(M+H)^+$ m/z=609.3; found 609.2.

Example 21b. Diastereomer 2. Peak 2. LCMS calculated for $C_{36}H_{30}FN_8O$ $(M+H)^+$ m/z=609.3; found 609.2.

Example 22a and Example 22b. 3-(1-((endo)-2-Azabicyclo[2.1.1]hexan-5-yl)-2-ethyl-6-fluoro-7-(3-hydroxynaphthalen-1-yl)-4-(2-(4-methylpiperazin-1-yl)pyridin-4-yl)-1H-imidazo[4,5-c]quinolin-8-yl) propanenitrile

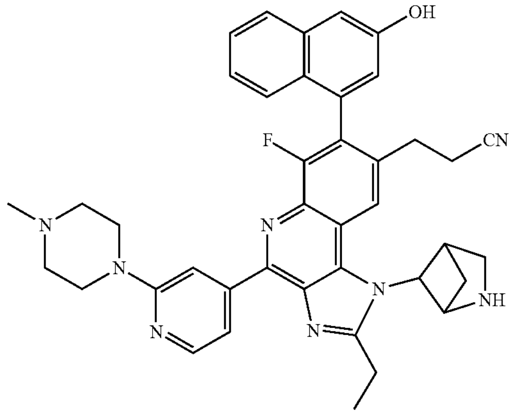 [SMILES: CCc1nc2c(-c3ccnc(N4CCN(C)CC4)c3)nc3c(F)c(-c4cc(O)cc5ccccc45)c(CCC#N)cc3c2n1C1C2CNC1C2]

This compound was prepared on 20 mg (0.029 mmol) scale according to the procedure described in Example 19, replacing N-methyl-5-(4,4,5,5-tetramethyl-1,3,2-dioxaborolan-2-yl)picolinamide with 1-methyl-4-(4-(4,4,5,5-tetramethyl-1,3,2-dioxaborolan-2-yl)pyridin-2-yl)piperazine (22 mg, 0.073 mmol), and with the purification altered as described below. LCMS calculated for intermediate $C_{47}H_{52}FN_8O_4(M+H)^+$: m/z=811.4; found: 811.3.

After deprotection as described above, the solution was concentrated in vacuo and diluted with 4:1 acetonitrile/water, filtered through a SiliaPrep Thiol cartridge, and purified by HPLC (pH=2 method) to afford 3-(1-((endo)-2-azabicyclo[2.1.1]hexan-5-yl)-2-ethyl-6-fluoro-7-(3-hydroxynaphthalen-1-yl)-4-(2-(4-methylpiperazin-1-yl)pyridin-4-yl)-1H-imidazo[4,5-c]quinolin-8-yl)propanenitrile as two diastereomers (Peak 1: 0.9 mg, 1.4 μmol, 5% yield; Peak 2: 1.5 mg, 2.3 μmol, 8% yield). Both diastereomers were isolated as their corresponding TFA salt.

Example 22a. Diastereomer 1. Peak 1. LCMS calculated for $C_{40}H_{40}FN_5O$ $(M+H)^+$ m/z=667.3; found 667.3.

Example 22b. Diastereomer 2. Peak 2. LCMS calculated for $C_{40}H_{40}FN_5O$ $(M+H)^+$ m/z=667.3; found 667.3.

Example 23a and Example 23b. 3-(1-((endo)-2-Azabicyclo[2.1.1]hexan-5-yl)-2-ethyl-6-fluoro-7-(3-hydroxynaphthalen-1-yl)-4-methyl-1H-imidazo[4,5-c]quinolin-8-yl)propanenitrile

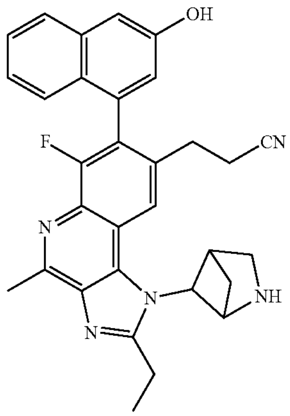 [SMILES: CCc1nc2c(C)nc3c(F)c(-c4cc(O)cc5ccccc45)c(CCC#N)cc3c2n1C1C2CNC1C2]

The title compound was prepared as the unexpected byproduct of the following coupling reaction.

A sample of 4-bromooxazole (40 mg, 0.27 mmol) was dissolved in 1,4-dioxane (0.9 mL) and treated with hexamethylditin (84 μl, 0.41 mmol) and tetrakis(triphenylphosphine)palladium(0) (31 mg, 0.027 mmol). The solution was heated to 100° C. and stirred overnight. The mixture was cooled to room temperature, diluted with EtOAc, then filtered over a pad of Celite twice. The filtrate was concentrated and used as is. A mass corresponding to the desired product, 4-(trimethylstannyl)oxazole, was not observed. A mass that corresponds to trimethyltin radical or anion was observed. LCMS calculated for $C_3H_9Sn$ $(M+H)^+$ m/z=165.0, 163.0, 161.0; found 164.9, 162.9, 160.9.

The crude material was dissolved in 1,4-dioxane (0.44 mL) and treated with a sample of tert-butyl (endo)-5-(8-(2-cyanoethyl)-2-ethyl-6-fluoro-7-(3-(methoxymethoxy)naphthalen-1-yl)-4-(methylthio)-1H-imidazo[4,5-c]quinolin-1-yl)-2-azabicyclo[2.1.1]hexane-2-carboxylate (Example 18, Step 5; 30 mg, 0.044 mmol) in a vial with a stir bar and stirred at room temperature. The solution was treated with tetrakis(triphenylphosphine)palladium(0) (10 mg, 0.009 mmol) and copper(I) 3-methylsalicylate (34 mg, 0.16 mmol). The vial was capped and the solution was stirred at 90° C.

After 3 hours, LCMS showed complete conversion to tert-butyl (endo)-5-(8-(2-cyanoethyl)-2-ethyl-6-fluoro-7-(3-(methoxymethoxy)naphthalen-1-yl)-4-methyl-1H-imidazo[4,5-c]quinolin-1-yl)-2-azabicyclo[2.1.1]hexane-2-carboxylate. The reaction was cooled to room temperature, quenched with aq. $NH_4OH$ and diluted with DCM. The layers were separated, and the aqueous layer was extracted with additional DCM. The combined organic fractions were dried over $MgSO_4$, filtered, and concentrated in vacuo. LCMS calculated for $C_{38}H_{41}FN_5O_4(M+H)^+$: m/z=650.3; found: 650.4.

The crude material was dissolved in 1 mL of 50% TFA in DCM and stirred at room temperature. After 30 minutes, LCMS indicated complete deprotection. The solution was concentrated in vacuo and diluted with 4:1 acetonitrile/water, filtered through a SiliaPrep Thiol cartridge, and purified by HPLC (pH=2 method) to afford 3-(1-((endo)-2-azabicyclo[2.1.1]hexan-5-yl)-2-ethyl-6-fluoro-7-(3-hydroxynaphthalen-1-yl)-4-methyl-1H-imidazo[4,5-c]quinolin-8-yl)propanenitrile as two diastereomers (Peak 1: 0.6 mg, 1.2 μmol, 3% yield; Peak 2: 1.4 mg, 2.8 μmol, 6% yield). Both diastereomers were isolated as their corresponding TFA salt.

Example 23a. Diastereomer 1. Peak 1. LCMS calculated for $C_{31}H_{29}FN_5O$ $(M+H)^+$ m/z=506.2; found 506.2.

Example 23b. Diastereomer 2. Peak 2. LCMS calculated for $C_{31}H_{29}FN_5O$ $(M+H)^+$ m/z=506.2; found 506.2.

Example 24a and Example 24b. 3-(1-((endo)-2-Azabicyclo[2.1.1]hexan-5-yl)-2-ethyl-6-fluoro-7-(3-hydroxynaphthalen-1-yl)-4-phenoxy-1H-imidazo[4,5-c]quinolin-8-yl)propanenitrile

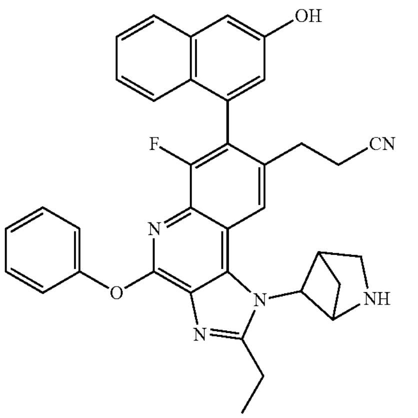 [SMILES: CCc1nc2c(Oc3ccccc3)nc3c(F)c(-c4cc(O)cc5ccccc45)c(CCC#N)cc3c2n1C1C2CNC1C2]

Step 1. tert-Butyl (endo)-5-(8-(2-cyanoethyl)-2-ethyl-6-fluoro-7-(3-(methoxymethoxy)naphthalen-1-yl)-4-(methylsulfinyl)-1H-imidazo[4,5-c]quinolin-1-yl)-2-azabicyclo[2.1.1]hexane-2-carboxylate

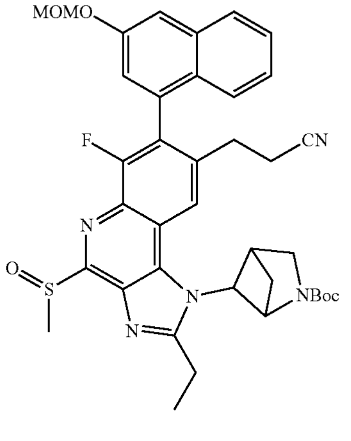

A sample of tert-butyl (endo)-5-(8-(2-cyanoethyl)-2-ethyl-6-fluoro-7-(3-(methoxymethoxy)naphthalen-1-yl)-4-(methylthio)-1H-imidazo[4,5-c]quinolin-1-yl)-2-azabicyclo[2.1.1]hexane-2-carboxylate (Example 18, Step 5; 460 mg, 0.675 mmol) was dissolved in dichloromethane (7 mL) and stirred at 0° C. The solution was treated with m-CPBA (160 mg, 75% w/w, 0.71 mmol).

After 45 minutes, LCMS indicated complete conversion to the desired product, with ~10% of the corresponding sulfone. The reaction was quenched with saturated aq. $NaHCO_3$ and diluted with DCM. The layers were separated, and the aqueous layer was extracted with additional DCM. The combined organic layers were dried over $MgSO_4$, filtered, and concentrated in vacuo to give tert-butyl (endo)-5-(8-(2-cyanoethyl)-2-ethyl-6-fluoro-7-(3-(methoxymethoxy)naphthalen-1-yl)-4-(methylsulfinyl)-1H-imidazo[4,5-c]quinolin-1-yl)-2-azabicyclo[2.1.1]hexane-2-carboxylate (220 mg, 0.31 mmol, 46% yield). LCMS calculated for $C_{38}H_{41}FN_5O_5S$ $(M+H)^+$: m/z=698.3; found: 698.2.

Step 2. 3-(1-((endo)-2-Azabicyclo[2.1.1]hexan-5-yl)-2-ethyl-6-fluoro-7-(3-hydroxynaphthalen-1-yl)-4-phenoxy-1H-imidazo[4,5-c]quinolin-8-yl)propanenitrile A sample of tert-butyl (endo)-5-(8-(2-cyanoethyl)-2-ethyl-6-fluoro-7-(3-(methoxymethoxy)naphthalen-1-yl)-4-(methylsulfinyl)-1H-imidazo[4,5-c]quinolin-1-yl)-2-azabicyclo[2.1.1]hexane-2-carboxylate (20 mg, 0.03 mmol) was dissolved in anhydrous THF (0.3 mL) in a vial with a stir bar and stirred at room temperature. The solution was treated with solid sodium phenolate (7 mg, 0.06 mmol) and stirred at 22° C.

After 1 hour, LCMS showed complete conversion to the desired product. The reaction was quenched with saturated aq. $NH_4Cl$ and diluted with DCM. The layers were separated, and the aqueous layer was extracted with additional DCM. The combined organic layers were dried over $MgSO_4$, filtered, and concentrated in vacuo. LCMS calculated for $C_{43}H_{43}FN_5O_5(M+H)^+$: m/z=728.3; found: 728.3.

The crude material was dissolved in 1 mL of 50% TFA in DCM and stirred at room temperature. After 30 minutes, LCMS indicated complete deprotection. The solution was concentrated in vacuo, diluted with 4:1 acetonitrile/water, filtered through a SiliaPrep Thiol cartridge, and purified by HPLC (pH=2 method) to afford 3-(1-((endo)-2-azabicyclo[2.1.1]hexan-5-yl)-2-ethyl-6-fluoro-7-(3-hydroxynaphthalen-1-yl)-4-phenoxy-1H-imidazo[4,5-c]quinolin-8-yl)propanenitrile as two diastereomers (Peak 1: 1.7 mg, 2.9 μmol, 10% yield; Peak 2: 2.0 mg, 3.4 μmol, 12% yield). Both isomers were isolated as their corresponding TFA salt.

Example 24a. Diastereomer 1. Peak 1. LCMS calculated for $C_{36}H_{31}FN_5O_2(M+H)^+$ m/z=584.3; found 584.2.

Example 24b. Diastereomer 2. Peak 2. LCMS calculated for $C_{36}H_{31}FN_5O_2(M+H)^+$ m/z=584.3; found 584.2.

Example 25a and Example 25b. 3-(1-((endo)-2-Azabicyclo[2.1.1]hexan-5-yl)-2-cyclopropyl-4-(3-(dimethylamino)azetidin-1-yl)-6-fluoro-7-(3-hydroxynaphthalen-1-yl)-1H-imidazo[4,5-c]quinolin-8-yl)propanenitrile

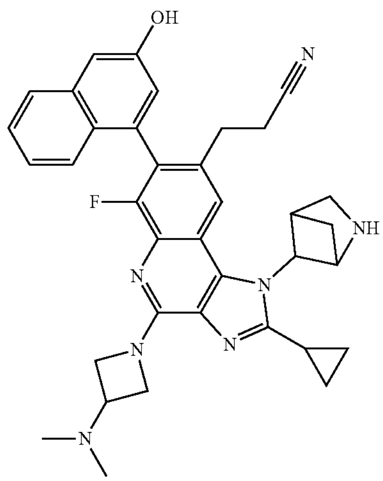 [SMILES: CN(C)C1CN(c2nc3c(F)c(-c4cc(O)cc5ccccc45)c(CCC#N)cc3c3c2nc(C2CC2)n3C2C3CNC2C3)C1]

To a solution of tert-butyl (endo)-5-((3-amino-6-(2-cyanoethyl)-2-(3-(dimethylamino)azetidin-1-yl)-8-fluoro-7-(3-hydroxynaphthalen-1-yl)quinolin-4-yl)amino)-2-azabicyclo[2.1.1]hexane-2-carboxylate (Intermediate 6, 20 mg, 0.031 mmol) in EtOH (2 mL) was added cyclopropanecarbaldehyde (21.5 mg, 0.307 mmol). After stirring at room temperature for 3 days, the solution was concentrated under reduced pressure. The residue was dissolved in EtOH (2 mL) and HCl (4M in 1,4-dioxane, 0.5 mL, 2 mmol). After heating at 40° C. for 1 hour, the mixture was diluted with acetonitrile/water and purified using prep-LCMS (XBridge column, eluting with a gradient of acetonitrile/water containing 0.1% $NH_4OH$, at flow rate of 60 mL/min). Fractions containing the desired diastereomers were then concentrated, and the material obtained was dissolved in acetonitrile and purified by prep-LCMS (Sunfire C18 column, eluting with a gradient of acetonitrile/water containing 0.1% TFA, at flow rate of 60 mL/min). The product was isolated as a pair of diastereomers.

Example 25a. Diastereomer 1. Peak 1. LCMS calculated for $C_{36}H_{37}FN_7O$ $(M+H)^+$ m/z=602.3; found 602.3.

Example 25b. Diastereomer 2. Peak 2. LCMS calculated for $C_{36}H_{37}FN_7O$ $(M+H)^+$ m/z=602.3; found 602.2.

Example 26a and Example 26b. 3-(1-((endo)-2-Azabicyclo[2.1.1]hexan-5-yl)-4-(3-(dimethylamino)azetidin-1-yl)-6-fluoro-7-(3-hydroxynaphthalen-1-yl)-2-(1-(piperidin-4-yl)-1H-1,2,3-triazol-4-yl)-1H-imidazo[4,5-c]quinolin-8-yl)propanenitrile

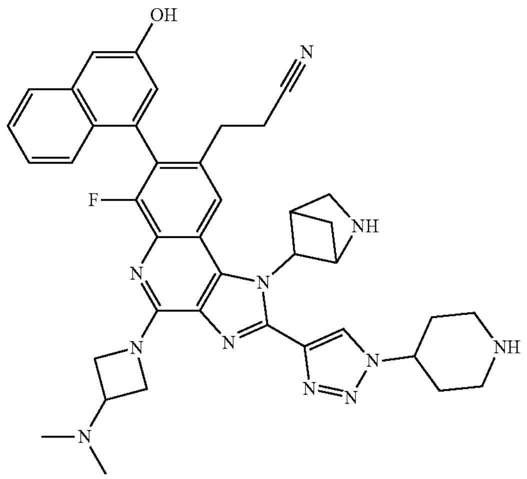 [SMILES: CN(C)C1CN(c2nc3c(F)c(-c4cc(O)cc5ccccc45)c(CCC#N)cc3c3c2nc(-c2cn(C4CCNCC4)nn2)n3C2C3CNC2C3)C1]

This compound was prepared according to the procedures described in Examples 25a and Example 25b, using tert-butyl 4-(4-formyl-1H-1,2,3-triazol-1-yl)piperidine-1-carboxylate instead of cyclopropanecarbaldehyde as a starting material. The product was isolated as a pair of diastereomers.

Example 26a. Diastereomer 1. Peak 1. LCMS calculated for $C_{40}H_{43}FN_{11}O$ $(M+H)^+$ m/z=712.4; found 712.4.

Example 26b. Diastereomer 2. Peak 2. LCMS calculated for $C_{40}H_{43}FN_{11}O$ $(M+H)^+$ m/z=712.4; found 712.4.

Example 27a and Example 27b, Example 27c, and Example 27d. 3-(1-((endo)-2-Azabicyclo[2.1.1]hexan-5-yl)-2-(1-cyclobutyl-1H-1,2,3-triazol-4-yl)-6-fluoro-7-(3-hydroxynaphthalen-1-yl)-4-(((S)-1-methylpyrrolidin-2-yl)methoxy)-1H-imidazo[4,5-c]quinolin-8-yl)propanenitrile

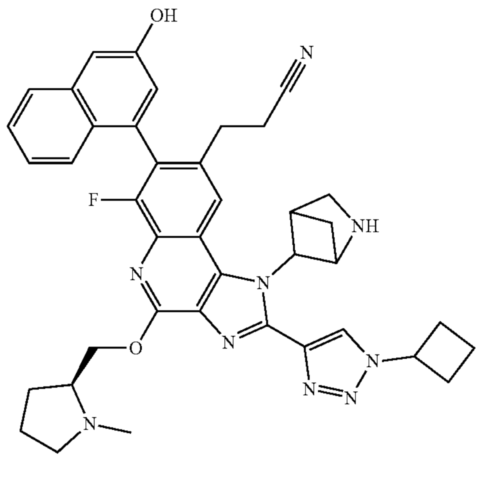 [SMILES: CN1CCC[C@H]1COc1nc2c(F)c(-c3cc(O)cc4ccccc34)c(CCC#N)cc2c2c1nc(-c1cn(C3CCC3)nn1)n2C1C2CNC1C2]

Step 1. tert-Butyl (endo)-5-((7-bromo-8-fluoro-6-iodo-2-(((S)-1-methylpyrrolidin-2-yl)methoxy)-3-nitroquinolin-4-yl)amino)-2-azabicyclo[2.1.1]hexane-2-carboxylate

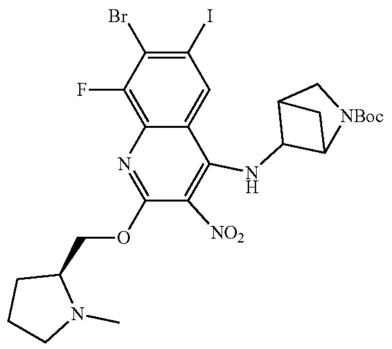 [SMILES: CN1CCC[C@H]1COc1nc2c(F)c(Br)c(I)cc2c(NC2C3CC2N(C(=O)OC(C)(C)C)C3)c1[N+](=O)[O-]]

This compound was prepared according to the procedures described for Intermediate 2, Step 1, using (S)-(1-methylpyrrolidin-2-yl)methanol and sodium hydride instead of N,N-dimethylazetidin-3-amine dihydrochloride as a starting material. LCMS calculated for $C_{25}H_{31}BrFIN_5O_5(M+H)^*$: m/z=706.1; found 706.3.

Step 2. tert-Butyl (endo)-5-((7-bromo-6-(2-cyanoethyl)-8-fluoro-2-(((S)-1-methylpyrrolidin-2-yl)methoxy)-3-nitroquinolin-4-yl)amino)-2-azabicyclo[2.1.1]hexane-2-carboxylate

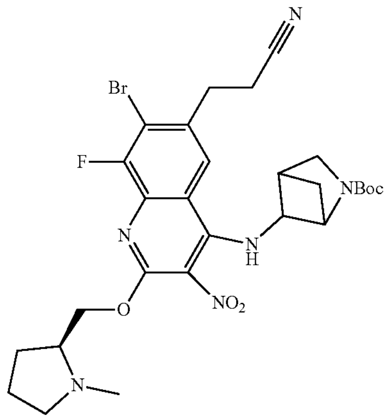 [SMILES: CN1CCC[C@H]1COc1nc2c(F)c(Br)c(CCC#N)cc2c(NC2C3CC2N(C(=O)OC(C)(C)C)C3)c1[N+](=O)[O-]]

This compound was prepared according to the procedures described for Intermediate 3, using tert-butyl (endo)-5-((7-bromo-8-fluoro-6-iodo-2-(((S)-1-methylpyrrolidin-2-yl)methoxy)-3-nitroquinolin-4-yl)amino)-2-azabicyclo[2.1.1]hexane-2-carboxylate instead of tert-butyl (endo)-5-((3-amino-7-bromo-2-(3-(dimethylamino)-azetidin-1-yl)-8-fluoro-6-iodoquinolin-4-yl)amino)-2-azabicyclo[2.1.1]hexane-2-carboxylate as a starting material. LCMS calculated for $C_{28}H_{35}BrFN_6O_5(M+H)^+$: m/z=633.2; found 633.4.

Step 3. tert-Butyl (endo)-5-((3-amino-7-bromo-6-(2-cyanoethyl)-8-fluoro-2-(((S)-1-methylpyrrolidin-2-yl)methoxy)quinolin-4-yl)amino)-2-azabicyclo[2.1.1]hexane-2-carboxylate

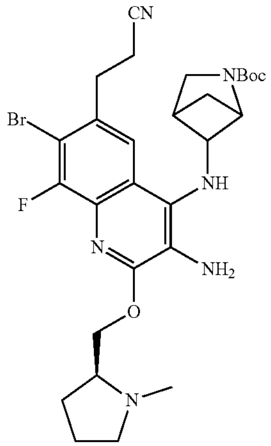 [SMILES: CN1CCC[C@H]1COc1nc2c(F)c(Br)c(CCC#N)cc2c(NC2C3CC2N(C(=O)OC(C)(C)C)C3)c1N]

In a 100 mL round-bottomed flask, tert-butyl (endo)-5-((7-bromo-6-(2-cyanoethyl)-8-fluoro-2-(((S)-1-methylpyrrolidin-2-yl)methoxy)-3-nitroquinolin-4-yl)amino)-2-azabicyclo[2.1.1]hexane-2-carboxylate (1.44 g, 2.27 mmol), ammonium chloride (1.27 g, 23.8 mmol), and iron (1.27 g, 22.7 mmol) were mixed in a solution of THF (10 mL), methanol (10 mL), and water (10 mL). The mixture was stirred at 60° C. for 1 hour. After cooling to room temperature, the resultant solution was filtered through Celite and the residue was washed with water, methanol, and DCM. The filtrate was concentrated under reduced pressure to remove the organic solvent. The remaining mixture was extracted with DCM (100 mL×3). The combined organic layers were washed with brine (100 mL×1), dried over $Na_2SO_4$, and concentrated under reduced pressure. The residue was diluted with MeOH and purified by prep-LCMS (XBridge column, eluting with a gradient of acetonitrile/water containing 0.1% $NH_4OH$, at flow rate of 60 mL/min) to afford the desired product (360 mg, 0.596 mmol) in 26% yield from Step 2. LCMS calculated for $C_{28}H_{37}BrFN_6O_3$ $(M+H)^+$ m/z=603.2; found 603.3.

Step 4. tert-Butyl (endo)-5-((3-amino-6-(2-cyanoethyl)-8-fluoro-7-(3-hydroxynaphthalen-1-yl)-2-(((S)-1-methylpyrrolidin-2-yl)methoxy)quinolin-4-yl)amino)-2-azabicyclo[2.1.1]hexane-2-carboxylate

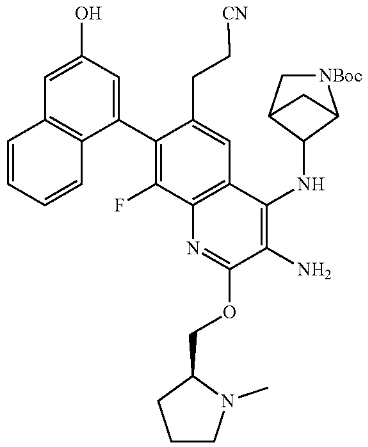 [SMILES: CN1CCC[C@H]1COc1nc2c(F)c(-c3cc(O)cc4ccccc34)c(CCC#N)cc2c(NC2C3CC2N(C(=O)OC(C)(C)C)C3)c1N]

This compound was prepared according to the procedures described for Intermediate 6, using tert-butyl (endo)-5-((3-amino-7-bromo-6-(2-cyanoethyl)-8-fluoro-2-(((S)-1-methylpyrrolidin-2-yl)methoxy)quinolin-4-yl)amino)-2-azabicyclo[2.1.1]hexane-2-carboxylate instead of tert-butyl (endo)-5-((3-amino-7-bromo-6-(2-cyanoethyl)-2-(3-(dimethylamino)azetidin-1-yl)-8-fluoroquinolin-4-yl) amino)-2-azabicyclo[2.1.1]hexane-2-carboxylate as a starting material. LCMS calculated for $C_{38}H_{44}FN_6O_4(M+H)^+$ m/z=667.3; found 667.6.

Step 5. 3-(1-((endo)-2-Azabicyclo[2.1.1]hexan-5-yl)-2-(1-cyclobutyl-1H-1,2,3-triazol-4-yl)-6-fluoro-7-(3-hydroxynaphthalen-1-yl)-4-(((S)-1-methylpyrrolidin-2-yl)methoxy)-1H-imidazo[4,5-c]quinolin-8-yl)propanenitrile This compound was prepared according to the procedures described in Examples 25a and Example 25b, using 1-cyclobutyl-1H-1,2,3-triazole-4-carbaldehyde instead of cyclopropanecarbaldehyde as a starting material. The products were isolated as single diastereomers.

Example 27a. Diastereomer 1. Peak 1. LCMS calculated for $C_{40}H_{41}FN_9O_2(M+H)^+$ m/z=698.3; found 698.5.

Example 27b. Diastereomer 2. Peak 2. LCMS calculated for $C_{40}H_{41}FN_9O_2(M+H)^+$ m/z=698.3; found 698.5.

Example 27c. Diastereomer 3. Peak 3. LCMS calculated for $C_{40}H_{41}FN_9O_2(M+H)^+$ m/z=698.3; found 698.5.

Example 27d. Diastereomer 4. Peak 4. LCMS calculated for $C_{40}H_{41}FN_9O_2(M+H)^+$ m/z=698.3; found 698.5.

Example 28. 3-(1-(2-azabicyclo[2.1.1]hexan-5-yl)-2-ethyl-6-fluoro-4-(((2R,7aS)-2-fluorotetrahydro-1H-pyrrolizin-7a(5H)-yl)methoxy)-7-(5-methyl-1H-indol-3-yl)-1H-imidazo[4,5-c]quinolin-8-yl) propanenitrile

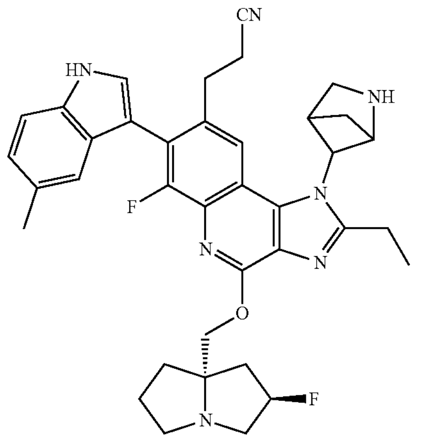 [SMILES: CCc1nc2c(OC[C@@]34CCCN3C[C@H](F)C4)nc3c(F)c(-c4c[nH]c5ccc(C)cc45)c(CCC#N)cc3c2n1C1C2CNC1C2]

Step 1. tert-butyl (endo)-5-(7-bromo-8-(2-cyanoethyl)-2-ethyl-6-fluoro-4-(methylsulfonyl)-1H-imidazo[4,5-c]quinolin-1-yl)-2-azabicyclo[2.1.1] hexane-2-carboxylate

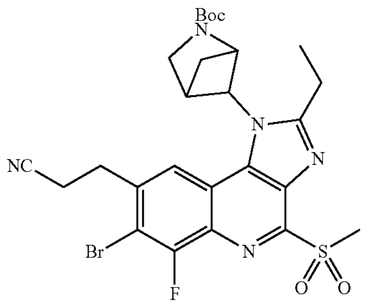 [SMILES: CCc1nc2c(S(C)(=O)=O)nc3c(F)c(Br)c(CCC#N)cc3c2n1C1C2CC1N(C(=O)OC(C)(C)C)C2]

To a 40 mL vial charged with a magnetic stir bar was added tert-butyl (endo)-5-(7-bromo-8-(2-cyanoethyl)-2-ethyl-6-fluoro-4-(methylthio)-1H-imidazo[4,5-c]quinolin-1-yl)-2-azabicyclo[2.1.1]hexane-2-carboxylate (Example 18, Step 4; 736.7 mg, 1.282 mmol) and ethyl acetate (12.82 ml). The solution was cooled to 0° C. before m-CPBA (1.32 g, 3.85 mmol) was added in one portion. The mixture was stirred at 0° C. for 90 min. The reaction was diluted with water and ethyl acetate, phases separated, and the aqueous phase extracted 3× with ethyl acetate. The combined organics were rinsed with saturated aq $NaHCO_3$ (2×), brine, dried over sodium sulfate, filtered and concentrated to the desired product as a white/light yellow powder (778 mg, 100%). This material was moved forward without additional purification. LCMS calculated for $C_{26}H_{29}BrFN_5O_4S$ $(M+H)^+$: m/z=606.5; found 607.4.

Step 2: tert-butyl (endo)-5-(7-bromo-8-(2-cyanoethyl)-2-ethyl-6-fluoro-4-(((2R,7aS)-2-fluorotetrahydro-1H-pyrrolizin-7a(5H)-yl)methoxy)-1H-imidazo[4,5-c]quinolin-1-yl)-2-azabicyclo[2.1.1] hexane-2-carboxylate

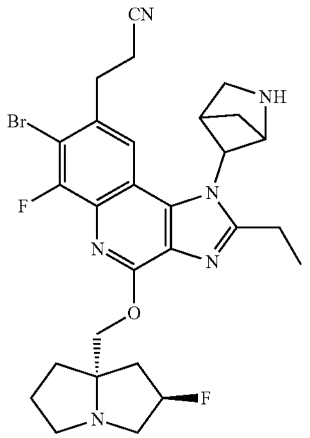 [SMILES: CCc1nc2c(OC[C@@]34CCCN3C[C@H](F)C4)nc3c(F)c(Br)c(CCC#N)cc3c2n1C1C2CNC1C2]

To a 40 ml vial charged with a magnetic stir bar was added tert-butyl (endo)-5-(7-bromo-8-(2-cyanoethyl)-2-ethyl-6-fluoro-4-(methylsulfonyl)-1H-imidazo[4,5-c]quinolin-1-yl)-2-azabicyclo[2.1.1]hexane-2-carboxylate (757 mg, 1.248 mmol), THF (24.96 ml), ((2R,7aS)-2-fluorotetrahydro-1H-pyrrolizin-7a(5H)-yl)methanol (298 mg, 1.872 mmol), and lastly potassium tert-butoxide (1 M in THF) (1872 μl, 1.872 mmol). The mixture was heated to 45° C. and stirred overnight (18 h). After the indicated time, the reaction was diluted with water and ethyl acetate, the phases were separated and the aqueous phase was extracted with ethyl acetate (2×). The combined organics were rinsed with saturated aq $NaHCO_3$ solution, brine, dried over sodium sulfate, filtered and concentrated. The residue was purified via flash column chromatography (0 to 100% ethyl acetate in hexanes then 0 to 15% MeOH in dichloromethane) to deliver the desired product as a brown foam (157 mg, 19%). LCMS calculated for $C_{33}H_{39}BrF_2N_6O_3$ $(M+H)^+$: m/z=685.6; found 686.2.

Step 3. 3-(1-(2-azabicyclo[2.1.1]hexan-5-yl)-2-ethyl-6-fluoro-4-(((2R,7aS)-2-fluorotetrahydro-1H-pyrrolizin-7a(5H)-yl)methoxy)-7-(5-methyl-1H-indol-3-yl)-1H-imidazo[4,5-c]quinolin-8-yl)propanenitrile To a 1-dram vial equipped with a stir bar was added tert-butyl (endo)-5-(7-bromo-8-(2-cyanoethyl)-2-ethyl-6-fluoro-4-(((2R,7aS)-2-fluorotetrahydro-1H-pyrrolizin-7a(5H)-yl)methoxy)-1H-imidazo[4,5-c]quinolin-1-yl)-2-azabicyclo[2.1.1]hexane-2-carboxylate (15 mg, 0.022 mmol), 5-methyl-3-(4,4,5,5-tetramethyl-1,3,2-dioxaborolan-2-yl)-1H-indole (11.25 mg, 0.044 mmol), $Na_2CO_3$ (6.96 mg, 0.066 mmol), XPhos Pd G2 (0.861 mg, 1.094 μmol), dioxane (0.122 ml), and water (0.024 ml). The mixture was capped and stirred at 100° C. for 1 h. After this time, the reaction was cooled to rt, filtered to remove solids, and diluted with MeCN/water. To the mixture was added HCl (4 M in dioxane) (400 μl, 1.600 mmol). The whole was stirred at 60° C. After 30 min, the mixture was purified using prep-LCMS (XBridge C18 column, eluting with a gradient of acetonitrile/water containing 0.1% TFA, at flow rate of 60 mL/min) to afford the desired product as the TFA salt and a mixture of diastereomers. Example 28. LCMS calculated for $C_{37}H_{39}F_2N_7O$ $(M+H)^+$ m/z=635.8; found 636.5.

Example 29. 4-((1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(methylamino)ethyl)-1H-imidazo[4,5-c]quinolin-8-yl)methyl)benzonitrile

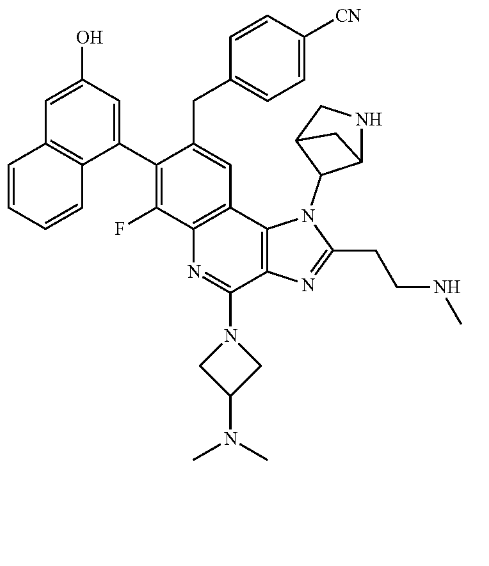 [SMILES: CNCCc1nc2c(N3CC(N(C)C)C3)nc3c(F)c(-c4cc(O)cc5ccccc45)c(Cc4ccc(C#N)cc4)cc3c2n1C1C2CNC1C2]

Step 1. tert-butyl 5-(7-bromo-2-(2-((tert-butoxycarbonyl)(methyl)amino)ethyl)-4-(3-(dimethylamino)azetidin-1-yl)-6-fluoro-8-iodo-1H-imidazo[4,5-c]quinolin-1-yl)-(endo)-2-azabicyclo[2.1.1]hexane-2-carboxylate

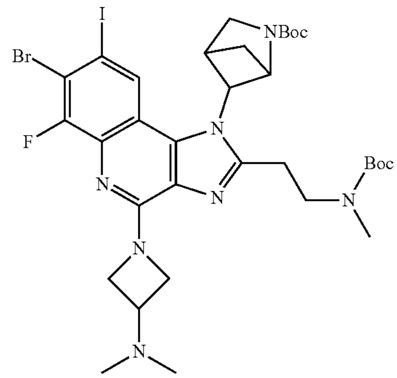 [SMILES: CN(CCc1nc2c(N3CC(N(C)C)C3)nc3c(F)c(Br)c(I)cc3c2n1C1C2CC1N(C(=O)OC(C)(C)C)C2)C(=O)OC(C)(C)C]

To a 40 ml vial charged with a magnetic stir bar was added tert-butyl (endo)-5-((3-amino-7-bromo-2-(3-(dimethylamino)azetidin-1-yl)-8-fluoro-6-iodoquinolin-4-yl)amino)-2-azabicyclo[2.1.1]hexane-2-carboxylate (Intermediate 2, 600 mg, 0.907 mmol), ethanol (4.54 ml), tert-butyl methyl (3-oxopropyl)carbamate (255 mg, 1.361 mmol), and acetic acid (51.9 μl, 0.907 mmol). The mixture was capped and stirred at 75° C. overnight (16 h). After the indicated time, the reaction was diluted with water and ethyl acetate. The phases were separated and the aqueous layer was extracted 2× more with ethyl acetate. The combined organics were rinsed with saturated aq. $NaHCO_3$, brine, dried over sodium sulfate filtered and concentrated to give the desired product as a light yellow foam. This material was moved forward to the next step without additional purification. LCMS calculated for $C_{33}H_{44}BrFIN_7O_4(M+H)^+$: m/z=828.6; found 829.6.

Step 2. tert-butyl 5-(7-bromo-2-(2-((tert-butoxycarbonyl)(methyl)amino)ethyl)-8-(4-cyanobenzyl)-4-(3-(dimethylamino)azetidin-1-yl)-6-fluoro-1H-imidazo[4,5-c]quinolin-1-yl)(endo)-2-azabicyclo[2.1.1]hexane-2-carboxylate

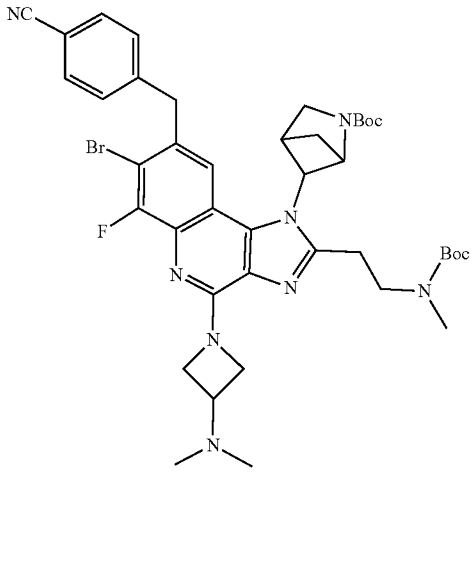 [SMILES: CN(CCc1nc2c(N3CC(N(C)C)C3)nc3c(F)c(Br)c(Cc4ccc(C#N)cc4)cc3c2n1C1C2CC1N(C(=O)OC(C)(C)C)C2)C(=O)OC(C)(C)C]

To a 40 mL vial charged with a magnetic stir bar was added tert-butyl 5-(7-bromo-2-(2-((tert-butoxycarbonyl)(methyl)amino)ethyl)-4-(3-(dimethylamino)azetidin-1-yl)-6-fluoro-8-iodo-1H-imidazo[4,5-c]quinolin-1-yl)(endo)-2-azabicyclo[2.1.1]hexane-2-carboxylate (50 mg, 0.060 mmol), THF (1.207 ml), $Pd(Cl)_2(PPh_3)_2$(8.47 mg, 0.012 mmol) and (2-cyanobenzyl)zinc(II) bromide (0.5 M in THF) (241 μl, 0.121 mmol). The mixture was degassed with $N_2$ for 5 min, capped and stirred at 60° C. After 1 h, the reaction was filtered to remove solids and the filtrate was concentrated in vacuo to give the crude product as a yellow foam. This material was moved forward to the next step without additional purification. LCMS calculated for $C_{41}H_{50}BrFN_8O_4(M+H)^+$: m/z=817.8; found 818.3.

Step 3. 4-((1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(methylamino)ethyl)-1H-imidazo[4,5-c]quinolin-8-yl)methyl)benzonitrile To a 1-dram vial equipped with a stir bar was added 4-((1-((endo)-2-azabicyclo[2.1.1]hexan-5-yl)-7-bromo-4-(3-(dimethylamino)azetidin-1-yl)-6-fluoro-2-(2-(methylamino)ethyl)-1H-imidazo[4,5-c]quinolin-8-yl)methyl)benzonitrile (15 mg, 0.024 mmol), 4-(4,4,5,5-tetramethyl-1,3,2-dioxaborolan-2-yl)naphthalen-2-ol (13.12 mg, 0.049 mmol), $Na_2CO_3$ (7.72 mg, 0.073 mmol), XPhos Pd G2 (0.956 mg, 1.214 μmol), dioxane (0.135 ml), and water (0.027 ml). The mixture was capped and stirred at 100° C. for 1 h. After this time, the reaction was cooled to rt, filtered to remove solids, and diluted with acetonitrile/water. HCl (4 M in dioxane) (267 μl, 1.069 mmol) was added to the mixture. The whole was stirred at 50° C. After 30 min, the mixture was purified using prep-LCMS (XBridge C18 column, eluting with a gradient of acetonitrile/water containing 0.1% $NH_4OH$, at flow rate of 60 mL/min) to afford the desired product. The product was isolated as a mixture of diastereomers. Example 29. LCMS calculated for $C_{41}H_{41}FN_8O$ $(M+H)^+$ m/z=680.8; found 681.5.

Example 30. 3-(1-((endo)-2-azabicyclo[2.1.1]hexan-5-yl)-2-ethyl-6-fluoro-7-(5-fluoro-1H-indol-3-yl)-4-(((2R,7aS)-2-fluorotetrahydro-1H-pyrrolizin-7a(5H)-yl)methoxy)-1H-imidazo[4,5-c]quinolin-8-yl)propanenitrile

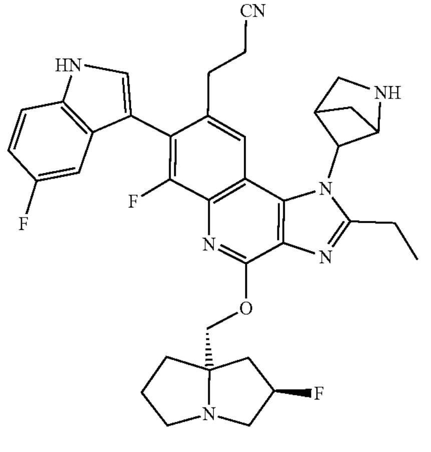

This compound was prepared according to the procedure described for Example 28, replacing tert-butyl 5-fluoro-3-(4,4,5,5-tetramethyl-1,3,2-dioxaborolan-2-yl)-1H-indole-1-carboxylate with tert-butyl 5-fluoro-3-(4,4,5,5-tetramethyl-1,3,2-dioxaborolan-2-yl)-1H-indole-1-carboxylate in Step 7.

To a 1-dram vial equipped with a stir bar was added tert-butyl (endo)-5-(7-bromo-8-(2-cyanoethyl)-2-ethyl-6-fluoro-4-(((2R,7aS)-2-fluorotetrahydro-1H-pyrrolizin-7a(5H)-yl)methoxy)-1H-imidazo[4,5-c]quinolin-1-yl)-2-azabicyclo[2.1.1]hexane-2-carboxylate (117 μl, 0.029 mmol), tert-butyl 5-fluoro-3-(4,4,5,5-tetramethyl-1,3,2-dioxaborolan-2-yl)-1H-indole-1-carboxylate (21.07 mg, 0.058 mmol), $Na_2CO_3$ (9.28 mg, 0.088 mmol), XPhos Pd G2 (1.148 mg, 1.459 μmol), dioxane (0.162 ml), and water (0.032 ml). The mixture was capped and stirred at 100° C. for 1 h. After this time, the reaction was cooled to rt, filtered to remove solids, and diluted with MeCN/water. To the mixture was added TFA (200 μl, 2.60 mmol). The whole was stirred at 70° C. After 30 min, the mixture was purified using prep-LCMS (XBridge C18 column, eluting with a gradient of acetonitrile/water containing 0.1% TFA, at flow rate of 60 mL/min) to afford the desired product. The product was isolated as the TFA salt and a mixture of diastereomers. Example 30. LCMS calculated for $C_{36}H_{36}F_3N_7O$ $(M+H)^-$ m/z=639.7; found 640.3.

Example 31a and Example 31b. 3-(7-(3-aminoisoquinolin-1-yl)-1-endo-(2-azabicyclo[2.1.1]hexan-5-yl)-8-(2-cyanoethyl)-4-(3-(dimethylamino)azetidin-1-yl)-6-fluoro-1H-imidazo[4,5-c]quinolin-2-yl)-N,N-dimethylpropanamide

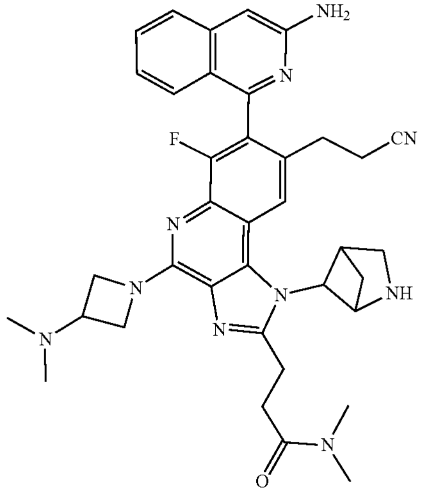 [SMILES: CN(C)C(=O)CCc1nc2c(N3CC(N(C)C)C3)nc3c(F)c(-c4nc(N)cc5ccccc45)c(CCC#N)cc3c2n1C1C2CNC1C2]

Step 1. tert-butyl 5-(7-(3-aminoisoquinolin-1-yl)-8-(2-cyanoethyl)-2-(3-(dimethylamino)-3-oxopropyl)-4-(3-(dimethylamino)azetidin-1-yl)-6-fluoro-1H-imidazo[4,5-c]quinolin-1-yl)-2-endo-azabicyclo[2.1.1]hexane-2-carboxylate

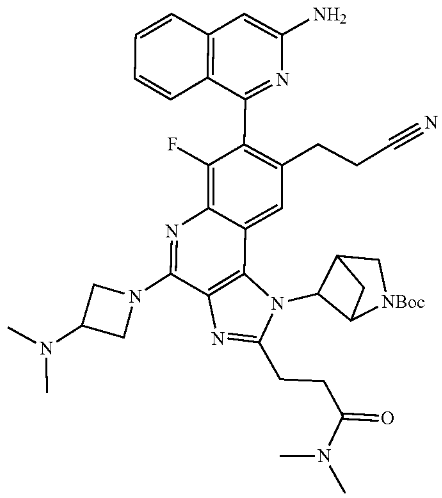 [SMILES: CN(C)C(=O)CCc1nc2c(N3CC(N(C)C)C3)nc3c(F)c(-c4nc(N)cc5ccccc45)c(CCC#N)cc3c2n1C1C2CC1N(C(=O)OC(C)(C)C)C2]

To a solution of tert-butyl 5-(8-(2-cyanoethyl)-2-(3-(dimethylamino)-3-oxopropyl)-4-(3-(dimethylamino)azetidin-1-yl)-6-fluoro-7-(4,4,5,5-tetramethyl-1,3,2-dioxaborolan-2-yl)-1H-imidazo[4,5-c]quinolin-1-yl)-2-endo-azabicyclo[2.1.1]hexane-2-carboxylate (Example 10, Step 1, 100 mg, 0.060 mmol, 1.00 equiv.) in 1,4-dioxane (1.0 mL) and 0.5 M $K_3PO_4$ (0.25 mL) was added 1-bromoisoquinolin-3-amine (40.4 mg, 0.181 mmol, 3.0 equiv.) followed by SPhos Pd G4 (10.0 mg, 12.6 μmol, 0.21 equiv.). The vial headspace was purged with a stream of nitrogen and the mixture was stirred at 60° C. for 30 min. After this time, the mixture was diluted with MeOH, filtered through a SiliaPrep Thiol cartridge, and purified via prep-LCMS (XBridge C18 column, eluting with a gradient of acetonitrile/water containing 0.1% TFA, at flow rate of 60 mL/min) to afford Peak 1 and Peak 2. Each solution was lyophilized to afford the desired product. LCMS calculated for $C_{42}H_{50}FN_{10}O_3(M+H)^+$: m/z=761.4; found: 761.4.

Step 2. 3-(7-(3-aminoisoquinolin-1-yl)-1-endo-(2-azabicyclo[2.1.1]hexan-5-yl)-8-(2-cyanoethyl)-4-(3-(dimethylamino)azetidin-1-yl)-6-fluoro-1H-imidazo[4,5-c]quinolin-2-yl)-N,N-dimethylpropanamide To individual 40 mL vials containing Peak 1 and Peak 2 (separately) from Step 1 was added 0.5 mL TFA and the mixtures were stirred at 21° C. for 30 min. After this time, the mixtures were diluted with MeOH and purified via prep-LCMS (XBridge C18 column, eluting with a gradient of acetonitrile/water containing 0.1% TFA, at flow rate of 60 mL/min) to afford Peak 1 and Peak 2 as white flocculent solids after lyophilization.

Example 31a. Diastereomer 1. Peak 1. LCMS calculated for $C_{37}H_{42}FN_{10}O^+$ $(M+H)^+$ m/z=661.4; found 661.3.

Example 31b. Diastereomer 2. Peak 2. LCMS calculated for $C_{37}H_{42}FN_{10}O^+$ $(M+H)^+$ m/z=661.4; found 661.3.

Example 32a and Example 32b. 3-(7-(6-amino-3-(trifluoromethyl)pyridin-2-yl)-1-endo-(2-azabicyclo[2.1.1]hexan-5-yl)-8-(2-cyanoethyl)-4-(3-(dimethylamino)azetidin-1-yl)-6-fluoro-1H-imidazo[4,5-c]quinolin-2-yl)-N,N-dimethylpropanamide

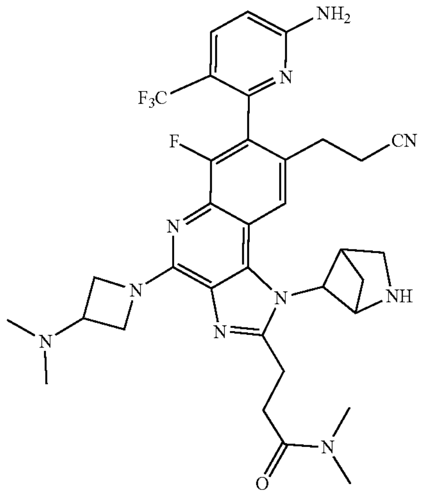 [SMILES: CN(C)C(=O)CCc1nc2c(N3CC(N(C)C)C3)nc3c(F)c(-c4nc(N)ccc4C(F)(F)F)c(CCC#N)cc3c2n1C1C2CNC1C2]

This compound was prepared using protocols identical to those reported for Example 31a and Example 31b, replacing 1-bromoisoquinolin-3-amine with 6-chloro-5-(trifluoromethyl)pyridin-2-amine in Step 1.

Example 32a. Diastereomer 1. Peak 1. LCMS calculated for $C_{34}H_{39}F_4N_{10}O^+$ $(M+H)^+$ m/z=679.3; found 679.3.

Example 32b. Diastereomer 2. Peak 2. LCMS calculated for $C_{34}H_{39}F_4N_{10}O^+$ $(M+H)^+$ m/z=679.3; found 679.3.

Example 33. 3-(1-endo-(2-azabicyclo[2.1.1]hexan-5-yl)-8-(2-cyanoethyl)-7-(7,7-difluoro-5,6,7,8-tetrahydronaphthalen-1-yl)-4-(3-(dimethylamino)azetidin-1-yl)-6-fluoro-1H-imidazo[4,5-c]quinolin-2-yl)-N,N-dimethylpropanamide

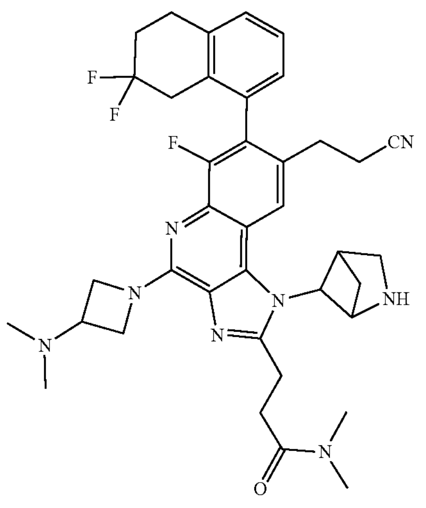 [SMILES: CN(C)C(=O)CCc1nc2c(N3CC(N(C)C)C3)nc3c(F)c(-c4cccc5c4CC(F)(F)CC5)c(CCC#N)cc3c2n1C1C2CNC1C2]

Step 1. 8-bromo-2,2-difluoro-1,2,3,4-tetrahydronaphthalene

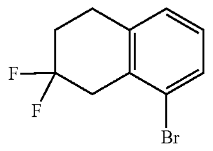 [SMILES: FC1(F)CCc2cccc(Br)c2C1]

8-Bromo-3,4-dihydronaphthalen-2(1H)-one (357 mg, 1.59 mmol, 1.0 equiv.) was dissolved in 1.0 mL of DCM. EtOH (9.3 μL, 0.159 mmol, 0.1 equiv.) followed by bis(2-methoxyethyl)aminosulfur trifluoride (0.733 mL, 3.98 mmol, 2.5 equiv.) were added sequentially to the reaction mixture. The mixture was stirred at 21° C. and after 20 h. The reaction was quenched by addition of saturated aqueous sodium bicarbonate (2.0 mL) and extracted with DCM (3×4 mL). The organic extracts were dried over $MgSO_4$, filtered, and concentrated in vacuo. The crude residue was purified by automated flash column chromatography on silica gel (0-100% DCM/heptane) to afford the desired product as a clear, viscous oil (80 mg, 1.59 mmol, 20%).

Step 2. 2-(7,7-difluoro-5,6,7,8-tetrahydronaphthalen-1-yl)-4,4,5,5-tetramethyl-1,3,2-dioxaborolane

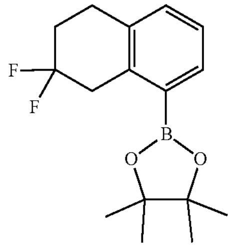 [SMILES: CC1(C)OB(c2cccc3c2CC(F)(F)CC3)OC1(C)C]

A solution of 8-bromo-2,2-difluoro-1,2,3,4-tetrahydronaphthalene (80 mg, 0.324 mmol, 1.00 equiv.), Pd(dppf)$Cl_2$.$CH_2Cl_2$ (26.4 mg, 0.032 mmol, 0.1 equiv.), potassium acetate (63.6 mg, 0.648 mmol, 2.0 equiv.), and bis(pinacolato)diboron (103 mg, 0.405 mmol, 1.25 equiv) in dioxane (2.0 mL) was heated at 85° C. for 3 h. The reaction mixture was cooled to 21° C., diluted with water (4 mL) and extracted into DCM (3×4 mL). The organic layer was dried over $MgSO_4$, filtered, and dried to provide a residue that was purified by automated flash column chromatography (0-100% DCM/heptane) to yield the title compound as a clear oil (95.0 mgs, 0.324 mmol, quant.).

Step 3: 3-(1-endo-(2-azabicyclo[2.1.1]hexan-5-yl)-8-(2-cyanoethyl)-7-(7,7-difluoro-5,6,7,8-tetrahydronaphthalen-1-yl)-4-(3-(dimethylamino)azetidin-1-yl)-6-fluoro-1H-imidazo[4,5-c]quinolin-2-yl)-N,N-dimethylpropanamide To a solution of tert-butyl 5-(7-bromo-8-(2-cyanoethyl)-2-(3-(dimethylamino)-3-oxopropyl)-4-(3-(dimethylamino)azetidin-1-yl)-6-fluoro-1H-imidazo[4,5-c]quinolin-1-yl)-2-endo-azabicyclo[2.1.1]hexane-2-carboxylate (Intermediate 9, 20.0 mg, 0.043 mmol, 1.0 equiv.) in 1,4-dioxane (1.0 mL) and 0.5 M $K_3PO_4$ (0.25 mL) was added 2-(7,7-difluoro-5,6,7,8-tetrahydronaphthalen-1-yl)-4,4,5,5-tetramethyl-1,3,2-dioxaborolane (12.7 mg, 0.181 mmol, 3.0 equiv.) followed by XPhos Pd G4 (4.9 mg, 5.73 μmol, 0.20 equiv.). The vial headspace was purged with a stream of nitrogen and the mixture was stirred at 75° C. for 1 h. After this time, the mixture was diluted with water (2 mL), extracted into DCM (3×3 mL), dried over $MgSO_4$ and then dried in vacuo. The residue was treated with TFA (0.5 mL) and stirred for 30 minutes, then diluted with MeOH, and purified via prep-LCMS (XBridge C18 column, eluting with a gradient of acetonitrile/water containing 0.1% TFA, at flow rate of 60 mL/min) to afford the title compound and the TFA salt and mixture of diastereomers. Example 33. LCMS calculated for $C_{38}H_{44}F_3N_8O^+$ $(M+H)^+$ m/z=685.4; found 685.4.

Example 34a and Example 34b. 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(1-phenyl-1H-pyrazol-3-yl)-1H-imidazo[4,5-c]quinolin-8-yl)propanenitrile

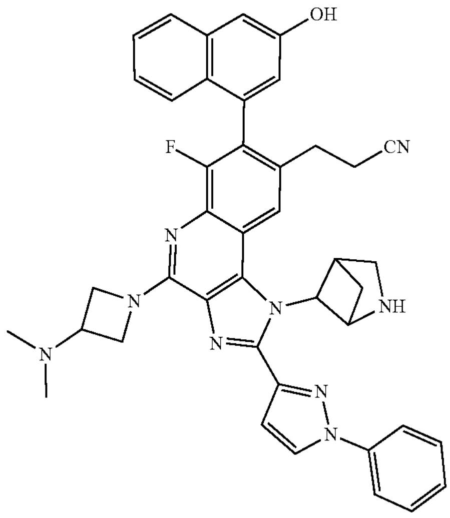 [SMILES: CN(C)C1CN(c2nc3c(F)c(-c4cc(O)cc5ccccc45)c(CCC#N)cc3c3c2nc(-c2ccn(-c4ccccc4)n2)n3C2C3CNC2C3)C1]

To a vial containing tert-butyl (endo)-5-((3-amino-6-(2-cyanoethyl)-2-(3-(dimethylamino)azetidin-1-yl)-8-fluoro-7-(3-hydroxynaphthalen-1-yl)quinolin-4-yl)amino)-2-azabicyclo[2.1.1]hexane-2-carboxylate (Intermediate 6, 40.0 mg, 0.061 mmol) in ethanol (0.5 mL, 0.12 M) was added 1-phenyl-1H-pyrazole-3-carbaldehyde (26.4 mg, 0.153 mmol, 2.5 equiv). After stirring at 23° C. for 18 h, HCl (4.0 M in dioxane, 0.2 mL) was added and the mixture continued to stir at 23° C. After 6 h, the mixture was diluted with methanol and purified by prep-LCMS (Sunfire C18 column, eluting with a gradient of acetonitrile/water containing 0.1% TFA, at a flow rate of 60 mL/min) to afford the desired product as a TFA salt. The product was isolated as a pair of diastereomers.

Example 34a. Diastereomer 1. Peak 1. LCMS calculated for $C_{42}H_{38}FN_9O$ $(M+H)^+$ m/z=704.3; found 704.3.

Example 34b. Diastereomer 2. Peak 2. LCMS calculated for $C_{42}H_{38}FN_9O$ $(M+H)^+$ m/z=704.3; found 704.3.

Example 35a and Example 35b. 3-(1-((endo)-2-azabicyclo[2.1.1]hexan-5-yl)-4-(3-(dimethylamino)azetidin-1-yl)-2-(1-ethyl-1H-pyrazol-3-yl)-6-fluoro-7-(3-hydroxynaphthalen-1-yl)-1H-imidazo[4,5-c]quinolin-8-yl)propanenitrile

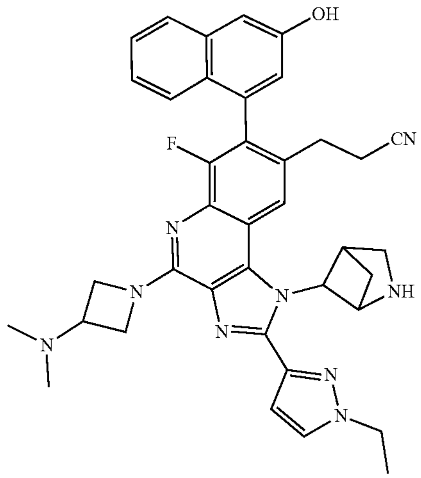 [SMILES: CCn1ccc(-c2nc3c(N4CC(N(C)C)C4)nc4c(F)c(-c5cc(O)cc6ccccc56)c(CCC#N)cc4c3n2C2C3CNC2C3)n1]

This compound was prepared according to the procedure described for Example 34, replacing 1-phenyl-1H-pyrazole-3-carbaldehyde with 1-ethyl-1H-pyrazole-3-carbaldehyde. The compound was purified using prep-LCMS (Sunfire C18 column, eluting with a gradient of acetonitrile/water containing 0.1% TFA, at a flow rate of 60 mL/min) to afford the desired product as a TFA salt. The product was isolated as a pair of diastereomers.

Example 35a. Diastereomer 1. Peak 1. LCMS calculated for $C_{38}H_{38}FN_9O$ $(M+H)^+$ m/z=656.3; found 656.3.

Example 35b. Diastereomer 2. Peak 2. LCMS calculated for $C_{38}H_{38}FN_9O$ $(M+H)^+$ m/z=656.3; found 656.3.

Example 36a and Example 36b. 3-(2-(1-benzyl-1H-pyrazol-3-yl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-8-yl)propanenitrile

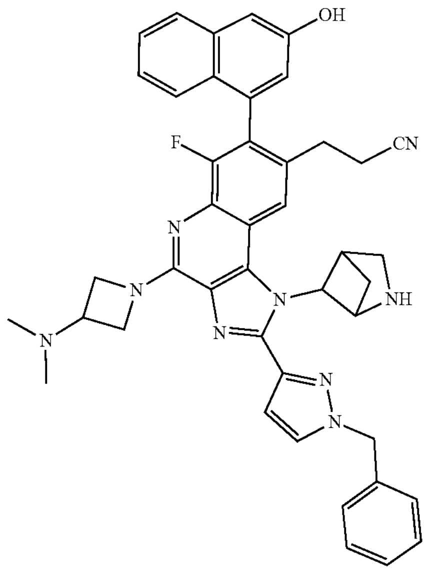 [SMILES: CN(C)C1CN(c2nc3c(F)c(-c4cc(O)cc5ccccc45)c(CCC#N)cc3c3c2nc(-c2ccn(Cc4ccccc4)n2)n3C2C3CNC2C3)C1]

To a vial containing tert-butyl (endo)-5-((3-amino-6-(2-cyanoethyl)-2-(3-(dimethylamino)azetidin-1-yl)-8-fluoro-7-(3-hydroxynaphthalen-1-yl)quinolin-4-yl)amino)-2-azabicyclo[2.1.1]hexane-2-carboxylate (Intermediate 6, 30.0 mg, 0.046 mmol) in ethanol (0.4 mL, 0.12 M) was added 1-benzyl-1H-pyrazole-4-carbaldehyde (42.9 mg, 0.230 mmol, 5.0 equiv). After stirring at 23° C. for 18 h, the mixture was diluted with methanol and purified using prep-LCMS (XBridge C18 column, eluting with a gradient for acetonitrile/water containing 0.1% $NH_4OH$ at a flow rate of 60 mL/min). LCMS calculated for $C_{48}H_{48}FN_903$ $(M+H)^+$ m/z=818.4; found 818.4. The purified material was concentrated and dissolved in ethanol (0.4 mL), followed by addition of HCl (4.0 M in dioxane, 0.2 mL). After stirring at 23° C. for 3 h, the mixture was diluted with methanol and purified by prep-LCMS (Sunfire C18 column, eluting with a gradient of acetonitrile/water containing 0.1% TFA, at a flow rate of 60 mL/min) to afford the desired product as a TFA salt. The product was isolated as a pair of diastereomers.

Example 36a. Diastereomer 1. Peak 1. LCMS calculated for $C_{43}H_{40}FN_9O$ $(M+H)^+$ m/z=718.3; found 718.3.

Example 36b. Diastereomer 2. Peak 2. LCMS calculated for $C_{43}H_{40}FN_9O$ $(M+H)^+$ m/z=718.3; found 718.3.

Example 37. 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(pyrimidin-2-yl)ethyl)-1H-imidazo[4,5-c]quinolin-8-yl)propanenitrile

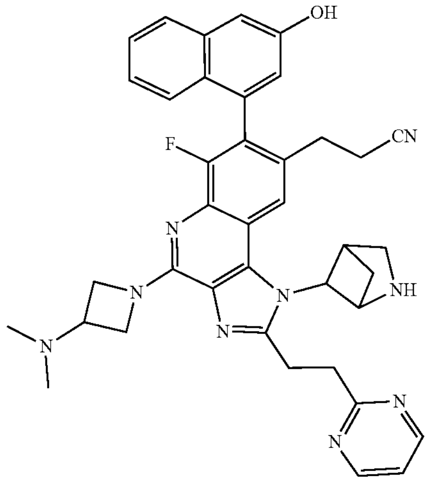 [SMILES: CN(C)C1CN(c2nc3c(F)c(-c4cc(O)cc5ccccc45)c(CCC#N)cc3c3c2nc(CCc2ncccn2)n3C2C3CNC2C3)C1]

This compound was prepared according to the procedure described in Example 34, replacing 1-phenyl-1H-pyrazole-3-carbaldehyde with 3-(pyrimidin-2-yl)propanal. The compound was purified using prep-LCMS (XBridge C18 column, eluting with a gradient for acetonitrile/water containing 0.1% $NH_4OH$ at a flow rate of 60 mL/min), followed by prep-LCMS (Sunfire C18 column, eluting with a gradient of acetonitrile/water containing 0.1% TFA, at a flow rate of 60 mL/min) to afford the desired product as a TFA salt. The product was isolated as a single diastereomer. LCMS calculated for $C_{39}H_{38}FN_9O$ $(M+H)^+$ m/z=668.3; found 668.3.

Example 38a and Example 38b. (3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(1H-indazol-5-yl)-1H-imidazo[4,5-c]quinolin-8-yl)propanenitrile

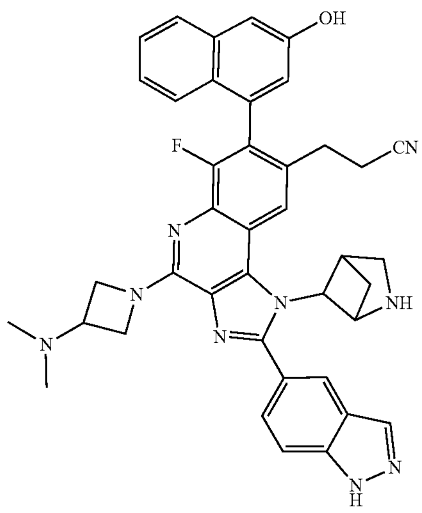 [SMILES: CN(C)C1CN(c2nc3c(F)c(-c4cc(O)cc5ccccc45)c(CCC#N)cc3c3c2nc(-c2ccc4[nH]ncc4c2)n3C2C3CNC2C3)C1]

To a vial containing tert-butyl (endo)-5-((3-amino-6-(2-cyanoethyl)-2-(3-(dimethylamino)azetidin-1-yl)-8-fluoro-7-(3-hydroxynaphthalen-1-yl)quinolin-4-yl)amino)-2-azabicyclo[2.1.1]hexane-2-carboxylate (Intermediate 6, 40.0 mg, 0.061 mmol) in ethanol (0.4 mL, 0.15 M) was added 1H-indazole-5-carbaldehyde (22.4 mg, 0.153 mmol, 2.5 equiv). After stirring at 50° C. for 18 h, the mixture was diluted with methanol and purified by prep-LCMS (XBridge C18 column, eluting with a gradient for acetonitrile/water containing 0.1% $NH_4OH$ at a flow rate of 60 mL/min), LCMS calculated for $C_{45}H_{44}FN_9O_3(M+H)^+$ m/z=778.4; found 778.4. The purified material was concentrated and dissolved in ethanol (0.4 mL), followed by addition of HCl (4.0 M in dioxane, 0.2 mL). After stirring at 23° C. for 18 h, the mixture was diluted with methanol and purified by prep-LCMS (Sunfire C18 column, eluting with a gradient of acetonitrile/water containing 0.1% TFA, at a flow rate of 60 mL/min) to afford the desired product as a TFA salt. The product was isolated as a pair of diastereomers.

Example 38a. Diastereomer 1. Peak 1. LCMS calculated for $C_{40}H_{36}FN_9O$ $(M+H)^+$ m/z=678.3; found 678.3.

Example 38b. Diastereomer 2. Peak 2. LCMS calculated for $C_{40}H_{36}FN_9O$ $(M+H)^+$ m/z=678.3; found 678.3.

Example 39a and Example 39b. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-imidazo[4,5-c]quinolin-7-yl)-1-naphthonitrile

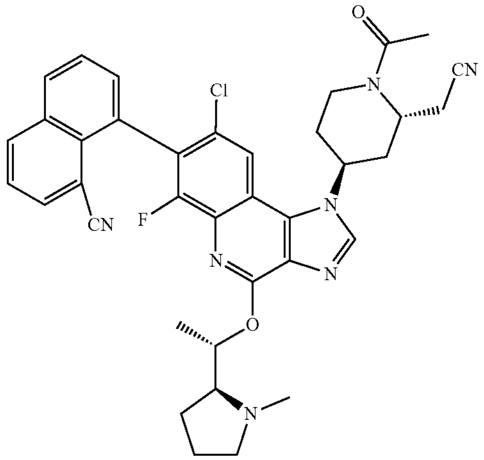 [SMILES: CC(=O)N1CC[C@H](n2cnc3c(O[C@@H](C)[C@@H]4CCCN4C)nc4c(F)c(-c5cccc6cccc(C#N)c56)c(Cl)cc4c32)C[C@H]1CC#N]

Step 1. tert-butyl (2S,4S)-4-((7-bromo-2,6-dichloro-8-fluoro-3-nitroquinolin-4-yl)amino)-2-(cyanomethyl)piperidine-1-carboxylate

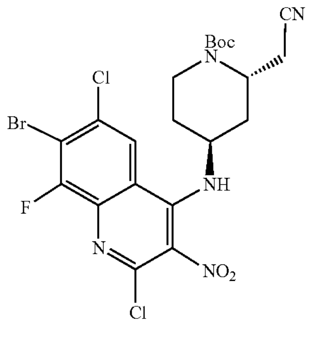 [SMILES: CC(C)(C)OC(=O)N1CC[C@H](Nc2c([N+](=O)[O-])c(Cl)nc3c(F)c(Br)c(Cl)cc23)C[C@H]1CC#N]

tert-Butyl (2S,4S)-4-amino-2-(cyanomethyl)piperidine-1-carboxylate (300 mg, 1.254 mmol) was added to 7-bromo-2,4,6-trichloro-8-fluoro-3-nitroquinoline (Intermediate 7; 469 mg, 1.254 mmol) in $CH_2Cl_2$ (6.27 ml) at rt. It was allowed to stir at 50° C. 1 h. The mixture was diluted with DCM and the organic phase was washed with water and brine. The organic layer was dried over sodium sulfate and it was concentrated. The residue was used in next step without further purification. LCMS calculated for $C_{21}H_{22}BrCl_2FN_5O_4(M+H)^+$: m/z=578.2; found 578.2.

Step 2. tert-butyl (2S,4S)-4-((7-bromo-6-chloro-8-fluoro-2-((S)-1-((S)-1-methylpyrrolidin-2-yl)ethoxy)-3-nitroquinolin-4-yl)amino)-2-(cyanomethyl)piperidine-1-carboxylate

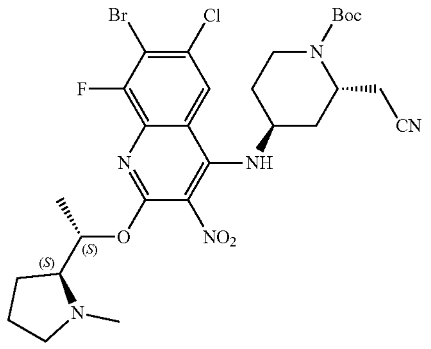

Sodium hydride (0.100 g, 2.500 mmol) was added to a THF (6.25 ml) solution of (S)-1-((S)-1-methylpyrrolidin-2-yl)ethan-1-ol (0.323 g, 2.500 mmol) at 0° C. After 15 min, tert-butyl (2S,4S)-4-((7-bromo-2,6-dichloro-8-fluoro-3-nitroquinolin-4-yl)amino)-2-(cyanomethyl)piperidine-1-carboxylate (0.722 g, 1.25 mmol) in THF (6.25 ml) was added at 0° C. It was allowed to warm to room temperature slowly. After 1 h, the mixture was quenched by addition of saturated $NH_4Cl$ aq and EtOAc. The mixture was extracted with EtOAc (50 mL×3). The combined organic layers were dried $Na_2SO_4$, filtered and concentrated. The residue was used in next step without further purification. LCMS calculated for $C_{28}H_{36}BrClFN_6O_5(M+H)^+$: m/z=671.2; found 671.2.

Step 3. tert-butyl (2S,4S)-4-((3-amino-7-bromo-6-chloro-8-fluoro-2-((S)-1-((S)-1-methylpyrrolidin-2-yl)ethoxy)quinolin-4-yl)amino)-2-(cyanomethyl)piperidine-1-carboxylate

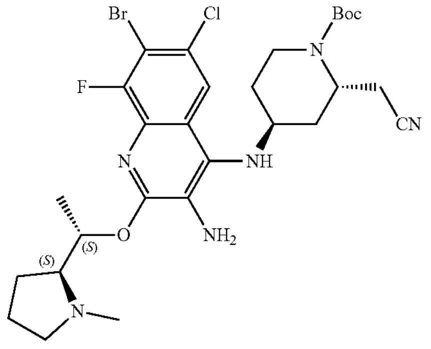

In a 50 mL round-bottomed flask, tert-butyl (2S,4S)-4-((7-bromo-6-chloro-8-fluoro-2-((S)-1-((S)-1-methylpyrrolidin-2-yl)ethoxy)-3-nitroquinolin-4-yl)amino)-2-(cyanomethyl)piperidine-1-carboxylate (0.837 g, 1.25 mmol), and iron (0.698 g, 12.50 mmol) were dissolved in a mixture of MeOH (2.083 ml)/THF (2.083 ml)/water (2.083 ml). The mixture was stirred at 70° C. for 0.5 hours. The mixture was filtered through Celite, and washed with MeOH. The solvent was removed under reduced pressure. The residue was taken into DCM and washed with water and brine. The combined organic layers were dried $Na_2SO_4$, filtered and concentrated. The residue was used in next step without further purification. LCMS calculated for $C_{28}H_{33}BrClFN_6O_3(M+H)^+$: m/z=641.2; found 641.1.

Step 4. tert-butyl (2S,4S)-4-(7-bromo-8-chloro-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxylate

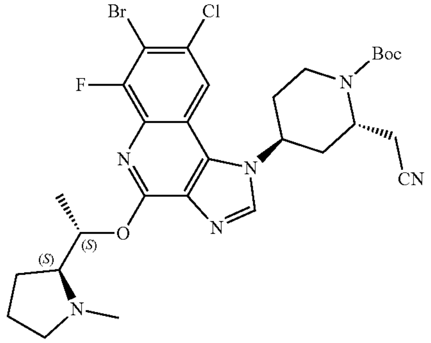

A mixture of tert-butyl (2S,4S)-4-((3-amino-7-bromo-6-chloro-8-fluoro-2-((S)-1-((S)-1-methylpyrrolidin-2-yl)ethoxy)quinolin-4-yl)amino)-2-(cyanomethyl)piperidine-1-carboxylate (30 mg, 0.047 mmol), triethyl orthoformate (390 μl, 2.344 mmol) in toluene (0.234 ml) was heated at 105° C. 3 h. The mixture was concentrated and the crude product was added to a silica gel column and was eluted with methanol/dichloromethane from 0% to 20% to give desired product. LCMS calculated for $C_{29}H_{36}BrClFN_6O_3(M+H)^+$: m/z=651.2; found 651.2.

Step 5. tert-butyl (2S,4S)-4-(8-chloro-7-(8-cyanonaphthalen-1-yl)-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxylate

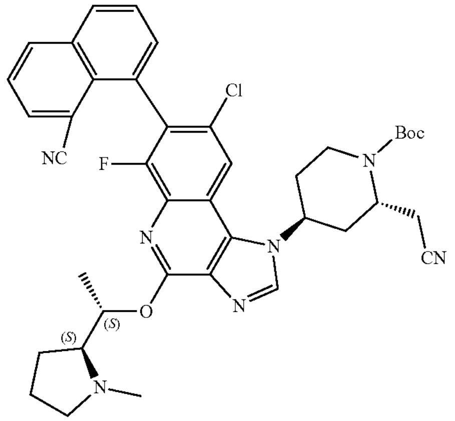

In a vial, a mixture of tert-butyl (2S,4S)-4-(7-bromo-8-chloro-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxylate (200 mg, 0.308 mmol), 8-(4,4,5,5-tetramethyl-1,3,2-dioxaborolan-2-yl)-1-naphthonitrile (129 mg, 0.462 mmol), Methanesulfonato(2-dicyclohexylphosphino-2',6'-dimethoxy-1,1'-biphenyl)(2'-methylamino-1,1'-biphenyl-2-yl)palladium(II) dichloromethane adduct (24.47 mg, 0.031 mmol), potassium phosphate (131 mg, 0.615 mmol) in 1,4-dioxane (1.399 ml)/water (0.140 ml) was purged with $N_2$ and it was heated at 75° C. 5 h. The mixture was diluted with water and extracted with DCM (20 mL×3), and then the combined organic layers were washed with $H_2O$ (50 mL), dried with $Na_2SO_4$, filtered and concentrated. The crude product was added to a silica gel column and was eluted with methanol/dichloromethane from 0% to 50% to give desired product. LCMS calculated for $C_{40}H_{42}ClFN_7O_3$ $(M+H)^+$: m/z=722.3; found 722.2.

Step 6. 8-(8-chloro-1-((2S,4S)-2-(cyanomethyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile

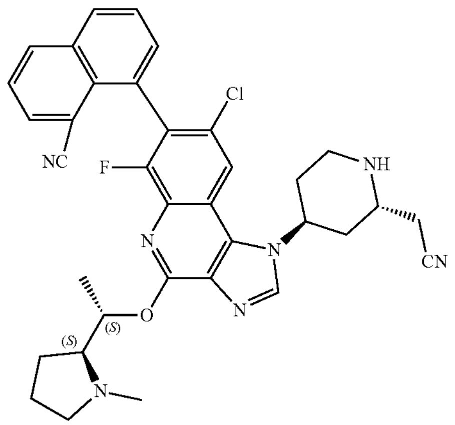

tert-butyl (2S,4S)-4-(8-chloro-7-(8-cyanonaphthalen-1-yl)-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxylate (170 mg, 0.3 mmol), was treated with 1 mL TFA/DCM (1:1). The mixture was allowed to stir at room temperature 30 min. The mixture was concentrated and used in next step without further purification. LCMS calculated for $C_{35}H_{34}ClFN_7O$ $(M+H)^+$: m/z=622.2; found 622.2.

Step 7. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-imidazo[4,5-c]quinolin-7-yl)-1-naphthonitrile Hunig's base (5.61 µl, 0.032 mmol) was added to a DMF (0.161 ml) solution of 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-imidazo[4,5-c]quinolin-7-yl)-1-naphthonitrile, BOP (8.53 mg, 0.019 mmol) and acetic acid (1.104 µl, 0.019 mmol). After 30 min, it was diluted with MeOH and purified using prep-LCMS (XBridge C18 column, eluting with a gradient of acetonitrile/water containing 0.1% TFA, at flow rate of 60 mL/min) to afford the desired products as a TFA salt. The product was isolated as a pair of diastereomers.

Example 39a. Diastereomer 1. Peak 1. LCMS calculated for $C_{37}H_{36}ClFN_7O_2(M+H)^+$ m/z=664.2; found 664.2.

Example 39b. Diastereomer 2. Peak 2. LCMS calculated for $C_{37}H_{36}ClFN_7O_2(M+H)^+$ m/z=664.2; found 664.2. This peak is the potent peak.

Example 40. 8-(8-chloro-1-((2S,4S)-1-(2-cyanoacetyl)-2-(cyanomethyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile

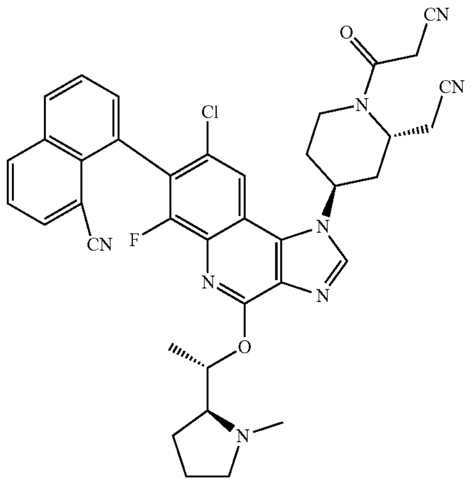 [SMILES: C[C@H](Oc1nc2c(F)c(-c3cccc4cccc(C#N)c34)c(Cl)cc2c2c1ncn2[C@H]1CCN(C(=O)CC#N)[C@H](CC#N)C1)[C@@H]1CCCN1C]

This compound was prepared according to the procedure described in Example 39, Step 7, replacing acetic acid with 2-cyanoacetic acid. It purified by prep-LCMS (XBridge C18 column, eluting with a gradient of acetonitrile/water containing 0.1% TFA, at flow rate of 60 mL/min) to afford the desired products as a TFA salt. The product was isolated as a mixture of diastereomers. LCMS calculated for $C_{38}H_{35}ClFN_8O_2(M+H)^+$ m/z=689.2; found 689.2.

Example 41. 8-(8-chloro-1-((2S,4S)-2-(cyanomethyl)-1-(1H-1,2,4-triazole-3-carbonyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile

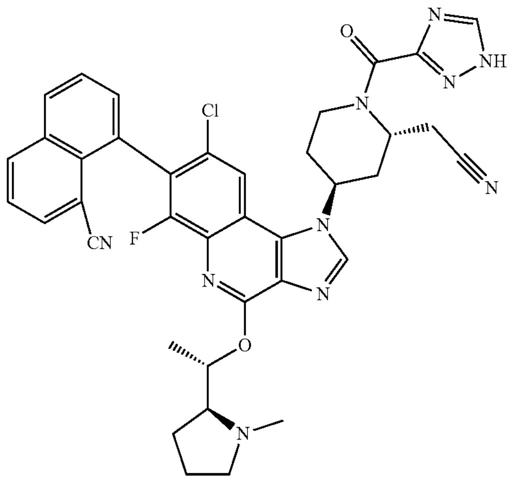 [SMILES: C[C@H](Oc1nc2c(F)c(-c3cccc4cccc(C#N)c34)c(Cl)cc2c2c1ncn2[C@H]1CCN(C(=O)c2nc[nH]n2)[C@H](CC#N)C1)[C@@H]1CCCN1C]

This compound was prepared according to the procedure described in Example 39, Step 7, replacing acetic acid with 1H-1,2,4-triazole-3-carboxylic acid. It purified by prep-LCMS (XBridge C18 column, eluting with a gradient of acetonitrile/water containing 0.1% TFA, at flow rate of 60 mL/min) to afford the desired products as a TFA salt. The product was isolated as a mixture of diastereomers. LCMS calculated for $C_{38}H_{35}ClFN_{10}O_2(M+H)^+$ m/z=717.2; found 717.2.

Example 42. (2S,4S)-4-(8-chloro-7-(8-cyanonaphthalen-1-yl)-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxamide

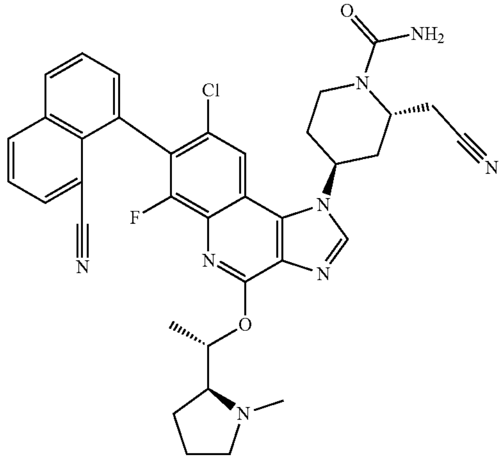 [SMILES: C[C@H](Oc1nc2c(F)c(-c3cccc4cccc(C#N)c34)c(Cl)cc2c2c1ncn2[C@H]1CCN(C(N)=O)[C@H](CC#N)C1)[C@@H]1CCCN1C]

Trimethylsilyl isocyanate (2.176 μl, 0.016 mmol) was added to 8-(8-chloro-1-((2S,4S)-2-(cyanomethyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile (Example 39, Step 6; 10 mg, 0.016 mmol), Hunig's base (5.61 μl, 0.032 mmol) in $CH_2Cl_2$ (0.8 ml) at room temperature. The reaction mixture was stirred overnight. Then the mixture was diluted with MeOH and purified by prep-LCMS (XBridge C18 column, eluting with a gradient of acetonitrile/water containing 0.1% TFA, at flow rate of 60 mL/min) to afford the desired products as a TFA salt. The product was isolated as a mixture of diastereomers. LCMS calculated for $C_{36}H_{35}ClFN_8O_2(M+H)^+$ m/z=665.2; found 665.2.

Example 43. 8-(8-chloro-1-((2S,4S)-2-(cyanomethyl)-1-(cyclopropanecarbonyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile

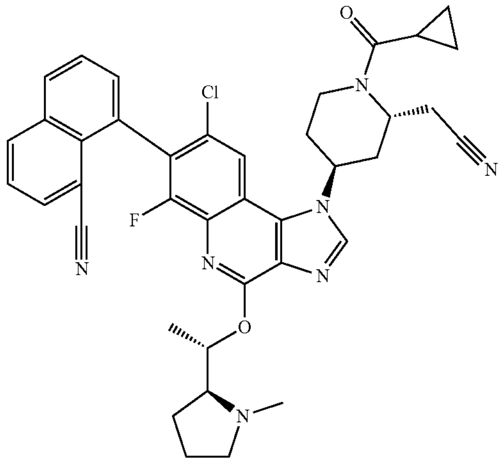 [SMILES: C[C@H](Oc1nc2c(F)c(-c3cccc4cccc(C#N)c34)c(Cl)cc2c2c1ncn2[C@H]1CCN(C(=O)C2CC2)[C@H](CC#N)C1)[C@@H]1CCCN1C]

Cyclopropyl acid chloride was added to a $CH_2Cl_2$ (0.8 ml) solution of 8-(8-chloro-1-((2S,4S)-2-(cyanomethyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile (Example 39, Step 6; 10 mg, 0.016 mmol) and Hunig's base (5.61 μl, 0.032 mmol) at room temperature. After 5 min, the reaction mixture was diluted with MeOH and purified by prep-LCMS (XBridge C18 column, eluting with a gradient of acetonitrile/water containing 0.1% TFA, at flow rate of 60 mL/min) to afford the desired products as a TFA salt. The product was isolated as a mixture of diastereomers. LCMS calculated for $C_{39}H_{38}ClFN_7O_2(M+H)^+$ m/z=690.2; found 690.2.

Example 44. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-[1,2,3]triazolo[4,5-c]quinolin-7-yl)-1-naphthonitrile

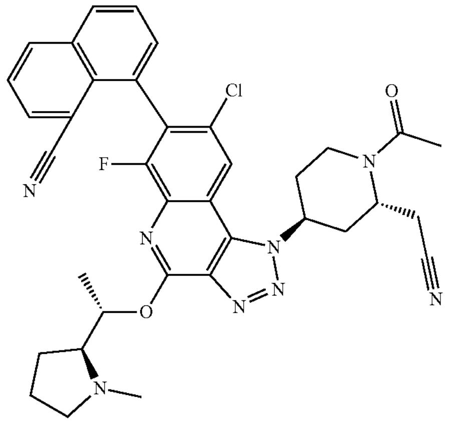 [SMILES: CC(=O)N1CC[C@H](n2nnc3c(O[C@@H](C)[C@@H]4CCCN4C)nc4c(F)c(-c5cccc6cccc(C#N)c56)c(Cl)cc4c32)C[C@H]1CC#N]

Step 1. tert-butyl (2S,4S)-4-(7-bromo-8-chloro-6-fluoro-4-((S)-1-((S)-1-methylpyrrolidin-2-yl)ethoxy)-1H-[1,2,3]triazolo[4,5-c]quinolin-1-yl)-2-(cyanomethyl)piperidine-1-carboxylate

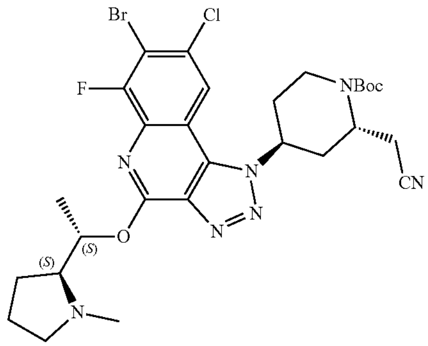

tert-Butyl (2S,4S)-4-((3-amino-7-bromo-6-chloro-8-fluoro-2-((S)-1-((S)-1-methylpyrrolidin-2-yl)ethoxy)quinolin-4-yl)amino)-2-(cyanomethyl)piperidine-1-carboxylate (Example 39, Step 3; 0.8 g, 1.25 mmol) was taken into 2 mL AcOH and 2 mL DCM. Sodium nitrite (0.259 g, 3.75 mmol) was added in one portion at 0° C. After 30 min, the reaction was diluted with water and extracted with DCM (50 mL×3), and then the combined organic layers were washed with $H_2O$ (50 mL), dried with $Na_2SO_4$, filtered and concentrated. The crude product was added to a silica gel column and was eluted with methanol/dichloromethane from 0% to 30% to give desired product. LCMS calculated for $C_{28}H_{35}BrClFN_7O_3(M+H)^+$: m/z=652.2; found 652.2.

Step 2. tert-butyl (2S,4S)-4-(8-chloro-7-(8-cyanonaphthalen-1-yl)-6-fluoro-4-((S)-1-((S)-1-methylpyrrolidin-2-yl)ethoxy)-1H-[1,2,3]triazolo[4,5-c]quinolin-1-yl)-2-(cyanomethyl)piperidine-1-carboxylate

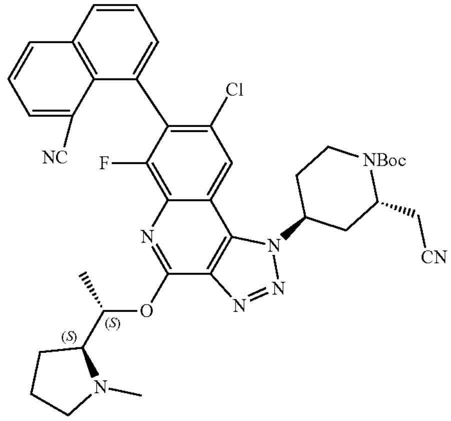

This compound was prepared according to the procedure described in Example 39, Step 5, replacing tert-butyl (2S,4S)-4-(7-bromo-8-chloro-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxylate with tert-butyl (2S,4S)-4-(7-bromo-8-chloro-6-fluoro-4-((S)-1-((S)-1-methylpyrrolidin-2-yl)ethoxy)-1H-[1,2,3]triazolo[4,5-c]quinolin-1-yl)-2-(cyanomethyl)piperidine-1-carboxylate. LCMS calculated for $C_{39}H_{41}ClFN_8O_3$ $(M+H)^+$ m/z=723.3; found 723.2.

Step 3. 8-(8-chloro-1-((2S,4S)-2-(cyanomethyl)piperidin-4-yl)-6-fluoro-4-((S)-1-((S)-1-methylpyrrolidin-2-yl)ethoxy)-1H-[1,2,3]triazolo[4,5-c]quinolin-7-yl)-1-naphthonitrile

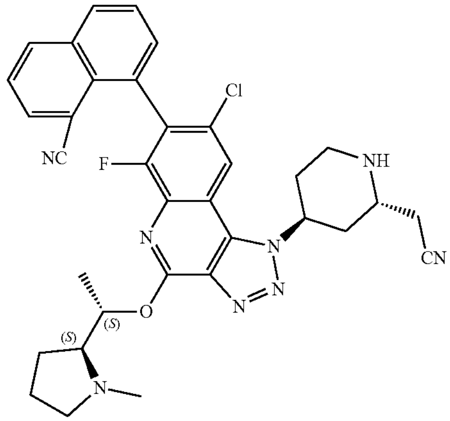

tert-Butyl (2S,4S)-4-(8-chloro-7-(8-cyanonaphthalen-1-yl)-6-fluoro-4-((S)-1-((S)-1-methylpyrrolidin-2-yl)ethoxy)-1H-[1,2,3]triazolo[4,5-c]quinolin-1-yl)-2-(cyanomethyl)piperidine-1-carboxylate was treated with 1 mL TFA/DCM (1:1). After stirring at room temperature 30 min, the mixture was concentrated and used in next step without further purification. LCMS calculated for $C_{34}H_{33}ClFN_8O$ $(M+H)^+$: m/z=623.2; found 623.2.

Step 4. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-[1,2,3]triazolo[4,5-c]quinolin-7-yl)-1-naphthonitrile Hunig's base (5.61 μl, 0.032 mmol) was added to a DMF (0.161 ml) solution of 8-(8-chloro-1-((2S,4S)-2-(cyanomethyl)piperidin-4-yl)-6-fluoro-4-((S)-1-((S)-1-methylpyrrolidin-2-yl)ethoxy)-1H-[1,2,3]triazolo[4,5-c]quinolin-7-yl)-1-naphthonitrile, BOP (8.53 mg, 0.019 mmol) and acetic acid (1.104 μl, 0.019 mmol). After 30 min, it was diluted with MeOH and purified using prep-LCMS (XBridge C18 column, eluting with a gradient of acetonitrile/water containing 0.1% TFA, at flow rate of 60 mL/min) to afford the desired products as a TFA salt. The product was isolated as a mixture of diastereomers. LCMS calculated for $C_{36}H_{35}ClFN_8O_2(M+H)^+$ m/z=665.2; found 665.2.

Example 45. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-2-oxo-2,3-dihydro-1H-imidazo[4,5-c]quinolin-7-yl)-1-naphthonitrile

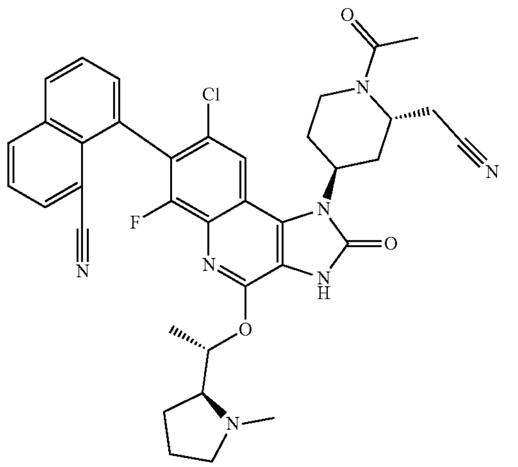 [SMILES: CC(=O)N1CC[C@H](n2c(=O)[nH]c3c(O[C@@H](C)[C@@H]4CCCN4C)nc4c(F)c(-c5cccc6cccc(C#N)c56)c(Cl)cc4c32)C[C@H]1CC#N]

Step 1. tert-butyl (2S,4S)-4-(7-bromo-8-chloro-6-fluoro-4-((S)-1-((S)-1-methylpyrrolidin-2-yl)ethoxy)-2-oxo-2,3-dihydro-1H-imidazo[4,5-c]quinolin-1-yl)-2-(cyanomethyl)piperidine-1-carboxylate

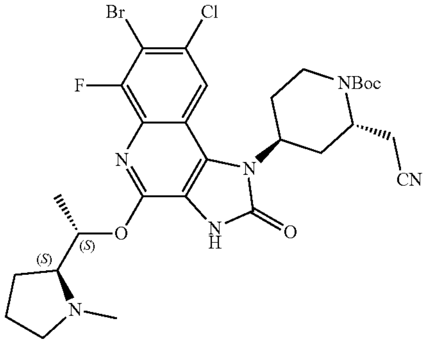

tert-Butyl (2S,4S)-4-((3-amino-7-bromo-6-chloro-8-fluoro-2-((S)-1-((S)-1-methylpyrrolidin-2-yl)ethoxy)quinolin-4-yl)amino)-2-(cyanomethyl)piperidine-1-carboxylate (Example 39, Step 3; 0.05 g, 0.075 mmol) was taken into 1 mL THF. After cooling to 0° C., triphosgene (33.2 mg, 0.112 mmol) was added in one portion. After 10 min, the reaction was diluted with saturated $NaHCO_3$ aq and extracted with DCM (10 mL×3) and then the combined organic layers were washed with $H_2O$ (50 mL), dried with $Na_2SO_4$, filtered and concentrated. The crude product was added to a silica gel column and was eluted with methanol/dichloromethane from 0% to 50% to give desired product LCMS calculated for $C_{29}H_{36}BrClFN_6O_4$ $(M+H)^+$: m/z=667.2; found 667.2.

Step 2. tert-butyl (2S,4S)-4-(8-chloro-7-(8-cyanonaphthalen-1-yl)-6-fluoro-4-((S)-1-((S)-1-methylpyrrolidin-2-yl)ethoxy)-2-oxo-2,3-dihydro-1H-imidazo[4,5-c]quinolin-1-yl)-2-(cyanomethyl)piperidine-1-carboxylate

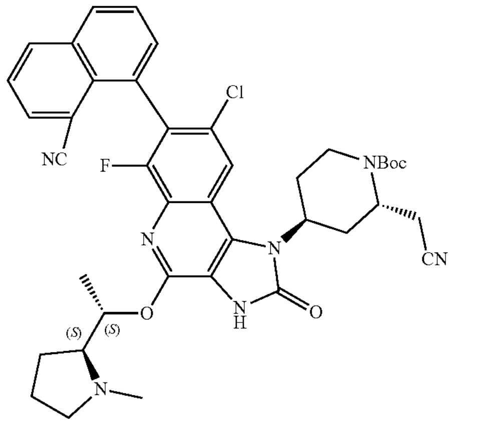

This compound was prepared according to the procedure described in Example 39, Step 5, replacing tert-butyl (2S,4S)-4-(7-bromo-8-chloro-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxylate with tert-butyl (2S,4S)-4-(7-bromo-8-chloro-6-fluoro-4-((S)-1-((S)-1-methylpyrrolidin-2-yl)ethoxy)-2-oxo-2,3-dihydro-1H-imidazo[4,5-c]quinolin-1-yl)-2-(cyanomethyl)piperidine-1-carboxylate. LCMS calculated for $CH_{42}ClFN_7O_4(M+H)^+$ m/z=738.3; found 738.2.

Step 3. 8-(8-chloro-1-((2S,4S)-2-(cyanomethyl)piperidin-4-yl)-6-fluoro-4-((S)-1-((S)-1-methylpyrrolidin-2-yl)ethoxy)-2-oxo-2,3-dihydro-1H-imidazo[4,5-c]quinolin-7-yl)-1-naphthonitrile

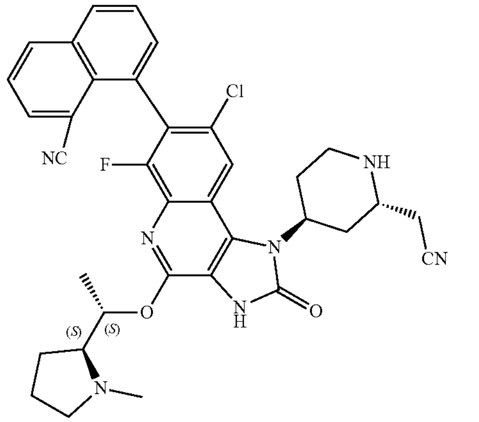

tert-butyl (2S,4S)-4-(8-chloro-7-(8-cyanonaphthalen-1-yl)-6-fluoro-4-((S)-1-((S)-1-methylpyrrolidin-2-yl)ethoxy)-2-oxo-2,3-dihydro-1H-imidazo[4,5-c]quinolin-1-yl)-2-(cyanomethyl)piperidine-1-carboxylate was treated with 1 mL TFA/DCM (1:1). The mixture was allowed to stir at room temperature 30 min. The mixture was concentrated and used in next step without further purification. LCMS calculated for $C_{35}H_{34}ClFN_7O_2(M+H)^+$: m/z=638.2; found 638.2.

Step 4. 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-2-oxo-2,3-dihydro-1H-imidazo[4,5-c]quinolin-7-yl)-1-naphthonitrile Hunig's base (5.61 μl, 0.032 mmol) was added to a DMF (0.161 ml) solution of 8-(8-chloro-1-((2S,4S)-2-(cyanomethyl)piperidin-4-yl)-6-fluoro-4-((S)-1-((S)-1-methylpyrrolidin-2-yl)ethoxy)-2-oxo-2,3-dihydro-1H-imidazo[4,5-c]quinolin-7-yl)-1-naphthonitrile, BOP (8.53 mg, 0.019 mmol) and acetic acid (1.104 μl, 0.019 mmol). After 30 min, it was diluted with MeOH and purified using prep-LCMS (XBridge C18 column, eluting with a gradient of acetonitrile/water containing 0.1% TFA, at flow rate of 60 mL/min) to afford the desired products as a TFA salt. The product was isolated as a mixture of diastereomers. LCMS calculated for $C_{37}H_{36}ClFN_7O_3(M+H)^+$ m/z=680.2; found 680.2.

Example A. GDP-GTP Exchange Assay

The inhibitor potency of the exemplified compounds was determined in a fluorescence based guanine nucleotide exchange assay, which measures the exchange of bodipy-GDP (fluorescently labeled GDP) for GppNHp (Non-hydrolyzable GTP analog) to generate the active state of KRAS in the presence of SOS1 (guanine nucleotide exchange factor). Inhibitors were serially diluted in DMSO and a volume of 0.1 μL was transferred to the wells of a black low volume 384-well plate. 5 μL/well volume of bodipy-loaded KRAS G12D diluted to 2.5 nM in assay buffer (25 mM Hepes pH 7.5, 50 mM NaCl, 10 mM $MgCl_2$ and 0.01% Brij-35) was added to the plate and pre-incubated with inhibitor for 4 hours at ambient temperature. Appropriate controls (enzyme with no inhibitor or with a G12D inhibitor) were included on the plate. The exchange was initiated by the addition of a 5 μL/well volume containing 1 mM GppNHp and 300 nM SOS1 in assay buffer. The 10 μL/well reaction concentration of the bodipy-loaded KRAS G12D, GppNHp, and SOS1 were 2.5 nM, 500 uM, and 150 nM, respectively. The reaction plates were incubated at ambient temperature for 2 hours, a time estimated for complete GDP-GTP exchange in the absence of inhibitor. For the KRAS G12V mutant, similar guanine nucleotide exchange assays were used with 2.5 nM as final concentration for the bodipy loaded KRAS proteins and 3 hours incubation after adding GppNHp-SOS1 mixture. A cyclic peptide described to selectively bind G12D mutant (Sakamoto et al., BBRC 484.3 (2017), 605-611) or internal compounds with confirmed binding were used as positive controls in the assay plates. Fluorescence intensities were measured on a PheraStar plate reader instrument (BMG Labtech) with excitation at 485 nm and emission at 520 nm.

Either GraphPad prism or Genedata Screener SmartFit was used to analyze the data. The $IC_{50}$ values were derived by fitting the data to a four parameter logistic equation producing a sigmoidal dose-response curve with a variable Hill coefficient.

The KRAS_G12D and KRAS_G12V exchange assay $IC_{50}$ data are provided in Table 1 below. The symbol "†" indicates $IC_{50}$≤100 nM, "††" indicates $IC_{50}$>100 nM but ≤1 μM; and "†††" indicates $IC_{50}$ is >1 μM but ≤5 μM, "††††" indicates $IC_{50}$ is >5 μM but ≤10 μM. "NA" indicates $IC_{50}$ not available.

TABLE 1

| Ex. No. | G12D_exchange | G12V_exchange |
|---|---|---|
| 1a | †† | NA |
| 2a | † | ††† |
| 3a | † | † |
| 4a | † | † |
| 5a | † | † |
| 6a | †† | †††† |
| 7a | † | †† |
| 8b | † | †† |
| 9 | † | † |
| 10 | † | †† |
| 11 | † | ††† |
| 12 | †† | †††† |
| 13 | †† | †††† |
| 14 | †† | †††† |
| 15 | † | ††† |
| 16 | †† | †††† |
| 17a | † | † |
| 18 | † | † |
| 19a | † | † |
| 20a | † | †† |
| 21a | † | † |
| 22a | † | †† |
| 23a | † | † |
| 24a | † | †† |
| 25a | † | †† |
| 26a | † | † |
| 27a | † | † |
| 28 | † | †† |
| 29 | †† | †††† |
| 30 | † | †† |
| 31a | †† | †††† |
| 32a | †† | †††† |
| 33 | † | ††† |
| 34a | † | † |
| 35a | † | † |
| 36a | †† | † |
| 37 | † | † |
| 38a | †† | † |
| 39b | † | † |
| 40 | † | † |
| 41 | †† | † |
| 42 | † | † |
| 43 | † | †† |
| 44 | † | † |
| 45 | †† | † |

Example B: Luminescent Viability Assay

MIA PaCa-2 (KRAS G12C; ATCC® CRL-1420), NCI-H358 (KRAS G12C; ATCC® CRL-5807), A427 (KRAS G12D; ATCC® HTB53), HPAFII (KRAS G12D; ATCC® CRL-1997), YAPC (KRAS G12V; DSMZ ACC382), SW480 (KRAS G12V; ATCC® CRL-228) and NCI-H838 (KRAS WT; ATCC® CRL-5844) cells are cultured in RPMI 1640 media supplemented with 10% FBS (Gibco/Life Technologies). Eight hundred cells per well in RPMI 1640 media supplemented with 2% FBS are seeded into white, clear bottomed 384-well Costar tissue culture plates containing 50 nL dots of test compounds (final concentration is a 1:500 dilution, with a final concentration in 0.2% DMSO). Plates are incubated for 3 days at 370° C., 5% $CO_2$. At the end of the assay, 25 ul/well of CellTiter-Glo reagent (Promega) is added. Luminescence is read after 15 minutes with a PHERAstar (BMG). Data are analyzed in Genedata Screener using SmartFit for $IC_{50}$ values.

Example C: Cellular pERK HTRF Assay

MIA PaCa-2 (KRAS G12C; ATCC® CRL-1420), NCI-H358 (KRAS G12C; ATCC® CRL-5807), A427 (KRAS G12D; ATCC® HTB53), HPAFII (KRAS G12D; ATCC®

CRL-1997), YAPC (KRAS G12V; DSMZ ACC382), SW480 (KRAS G12V; ATCC® CRL-228) and NCI-H838 (KRAS WT; ATCC® CRL-5844) cells are purchased from ATCC and maintained in RPMI 1640 media supplemented with 10% FBS (Gibco/Life Technologies). The cells are plated at 5000 cells per well (8 uL) into Greiner 384-well low volume, flat-bottom, and tissue culture treated white plates and incubated overnight at 370° C., 5% $CO_2$. The next morning, test compound stock solutions are diluted in media at 3× the final concentration and 4 uL are added to the cells, with a final concentration of 0.1% of DMSO. The cells are incubated with the test compounds for 4 hours (G12C and G12V) or 2 hrs (G12D) at 37° C., 5% $CO_2$. Four uL of 4× lysis buffer with blocking reagent (Cisbio) are added to each well and plates are rotated gently (300 rpm) for 30 minutes at room temperature. Four uL per well of Cisbio anti Phospho-ERK 1/2 d2 is mixed with anti Phospho-ERK 1/2 Cryptate (1:1), and added to each well, incubated overnight in the dark at room temperature. Plates are read on the Pherastar plate reader at 665 nm and 620 nm wavelengths. Data are analyzed in Genedata Screener using SmartFit for $IC_{50}$ values.

Example D: Whole Blood pERK1/2 HTRF Assay

MIA PaCa-2 cells (KRAS G12C; ATCC® CRL-1420), HPAF-II (KRAS G12D; ATCC® CRL-1997) and YAPC (KRAS G12V; DSMZ ACC382) are maintained in RPMI 1640 with 10% FBS (Gibco/Life Technologies). For MIA PaCa-2 assay, cells are seeded into 96 well tissue culture plates (Corning #3596) at 25000 cells per well in 100 uL media and cultured for 2 days at 37° C., 5% $CO_2$ before the assay. For HPAF-II and YAPC assay, cells are seeded in 96 well tissue culture plates at 50000 cells per well in 100 uL media and cultured for 1 day before the assay. Whole Blood are added to the 1 uL dots of compounds (prepared in DMSO) in 96 well plates and mixed gently by pipetting up and down so that the concentration of the compound in blood is 1× of desired concentration, in 0.5% DMSO. The media is aspirated from the cells and 50 uL per well of whole blood with test compound is added and incubated for 4 hours for MIA PaCa and YAPC assay; or 2 hours for HPAF-II assay, respectively at 37° C., 5% $CO_2$. After dumping the blood, the plates are gently washed twice by adding PBS to the side of the wells and dumping the PBS from the plate onto a paper towel, tapping the plate to drain well. Fifty ul/well of 1× lysis buffer #1 (Cisbio) with blocking reagent (Cisbio) and Benzonase nuclease (Sigma Cat #E1014-5KU, 1: 10000 final concentration) is then added and incubated at room temperature for 30 minutes with shaking (250 rpm). Following lysis, 16 uL of lysate is transferred into 384-well Greiner small volume white plate using an Assist Plus (Integra Biosciences, NH). Four uL of 1:1 mixture of anti Phospho-ERK 1/2 d2 and anti Phospho-ERK 1/2 Cryptate (Cisbio) is added to the wells using the Assist Plus and incubated at room temperature overnight in the dark. Plates are read on the Pherastar plate reader at 665 nm and 620 nm wavelengths. Data are analyzed in Genedata Screener using SmartFit for $IC_{50}$ values.

Example E: Ras Activation Elisa

The 96-Well Ras Activation ELISA Kit (Cell Biolabs Inc; #STA441) uses the Raf1 RBD (Rho binding domain) bound to a 96-well plate to selectively pull down the active form of Ras from cell lysates. The captured GTP-Ras is then detected by a pan-Ras antibody and HRP-conjugated secondary antibody.

MIA PaCa-2 (KRAS G12C; ATCC® CRL-1420), NCI-H358 (KRAS G12C; ATCC® CRL-5807), A427 (KRAS G12D; ATCC® HTB53), HPAFII (KRAS G12D; ATCC® CRL-1997), YAPC (KRAS G12V; DSMZ ACC382), SW480 (KRAS G12V; ATCC® CRL-228) and NCI-H838 (KRAS WT; ATCC® CRL-5844) cells are maintained in RPMI 1640 with 10% FBS (Gibco/Life Technologies). The cells are seeded into 96 well tissue culture plates (Corning #3596) at 25000 cells per well in 100 uL media and cultured for 2 days at 37° C., 5% $CO_2$ so that they are approximately 80% confluent at the start of the assay. The cells are treated with compounds for either 4 hours or overnight at 37° C., 5% $CO_2$. At the time of harvesting, the cells are washed with PBS, drained well and then lysed with 50 uL of the 1× Lysis buffer (provided by the kit) plus added Halt Protease and Phosphatase inhibitors (1:100) for 1 hour on ice.

The Raf-1 RBD is diluted 1:500 in Assay Diluent (provided in kit) and 100 μL of the diluted Raf-1 RBD is added to each well of the Raf-1 RBD Capture Plate. The plate is covered with a plate sealing film and incubated at room temperature for 1 hour on an orbital shaker. The plate is washed 3 times with 250 μL 1× Wash Buffer per well with thorough aspiration between each wash. 50 μL of Ras lysate sample (10-100 μg) is added per well in duplicate. A "no cell lysate" control is added in a couple of wells for background determination. 50 μL of Assay Diluent is added to all wells immediately to each well and the plate is incubated at room temperature for 1 hour on an orbital shaker. The plate is washed 5 times with 250 μL 1× Wash Buffer per well with thorough aspiration between each wash. 100 μL of the diluted Anti-pan-Ras Antibody is added to each well and the plate is incubated at room temperature for 1 hour on an orbital shaker. The plate is washed 5 times as previously. 100 μL of the diluted Secondary Antibody, HRP Conjugate is added to each well and the plate is incubated at room temperature for 1 hour on an orbital shaker. The plate is washed 5 times as previously and drained well. 100 μL of Chemiluminescent Reagent (provided in the kit) is added to each well, including the blank wells. The plate is incubated at room temperature for 5 minutes on an orbital shaker before the luminescence of each microwell is read on a plate luminometer. The % inhibition is calculated relative to the DMSO control wells after a background level of the "no lysate control" is subtracted from all the values. $IC_{50}$ determination is performed by fitting the curve of inhibitor percent inhibition versus the log of the inhibitor concentration using the GraphPad Prism 7 software.

Example F: Inhibition of RAS-RAF and PI3K-AKT Pathways

The cellular potency of compounds was determined by measuring phosphorylation of KRAS downstream effectors extracellular-signal-regulated kinase (ERK), ribosomal S6 kinase (RSK), AKT (also known as protein kinase B, PKB) and downstream substrate S6 ribosomal protein.

To measure phosphorylated extracellular-signal-regulated kinase (ERK), ribosomal S6 kinase (RSK), AKT and S6 ribosomal protein, cells (details regarding the cell lines and types of data produced are further detailed in Table 2) were seeded overnight in Corning 96-well tissue culture treated plates in RPMI medium with 10% FBS at 4×104 cells/well. The following day, cells were incubated in the presence or absence of a concentration range of test compounds for 4 hours at 37° C., 5% $CO_2$. Cells were washed with PBS and lysed with 1× lysis buffer (Cisbio) with protease and phosphatase inhibitors (Thermo Fisher, 78446). Ten or twenty μg of total protein lysates was subjected to SDS-PAGE and immunoblot analysis using following antibodies: phospho-ERK1/2-Thr202/Tyr204 (#9101L), total-ERK1/2 (#9102L), phosphor-AKT-Ser473 (#4060L), phospho-p90RSK-Ser380 (#11989S) and phospho-S6 ribosomal protein-Ser235/Ser236 (#2211S) are from Cell Signaling Technologies (Danvers, Mass.).

TABLE 2

| Cell Line | Histology | KRAS alteration | Readout |
|---|---|---|---|
| H358 | Lung | G12C | pERK, pAKT, p-S6, p-p90RSK |
| MIA PaCa-2 | Pancreas | G12C | pERK, pAKT, p-S6, p-p90RSK |
| HPAF II | Pancreas | G12D | pERK, pAKT, p-S6, p-p90RSK |
| A427 | Lung | G12D | pERK, pAKT, p-S6, p-p90RSK |
| AGS | Stomach | G12D | pERK, pAKT, p-S6, p-p90RSK |
| PaTu 8988s | Pancreas | G12V | pERK, pAKT, p-S6, p-p90RSK |
| H441 | Lung | G12V | pERK, pAKT, p-S6, p-p90RSK |
| YAPC | Pancreas | G12V | pERK, pAKT, p-S6, p-p90RSK |
| SW480 | Colorectal | G12V | pERK, pAKT, p-S6, p-p90RSK |

Example G: In Vivo Efficacy Studies

MIA-PaCa-2 (KRAS G12C), H358 (KRAS G12C), HPAF-II (KRAS G12D), AGS (KRAS G12D), SW480 (KRAS G12V) or YAPC(KRAS G12V) human cancer cells are obtained from the American Type Culture Collection and maintained in RPMI media supplemented with 10% FBS. For efficacy studies experiments, 5×106 cells are inoculated subcutaneously into the right hind flank of 6- to 8-week-old BALB/c nude mice (Charles River Laboratories, Wilmington, Mass., USA). When tumor volumes are approximately 150-250 mm3, mice are randomized by tumor volume and compounds are orally administered. Tumor volume is calculated using the formula (L×W2)/2, where L and W refer to the length and width dimensions, respectively. Tumor growth inhibition is calculated using the formula (1−(VT/VC))×100, where VT is the tumor volume of the treatment group on the last day of treatment, and VC is the tumor volume of the control group on the last day of treatment. Two-way analysis of variance with Dunnett's multiple comparisons test is used to determine statistical differences between treatment groups (GraphPad Prism). Mice are housed at 10-12 animals per cage, and are provided enrichment and exposed to 12-hour light/dark cycles. Mice whose tumor volumes exceeded limits (10% of body weight) are humanely euthanized by $CO_2$ inhalation. Animals are maintained in a barrier facility fully accredited by the Association for Assessment and Accreditation of Laboratory Animal Care, International. All of the procedures are conducted in accordance with the US Public Service Policy on Human Care and Use of Laboratory Animals and with Incyte Animal Care and Use Committee Guidelines.

Example H: Caco2 Assay

Caco-2 cells are grown at 37° C. in an atmosphere of 5% $CO_2$ in DMEM growth medium supplemented with 10% (v/v) fetal bovine serum, 1% (v/v) nonessential amino acids, penicillin (100 U/mL), and streptomycin (100 μg/mL). Confluent cell monolayers are subcultured every 7 days or 4 days for Caco-2 by treatment with 0.05% trypsin containing 1 μM EDTA. Caco-2 cells are seeded in 96-well Transwell plates. The seeding density for Caco-2 cells is 14,000 cells/well. DMEM growth medium is replaced every other day after seeding. Cell monolayers are used for transport assays between 22 and 25 days for Caco-2 cells.

Cell culture medium is removed and replaced with HBSS. To measure the TEER, the HBSS is added into the donor compartment (apical side) and receiver compartment (basolateral side). The TEER is measured by using a REMS Autosampler to ensure the integrity of the cell monolayers. Caco-2 cell monolayers with TEER values≥300 $\Omega \cdot cm^2$ are used for transport experiments. To determine the $P_{app}$ in the absorptive direction (A-B), solution of test compound (50 μM) in HBSS is added to the donor compartment (apical side), while HBSS solution with 4% BSA is added to the receiver compartment (basolateral side). The apical volume was 0.075 mL, and the basolateral volume is 0.25 mL. The incubation period is 120 minutes at 37° C. in an atmosphere of 5% $CO_2$. At the end of the incubation period, samples from the donor and receiver sides are removed and an equal volume of acetonitrile is added for protein precipitation. The supernatants are collected after centrifugation (3000 rpm, Allegra X-14R Centrifuge from Beckman Coulter, Indianapolis, Ind.) for LCMS analysis. The permeability value is determined according to the equation:

$$P_{app}\ (\text{cm/s})=(F*VD)/(\text{SA}*MD),$$

where the flux rate (F, mass/time) is calculated from the slope of cumulative amounts of compound of interest on the receiver side, SA is the surface area of the cell membrane, VD is the donor volume, and MD is the initial amount of the solution in the donor chamber.

Example I: Human Whole Blood Stability

The whole blood stability of the exemplified compounds is determined by LC-MS/MS. The 96-Well Flexi-Tier™ Block (Analytical Sales & Services, Inc, Flanders, N.J.) is used for the incubation plate containing 1.0 mL glass vials with 0.5 mL of blood per vial (pooled gender, human whole blood sourced from BIOIVT, Hicksville, N.Y. or similar). Blood is pre-warmed in water bath to 37° C. for 30 minutes. 96-deep well analysis plate is prepared with the addition of 100 μL ultrapure water/well. 50 μL chilled ultrapure water/well is added to 96-deep well sample collection plate and covered with a sealing mat. 1 μL of 0.5 mM compound working solution (DMSO:water) is added to the blood in incubation plate to reach final concentrations of 1 μM, mixed by pipetting thoroughly and 50 μL is transferred 50 into the T=0 wells of the sample collection plate. Blood is allowed to sit in the water for 2 minutes and then 400 μL stop solution/well is added (acetonitrile containing an internal standard). The incubation plate is placed in the Incu-Shaker $CO_2$ Mini incubator (Benchmark Scientific, Sayreville, N.J.) at 37° C. with shaking at 150 rpm. At 1, 2 and 4-hr, the blood samples are mixed thoroughly by pipetting and 50 μL is transferred into the corresponding wells of the sample collection plate. Blood is allowed to sit in the water for 2 minutes and then 400 μL of stop solution/well is added. The collection plate is sealed and vortexed at 1700 rpm for 3 minutes (VX-2500 Multi-Tube Vortexer, VWR International, Radnor, Pa.), and samples are then centrifuged in the collection plate at 3500 rpm for 10 minutes (Allegra X-14R Centrifuge Beckman Coulter, Indianapolis, Ind.). 100 μL of supernatant/well is transferred from the sample collection plate into the corresponding wells of the analysis plate. The final plate is vortexed at 1700 rpm for 1 minute and analyze samples by LC-MS/MS. The peak area ratio of the 1, 2, and 4 hr samples relative to T=0 is used to determine the percent remaining. The natural log of the percent remaining versus time is used determine a slope to calculate the compounds half-life in blood ($t_{1/2}$=0.693/slope).

Example J: In Vitro Intrinsic Clearance Protocol

For in vitro metabolic stability experiments, test compounds are incubated with human liver microsomes at 37° C. The incubation mixture contains test compounds (1 μM), NADPH (2 mM), and human liver microsomes (0.5 mg protein/mL) in 100 mM phosphate buffer (pH 7.4). The mixture is pre-incubated for 2 min at 37° C. before the addition of NADPH. Reactions are commenced upon the addition of NADPH and quenched with ice-cold methanol at 0, 10, 20, and 30 min. Terminated incubation mixtures are analyzed using LC-MS/MS system. The analytical system consisted of a Shimadzu LC-30AD binary pump system and SIL-30AC autosampler (Shimadzu Scientific Instruments, Columbia, Md.) coupled with a Sciex Triple Quad 6500+ mass spectrometer from Applied Biosystems (Foster City, Calif.). Chromatographic separation of test compounds and internal standard is achieved using a Hypersil Gold C18 column (50×2.1 mm, 5 μM, 175 Å) from ThermoFisher Scientific (Waltham, Mass.). Mobile phase A consists of 0.1% formic acid in water, and mobile phase B consists of 0.1% formic acid in acetonitrile. The total LC-MS/MS runtime can be 2.75 minutes with a flow rate of 0.75 mL/min. Peak area integrations and peak area ratio calculations are performed using Analyst software (version 1.6.3) from Applied Biosystems.

The in vitro intrinsic clearance, $CL_{int,\ in\ vitro}$, is calculated from the $t_{1/2}$ of test compound disappearance as $CL_{int,\ in\ vitro}=(0.693/t_{1/2})\times(1/C_{protein})$, where $C_{protein}$ is the protein concentration during the incubation, and $t_{1/2}$ is determined by the slope (k) of the log-linear regression analysis of the concentration versus time profiles; thus, $t_{1/2}$=ln 2/k. The $CL_{int\ in\ vitro}$ values are scaled to the in vivo values for human by using physiologically based scaling factors, hepatic microsomal protein concentrations (45 mg protein/g liver), and liver weights (21 g/kg body weight). The equation $CL_{int}=CL_{int,\ in\ vitro}\times$ (mg protein/g liver weight)×(g liver weight/kg body weight) is used. The in vivo hepatic clearance ($CL_H$) is then calculated by using $CL_{int}$ and hepatic blood flow, Q (20 mL·min$^{-1}$·kg$^{-1}$ in humans) in the well-stirred liver model disregarding all binding from $CL_H=(Q\times CL_{int})/(Q+CL_{int})$. The hepatic extraction ratio was calculated as $CL_H$ divided by Q.

Example K: In Vivo Pharmacokinetics Protocol

For in vivo pharmacokinetic experiments, test compounds are administered to male Sprague Dawley rats or male and female Cynomolgus monkeys intravenously or via oral gavage. For intravenous (IV) dosing, test compounds are dosed at 0.5 to 1 mg/kg using a formulation of 10% dimethylacetamide (DMAC) in acidified saline via IV bolus for rat and 5 min or 10 min IV infusion for monkey. For oral (PO) dosing, test compounds are dosed at 1.0 to 3.0 mg/kg using 5% DMAC in 0.5% methylcellulose in citrate buffer (pH 2.5). Blood samples are collected at predose and various time points up to 24 hours postdose. All blood samples are collected using EDTA as the anticoagulant and centrifuged to obtain plasma samples. The plasma concentrations of test compounds are determined by LC-MS methods. The measured plasma concentrations are used to calculate PK parameters by standard noncompartmental methods using Phoenix® WinNonlin software program (version 8.0, Pharsight Corporation).

In rats and monkeys, cassette dosing of test compounds are conducted to obtain preliminary PK parameters.

In vivo pharmacokinetic experiments with male beagle dogs may be performed under the conditions described above.

Example L: Time Dependent Inhibition (TDI) of CYP Protocol

This assay is designed to characterize an increase in CYP inhibition as a test compounds is metabolized over time. Potential mechanisms for this include the formation of a tight-binding, quasi-irreversible inhibitory metabolite complex or the inactivation of P450 enzymes by covalent adduct formation of metabolites. While this experiment employs a 10-fold dilution to diminish metabolite concentrations and therefore effects of reversible inhibition, it is possible (but not common) that a metabolite that is an extremely potent CYP inhibitor could result in a positive result.

The results are from a cocktail of CYP specific probe substrates at 4 times their Km concentrations for CYP2C9, 2C19, 2D6 and 3A4 (midazolam) using human liver microsomes (HLM). The HLMs can be pre-incubated with test compounds at a concentration 10 μM for 30 min in the presence (+N) or absence (−N) of a NADPH regenerating system, diluted 10-fold, and incubated for 8 min in the presence of the substrate cocktail with the addition of a fresh aliquot of NADPH regenerating system. A calibration curve of metabolite standards can be used to quantitatively measure the enzyme activity using LC-MS/MS. In addition, incubations with known time dependent inhibitors, tienilic acid (CYP2C9), ticlopidine (CYP2C19), paroxetine (CYP2D6), and troleandomycin (CYP3A4), used as positive controls are pre-incubated 30 min with or without a NADPH regenerating system.

The analytical system consists of a Shimadzu LC-30AD binary pump system and SIL-30AC autosampler (Shimadzu Scientific Instruments, Columbia, Md.) coupled with a Sciex Triple Quad 6500+ mass spectrometer from Applied Biosystems (Foster City, Calif.). Chromatographic separation of test compounds and internal standard can be achieved using an ACQUITY UPLC BEH 130A, 2.1×50 mm, 1.7 μm HPLC column (Waters Corp, Milford, Mass.). Mobile phase A consists of 0.1% formic acid in water, and mobile phase B consists of 0.1% formic acid in acetonitrile. The total LC-MS/MS runtime will be 2.50 minutes with a flow rate of 0.9 mL/min. Peak area integrations and peak area ratio calculations are performed using Analyst software (version 1.6.3) from Applied Biosystems.

The percentage of control CYP2C9, CYP2C19, CYP2D6, and CYP3A4 activity remaining following preincubation of the compounds with NADPH is corrected for the corresponding control vehicle activity and then calculated based on 0 minutes as 100%. A linear regression plot of the natural log of % activity remaining versus time for each isozyme is used to calculate the slope. The −slope is equal to the rate of enzyme loss, or the $K_{obs}$.

Various modifications of the invention, in addition to those described herein, will be apparent to those skilled in the art from the foregoing description. Such modifications are also intended to fall within the scope of the appended claims. Each reference, including without limitation all patent, patent applications, and publications, cited in the present application is incorporated herein by reference in its entirety.

What is claimed is:

1. A compound having Formula (1):

I

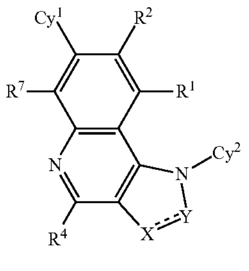

or a pharmaceutically acceptable salt thereof, wherein:

X ⎓ Y is selected from —$NR^5$—C(=O)—, —N=N—, and —N=$CR^6$—;

$R^1$ is selected from H, D, $C_{1-2}$ alkyl, and $C_{1-2}$ haloalkyl; wherein said $C_{1-2}$ alkyl is optionally substituted with 1 or 2 substituents independently selected from $R^{11}$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, or 3 substituents independently selected from $R^{10}$;

$R^4$ is selected from H, $C_{1-3}$ alkyl, $C_{1-3}$ haloalkyl, 5-10 membered heteroaryl, $OR^{a3}$, and $NR^{c3}R^{d3}$; wherein said $C_{1-3}$ alkyl and 5-10 membered heteroaryl are each optionally substituted with 1 or 2 substituents independently selected from $R^{30}$; or $R^4$ is selected from $R^4$-a

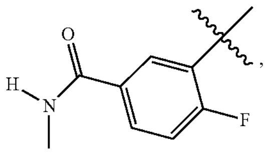

$R^4$-b

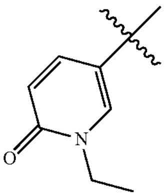

and

-continued $R^4$-c

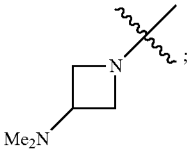

$R^5$ is selected from H, $C_{1-2}$ alkyl, and $C_{1-2}$ haloalkyl;

$R^7$ is selected from H, $C_{1-3}$ alkyl, $C_{1-3}$ haloalkyl, phenyl, 5-6 membered heteroaryl, F, Cl, D, CN, $OR^{a7}$, and $NR^{c7}R^{d7}$; wherein said phenyl and 5-6 membered heteroaryl are each optionally substituted with 1 or 2 substituents independently selected from $R^{70}$;

$Cy^2$ is selected from $Cy^2$-a

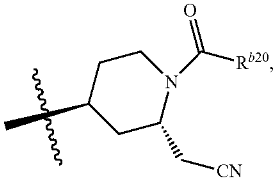

and $Cy^2$-b

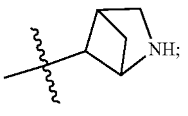

when $Cy^2$ is $Cy^2$-a and X ⎓ Y is —N=$CR^6$—, then, $R^6$ is selected from H, D, $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl are each optionally substituted with 1 or 2 substituents independently selected from $R^{60}$;

when $Cy^2$ is $Cy^2$-a, then $R^2$ is selected from H, $C_{1-2}$ alkyl, $C_{1-2}$ haloalkyl, F, Cl, and —$CH_2CH_2CN$;

when $Cy^2$ is $Cy^2$-b and X ⎓ Y is —N=$CR^6$—, then $R^6$ is selected from $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl are each optionally substituted with 1 or 2 substituents independently selected from $R^{60}$;

when $Cy^2$ is $Cy^2$-b, then $R^2$ is selected from H, $C_{1-2}$ alkyl, $C_{1-2}$ haloalkyl, F, —$CH_2CH_2CN$, $R^2$-a

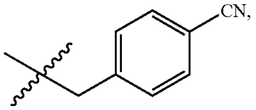

$R^2$-b

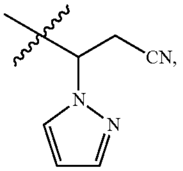

-continued

R$^2$-c

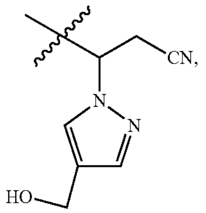

R$^2$-d

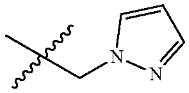

, and

R$^2$-e

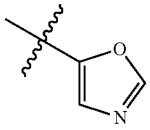

;

each $R^{10}$ is independently selected from $C_{1-3}$ alkyl, $C_{1-3}$ haloalkyl, $C_{3-6}$ cycloalkyl, halo, D, CN, $OR^{a10}$, C(O)$NR^{c10}R^{d10}$, $NR^{c10}C(O)OR^{a10}$, $NR^{c10}C(O)NR^{c10}R^{d10}$, and $NR^{c10}R^{d10}$; wherein said $C_{1-3}$ alkyl and $C_{3-6}$ cycloalkyl are each optionally substituted with 1 or 2 substituents independently selected from $R^g$;

each $R^{11}$ is independently selected from $C_{1-2}$ alkyl, $C_{1-2}$ haloalkyl, $C_{3-6}$ cycloalkyl, 4-6 membered heterocycloalkyl, halo, D, CN, $OR^{a11}$, and $NR^{c11}R^{d11}$; wherein said $C_{12}$ alkyl, $C_{3-6}$ cycloalkyl, and 4-6 membered heterocycloalkyl are each optionally substituted with 1 or 2 substituents independently selected from $R^g$;

each $R^{21}$ is independently selected from $C_{1-3}$ alkyl, $C_{1-3}$ haloalkyl, halo, D, CN, $OR^{a21}$ and $NR^{c21}R^{d21}$;

each $R^{30}$ is independently selected from $C_{1-3}$ alkyl, $C_{1-3}$ haloalkyl, 4-10 membered heterocycloalkyl, halo, D, CN, $OR^{a30}$, $C(O)NR^{c30}R^{d30}$, $NR^{c30}C(O)OR^{a30}$, $NR^{c30}C(O)NR^{c30}R^{d30}$, and $NR^{c30}R^{d30}$; wherein said $C_{1-3}$ alkyl and 4-10 membered heterocycloalkyl are each optionally substituted with 1 or 2 substituents independently selected from $R^{31}$ each $R^{31}$ is independently selected from $C_{1-3}$ alkyl, $C_{1-3}$ haloalkyl, halo, D, and CN;

each $R^{60}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a60}$, $C(O)R^{b60}$, $C(O)NR^{c60}R^{d60}$, and $NR^{c60}R^{d60}$; wherein said $C_{1-3}$ alkyl, $C_{3-6}$cycloalkyl, 4-6 membered heterocycloalkyl, phenyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a61}$, $C(O)R^{b61}$, and $NR^{c61}R^{d61}$;

each $R^{70}$ is independently selected from $C_{1-3}$ alkyl, $C_{1-3}$ haloalkyl, phenyl, 5-6 membered heteroaryl, halo, D, CN, $OR^{a70}$, and $NR^{c70}R^{d70}$;

each $R^{a3}$ and $R^{c3}$ is independently selected from H, $C_{1-3}$ alkyl, $C_{1-3}$ haloalkyl, 5-6 membered heteroaryl, and phenyl; wherein said $C_{1-3}$ alkyl, 5-6 membered heteroaryl, and phenyl are each optionally substituted with 1 or 2 substituents independently selected from $R^{30}$;

each $R^{f3}$ is independently selected from $C_{1-3}$ alkyl and $C_{1-3}$ haloalkyl;

each $R^{a7}$, $R^{c7}$ and $R^{d7}$ is independently selected from H, $C_{1-3}$ alkyl, and $C_{1-3}$ haloalkyl;

wherein said $C_{1-3}$ alkyl is optionally substituted with 1 or 2 substituents independently selected from $R^{70}$;

each $R^{a10}$, $R^{c10}$ and $R^{d10}$ is independently selected from H, $C_{1-3}$ alkyl, and $C_{1-3}$ haloalkyl;

each $R^{a11}$, $R^{c11}$ and $R^{d11}$, is independently selected from H, $C_{1-3}$ alkyl, and $C_{1-3}$ haloalkyl;

$R^{b20}$ is selected from $NH_2$, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{21}$;

each $R^{a21}$, $R^{c21}$ and $R^{d21}$, is independently selected from H, $C_{1-3}$ alkyl, and $C_{1-3}$ haloalkyl;

each $R^{a30}$, $R^{c30}$ and $R^{d30}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, 6-, 7-, 8-, or 9-membered heterocycloalkyl group optionally substituted with 1 or 2 substituents independently selected from $R^{61}$;

each $R^{a61}$, $R^{b61}$ $R^{c61}$ and $R^{d61}$ is independently selected from H, $C_{1-3}$ alkyl, and $C_{1-3}$ haloalkyl;

each $R^{a70}$, $R^{c70}$ and $R^{d70}$ is independently selected from H, $C_{1-3}$ alkyl, and $C_{1-3}$ haloalkyl; and each $R^g$ is independently selected from D, OH, CN, halo, $C_{1-2}$ alkyl, amino, and $C_{1-2}$ haloalkyl;

provided that the compound of Formula I is other than 3-(1-((endo)-2-azabicyclo[2.1.1]hexan-5-yl)-8-(2-cyanoethyl)-4-(3-(dimethylamino)azetidin-1-yl)-6-fluoro-7-(7-fluoronaphthalen-1-yl)-1H-imidazo[4,5-c]quinolin-2-yl)-N,N-dimethylpropanamide, 3-(1-((endo)-2-azabicyclo[2.1.1]hexan-5-yl)-4-(3-(dimethylamino)azetidin-1-yl)-2-ethyl-6-fluoro-7-(7-fluoro-3-hydroxynaphthalen-1-yl)-1H-imidazo[4,5-c]quinolin-8-yl)propanenitrile, 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-((3-oxomorpholino)methyl)-1H-imidazo[4,5-c]quinolin-8-yl)propanenitrile, 3-(1-((endo)-2-azabicyclo[2.1.1]hexan-5-yl)-8-(2-cyanoethyl)-4-(3-(dimethylamino)azetidin-1-yl)-6-fluoro-7-(3-hydroxynaphthalen-1-yl)-1H-imidazo[4,5-c]quinolin-2-yl)-N-methyl-N-(pyridin-2-ylmethyl)propanamide, and -continued 3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(piperazin-1-yl)thiazol-4-yl)-1H-imidazo[4,5-c]quinolin-8-yl)propanenitrile.

2. The compound of claim 1, or a pharmaceutically acceptable salt thereof, wherein:

X ═ Y is selected from —$NR^5$—C(═O)—, —N═N—, and —N═$CR^6$—;

$R^1$ is selected from H, D, $C_{1-2}$ alkyl, and $C_{1-2}$ haloalkyl; wherein said $C_{1-2}$ alkyl is optionally substituted with 1 or 2 substituents independently selected from $R^{11}$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, or 3 substituents independently selected from $R^{10}$;

$R^4$ is selected from $OR^{a3}$;

$R^5$ is selected from H, $C_{1-2}$ alkyl, and $C_{1-2}$ haloalkyl;

$R^7$ is selected from H, $C_{1-3}$ alkyl, $C_{1-3}$ haloalkyl, phenyl, 5-6 membered heteroaryl, F, Cl, D, CN, $OR^{a7}$, and $NR^{c7}R^{d7}$; wherein said phenyl and 5-6 membered heteroaryl are each optionally substituted with 1 or 2 substituents independently selected from $R^{70}$;

$Cy^2$ is selected from

Cy²-a

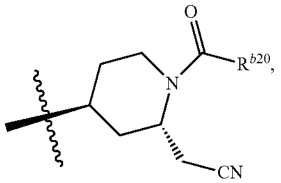

, and

Cy²-b

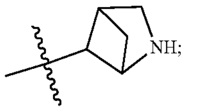

;

when $Cy^2$ is $Cy^2$-a and X ═ Y is —N═$CR^6$—, then, $R^6$ is selected from H, D, $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl are each optionally substituted with 1 or 2 substituents independently selected from $R^{60}$;

when $Cy^2$ is $Cy^2$-a, then $R^2$ is selected from H, $C_{1-2}$ alkyl, $C_{1-2}$ haloalkyl, F, Cl, and —$CH_2CH_2CN$;

when $Cy^2$ is $Cy^2$-b and X ═ Y is —N═$CR^6$—, then $R^6$ is selected from $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl are each optionally substituted with 1 or 2 substituents independently selected from $R^{60}$;

when $Cy^2$ is $Cy^2$-b then $R^2$ is selected from H, $C_{1-2}$ alkyl $C_{1-2}$ haloalkyl, F, —$CH_2CH_2CN$, R²-a

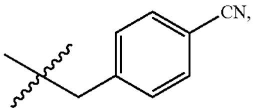

,

R²-b

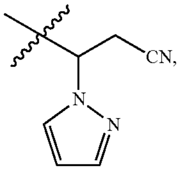

,

R²-c

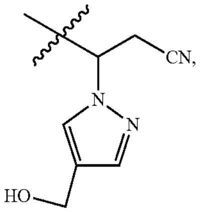

,

R²-d

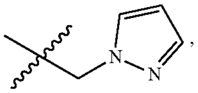

, and

R²-e

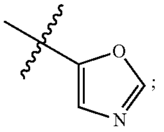

;

each $R^{10}$ is independently selected from $C_{1-3}$ alkyl, $C_{1-3}$ haloalkyl, $C_{3-6}$ cycloalkyl, halo, D, CN, $OR^{a10}$, C(O)$NR^{c10}R^{d10}$, $NR^{c10}$C(O)$OR^{a10}$, $NR^{c10}$C(O)$NR^{c10}R^{d10}$, and $NR^{c10}R^{d10}$; wherein said $C_{1-3}$ alkyl and $C_{3-6}$ cycloalkyl are each optionally substituted with 1 or 2 substituents independently selected from $R^9$;

each $R^{11}$ is independently selected from $C_{1-2}$ alkyl, $C_{1-2}$ haloalkyl, $C_{3-6}$ cycloalkyl, 4-6 membered heterocycloalkyl, halo, D, CN, $OR^{a11}$, and $NR^{c11}R^{d11}$; wherein said $C_{1-2}$ alkyl, $C_{3-6}$ cycloalkyl, and 4-6 membered heterocycloalkyl are each optionally substituted with 1 or 2 substituents independently selected from $R^9$;

each $R^{21}$ is independently selected from $C_{1-3}$ alkyl, $C_{1-3}$ haloalkyl, halo, D, CN, $OR^{a21}$ and $NR^{c21}R^{d21}$;

each $R^{30}$ is independently selected from $C_{1-3}$ alkyl, $C_{1-3}$ haloalkyl, 4-10 membered heterocycloalkyl, halo, D, CN, $OR^{a30}$, C(O)$NR^{c30}R^{d30}$, $NR^{c30}$C(O)$OR^{a30}$, $NR^{c30}$C(O)$NR^{c30}R^{d30}$ and $NR^{c30}R^{d30}$; wherein said 1-3 alkyl and 4-6 membered heterocycloalkyl are each optionally substituted with 1 or 2 substituents independently selected from $R^{31}$;

each $R^{31}$ is independently selected from $C_{1-3}$ alkyl, $C_{1-3}$ haloalkyl, halo, D, and CN;

each $R^{60}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a60}$, $C(O)R^{b60}$, $C(O)NR^{c60}R^{d60}$, and $NR^{c60}R^{d60}$; wherein said $C_{1-3}$ alkyl, $C_{3-6}$cycloalkyl, 4-6 membered heterocycloalkyl, phenyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a61}$, $C(O)R^{b61}$, and $NR^{c61}R^{d61}$;

each $R^{70}$ is independently selected from $C_{1-3}$ alkyl, $C_{1-3}$ haloalkyl, phenyl, 5-6 membered heteroaryl, halo, D, CN, $OR^{a70}$, and $NR^{c70}R^{d70}$;

each $R^{a3}$ is independently selected from H, $C_{1-3}$ alkyl, $C_{1-3}$ haloalkyl, 5-6 membered heteroaryl, and phenyl; wherein said $C_{1-3}$ alkyl, 5-6 membered heteroaryl, and phenyl are each optionally substituted with 1 or 2 substituents independently selected from $R^{30}$;

each $R^{a7}$, $R^{c7}$ and $R^{d7}$ is independently selected from H, $C_{1-3}$ alkyl, and $C_{1-3}$ haloalkyl;

wherein said $C_{1-3}$ alkyl is optionally substituted with 1 or 2 substituents independently selected from $R^{70}$;

each $R^{a10}$, $R^{c10}$ and $R^{d10}$ is independently selected from H, $C_{1-3}$ alkyl, and $C_{1-3}$ haloalkyl;

each $R^{a11}$, $R^{c11}$ and $R^{d11}$, is independently selected from H, $C_{1-3}$ alkyl, and $C_{1-3}$ haloalkyl;

$R^{b20}$ is selected from $NH_2$, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{21}$;

each $R^{a21}$, $R^{c21}$ and $R^{d21}$, is independently selected from H, $C_{1-3}$ alkyl, and $C_{1-3}$ haloalkyl;

each $R^{a30}$, $R^{c30}$ and $R^{d30}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, $C_{1-3}$ haloalkyl, $C_{3-6}$ cycloalkyl, 4-6 membered heterocycloalkyl, phenyl, and 5-6 membered heteroaryl; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{61}$;

or any $R^{c60}$ and $R^{d60}$ attached to the same N atom, together with the N atom to which they are attached, form a 4-, 5-, 6-, 7-, 8-, or 9-membered heterocycloalkyl group optionally substituted with 1 or 2 substituents independently selected from $R^{61}$;

each $R^{a61}$, $R^{b61}$ $R^{c61}$ and $R^{d61}$ is independently selected from H, $C_{1-3}$ alkyl, and $C_{1-3}$ haloalkyl;

each $R^{a70}R^{c70}$ and $R^{d70}$ is independently selected from H, $C_{1-3}$ alkyl, and $C_{1-3}$ haloalkyl; and each $R^{g}$ is independently selected from D, OH, CN, halo, $C_{1-2}$ alkyl, amino, and $C_{1-2}$ haloalkyl.

3. The compound of claim 1, or a pharmaceutically acceptable salt thereof, wherein:

X ═ Y is selected from —$NR^5$—C(═O)—, —N═N—, and —N═$CR^6$—;

$R^1$ is selected from H, D, $C_{1-2}$ alkyl, and $C_{1-2}$ haloalkyl; wherein said $C_{1-2}$ alkyl is optionally substituted with 1 or 2 substituents independently selected from $R^{11}$;

$Cy^1$ is selected from $C_{3-10}$ cycloalkyl, 4-10 membered heterocycloalkyl, $C_{6-10}$ aryl and 6-10 membered heteroaryl; wherein the 4-10 membered heterocycloalkyl and 6-10 membered heteroaryl each has at least one ring-forming carbon atom and 1, 2, 3, or 4 ring-forming heteroatoms independently selected from N, O, and S; wherein a ring-forming carbon atom of 6-10 membered heteroaryl and 4-10 membered heterocycloalkyl is optionally substituted by oxo to form a carbonyl group; and wherein the $C_{3-10}$ cycloalkyl, 4-10 membered heterocycloalkyl, $C_{6-10}$ aryl and 6-10 membered heteroaryl are each optionally substituted with 1, 2, or 3 substituents independently selected from $R^{10}$;

$R^4$ is selected from $OR^{a3}$;

$R^5$ is selected from H, $C_{1-2}$ alkyl, and $C_{1-2}$ haloalkyl;

$R^7$ is selected from H, $C_{1-3}$ alkyl, $C_{1-3}$ haloalkyl, phenyl, 5-6 membered heteroaryl, F, Cl, D, CN, $OR^{a7}$, and $NR^{c7}R^{d7}$; wherein said phenyl and 5-6 membered heteroaryl are each optionally substituted with 1 or 2 substituents independently selected from $R^{70}$;

$Cy^2$ is selected from $Cy^2$-a

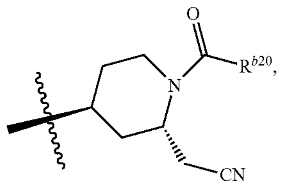

and $Cy^2$-b

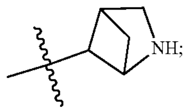

when $Cy^2$ is $Cy^2$-a and X ═ Y is —N═$CR^6$—, then, $R^6$ is selected from H, D, $C_{1-3}$ alkyl, and $C_{1-3}$ haloalkyl; wherein said $C_{1-3}$ alkyl is optionally substituted with 1 or 2 substituents independently selected from $R^{60}$;

when $Cy^2$ is $Cy^2$-a, then $R^2$ is selected from H, $C_{1-2}$ alkyl, $C_{1-2}$ haloalkyl, F, Cl, and —$CH_2CH_2CN$;

when $Cy^2$ is $Cy^2$-b and X ═ Y is —N═$CR^6$—, then $R^6$ is selected from $C_{1-3}$ alkyl, $C_{1-3}$ haloalkyl, $C_{3-6}$ cycloalkyl, 4-6 membered heterocycloalkyl, phenyl, and 5-10 membered heteroaryl; wherein said $C_{1-3}$ alkyl, $C_{3-6}$ cycloalkyl, 4-6 membered heterocycloalkyl, phenyl, and 5-10 membered heteroaryl, are each optionally substituted with 1 or 2 substituents independently selected from $R^{60}$;

when $Cy^2$ is $Cy^2$-b, then $R^2$ is selected from H, $C_{1-2}$ alkyl, $C_{1-2}$ haloalkyl, F, —$CH_2CH_2CN$, $R^2$-a

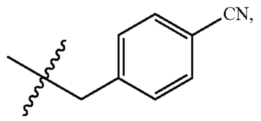

-continued

R²-b

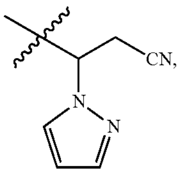

R²-c

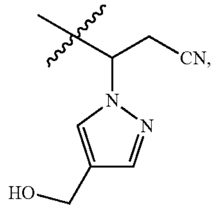

R²-d

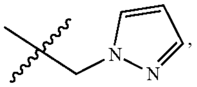

and

R²-e

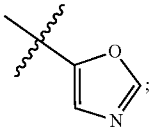

each $R^{10}$ is independently selected from $C_{1-3}$ alkyl, $C_{1-3}$ haloalkyl, $C_{3-6}$ cycloalkyl, halo, D, CN, $OR^{a10}$, C(O)$NR^{c10}R^{d10}$, and $NR^{c10}R^{d10}$; wherein said $C_{1-3}$ alkyl and $C_{3-6}$cycloalkyl are each optionally substituted with 1 or 2 substituents independently selected from $R^9$;

each $R^{11}$ is independently selected from $C_{1-2}$ alkyl, $C_{1-2}$ haloalkyl, $C_{3-6}$ cycloalkyl, 4-6 membered heterocycloalkyl, halo, D, CN, $OR^{a11}$, and $NR^{c11}R^{d11}$; wherein said $C_{12}$ alkyl, $C_{3-6}$ cycloalkyl, and 4-6 membered heterocycloalkyl are each optionally substituted with 1 or 2 substituents independently selected from $R^g$;

each $R^{21}$ is independently selected from $C_{1-3}$ alkyl, $C_{1-3}$ haloalkyl, halo, D, and CN;

each $R^{30}$ is independently selected from $C_{1-3}$ alkyl, $C_{1-3}$ haloalkyl, 4-10 membered heterocycloalkyl, halo, D, CN, $OR^{a30}$, C(O)$NR^{c30}R^{d30}$, and $NR^{c30}R^{d30}$; wherein said $C_{1-3}$ alkyl and 4-10 membered heterocycloalkyl are each optionally substituted with 1 or 2 substituents independently selected from $R^{31}$;

each $R^{31}$ is independently selected from $C_{1-3}$ alkyl, $C_{1-3}$ haloalkyl, halo, D, and CN;

each $R^{60}$ is independently selected from $C_{1-3}$ alkyl, $C_{1-3}$ haloalkyl, $C_{3-6}$ cycloalkyl, 4-6 membered heterocycloalkyl, phenyl, 5-6 membered heteroaryl, halo, D, CN, $OR^{a60}$, C(O)$R^{b60}$, C(O)$NR^{60}R^{d60}$, and $NR^{c60}R^{d60}$; wherein said $C_{1-3}$ alkyl, $C_{3-6}$cycloalkyl, 4-6 membered heterocycloalkyl, phenyl, and 5-6 membered heteroaryl are each optionally substituted with 1 or 2 substituents independently selected from $R^{61}$;

each $R^{61}$ is independently selected from $C_{1-3}$ alkyl, $C_{1-3}$ haloalkyl, phenyl, 5-6 membered heteroaryl, halo, D, CN, $OR^{a61}$, C(O)$R^{b61}$, and $NR^{c61}R^{d61}$;

each $R^{70}$ is independently selected from $C_{1-3}$ alkyl, $C_{1-3}$ haloalkyl, phenyl, 5-6 membered heteroaryl, halo, D, and CN;

each $R^{a3}$ is independently selected from H, $C_{1-3}$ alkyl, $C_{1-3}$ haloalkyl, 5-6 membered heteroaryl, and phenyl; wherein said $C_{1-3}$ alkyl, 5-6 membered heteroaryl, and phenyl are each optionally substituted with 1 or 2 substituents independently selected from $R^{30}$;

each $R^{a7}$, $R^{c7}$ and $R^{d7}$ is independently selected from H, $C_{1-3}$ alkyl, and $C_{1-3}$ haloalkyl; wherein said $C_{1-3}$ alkyl is optionally substituted with 1 or 2 substituents independently selected from $R^{70}$;

each $R^{a10}$, $R^{c10}$ and $R^{d10}$ is independently selected from H, $C_{1-3}$ alkyl, and $C_{1-3}$ haloalkyl;

each $R^{a11}$, $R^{c11}$ and $R^{d11}$, is independently selected from H, $C_{1-3}$ alkyl, and $C_{1-3}$ haloalkyl;

$R^{b20}$ is selected from $NH_2$, $C_{1-3}$ alkyl, $C_{1-3}$ haloalkyl, $C_{3-6}$ cycloalkyl, 4-6 membered heterocycloalkyl, phenyl and 5-6 membered heteroaryl; wherein said $C_{1-3}$ alkyl, $C_{3-6}$ cycloalkyl, 4-6 membered heterocycloalkyl, phenyl and 5-6 membered heteroaryl are each optionally substituted with 1 or 2 substituents independently selected from $R^{21}$;

each $R^{a21}$, $R^{c21}$ and $R^{d21}$ is independently selected from H, $C_{1-3}$ alkyl, and $C_{1-3}$ haloalkyl;

each $R^{a30}$, $R^{c30}$ and $R^{d30}$ is independently selected from H, $C_{1-3}$ alkyl, and $C_{1-3}$ haloalkyl;

each $R^{a60}$, $R^{b60}$, $R^{c60}$ and $R^{d60}$ is independently selected from H, $C_{1-3}$ alkyl, and $C_{1-3}$ haloalkyl; wherein said $C_{1-3}$ alkyl is optionally substituted with 1 or 2 substituents independently selected from $R^{61}$;

or any $R^{c60}$ and $R^{d60}$ attached to the same N atom, together with the N atom to which they are attached, form a 4-, 5-, 6-, or 9-membered heterocycloalkyl group optionally substituted with 1 or 2 substituents independently selected from $R^{61}$;

each $R^{a61}$, $R^{b61}$ $R^{c61}$ and $R^{d61}$ is independently selected from H, $C_{1-3}$ alkyl, and $C_{1-3}$ haloalkyl; and each $R^g$ is independently selected from D, OH, CN, halo, $C_{1-2}$ alkyl, amino, and $C_{1-2}$ haloalkyl.

4. The compound of claim 1, or a pharmaceutically acceptable salt thereof, wherein:

X ⎓ Y is selected from —$NR^5$—C(═O)—, —N═N—, and —N═$CR^6$—;

$R^1$ is selected from H, and $C_{1-2}$ alkyl; wherein said $C_{1-2}$ alkyl is optionally substituted with 1 or 2 substituents independently selected from $R^{11}$;

$Cy^1$ is selected from $C_{3-10}$ cycloalkyl, $C_{6-10}$ aryl and 6-10 membered heteroaryl; wherein the 6-10 membered heteroaryl each has at least one ring-forming carbon atom and 1, 2, or 3 ring-forming heteroatoms independently selected from N, O, and S; wherein a ring-forming carbon atom of 6-10 membered heteroaryl is optionally substituted by oxo to form a carbonyl group; and wherein the $C_{3-10}$ cycloalkyl, $C_{6-10}$ aryl and 6-10 membered heteroaryl are each optionally substituted with 1, 2, or 3 substituents independently selected from $R^{10}$;

$R^4$ is selected from $OR^{a3}$;

$R^5$ is H;

$R^7$ is selected from phenyl, 5-6 membered heteroaryl, F, and $OR^{a7}$; wherein said phenyl and 5-6 membered heteroaryl are each optionally substituted with 1 or 2 substituents independently selected from $R^{70}$;

$Cy^2$ is selected from

Cy²-a

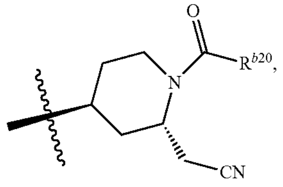

and

-continued $Cy^2$-b

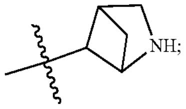

when $Cy^2$ is $Cy^2$-a and X ⎓ Y is —N═$CR^6$—, then, $R^6$ is H;

when $Cy^2$ is $Cy^2$-a, then $R^2$ is Cl;

when $Cy^2$ is $Cy^2$-b and X ⎓ Y is —N═$CR^6$—, then $R^6$ is selected from $C_{1-3}$ alkyl, $C_{3-6}$ cycloalkyl, 4-6 membered heterocycloalkyl, and 5-10 membered heteroaryl; wherein said $C_{1-3}$ alkyl, $C_{3-6}$ cycloalkyl, 4-6 membered heterocycloalkyl, and 5-10 membered heteroaryl are each optionally substituted with 1 or 2 substituents independently selected from $R^{60}$;

when $Cy^2$ is $Cy^2$-b, then $R^2$ is selected from H, $C_{1-2}$ alkyl, —$CH_2CH_2CN$, $R^2$-a

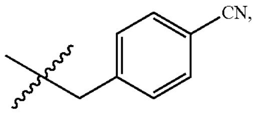

$R^2$-b

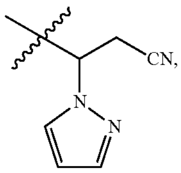

$R^2$-c

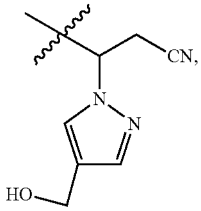

$R^2$-d

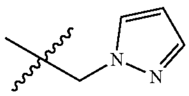

, and $R^2$-e

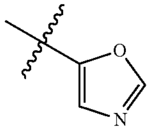

;

each $R^{10}$ is independently selected from $C_{1-3}$ alkyl, $C_{1-3}$ haloalkyl, $C_{3-6}$ cycloalkyl, halo, CN, $OR^{a10}$, and $NR^{c10}R^{d10}$; wherein said $C_{1-3}$ alkyl and $C_{3-6}$ cycloalkyl are each optionally substituted with 1 or 2 substituents independently selected from $R^9$;

each $R^{11}$ is independently selected from 4-6 membered heterocycloalkyl, and $OR^{a11}$;

wherein said 4-6 membered heterocycloalkyl is optionally substituted with 1 or 2 substituents independently selected from $R^g$;

each $R^{21}$ is CN;

each $R^{30}$ is independently selected from 4-10 membered heterocycloalkyl and $C(O)NR^{c30}R^{d30}$; wherein said 4-10 membered heterocycloalkyl is optionally substituted with 1 or 2 substituents independently selected from $R^{31}$;

each $R^{31}$ is independently selected from $C_{1-3}$ alkyl;

each $R^{60}$ is independently selected from $C_{1-3}$ alkyl, $C_{3-6}$ cycloalkyl, 4-6 membered heterocycloalkyl, phenyl, 5-6 membered heteroaryl, $C(O)R^{b60}$, $C(O)NR^{c60}R^{d60}$, and $NR^{c60}R^{d60}$; wherein said $C_{1-3}$ alkyl, $C_{3-6}$ cycloalkyl, 4-6 membered heterocycloalkyl, phenyl, and 5-6 membered heteroaryl are each optionally substituted with 1 or 2 substituents independently selected from $R^{61}$;

each $R^{61}$ is independently selected from phenyl, 5-6 membered heteroaryl, and $C(O)R^{b61}$;

each $R^{70}$ is independently selected from phenyl, 5-6 membered heteroaryl, and CN;

each $R^{a3}$ is independently selected from $C_{1-3}$ alkyl, and phenyl; wherein said $C_{1-3}$ alkyl and phenyl are each optionally substituted with 1 or 2 substituents independently selected from $R^{30}$;

each $R^{a7}$ is $C_{1-3}$ alkyl; wherein said $C_{1-3}$ alkyl is optionally substituted with 1 or 2 substituents independently selected from $R^{70}$;

each $R^{a10}$, $R^{c10}$ and $R^{d10}$ is H;

each $R^{a11}$ is H;

$R^{b20}$ is selected from $NH_2$, $C_{1-3}$ alkyl, $C_{3-6}$cycloalkyl, and 5-6 membered heteroaryl; wherein said $C_{1-3}$ alkyl, $C_{3-6}$ cycloalkyl, and 5-6 membered heteroaryl are each optionally substituted with 1 or 2 substituents independently selected from $R^{21}$;

each $R^{c30}$ and $R^{d30}$ is independently selected from H and $C_{1-3}$ alkyl;

each $R^{b60}$, $R^{c60}$ and $R^{d60}$ is independently selected from H and $C_{1-3}$ alkyl; wherein said $C_{1-3}$ alkyl is optionally substituted with 1 or 2 substituents independently selected from $R^{61}$;

or any $R^{c60}$ and $R^{d60}$ attached to the same N atom, together with the N atom to which they are attached, form a 6- or 9-membered heterocycloalkyl group optionally substituted with 1 or 2 substituents independently selected from $R^{61}$;

each $R^{b61}$ is $C_{1-3}$ alkyl; and each $R^g$ is CN.

5. The compound of claim 1, or a pharmaceutically acceptable salt thereof, wherein X ⎓ Y is —$NR^5$—C(═O)— or —N═N—.

6. The compound of claim 1, or a pharmaceutically acceptable salt thereof, wherein X ⎓ Y is —N═$CR^6$—.

7. The compound of claim 1, or a pharmaceutically acceptable salt thereof, wherein $R^1$ is H.

8. The compound of claim 1, or a pharmaceutically acceptable salt thereof, wherein $Cy^1$ is selected from $C_{6-10}$ aryl and 6-10 membered heteroaryl; wherein the 6-10 membered heteroaryl has at least one ring-forming carbon atom and 1, 2, 3, or 4 ring-forming heteroatoms independently selected from N, O, and S; wherein a ring-forming carbon atom of 6-10 membered heteroaryl is optionally substituted by oxo to form a carbonyl group; and wherein the $C_{6-10}$ aryl and 6-10 membered heteroaryl are each optionally substituted with 1, 2, or 3 substituents independently selected from $R^{10}$.

9. The compound of claim 1, or a pharmaceutically acceptable salt thereof, wherein $Cy^1$ is selected from $Cy^1$-a

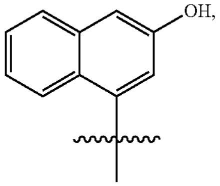

$Cy^1$-b

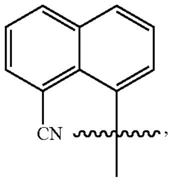

and $Cy^1$-c

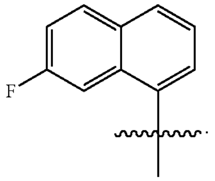

10. The compound of claim 1, or a pharmaceutically acceptable salt thereof, wherein $R^4$ is selected from $R^4$-a

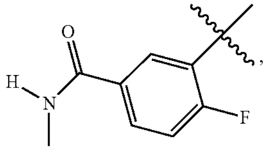

$R^4$-b

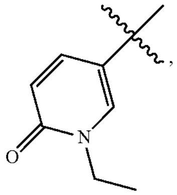

and $R^4$-c

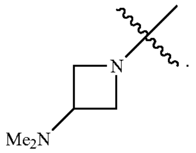

11. The compound of claim 1, or a pharmaceutically acceptable salt thereof, wherein $R^4$ is selected from H, $C_{1-3}$ alkyl, $C_{1-3}$ haloalkyl, 5-10 membered heteroaryl, $OR^{a3}$, and $NR^{c3}R^{d3}$; wherein said $C_{1-3}$ alkyl and 5-10 membered heteroaryl are each optionally substituted with 1 or 2 substituents independently selected from $R^{30}$.

12. The compound of claim 1, or a pharmaceutically acceptable salt thereof, wherein $R^7$ is selected from phenyl, 5-6 membered heteroaryl, F and $OR^{a7}$; wherein said phenyl and 5-6 membered heteroaryl are each optionally substituted with 1 or 2 substituents independently selected from $R^{70}$.

13. The compound of claim 1, or a pharmaceutically acceptable salt thereof, wherein when $Cy^2$ is $Cy^2$-a and X ⎓ Y is —N═$CR^6$—, then, $R^6$ is H.

14. The compound of claim 1, or a pharmaceutically acceptable salt thereof, wherein when $Cy^2$ is $Cy^2$-a, then $R^2$ is Cl.

15. The compound of claim 1, or a pharmaceutically acceptable salt thereof, wherein when $Cy^2$ is $Cy^2$-b and X ⎓ Y is —N═$CR^6$—, then $R^6$ is selected from $C_{1-3}$ alkyl, and $C_{1-3}$ haloalkyl; wherein said $C_{1-3}$ alkyl is optionally substituted with 1 or 2 substituents independently selected from $R^{60}$.

16. The compound of claim 1, or a pharmaceutically acceptable salt thereof, wherein when $Cy^2$ is $Cy^2$-b, then $R^2$ is selected from H, $C_{1-2}$ alkyl, —$CH_2CH_2CN$, $R^2$-a

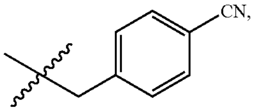

$R^2$-b

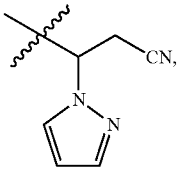

$R^2$-c

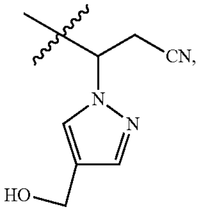

$R^2$-d

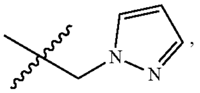

and $R^2$-e

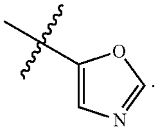

17. The compound of claim 1, or a pharmaceutically acceptable salt thereof, wherein each $R^{10}$ is independently selected from $C_{1-3}$ alkyl, $C_{1-3}$ haloalkyl, $C_{3-6}$ cycloalkyl, halo, CN, $OR^{a10}$, and $NR^{c10}R^{d10}$; wherein said $C_{1-3}$ alkyl and $C_{3-6}$cycloalkyl are each optionally substituted with 1 or 2 substituents independently selected from $R^g$.

18. The compound of claim 1, or a pharmaceutically acceptable salt thereof, wherein each $R^{11}$ is independently selected from 4-6 membered heterocycloalkyl and $OR^{a11}$, wherein said 4-6 membered heterocycloalkyl is optionally substituted with 1 or 2 substituents independently selected from $R^g$.

19. The compound of claim 1, or a pharmaceutically acceptable salt thereof, wherein each $R^{21}$ is independently selected from halo, CN, and $OR^{a21}$.

20. The compound of claim 1, or a pharmaceutically acceptable salt thereof, wherein each $R^{30}$ is independently selected from 4-10 membered heterocycloalkyl and C(O) $NR^{c30}R^{d30}$; wherein said 4-10 membered heterocycloalkyl is optionally substituted with 1 or 2 substituents independently selected from $R^{31}$.

21. The compound of claim 1, or a pharmaceutically acceptable salt thereof, wherein each $R^{31}$ is independently selected from $C_{1-3}$ alkyl and $C_{1-3}$ haloalkyl.

22. The compound of claim 1, or a pharmaceutically acceptable salt thereof, wherein each $R^{60}$ is independently selected from $C_{1-3}$ alkyl, C(O)$NR^{c60}R^{d60}$, and $NR^{c60}R^{d60}$; wherein said $C_{1-3}$ alkyl is optionally substituted with 1 or 2 substituents independently selected from $R^{61}$.

23. The compound of claim 1, or a pharmaceutically acceptable salt thereof, wherein each $R^{61}$ is independently selected from phenyl, 5-6 membered heteroaryl, and C(O)$R^{b61}$.

24. The compound of claim 1, or a pharmaceutically acceptable salt thereof, wherein each $R^{70}$ is independently selected from phenyl, 5-6 membered heteroaryl, and CN.

25. The compound of claim 1, or a pharmaceutically acceptable salt thereof, wherein $R^g$ is independently selected from OH, CN, and halo.

26. The compound of claim 1, or a pharmaceutically acceptable salt thereof, wherein each $R^{a3}$ is independently selected from $C_{1-3}$ alkyl; wherein said $C_{1-3}$ alkyl is optionally substituted with 1 or 2 substituents independently selected from $R^{30}$.

27. The compound of claim 1, or a pharmaceutically acceptable salt thereof, wherein $R^{b20}$ is selected from $NH_2$ and $C_{1-3}$ alkyl; wherein said $C_{1-3}$ alkyl is optionally substituted with 1 or 2 substituents independently selected from $R^{21}$.

28. The compound of claim 1, or a pharmaceutically acceptable salt thereof, wherein each $R^{b60}$, $R^{c60}$ and $R^{d60}$ is independently selected from H and $C_{1-3}$ alkyl; wherein said $C_{1-3}$ alkyl is optionally substituted with 1 or 2 substituents independently selected from $R^{61}$; or any $R^{c60}$ and $R^{d60}$ attached to the same N atom, together with the N atom to which they are attached, form a 6- or 9-membered heterocycloalkyl group optionally substituted with 1 or 2 substituents independently selected from $R^{61}$.

29. The compound of claim 1, wherein the compound of Formula I is selected from:

1-(3-(1-((endo)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)piperidin-1-yl)ethan-1-one;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-8-methyl-1H-imidazo[4,5-c]quinolin-2-yl)-1-(4-(pyrimidin-2-yl)piperazin-1-yl)propan-1-one;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(3-oxo-3-(7-oxa-2-azaspiro[3.5]nonan-2-yl)propyl)-1H-imidazo[4,5-c]quinolin-8-yl)propanenitrile;

3-(2-(3-(4-acetylpiperazin-1-yl)-3-oxopropyl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-8-yl)propanenitrile;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-((2-oxopyrrolidin-1-yl)methyl)-1H-imidazo[4,5-c]quinolin-8-yl)propanenitrile;

4-(1-((endo)-2-azabicyclo[2.1.1]hexan-5-yl)-4-(3-(dimethylamino)azetidin-1-yl)-2-ethyl-6-fluoro-8-(oxazol-5-yl)-1H-imidazo[4,5-c]quinolin-7-yl)naphthalen-2-ol;

3-(1-((endo)-2-azabicyclo[2.1.1]hexan-5-yl)-4-(3-(dimethylamino)azetidin-1-yl)-2-ethyl-6-fluoro-7-(3-hydroxynaphthalen-1-yl)-1H-imidazo[4,5-c]quinolin-8-yl)-3-(1H-pyrazol-1-yl)propanenitrile;

3-(1-((endo)-2-azabicyclo[2.1.1]hexan-5-yl)-4-(3-(dimethylamino)azetidin-1-yl)-2-ethyl-6-fluoro-7-(3-hydroxynaphthalen-1-yl)-1H-imidazo[4,5-c]quinolin-8-yl)-3-(4-(hydroxymethyl)-1H-pyrazol-1-yl)propanenitrile;

3-(8-((1H-pyrazol-1-yl)methyl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-2-yl)-N,N-dimethylpropanamide;

3-(1-(2-azabicyclo[2.1.1]hexan-5-yl)-8-(2-cyanoethyl)-7-(2,3-dichloro-6-hydroxyphenyl)-4-(3-(dimethylamino)azetidin-1-yl)-6-fluoro-1H-imidazo[4,5-c]quinolin-2-yl)-N,N-dimethylpropanamide;

3-(1-(2-azabicyclo[2.1.1]hexan-5-yl)-7-(3-chloro-2-cyclopropyl-5-hydroxyphenyl)-4-(3-(dimethylamino)azetidin-1-yl)-6-fluoro-1H-imidazo[4,5-c]quinolin-2-yl)-N,N-dimethylpropanamide;

3-(1-((endo)-2-azabicyclo[2.1.1]hexan-5-yl)-8-(2-cyanoethyl)-6-(3-cyanophenyl)-4-(3-(dimethylamino)azetidin-1-yl)-7-(3-hydroxynaphthalen-1-yl)-1H-imidazo[4,5-c]quinolin-2-yl)-N,N-dimethylpropanamide;

3-(1-((endo)-2-azabicyclo[2.1.1]hexan-5-yl)-8-(2-cyanoethyl)-4-(3-(dimethylamino)azetidin-1-yl)-7-(3-hydroxynaphthalen-1-yl)-6-(1-(pyridin-2-yl)-1H-pyrazol-4-yl)-1H-imidazo[4,5-c]quinolin-2-yl)-N,N-dimethylpropanamide;

3-(6-(benzyloxy)-1-((endo)-2-azabicyclo[2.1.1]hexan-5-yl)-8-(2-cyanoethyl)-4-(3-(dimethylamino)azetidin-1-yl)-7-(7-fluoronaphthalen-1-yl)-1H-imidazo[4,5-c]quinolin-2-yl)-N,N-dimethylpropanamide;

3-(1-((endo)2-azabicyclo[2.1.1]hexan-5-yl)-4-(3-(dimethylamino)azetidin-1-yl)-6-fluoro-9-(hydroxymethyl)-7-(3-hydroxynaphthalen-1-yl)-1H-imidazo[4,5-c]quinolin-2-yl)-N,N-dimethylpropanamide;

3-(1-((endo)2-azabicyclo[2.1.1]hexan-5-yl)-9-((3-cyanopyrrolidin-1-yl)methyl)-4-(3-(dimethylamino)azetidin-1-yl)-6-fluoro-7-(3-hydroxynaphthalen-1-yl)-1H-imidazo[4,5-c]quinolin-2-yl)-N,N-dimethylpropanamide;

3-(1-((endo)-2-Azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-4-fluoro-N-methylbenzamide;

3-(1-((endo)-2-Azabicyclo[2.1.1]hexan-5-yl)-2-ethyl-4-(1-ethyl-6-oxo-1,6-dihydropyridin-3-yl)-6-fluoro-7-(3-hydroxynaphthalen-1-yl)-1H-imidazo[4,5-c]quinolin-8-yl)propanenitrile;

5-(1-((endo)-2-Azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-N-methylpicolinamide;

3-(1-((endo)-2-Azabicyclo[2.1.1]hexan-5-yl)-2-ethyl-6-fluoro-7-(3-hydroxynaphthalen-1-yl)-4-(oxazol-2-yl)-1H-imidazo[4,5-c]quinolin-8-yl)propanenitrile;

3-(4-([1,2,4]Triazolo[1,5-a]pyridin-7-yl)-1-((endo)-2-azabicyclo[2.1.1]hexan-5-yl)-2-ethyl-6-fluoro-7-(3-hydroxynaphthalen-1-yl)-1H-imidazo[4,5-c]quinolin-8-yl)propanenitrile;

3-(1-((endo)-2-Azabicyclo[2.1.1]hexan-5-yl)-2-ethyl-6-fluoro-7-(3-hydroxynaphthalen-1-yl)-4-(2-(4-methylpiperazin-1-yl)pyridin-4-yl)-1H-imidazo[4,5-c]quinolin-8-yl)propanenitrile;

3-(1-((endo)-2-Azabicyclo[2.1.1]hexan-5-yl)-2-ethyl-6-fluoro-7-(3-hydroxynaphthalen-1-yl)-4-methyl-1H-imidazo[4,5-c]quinolin-8-yl)propanenitrile;

3-(1-((endo)-2-Azabicyclo[2.1.1]hexan-5-yl)-2-ethyl-6-fluoro-7-(3-hydroxynaphthalen-1-yl)-4-phenoxy-1H-imidazo[4,5-c]quinolin-8-yl)propanenitrile;

3-(1-((endo)-2-Azabicyclo[2.1.1]hexan-5-yl)-2-cyclopropyl-4-(3-(dimethylamino)azetidin-1-yl)-6-fluoro-7-(3-hydroxynaphthalen-1-yl)-1H-imidazo[4,5-c]quinolin-8-yl)propanenitrile;

3-(1-((endo)-2-Azabicyclo[2.1.1]hexan-5-yl)-4-(3-(dimethylamino)azetidin-1-yl)-6-fluoro-7-(3-hydroxynaphthalen-1-yl)-2-(1-(piperidin-4-yl)-1H-1,2,3-triazol-4-yl)-1H-imidazo[4,5-c]quinolin-8-yl)propanenitrile;

3-(1-((endo)-2-Azabicyclo[2.1.1]hexan-5-yl)-2-(1-cyclobutyl-1H-1,2,3-triazol-4-yl)-6-fluoro-7-(3-hydroxynaphthalen-1-yl)-4-(((S)-1-methylpyrrolidin-2-yl)methoxy)-1H-imidazo[4,5-c]quinolin-8-yl)propanenitrile;

3-(1-(2-azabicyclo[2.1.1]hexan-5-yl)-2-ethyl-6-fluoro-4-(((2R,7aS)-2-fluorotetrahydro-1H-pyrrolizin-7a(5H)-yl)methoxy)-7-(5-methyl-1H-indol-3-yl)-1H-imidazo[4,5-c]quinolin-8-yl)propanenitrile;

4-((1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(methylamino)ethyl)-1H-imidazo[4,5-c]quinolin-8-yl)methyl)benzonitrile;

3-(1-((endo)-2-azabicyclo[2.1.1]hexan-5-yl)-2-ethyl-6-fluoro-7-(5-fluoro-1H-indol-3-yl)-4-(((2R,7aS)-2-fluorotetrahydro-1H-pyrrolizin-7a(5H)-yl)methoxy)-1H-imidazo[4,5-c]quinolin-8-yl)propanenitrile;

3-(7-(3-aminoisoquinolin-1-yl)-1-endo-(2-azabicyclo[2.1.1]hexan-5-yl)-8-(2-cyanoethyl)-4-(3-(dimethylamino)azetidin-1-yl)-6-fluoro-1H-imidazo[4,5-c]quinolin-2-yl)-N,N-dimethylpropanamide;

3-(7-(6-amino-3-(trifluoromethyl)pyridin-2-yl)-1-endo-(2-azabicyclo[2.1.1]hexan-5-yl)-8-(2-cyanoethyl)-4-(3-(dimethylamino)azetidin-1-yl)-6-fluoro-1H-imidazo[4,5-c]quinolin-2-yl)-N,N-dimethylpropanamide;

3-(1-endo-(2-azabicyclo[2.1.1]hexan-5-yl)-8-(2-cyanoethyl)-7-(7,7-difluoro-5,6,7,8-tetrahydronaphthalen-1-yl)-4-(3-(dimethylamino)azetidin-1-yl)-6-fluoro-1H-imidazo[4,5-c]quinolin-2-yl)-N,N-dimethylpropanamide;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(1-phenyl-1H-pyrazol-3-yl)-1H-imidazo[4,5-c]quinolin-8-yl)propanenitrile;

3-(1-((endo)-2-azabicyclo[2.1.1]hexan-5-yl)-4-(3-(dimethylamino)azetidin-1-yl)-2-(1-ethyl-1H-pyrazol-3-yl)-6-fluoro-7-(3-hydroxynaphthalen-1-yl)-1H-imidazo[4,5-c]quinolin-8-yl)propanenitrile;

3-(2-(1-benzyl-1H-pyrazol-3-yl)-1-((endo)-2-azabicyclo[2.1.1]hexan-5-yl)-4-(3-(dimethylamino)azetidin-1-yl)-6-fluoro-7-(3-hydroxynaphthalen-1-yl)-1H-imidazo[4,5-c]quinolin-8-yl)propanenitrile;

3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(2-(pyrimidin-2-yl)ethyl)-1H-imidazo[4,5-c]quinolin-8-yl)propanenitrile;

(3-(1-((endo)-2-azabicyclo[2.1.1]hexan-5-yl)-4-(3-(dimethylamino)azetidin-1-yl)-6-fluoro-7-(3-hydroxynaphthalen-1-yl)-2-(1H-indazol-5-yl)-1H-imidazo[4,5-c]quinolin-8-yl)propanenitrile;

8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-imidazo[4,5-c]quinolin-7-yl)-1-naphthonitrile;

8-(8-chloro-1-((2S,4S)-1-(2-cyanoacetyl)-2-(cyanomethyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

8-(8-chloro-1-((2S,4S)-2-(cyanomethyl)-1-(1H-1,2,4-triazole-3-carbonyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

(2S,4S)-4-(8-chloro-7-(8-cyanonaphthalen-1-yl)-6-fluoro-4-((S)-1-((S)-1-methylpyrrolidin-2-yl)ethoxy)-1H-imidazo[4,5-c]quinolin-1-yl)-2-(cyanomethyl)piperidine-1-carboxamide;

8-(8-chloro-1-((2S,4S)-2-(cyanomethyl)-1-(cyclopropanecarbonyl)piperidin-4-yl)-6-fluoro-4-((S)-1-((S)-1-methylpyrrolidin-2-yl)ethoxy)-1H-imidazo[4,5-c]quinolin-7-yl)-1-naphthonitrile;

8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-1H-[1,2,3]triazolo[4,5-c]quinolin-7-yl)-1-naphthonitrile; and 8-(1-((2S,4S)-1-acetyl-2-(cyanomethyl)piperidin-4-yl)-8-chloro-6-fluoro-4-((S)-1-((S)-1-methylpyrrolidin-2-yl)ethoxy)-2-oxo-2,3-dihydro-1H-imidazo[4,5-c]quinolin-7-yl)-1-naphthonitrile;

or a pharmaceutically acceptable salt thereof.

30. A pharmaceutical composition comprising a compound of claim 1, or a pharmaceutically acceptable salt thereof, and at least one pharmaceutically acceptable carrier or excipient.

31. A method of inhibiting KRAS activity, said method comprising contacting a compound of claim 1 with KRAS.

32. A method of treating a KRAS-mediated disease or disorder associated with abnormal expression or activity of KRAS interaction, said method comprising administering to a patient in need thereof a therapeutically effective amount of a compound of claim 1, wherein the KRAS-mediated disease or disorder is selected from pancreatic cancer, colorectal cancer and lung cancer.

33. A method of treating a KRAS-mediated disease or disorder wherein the KRAS protein harbors a G12D mutation, said method comprising administering to a patient in need thereof a therapeutically effective amount of a compound of claim 1, wherein the KRAS-mediated disease or disorder is selected from pancreatic cancer, colorectal cancer and lung cancer.

34. The compound of claim 1, wherein the compound of Formula I is 5-(1-((endo)-2-azabicyclo[2.1.1]hexan-5-yl)-8-(2-cyanoethyl)-2-ethyl-6-fluoro-7-(3-hydroxynaphthalen-1-yl)-1H-imidazo[4,5-c]quinolin-4-yl)-N-methylpicolinamide, or a pharmaceutically acceptable salt thereof.

* * * * *